(12) United States Patent
Sederoff et al.

(10) Patent No.: US 11,248,235 B2
(45) Date of Patent: Feb. 15, 2022

(54) RE-ENGINEERING OF MYCORRHIZAL SYMBIOSIS IN PLANTS

(71) Applicant: NORTH CAROLINA STATE UNIVERSITY, Raleigh, NC (US)

(72) Inventors: Heike Sederoff, Raleigh, NC (US); Eli Hornstein, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 16/623,962

(22) PCT Filed: Jun. 19, 2018

(86) PCT No.: PCT/US2018/038173
§ 371 (c)(1),
(2) Date: Dec. 18, 2019

(87) PCT Pub. No.: WO2018/236792
PCT Pub. Date: Dec. 27, 2018

(65) Prior Publication Data
US 2020/0199614 A1    Jun. 25, 2020

Related U.S. Application Data

(60) Provisional application No. 62/522,917, filed on Jun. 21, 2017.

(51) Int. Cl.
*C12N 15/82* (2006.01)
*A01H 17/00* (2006.01)
*C07K 14/415* (2006.01)

(52) U.S. Cl.
CPC ......... *C12N 15/8282* (2013.01); *A01H 17/00* (2013.01); *C07K 14/415* (2013.01); *C12N 15/8281* (2013.01)

(58) Field of Classification Search
None
See application file for complete search history.

(56) References Cited

U.S. PATENT DOCUMENTS

| 2013/0067975 | A1  | 3/2013  | Herrera-Estrella et al. |
| 2013/0333061 | A1* | 12/2013 | Wu .......................... A01H 5/10 800/260 |

FOREIGN PATENT DOCUMENTS

| WO | 2012/028673 | 3/2012 |

OTHER PUBLICATIONS

Chen, et al. (New Phytologist 180.2 (2008): 311-315). (Year: 2008).*
GenBank Accession XM_003612555 dated Aug. 25, 2015. (Year: 2015).*
Horváth et al. (Molecular plant-microbe interactions 24.11 (2011): 1345-1358. (Year: 2011).*
Chen et al. "OsIPD3, an ortholog of the Medicago truncatula DMI3 interacting protein IPD3, is required for mycorrhizal symbiosis in rice" New Phytologist, 80(2):311-315 (2008).
Horvath et al. "Medicago truncatula IPD3 is a member of the common symbiotic signaling pathway required for rhizobial and mycorrhizal symbioses" Mol Plant Microbe Interact, 24(11):1345-1358 (2011).
Messinese et al. "A novel nuclear protein interacts with the symbiotic DMI3 calcium- and calmodulin-dependent protein kinase of Medicago truncatula" Mol Plant Microbe Interact, 20(8):912-921 (2007).
Ovchinnikova et al. "IPD3 controls the formation of nitrogen-fixing symbiosomes in pea and *Medicago* Spp." Mol Plant Microbe Interact, 24(11):1333-1344 (2011).
Prihatna et al. "A Novel Tomato Fusarium Wilt Tolerance Gene" Frontiers in Microbiology. vol. 9. p. 1226 (2018).
Yano et al. "CYCLOPS, a mediator of symbiotic intracellular accommodation" Proc. Natl. Acad. Sci. U.S.A, 105(51):2040-2045 (2008).
International Search Report, and Written Opinion corresponding to International Application No. PCT/US2018/038173, dated Oct. 30, 2018, 17 pages.
Das et al. "Functional conservation of CYCLOPS in crack entry legume Arachis hypogaea" Plant Science, 281:232-241 (2019).
Delaux et al. "Comparative Phylogenomics Uncovers the Impact of Symbiotic Associations on Host Genome Evolution" PLoS Genet, 10(7):e1004487 (2014).
Delaux et al. Supplemental Data from "Comparative Phylogenomics Uncovers the Impact of Symbiotic Associations on Host Genome Evolution" PLoS Genet, 10(7):e1004487 (2014) (11 pages).
Forsberg et al. "Fertile somatic hybrids between Brassica napus and *Arabidopsis thaliana*" Plant Science 95(2):213-223 (1994).
Jiang et al. "Intertribal somatic hybrids between *Brassica napus* and Camelina sativa with high linolenic acid content" Plant Cell Tissue and Organ Culture, 99(1):91-95 (2009).
Jin et al. "IPD3 and IPD3L Function Redundantly in Rhizobial and Mycorrhizal Symbioses" Frontiers in Plant Science, 9(article 267) (2018).
Larkan et al. "The reduced mycorrhizal colonisation (rmc) mutation of tomato disrupts five gene sequences including the CYCLOPS/IPD3 homologue" Mycorrhiza, 23(7):573-584 (2013).

(Continued)

*Primary Examiner* — Charles Logsdon
(74) *Attorney, Agent, or Firm* — Myers Bigel, P.A.

(57) ABSTRACT

The invention relates to methods and compositions for modifying naturally non-mycorrhizal plants to produce modified plants that can be colonized by a mycorrhizal fungus having increased nitrogen and phosphorus uptake, increased drought tolerance/resistance, increased resistance to fungal and/or bacterial pathogens, and/or increased growth rate, yield and/or biomass production of a naturally non-mycorrhizal plant. The invention further relates to plants, plant parts, and/or plant cells produced by the methods of the invention as well as harvested and processed products from the plants, plant parts, and/or plant cells.

9 Claims, No Drawings
Specification includes a Sequence Listing.

(56) References Cited

OTHER PUBLICATIONS

Lindsay et al. "A Phosphate-Dependent Requirement for Transcription Factors IPD3 and IPD3L During Arbuscular Mycorrhizal Symbiosis in Medicago truncatula" MPMI, 32(10):1277-1290 (2019).
Marchler-Bauer et al. "CDD/SPARCLE: functional classification of proteins via subfamily domain architectures" Nucleic Acids Research, 45:D200-D203 (2016).
Napier et al. "Transgenic plants as a sustainable, terrestrial source of fish oils" Eur. J. Lipid Sci. Technol. 117(9):1317-1324 (2015).
NCBI GenBank Accession No. ADV78033.1, "cyclops [Diphasiastrum digitatum]—Protein", 2 pages. Retrieved from URL: https://www.ncbi.nlm.nih.gov/protein/319917983/ (Retrieved on Jun. 25, 2021).
NCBI Reference Sequence NC_016411.2, "Medicago truncatula strain A17 chromosome 5, MedtrA17_4.0, whole genome shotgun sequence", 3 pages. Retrieved from URL: https://www.ncbi.nlm.nih.gov/nuccore/NC_016411.2?report=genbank (Retrieved on Jun. 30, 2021).
NCBI Reference Sequence NP_001269245.1, "CYCLOPS/IPD3-like protein [Solanum lycopersicum]", 2 pages. Retrieved from URL: https://www.ncbi.nlm.nih.gov/protein/536290943 (Retrieved on Jun. 30, 2021).
Pimprikar et al. "A CCaMK-CYCLOPS-DELLA Complex Activates Transcription of RAM1 to Regulate Arbuscule Branching" Current Biology, 26:987-998 (2016).
Prihatna et al. "Tomato CYCLOPS/IPD3 is required for mycorrhizal symbiosis but not tolerance to Fusarium wilt in mycorrhiza-deficient tomato mutant rmc" Mycorrhiza, 28:495-507 (2018).
Radhakrishnan et al. "An ancestral signalling pathway is conserved in intracellular symbioses-forming plant lineages" Nature Plants, 6:280-289 (2020).
Sharma et al. "Comparative genomics of Brassicaceae crops" Breeding Science, 64(1):3-13 (May 2014).
Singh et al. "CYCLOPS, a DNA-Binding Transcriptional Activator, Orchestrates Symbiotic Root Nodule Development" Cell Host & Microbe 15(2):139-152 (2014).
UniProt entry reference A9XMT3.1 (CCLOP_LOTJA); last modified on Feb. 5, 2008. Retrieved from URL: https://www.uniprot.org/uniprot/A9XMT3 (Retrieved on Jun. 30, 2021).
UniProt entry reference A9XMT4.1 (CCLOP_PEA); last modified on Feb. 5, 2008. Retrieved from URL: https://www.uniprot.org/uniprot/A9XMT4 (Retrieved on Jun. 30, 2021).
Wang et al. "Phylogenetic distribution and evolution of mycorrhizas in land plants" Mycorrhiza, 16(5):299-363 (2006).
Wang et al. "Presence of three mycorrhizal genes in the common ancestor of land plants suggests a key role of mycorrhizas in the colonization of land by plants" New Phytologist, 186(2):514-525 (2010).
Wu et al. "Stepwise engineering to produce high yields of very long-chain polyunsaturated fatty acids in plants" Nature Biotechnology, 23(8):1013-1017 (2005).
Yano et al. "CYCLOPS, a mediator of symbiotic intracellular accommodation" PNAS, 105(51):20540-20545 (2008).
Yano et al. Supplemental Information for "CYCLOPS, a mediator of symbiotic intracellular accommodation" PNAS, 105(51):20540-20545 (2008) (14 pages).

\* cited by examiner

RE-ENGINEERING OF MYCORRHIZAL SYMBIOSIS IN PLANTS

STATEMENT OF PRIORITY

This application claims the benefit, under 35 U.S.C. § 119 (e), of U.S. Provisional Application No. 62/522,917 filed on Jun. 21, 2017, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-921WO_ST25.txt, 307,357 bytes in size, generated on Jun. 19, 2018 and filed via EFS-Web, is provided in lieu of a paper copy. This Sequence Listing is hereby incorporated herein by reference into the specification for its disclosures.

FIELD OF THE INVENTION

The invention relates to methods and compositions for modifying naturally non-mycorrhizal plants to produce modified plants comprising in their genome a heterologous polynucleotide encoding an IPD3 (Interacting Protein of DMI3) polypeptide, which can be colonized by a mycorrhizal fungus.

BACKGROUND OF THE INVENTION

Mycorrhizae are symbiotic interfaces between plant roots and soil fungi in which the fungus provides increased uptake of nitrogen, phosphorous, and water. This relationship is an integral part of the biology of most plants, being present in about 80-95% of all plant species. However, this symbiotic relationship is not found in many plants of economic importance, including plants in the Brassicaceae and the Amaranthaceae families.

SUMMARY OF THE INVENTION

One aspect of the invention provides a modified naturally non-mycorrhizal plant, comprising in its genome a heterologous polynucleotide encoding an IPD3 (Interacting Protein of DMI3) polypeptide or a heterologous polynucleotide encoding an IPD3 phosphomimic polypeptide.

A second aspect provides a method of modifying a naturally non-mycorrhizal plant to produce a modified plant that is colonized by a mycorrhizal fungus when in contact with the mycorrhizal fungus, comprising: introducing into a naturally non-mycorrhizal plant, plant part or plant cell a heterologous polynucleotide encoding an IPD3 (Interacting Protein of DMI3) polypeptide or a heterologous polynucleotide encoding an IPD3 phosphomimic polypeptide, thereby producing the modified naturally non-mycorrhizal plant that is colonized by the mycorrhizal fungus when in contact with the mycorrhizal fungus.

A third aspect provides a method of producing a modified plant that is colonized by a mycorrhizal fungus from a plant that is a naturally non-mycorrhizal plant, comprising: introducing into a naturally non-mycorrhizal plant, or plant part or plant cell thereof; a heterologous polynucleotide encoding an IPD3 (Interacting Protein of DMI3) polypeptide or a heterologous polynucleotide encoding an IPD3 phosphomimic polypeptide, thereby producing the modified naturally non-mycorrhizal plant that is colonized by the mycorrhizal fungus.

A fourth aspect provides a method of producing a modified naturally non-mycorrhizal plant having increased nitrogen uptake, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased nitrogen uptake.

A fifth aspect of the invention provides a method of producing a modified naturally non-mycorrhizal plant having increased phosphorus uptake, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased phosphorus uptake.

A sixth aspect provides a method of producing a modified naturally non-mycorrhizal plant having increased drought tolerance/resistance, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased drought tolerance/resistance.

A seventh aspect provides a method of producing a modified naturally non-mycorrhizal plant having increased resistance to fungal and/or bacterial pathogens, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased resistance to fungal and/or bacterial pathogens.

A eighth aspect of the invention provides a method of producing a modified naturally non-mycorrhizal plant having an increased growth rate, yield and/or biomass production, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased growth rate, yield and/or biomass production.

A ninth aspect of the invention provides a method of increasing nitrogen uptake, phosphorus uptake, drought tolerance/resistance, resistance to fungal and/or bacterial pathogens, and/or growth rate, yield and/or biomass production of a naturally non-mycorrhizal plant, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce a modified naturally non-mycorrhizal plant, and contacting the modified naturally non-mycorrhizal plant with a mycorrhizal fungus, wherein the modified naturally non-mycorrhizal plant has increased nitrogen uptake, phosphorus uptake, drought tolerance/resistance, resistance to fungal and/or bacterial pathogens, and/or growth rate, yield and/or biomass production.

A tenth aspect of the invention provides a recombinant nucleic acid molecule comprising at least one polynucleotide selected from the group of polynucleotides consisting of:

(a) a polynucleotide encoding an IPD3 (DMI3-interacting protein IPD3/CYCLOPS) having a nucleotide sequence of any one of SEQ ID NOs:1-5;

(b) a polynucleotide encoding an IPD3 phosphomimic having a nucleotide sequence of any one of SEQ ID NOs: 6-9;

(c) a polynucleotide encoding a DMI3 (Doesn't Make Infections 3) polypeptide having a nucleotide sequence of any one of SEQ ID NOs:19-25;

(d) a polynucleotide encoding an DMI3 phosphomimic having a nucleotide sequence of SEQ ID NO:26, or SEQ ID NO:27;

(e) a polynucleotide encoding an isoflavone synthase (IFS) having a nucleotide sequence of any one of SEQ ID NOs:37-45;

(f) a polynucleotide encoding a flavone synthase 1 (FS1) having a nucleotide sequence of any one of SEQ ID NOs: 55-61; and/or (g) a polynucleotide encoding a flavone synthase 2 (FS2) having a nucleotide sequence of any one of SEQ ID NOs: 69-79;

(h) a polynucleotide having at least 70% identity to any one of the polynucleotides of (a)-(g);

(i) a polynucleotide that is complementary to any one of the polynucleotides of (a) to (h) above;

(j) a polynucleotide that hybridizes to any one of the polynucleotides of (a) to (i) above under stringent hybridization conditions;

(k) a functional fragment of any one of the polynucleotides of (a) to (j) above; or (l) any combination of the polynucleotides of (a) to (k) above.

An eleventh aspect of the invention provides a recombinant nucleic acid molecule comprising at least one polynucleotide selected from the group of polynucleotides consisting of:

(a) a polynucleotide encoding an IPD3 (DMI3-interacting protein IPD3/CYCLOPS) having an amino acid sequence of any one of SEQ ID NOs:10-14;

(b) a polynucleotide encoding an IPD3 phosphomimic having an amino acid sequence of SEQ ID NOs:15-18;

(c) a polynucleotide encoding a DMI3 (Doesn't Make Infections 3) polypeptide having an amino acid sequence of any one of SEQ ID NOs:28-34;

(d) a polynucleotide encoding an DMI3 phosphomimic having an amino acid sequence of SEQ ID NO:35 or SEQ ID NO:36;

(e) a polynucleotide encoding an isoflavone synthase (IFS) having an amino acid sequence of any one of SEQ ID NOs:46-54;

(f) a polynucleotide encoding a FS1 flavone synthase 1 having an amino acid sequence of any one of SEQ ID NO:62-68; and/or (g) a polynucleotide encoding a FS2 flavone synthase having an amino acid sequence of any one of SEQ ID NO:80-90;

(h) a polynucleotide having at least 70% identity to any one of the polynucleotides of (a)-(g);

(i) a polynucleotide that is complementary to any one of the polynucleotides of (a) to (h) above;

(j) a polynucleotide that hybridizes to any one of the polynucleotides of (a) to (i) above under stringent hybridization conditions;

(k) a functional fragment of any one of the polynucleotides of (a) to (j) above; or (l) any combination of the polynucleotides of (a) to (k) above.

Further provided are expression cassettes and vectors comprising a recombinant nucleic acid molecule of the invention and plants, plant parts and plant cells comprising a recombinant nucleic acid molecule, expression cassette or vector of the invention as well as crops comprising the plants of the invention and harvested and processed products produced from plants and plant parts thereof of the invention.

These and other aspects of the invention are set forth in more detail in the description of the invention below.

BRIEF DESCRIPTION OF THE SEQUENCES IN THE SEQUENCE LISTING

SEQ ID NOs:1-5 are IPD3 cDNA sequences.

SEQ ID NOs:6-9 are synthetic IPD3 phosphomimic polynucleotides.

SEQ ID NOs:10-14 are IPD3 polypeptides encoded by the nucleotide sequences of SEQ ID NOs:1-5.

SEQ ID NOs:15-18 are IPD3 phosphomimic polypeptides encoded by the nucleotide sequences of SEQ ID NOs:6-9.

SEQ ID NOs:19-25 are DMI3 cDNA sequences.

SEQ ID NOs:26-27 are synthetic DMI3 phosphomimic polynucleotides.

SEQ ID NOs:28-34 are DMI3 polypeptides encoded by the nucleotide sequences of SEQ ID NOs:19-25.

SEQ ID NOs:35-36 are DMI3 phosphomimic polypeptides encoded by the nucleotide sequences of SEQ ID NOs:26-27.

SEQ ID NOs:37-45 are IFS cDNA sequences.

SEQ ID NOs:46-54 are IFS polypeptides encoded by the nucleotide sequences of SEQ ID NOs:37-45.

SEQ ID NOs:55-61 are FS1 cDNA sequences.

SEQ ID NOs:62-68 are FS1 polypeptides encoded by the nucleotide sequences of SEQ ID NOs:55-61.

SEQ ID NOs:69-79 are FS2 cDNA sequences.

SEQ ID NOs:80-90 are FS2 polypeptides encoded by the nucleotide sequences of SEQ ID NOs:69-79.

SEQ ID NO:91 is an IPD3 promoter sequence.

SEQ ID NO:92 is an IPD3 terminator sequence.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 500% or more as compared to a control (e.g., the native or wild type non-mycorrhizal plant that is not transformed with the heterologous polynucleotides of the invention (e.g., heterologous polynucleotides encoding IPD3, IPD3 phosphomimic, DMI3, DMI3 phosphomimic, IFS, FS1, FS2 polypeptides) or that is transformed with an inactive or inactivated form of the heterologous polynucleotides of the invention).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control (e.g., the native or wild type non-mycorrhizal plant that is not transformed with the heterologous polynucleotides of the invention (e.g., heterologous polynucleotides encoding IPD3, IPD3 phosphomimic, DMI3, DMI3 phosphomimic, IFS, FS1, FS2 polypeptides) or that is transformed with an inactive or inactivated form of the heterologous polynucleotides of the invention). In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression. Such functional RNAs include but are not limited to RNAi (e.g., siRNA, shRNA), miRNA, antisense RNA, ribozymes, RNA aptamers, and the like.

The terms "contact" or "contacting" (or grammatical variations thereof) as used herein to refer to contacting a plant with a mycorrhizal fungus means any method by which mycorrhizal fungi may be delivered to or placed in proximity to a plant of the present invention so as to allow the plant and fungus to form mycorrhizae. Thus, this may occur in culture in a laboratory, a greenhouse, and/or growth chamber using any synthetic or naturally occurring media (e.g., culture media or soil) or it may occur naturally by planting the modified plants of the invention in soil in a field. Additionally, in some embodiments, mycorrhizal fungi may be delivered to a plant as a seed coating or by mixing a mycorrhizal fungal inoculum with seeds prior to planting. In some embodiments, mycorrhizal fungi may be delivered to a plant as a soil inoculum or amendment.

"Yield" as used herein, refers to the amount (as measured by weight or number) of tissue produced per plant. Plant tissues can include any plant part (e.g., leaves, stems, stalks, seeds, fruits, and the like) or the whole plant itself. An increase in yield can be an increase of about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 500% or more as compared to a control (e.g., the native or wild type non-mycorrhizal plant that is not transformed with the heterologous polynucleotides of the invention (e.g., heterologous polynucleotides encoding IPD3, IPD3 phosphomimic, DMI3, DMI3 phosphomimic, IFS, FS1, FS2 polypeptides) or is transformed with an inactive or inactivated form of the heterologous polynucleotides of the invention).

Some proteins are activated or deactivated by phosphorylation. "Phosphomimic" proteins are modified polypeptides (or nucleic acids encoding the same) (non-naturally occurring polypeptides and polynucleotides) that have amino acid substitutions that carry a negative charge on their side chain and therefore mimic a phosphorylated protein, such that the modified polypeptide no longer requires phosphorylation for activation or deactivation. IPD3 and DMI3 each require phosphorylation for activity. However, an IPD3 phosphomimic and a DMI3 phosphomimic as provided herein are active without requiring phosphorylation. Substitutions for the phosphorylation site amino acid (typically serine or threonine) in the native sequence are typically glutamate (glutamic acid) or aspartate (aspartic acid). To create a dephospho-mimic plant, the same amino acids (typically serine or threonine) would be replaced by an amino acid with a neutral (e.g. alanine, valine) or positively charged amino acid (e.g. lysine, arginine or histidine) or synthetic amino acids.

"Increased biomass production" as used herein refers to a modified plant of the invention or plant part thereof having a greater dry weight over the entire plant or any organ of the plant (leaf, stem, roots, seeds, seed pods, flowers, etc), increased plant height, leaf number, and/or seed number or increased root volume compared to the native or wild type (e.g., a plant, plant part that is not transformed with the heterologous polynucleotides of the invention (e.g., heterologous polynucleotides encoding IPD3, IPD3 phosphomimic, DMI3, DMI3 phosphomimic, IFS, FS1, FS2 polypeptides). An increase in biomass production can be an increase of about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 200%, 250%, 300%, 350%, 400%, 500% or more as compared to a control (e.g., the native or wild type non-mycorrhizal plant that is not transformed with the heterologous polynucleotides of the invention (e.g., heterologous polynucleotides encoding IPD3, IPD3 phosphomimic, DMI3, DMI3 phosphomimic, IFS, FS1, FS2 polypeptides) or that is transformed with an inactive or inactivated form of the heterologous polynucleotides of the invention. Such an inactive form could be a dephospho-mimic where the phosphorylation site is replaced by an amino acid with a site chain that is neutral (e.g. alanine, glycine, valine) or positively charged (e.g. arginine, histidine, lysine)).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid is a nucleotide sequence that is naturally associated with a host cell into which it is introduced.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof.

In some embodiments, the heterologous or recombinant nucleic acid constructs of the invention may be "synthetic." A "synthetic" nucleic acid molecule, a "synthetic" nucleotide sequence or a "synthetic" polypeptide is a nucleic acid molecule, nucleotide sequence or polypeptide that is not found in nature but is created by the hand of a human (including synthetic sequences generated by robots) and is therefore not a product of nature. Thus, for example, phosphomimic polypeptides or cDNAs as described herein are not found in nature but are made by the hand of a human and therefore are synthetic.

In some embodiments, the heterologous or recombinant nucleic acids molecules, nucleotide sequences and/or polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In some embodiments, an isolated nucleic acid molecule, an isolated nucleotide sequence and/or an isolated polypeptide may be at least about 1%, 5%, 10%, 20%, 30%, 40%, 50%, 60%, 70%, 80%, 90%, 95% pure or more.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the heterologous nucleic acid constructs, nucleotide sequences and their encoded polypeptides are "isolated" in that, by the hand of a human, they exist apart from their native environment and therefore are not products of nature, however, in some embodiments, they can be introduced into and exist in a recombinant host cell.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "genome" as used herein includes an organism's chromosomal/nuclear genome as well as any mitochondrial, and/or plasmid genome.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

A "fragment" or "portion" of a nucleotide sequence refers to a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a functional fragment that encodes a polypeptide that retains its function (e.g., a fragment of an IPD3 polypeptide retains one or more of the activities of a native IPD3 polypeptide). In representative embodiments, the invention may comprise a functional fragment of an IPD3, DMI3, IFS, FS1 or FS2 polypeptide that is encoded by a fragment of an IPD3, DMI3, IFS, FS1 or FS2 polynucleotide, respectively.

Thus, as used herein, "fragment" means a portion of the reference polypeptide that retains the polypeptide activity of IPD3, IPD3 phosphomimic, DMI3, DMI3 phosphomimic, IFS, FS1, or FS2. A fragment also means a portion of a nucleic acid molecule encoding the reference polypeptide. An active fragment of the polypeptide can be prepared, for example, by isolating a portion of a polypeptide-encoding nucleic acid molecule that expresses the encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, or 2000 contiguous nucleotides, or up to the number of nucleotides present in a full-length polypeptide-encoding nucleic acid molecule. As such, polypeptide fragments can be at least about 100, 125, 150, 175, 200, 225, 250, 275, 300, 325, 350, 375, 400, 425, 450, 475, 500, or 525 contiguous amino acid residues, or up to the total number of amino acid residues present in the full-length polypeptide.

By "operably linked" or "operably associated," it is meant that the indicated elements are functionally related to each other, and are also generally physically related. Thus, the term "operably linked" or "operably associated" as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

In some embodiments, a "heterologous" or a "recombinant" nucleotide sequence is a nucleotide sequence not naturally associated with a host cell into which it is introduced, including non-naturally occurring multiple copies of a naturally occurring nucleotide sequence. In some embodiments, "heterologous" may refer to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence may include a nucleotide sequence derived from and inserted into the same natural, original cell type, but which is present in a non-natural state, e.g. present in a different copy number, and/or under the control of different regulatory sequences than that found in the native state of the nucleic acid molecule.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention. Thus, in some embodiments, a homologue of an IPD3, IPD3 phosphomimic, DMI3, DMI3 phosphomimic, IFS, FS1, or FS2 polynucleotide of the invention can be about 70% identical or more to an IPD3, IPD3 phosphomimic, DMI3, DMI3 phosphomimic, IFS, FS1, or FS2 polynucleotide or polypeptide as set forth herein. In some embodiments, an amino acid homologue of an IPD3, IPD3 phosphomimic, DMI3, DMI3 phosphomimic, IFS, FS1, or FS2 useful with this invention can be encoded by a polynucleotide having about 50% or more similarity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to an IPD3, IPD3 phosphomimic, DMI3, DMI3 phosphomimic, IFS, FS1, or FS2 polynucleotide as set forth herein.

As used herein, hybridization, hybridize, hybridizing, and grammatical variations thereof, refer to the binding of two fully complementary nucleotide sequences or substantially complementary sequences in which some mismatched base pairs may be present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 200 residues to about 500 residues in length. Thus, in some embodiments of the invention, the substantial identity (e.g., at least about 70% identity) exists over a region of the sequences that is at least about 200, about 250, about 300, about 350, about 400, about 450, about 500 or more residues in length, and any range therein. In some embodiments, sequences of the invention can be about 70% to about 100% identical over at least about 16 nucleotides to about 25 nucleotides. In some embodiments, sequences of the invention can be about 75% to about 100% identical over at least about 200 nucleotides to about 500 nucleotides. In further embodiments, sequences of the invention can be about 80% to about 100% identical over at least about 200 nucleotides to about 500 nucleotides. In some embodiments, the sequences may be substantially identical over the entire length of a coding region. Furthermore, a substantially identical nucleotide or polypeptide sequences perform substantially the same function.

As used herein, the phrase "substantially similar," or "substantial similarity" in the context of two amino acid sequences, refers to two or more sequences or subsequences that have at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci.* USA 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

Any nucleotide sequence to be transformed into a plant, plant part and/or plant cell can be modified for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications for the nucleotide sequences for selection are determined by comparing the species specific codon usage table with the codons present in the native polynucleotide sequences. In those embodiments in which each of codons in native polynucleotide sequence for selection are sufficiently used, then no modifications are needed (e.g., a frequency of more than 30% for a codon used for a specific amino acid in that species would indicate no need for modification). In other embodiments, wherein up to 3 nucleotides have to be modified in the polynucleotide sequence, site-directed mutagenesis can be used according to methods known in the art (Zheng et al. *Nucleic Acids Res.* 32:e115 (2004); Dammai, *Meth. Mol. Biol* 634:111-126 (2010); Davis and Vierstra. *Plant Mol. Biol.* 36(4): 521-528 (1998)). In still other embodiments, wherein more than three nucleotide changes are necessary, a synthetic nucleotide sequence can be generated using the same codon usage as the highly expressed genes that were used to develop the codon usage table. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in some embodiments of the invention, a heterologous polynucleotide or recombinant nucleic acid molecule of this invention may be codon optimized for expression in the particular species of interest.

The great majority (about 80-95%) of known plant species form beneficial relationships with fungi in the soil, known as mycorrhizae. The fungi grow into or around the plant's roots and provide increased uptake of nitrogen, phosphorous and water in return for carbohydrate compounds. The minority of plant species that do lack mycorrhizae are of notable economic interest including those in the mustard (Brassicaceae) family whose members are used for food (e.g., canola, broccoli, cabbage), biofuels (e.g., *Camelina*) and research (e.g., *Arabidopsis*) as well as those in the Amaranthaceae, which now includes the former Chenopodiaceae (goosefoot) family (e.g., spinach, beet, chard, quinoa, and sugar beet). Extant sister groups to the Brassicaceae possess mycorrhizae, indicating that the ancestors of this group previously had the ability to form mycorrhizae. Most of the pathways and genes required for the establishment of arbuscular mycorrhizal (AM)– in plants have been researched in AM-forming crops and thus, these pathways and genes are fairly well known. A study of the evolutionary loss of the ability of Brassicaceae to form AM concluded that Brassicaceae have lost/lack at least eleven genes needed to establish symbiosis (Delaux et al., *Plos Genetics* 10(7) (2014)). Based on that analysis, it would not be feasible to engineer all eleven genes back into a mustard plant. However, the present inventors have surprisingly found that many known genetic components of the mycorrhizal phenotype are still present in Brassicaceae species making restoration of this important phenotype achievable in naturally non-mycorrhizal plants.

The first implicated pathway is the Common Symbiosis Pathway (CSP), which is so named because it mediates accommodation of both mycorrhizal and rhizobial symbionts, allows host plants to perceive the presence of symbiotic fungal or bacterial partners. The upstream end of the pathway is a protein kinase (e.g. NFP in *Medicago truncatula*) activated by binding of an extracellular domain to chitin oligomers shed by the fungus. Activation of the pathway ultimately leads to upregulation of cutin synthesis (e.g. via RAM2 in *M. truncatula*) and production of other proteins and metabolites (e.g. carbohydrates and CWI in *Lotus japonicus*) in cells of the root cortex. Cutin concentrations guide the symbiont toward the appropriate cells for formation of symbiotic structures, and may also affect the cell wall chemistry at the site of infection.

Historically, research has asserted (a) that almost all gene members of the CSP must be expressed for symbiosis to function and (b) that large swathes of the CSP are completely absent from the genome of Brassicaceae plants (Delaux et al., *Plos Genetics* 10(7) (2014); and Delaux et al., *Trends in Plant Science* 18(6):298-304 (2013)). However, more recent research using functional-genetic methods, rather than phylogenomics has contradicted this view. Knockout studies at the individual gene level reveal that while loss of most genes in the CSP alters mycorrhization, only a single gene (contrary to assertion (a)), IPD3, clearly destroys mycorrhizal function when knocked out. Bioinformatic re-analysis of 'lost' CSP genes in Brassicaceae by the present inventors also reveals (contrary to assertion (b)) that putative orthologs of all but one 'lost' CSP gene are in fact present in these species. The single gene that is unambiguously missing from Brassicaceae is once again IPD3.

A second pathway that may be involved is flavonoid synthesis. Flavonoids affect mycorrhizae in multiple ways. Most importantly, molecular subclasses known as flavones and isoflavones are secreted into soil by the plant, where they recruit fungal symbionts to grow into root tissue (Hassan and Mathesius. *J. Exp. Bot.* 63(9):3429-3444 (2012)). As with IPD3, a few genes of the flavonoid synthesis pathway are conspicuously absent from the Brassicaceae while the majority of the genes in this pathway remain in place. The three absent genes are isoflavone synthase (IFS, production of isoflavones) and flavone synthases 1 and 2 (FS1, FS2, production of flavones). The immediate upstream enzyme that produces the substrate for synthesis of both flavones and isoflavones by IFS, FS1 and/or FS2 is chalcone synthase (CHS). CHS is not only already present in the genome of Brassicaceae plants, and in *Arabidopsis*, it has been found to be most highly expressed in the root cortex cells where mycorrhizal colonization takes place.

Thus, the present invention is directed to the discovery of one CSP gene and three flavonoid genes having functional roles in AM-positive plants of which one or more of these genes may be introduced into naturally non-mycorrhizal plants for restoration of mycorrhizae in whole or in part.

Accordingly, the present invention is directed in part to compositions and methods for modifying plants that do not naturally form symbiotic relationships with mycorrhizal fungi (e.g. naturally non-mycorrhizal plants (e.g., plants in the Brassicaceae and Amaranthaceae families)), wherein the modified plants can be colonized by and form a symbiotic relationship with mycorrhizal fungi.

In some embodiments, the present invention provides a modified naturally non-mycorrhizal plant, comprising in its genome a heterologous polynucleotide encoding an IPD3 (Interacting Protein of DMI3) polypeptide or a heterologous polynucleotide encoding an IPD3 phosphomimic polypeptide. In some embodiments, the modified plant is colonized by mycorrhizal fungi.

A modified naturally non-mycorrhizal plant comprising in its genome a heterologous polynucleotide encoding an IPD3 (Interacting Protein of DMI3) polypeptide or a heterologous polynucleotide encoding an IPD3 phosphomimic polypeptide of the invention may comprise additional genetic modifications. In some embodiments, the modified naturally non-mycorrhizal plant may further comprise in its genome (a) a heterologous polynucleotide encoding a DMI3 (Doesn't Make Infections 3) polypeptide or a heterologous polynucleotide encoding a DMI3 phosphomimic polypeptide, (b) a heterologous polynucleotide encoding an isoflavone synthase (IFS) polypeptide, (c) a heterologous polynucleotide encoding a flavone synthase 1 (FS1) polypeptide and/or (d) a heterologous polynucleotide encoding a flavone synthase 2 (FS2) polypeptide, or any combination thereof of (a), (b), (c) or (d). In some embodiments, a modified plant of this invention is colonized by mycorrhizal fungi.

Thus, in some embodiments, a modified naturally non-mycorrhizal plant of the invention may comprise in its genome a heterologous polynucleotide encoding an IPD3 polypeptide or a heterologous polynucleotide encoding an IPD3 phosphomimic polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome a heterologous polynucleotide encoding a DMI3 polypeptide or a DMI3 phosphomimic polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome a heterologous polynucleotide encoding an IFS polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome a heterologous polynucleotide encoding an FS1 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome a heterologous polynucleotide encoding an FS1 polypeptide and a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding an IFS polypeptide and (b) a heterologous polynucleotide encoding an FS1 polypeptide.

In some embodiments, a modified naturally non-mycorrhizal plant of the invention comprising in its genome a heterologous polynucleotide encoding an IPD3 polypeptide and/or a heterologous polynucleotide encoding an IPD3 phosphomimic polypeptide may further comprise in its genome (a) a heterologous polynucleotide encoding an IFS polypeptide and (b) a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding an IFS polypeptide, (b) a heterologous polynucleotide encoding an FS1 polypeptide, and (c) a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide, may further comprise in its genome (a) a heterologous polynucleotide encoding a DMI3 polypeptide or a DMI3 phosphomimic polypeptide, and (b) a heterologous polynucleotide encoding an IFS polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide and (b) a heterologous polynucleotide encoding an FS1 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide and (b) a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide and (b) a heterologous polynucleotide encoding an FS1 polypeptide, and(c) a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide, (b) a heterologous polynucleotide encoding an IFS polypeptide, and (c) a heterologous polynucleotide encoding an FS1 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide, (b) a heterologous polynucleotide encoding an IFS polypeptide, and (c) a heterologous polynucleotide encoding an FS2 polypeptide.

In some embodiments, a modified naturally non-mycorrhizal plant of the invention comprising in its genome a heterologous polynucleotide encoding an IPD3 polypeptide or a heterologous polynucleotide encoding an IPD3 phosphomimic polypeptide may further comprise in its genome (a) a heterologous polynucleotide encoding a DMI3 polypeptide or an DMI3 phosphomimic polypeptide, (b) a heterologous polynucleotide encoding an IFS polypeptide, (c) a heterologous polynucleotide encoding an FS1 polypeptide and (d) a heterologous polynucleotide encoding an FS2 polypeptide.

In some embodiments, one or more (e.g., 1, 2, 3, 4, 5, 6, or more) heterologous polynucleotides that encode an IPD3 polypeptide, an IPD3 phosphomimic polypeptide, a DMI3 polypeptide, a DMI3 phosphomimic polypeptide, an IFS polypeptide, a FS1 polypeptide or a FS1 polypeptide may be introduced into the genome of a modified naturally non-mycorrhizal plant of the invention on one or more nucleic acid constructs (e.g., expression cassettes and/or vectors).

The introduction of a heterologous polynucleotide encoding an IPD3 or IPD3 phosphomimic into a naturally non-mycorrhizal plant as described herein (with or without the introduction of DMI3, DMI3 phosphomimic, IFS, and/or FS1 and/or FS2) not only provides modified naturally non-mycorrhizal plants that now may form symbiotic relationships with mycorrhizal fungi but as a consequence of forming mycorrhizal symbiotic relationships with mycorrhizal fungi, the plants of the present invention also have characteristics associated with plants in mycorrhizal symbiotic relationships including, but not limited to, increased drought tolerance/resistance, increased nitrogen uptake, increased phosphorus uptake, increased resistance to fungal and/or bacterial pathogens and/or increased growth rate, yield and/or biomass production.

Thus, in some embodiments, the present invention provides a method of modifying a naturally non-mycorrhizal plant to produce a plant that is colonized by a mycorrhizal fungus when in contact with the mycorrhizal fungus, comprising: introducing into the naturally non-mycorrhizal plant, plant part or plant cell a heterologous polynucleotide encoding an IPD3 (Interacting Protein of DMI3) polypeptide or a heterologous polynucleotide encoding an IPD3 phosphomimic polypeptide, thereby producing a modified naturally non-mycorrhizal plant that is colonized by the mycorrhizal fungus when in contact with the mycorrhizal fungus.

In some embodiments, the invention provides a method of producing a modified plant that is colonized by a mycorrhizal fungus from a plant that is a naturally non-mycorrhizal plant, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide, thereby producing the modified naturally non-mycorrhizal plant that is colonized by the mycorrhizal fungus when in contact with the mycorrhizal fungus.

In some embodiments, a method of producing a modified naturally non-mycorrhizal plant having increased nitrogen uptake and/or increased phosphorus uptake is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased nitrogen uptake and/or increased phosphorus uptake.

In some embodiments, a method of producing a modified naturally non-mycorrhizal plant having increased drought tolerance/resistance is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased drought tolerance/resistance.

In some embodiments, a method of producing a modified naturally non-mycorrhizal plant having increased resistance to fungal and/or bacterial pathogens is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased resistance to fungal and/or bacterial pathogens.

A plant produced using the methods of the present invention may have increased resistance to any pathogenic fungus or bacterium. Example pathogenic fungi include, but are not limited to, the genera *Phytophthora* (e.g. *P. brassicae, P. porri, P. infestans*), *Pythium* (*P. irregular, P. ultimum, P. aphanidermatum*), *Colletotrichum* (e.g. *C. higginsianum, C. dematium* and other anthracnoses), *Aphanomyces* (e.g. *A. raphani*), *Ganoderma* (e.g. *G. orbiforme* and other pathogens causing 'damping-off'), *Fusarium* (e.g. *F. oxysporum*), *Cercospora* (e.g. *C. brassicicola*), *Plasmodiophora* (e.g. *P. brassicae*), *Thielaviopsis* (e.g. *T. basicola* syn. *Chalara elegans*), and/or *Rhizoctonia* (e.g. *R. solani*). Example pathogenic bacteria include, but are not limited to, the genera *Pseudomonas* (e.g. *P. syringae*, *P. marginalis*), *Xanthomonas* (e.g. *X. campestris campestris*, and/or *X. campestris raphani*).

In some embodiments, a method of producing a modified naturally non-mycorrhizal plant having an increased growth rate, yield and/or biomass production is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, and contacting the modified naturally non-mycorrhizal plant with a mycorrhizal fungus, thereby producing the modified naturally non-mycorrhizal plant having increased growth rate, yield and/or biomass production.

In some embodiments, a method of producing a modified naturally non-mycorrhizal plant having an increased nitrogen uptake, increased phosphorus uptake, increased drought tolerance/resistance, increased resistance to fungal and/or bacterial pathogens, and/or increased growth rate, yield and/or biomass may further comprise introducing into the naturally non-mycorrhizal plant, or plant part or plant cell thereof one or more additional heterologous polypeptides including, but not limited to, (a) a heterologous polynucleotide encoding a DMI3 (Doesn't Make Infections 3) polypeptide or a heterologous polynucleotide encoding a DMI3 phosphomimic polypeptide, (b) a heterologous polynucleotide encoding an isoflavone synthase (IFS) polypeptide, (c) a heterologous polynucleotide encoding a flavone synthase 1 (FS1) polypeptide, and/or (d) a heterologous polynucleotide encoding a flavone synthase 2 (FS2) polypeptide, or any combination thereof.

In some embodiments, a method of increasing nitrogen uptake and/or phosphorus uptake, of a naturally non-mycorrhizal plant is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce a modified naturally non-mycorrhizal plant, and contacting the modified naturally non-mycorrhizal plant with a mycorrhizal fungus, wherein the modified naturally non-mycorrhizal plant has increased nitrogen uptake and/or phosphorus uptake.

In some embodiments, a method of increasing drought tolerance/resistance of a naturally non-mycorrhizal plant is provided, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce a modified naturally non-mycorrhizal plant, and contacting the modified naturally non-mycorrhizal plant with a mycorrhizal fungus, wherein the modified naturally non-mycorrhizal plant has increased drought tolerance/resistance.

In some embodiments, a method of increasing resistance to fungal and/or bacterial pathogens of a naturally non-mycorrhizal plant, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce a modified naturally non-mycorrhizal plant, and contacting the modified naturally non-mycorrhizal plant with a mycorrhizal fungus, wherein the modified naturally non-mycorrhizal plant has resistance to fungal and/or bacterial pathogens.

In some embodiments, a method of increasing growth rate, yield and/or biomass production of a naturally non-mycorrhizal plant, comprising: introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce a modified naturally non-mycorrhizal plant, and contacting the modified naturally non-mycorrhizal plant with a mycorrhizal fungus, wherein the naturally non-mycorrhizal plant has an increased growth rate, yield and/or biomass production.

In some embodiments, a method of increasing phosphorus uptake, increasing drought tolerance/resistance, increasing resistance to fungal and/or bacterial pathogens, and/or increasing growth rate, yield and/or biomass of a naturally non-mycorrhizal plant having an increased nitrogen uptake, increased may further comprise introducing into the naturally non-mycorrhizal plant, or plant part or plant cell thereof, one or more additional heterologous polypeptides including, but not limited to, (a) a heterologous polynucleotide encoding a DMI3 (Doesn't Make Infections 3) polypeptide or a heterologous polynucleotide encoding a DMI3 phosphomimic polypeptide, (b) a heterologous polynucleotide encoding an IFS polypeptide, (c) a heterologous polynucleotide encoding a FS1 polypeptide and/or (d) a heterologous polynucleotide encoding a FS2 polypeptide, in any combination thereof. When one or more heterologous polypeptides are introduced into a plant, they may be introduced in a single recombinant nucleic acid construct (e.g., a single expression cassette/vector) or in two or more nucleic acid constructs (e.g., 2, 3, 4, 5, 6, 7, or more expression cassettes/vectors). The additional heterologous polynucleotides may be introduced on the same or different nucleic acid constructs as the heterologous polynucleotide encoding an IPD3 polypeptide and/or the heterologous polynucleotide encoding an IPD3 phosphomimic polypeptide.

A heterologous polynucleotide encoding an IPD3 polypeptide, a DMI3 polypeptide, an IFS, a FS1 and/or a FS2 for introducing into a naturally non-mycorrhizal plant, or plant cell or plant part thereof, may be obtained from any naturally mycorrhizal or rhizobial host plant including, but not limited to, *Medicago* spp. (e.g., *Medicago truncatula*), *Lotus* spp. (e.g., *Lotus japonicus*), *Zea* spp. (e.g., *Zea mays*), *Oryza* spp. (e.g., *Oryza sativa*), *Triticum* spp. (e.g., *Triticum aestivum*), *Lycopersicon* spp. (e.g., *Lycopersicon esculentum*), *Cucumis* spp. (e.g., *Cucumis sativus*), *Tropaeolum* spp. (e.g., *Tropaeolum majus*), *Carica* spp. (e.g., *Carica papaya*), *Moringa* spp. (e.g., *Moringa oleifera*), *Pisum* spp. (e.g., *Pisum sativum*), *Solanum* spp. (e.g., *Solanum lycopersicum*), *Diphasiastrum* spp. (e.g., *Diphasiastrum digitatum*), *Glycine* spp. (e.g., *Glycine max*), *Phaseolus* spp. (e.g., *Phaseolus vulgaris*), *Arachis* spp. (e.g., *Arachis hypogea*), *Petunia* spp. (e.g., *Petunia* x *hybrida*), *Sesbania* spp. (e.g., *Sesbania rostrate*), *Trifolium* spp. (e.g., *Trifolium pretense*), *Beta* spp. (e.g., *Beta vulgaris*), *Vicia* spp. (e.g., *Vicia villosa*), *Caragana* spp. (e.g., *Caragana arborescens*), *Vigna* spp. (e.g., *Vigna unguiculata*, *Petroselinum* spp. (e.g., *Petroselinum crispum*), *Cuminum* spp. (e.g., *Cuminum cyminum*), *Aethusa* spp. (e.g., *Aethusa cynapium*), *Angelica* spp. (e.g., *Angelica archangelica*), *Apium* spp. (e.g., *Apium graveolens*), *Conium* spp. (e.g., *Conium maculatum*), *Daucus* spp. (e.g., *Daucus carota*, e.g., *Daucus carota* var. *sativa*), *Perilla* spp. (e.g., *Perilla frutescens*, e.g., *Perilla frutescens* var. *crispa*),

*Gerbera* spp. (e.g., *Gerbera* x *hybrida*, e.g., cross between *Gerbera jamesonii* and *Gerbera viridifolia*), *Gentiana* spp. (e.g., *Gentiana triflora*), *Antirrhinum* spp. (e.g., *Antirrhinum majus*), *Theobroma* spp. (e.g., *Theobroma cacao*), *Camellia* spp. (e.g., *Camellia sinensis*), *Plectranthus* spp. (e.g., *Plectranthus barbatus*), and *Lonicera* spp. (e.g., *Lonicera japonica*). In some embodiments, a heterologous polynucleotide encoding an IPD3 polypeptide, a DMI3 polypeptide, an IFS, a FS1 and/or a FS2 useful with this invention may be obtained from, for example, *Medicago* spp., *Lotus* spp., and/or *Glycine* spp. In some embodiments, a heterologous polynucleotide encoding an IPD3 polypeptide, a DMI3 polypeptide, an IFS, a FS1 and/or a FS2 for introducing into a naturally non-mycorrhizal plant, or plant cell or plant part thereof, may also be obtained from a plant that naturally produces an IPD3 polypeptide, a DMI3 polypeptide, an IFS, a FS1 and/or a FS2 in the absence of a mycorrhizal or rhizobial phenotype (e.g., *Beta vulgaris, Lupinus* spp.). In some embodiments, an IPD3 phosphomimic polypeptide and/or a DMI3 phosphomimic polypeptide may be synthesized from any IPD3 and/or DMI3 polypeptide obtained from any naturally mycorrhizal or rhizobial host plant, including but not limited to the mycorrhizal or rhizobial host plants described above.

In some embodiments, a heterologous polynucleotide encoding an IPD3 may comprise a nucleotide sequence having at least about 70% identity to any one of SEQ ID NOs:1-5 and/or a nucleotide sequence having at least about 70% identity to a polynucleotide encoding an amino acid sequence of any one of SEQ ID NOs:10-14. In some embodiments, a heterologous polynucleotide encoding an IPD3 phosphomimic may comprise a nucleotide sequence having at least about 70% identity to any one of SEQ ID NOs:6-9, and/or a polynucleotide encoding an amino acid sequence having at least about 70% identity to any one of SEQ ID NOs:15-18. Thus, in some embodiments, the sequence of a homologue of a phosphomimic polypeptide may be less than 100% identical to a phosphomimic polypeptide of the invention while maintaining the phosphomimic site(s) in the polypeptide.

In some embodiments, a heterologous polynucleotide encoding an DMI3 may comprise a nucleotide sequence having at least about 70% identity to any one of SEQ ID NOs:19-25 and/or a nucleotide sequence having at least about 70% identity to a polynucleotide encoding an amino acid sequence of any one of SEQ ID NOs:28-34. In some embodiments, a heterologous polynucleotide encoding an DMI3 phosphomimic may comprise a nucleotide sequence having at least about 70% identity to the nucleotide sequence of SEQ ID NO:26 or SEQ ID NO:27, and/or a nucleotide sequence having at least about 70% identity to a polynucleotide encoding an amino acid sequence of SEQ ID NO 35 or SEQ ID NO:36.

Thus, in some embodiments, the polypeptide or polynucleotide sequence of a homologue of a phosphomimic polypeptide (e.g., an IPD3 or a DMI3 phsophomimic) may be less than 100% identical to a phosphomimic polypeptide or polynucleotide of the invention, while maintaining the phosphomimic site(s).

In some embodiments, a heterologous polynucleotide encoding an IFS may comprise a nucleotide sequence having at least about 70% identity to a nucleotide sequence of any one of SEQ ID NOs:37-45 and/or a nucleotide sequence having at least about 70% identity to a polynucleotide encoding an amino acid sequence of any one of SEQ ID NOs: 46-54.

In some embodiments, a heterologous polynucleotide encoding an FS1 may comprise a nucleotide sequence having at least about 70% identity to a nucleotide sequence of any one of SEQ ID NOs:55-61 and/or having at least about 70% identity to a polynucleotide encoding an amino acid sequence of any one of SEQ ID NOs:62-68.

In some embodiments, a heterologous polynucleotide encoding an FS2 may comprise a nucleotide sequence having at least about 70% identity to a nucleotide sequence of any one of SEQ ID NOs:69-79 and/or having at least about 70% identity to a polynucleotide encoding an amino acid sequence of any one of SEQ ID NOs:80-90.

Also provided herein are plants, plant parts, or plant cells produced by any of the methods of the present invention, plants derived from the plants, plant parts, or plant cells produced by this invention, seeds produced from plants of the invention, and crops comprising plants of the present invention, as well as products harvested from the plants or parts thereof, or crops, and processed products produced from the seeds and other harvested products.

As used herein, "a naturally non-mycorrhizal plant" may be any plant that lacks arbuscular mycorrhizae and does not naturally form a symbiotic relationship with an arbuscular mycorrhizal fungus. The term "naturally non-mycorrhizal plant" also includes plants having incidental or limited colonization by mycorrhizal fungi, plants that may be colonized by mycorrhizal fungi in a non-symbiotic role, and plants that may be colonized by fungi but that do not complete the fungal lifecycle or where the fungi do not colonize significant portions of the root system, form intraradical hyphae, vesicles, intracellular hyphae, and spores, and complete nutrient exchange with the host.

In some embodiments, a naturally non-mycorrhizal plant may be a species in the Brassicaceae plant family. Members of the family Brassicaceae do not undergo symbiosis and are not typically colonized by mycorrhizal fungi in other capacities. Example plants in the Brassicaceae family include, but are not limited to, *Brassica napus* (canola), *Brassica oleraceae* (e.g., broccoli, cabbage, cauliflower, kale, Brussels sprouts, collard), *Brassica juncea* (e.g., mustard, e.g., brown mustard, Chinese mustard, Indian mustard, leaf mustard, Oriental mustard and vegetable mustard), *Camelina sativa, Brassica rapa* (e.g., turnip, napa cabbage, bomdong, bok choy), *Arabidopsis thaliana, Alliaria petiolata, Sinapis alba, Thlaspi arvense, Raphanus sativus* (e.g., radish), or *Cleome spinosa*.

In some embodiments, a naturally non-mycorrhizal plant may be a species in the Amaranthaceae plant family. Members of the family Amaranthaceae are not known to undergo typical AM symbiosis but may be colonized at low levels, commensally, in limited circumstances, and/or without all anatomical or physiological features of the functional AM relationship, by mycorrhizal fungi. Example plants in the Amaranthaceae plant family include, but are not limited to, *Beta vulgaris* (e.g., beet, sugar beet), *Amaranthus caudatus, Amaranthus tricolor, Hebanthe ariantha, Spinacia oleraceae* (e.g., spinach), *Haloxylon ammodendron, Kalidium gracile, Suaeda californica*, or *Chenopodium quinoa*.

Members of families and genera with mixed species-level mycorrhizal status that may also be useful with this invention include those from any one of the plant families of *Caryophyllaceae, Crassulaceae, Lupinus, Proteaceae, Cyperaceae*, or *Juncaceae*. Thus, in some embodiments, a naturally non-mycorrhizal plant of the invention may be any naturally nonmycorrhizal species as defined herein that is in any one of the plant families of *Caryophyllaceae, Crassulaceae, Lupinus, Proteaceae, Cyperaceae*, or *Juncaceae*.

The modified plants produced by the methods of the present invention are expected to form relationships with any fungus otherwise capable of forming natural arbuscular-mycorrhizal relationships with a photosynthetic partner. Accordingly, in some embodiments, the modified plants of the present invention may be colonized by, and form a symbiotic mycorrhizal relationship with any member of the clade Glomeromycota. In some embodiments, the fungi that the modified plants of the present invention may be colonized by, and form a symbiotic mycorrhizal relationship include, but are not limited to, *Rhizophagus irregularis* (formerly *Glomus intraradices*), *Glomus mosseae, Glomus clarum, Glomus clavisporum, Gigaspora margarita, Acaulospora dilatata, Pacispora scintillans, Diversispora spurca, Funneliformis mosseae, Claroideoglomus claroideum, Archaeospora gerdemannii, Ambispora appendicula, Geosiphon pyriformis, Diskagma buttonii, Paraglomus laccatum*, any common model and or commercial strains thereof, or any combination thereof. If the clade Glomeromycota is reorganized by taxonomists, any former member and any fungus displaying a similar symbiotic lifestyle would still be included among those fungi that are capable of forming a symbiotic mycorrhizal relationship with the modified plants of the present invention.

Also provided herein are plants, plant parts, or plant cells produced by any of the methods of the present invention, plants derived from the plants, plant parts, or plant cells produced by this invention, seeds produced from plants of the invention, and crops comprising plants of the present invention, as well as products harvested from the plants or parts thereof, or crops, and processed products produced from the seeds and other harvested products.

In some embodiments, the present invention further provides a recombinant nucleic acid molecule comprising at least one of the following polynucleotides:

(a) a polynucleotide encoding an IPD3 (DMI3-interacting protein IPD3/CYCLOPS) having a nucleotide sequence of any one of SEQ ID NOs:1-5;

(b) a polynucleotide encoding an IPD3 phosphomimic having a nucleotide sequence of any one of SEQ ID NOs: 6-9;

(c) a polynucleotide encoding a DMI3 (Doesn't Make Infections 3) polypeptide having a nucleotide sequence of any one of SEQ ID NOs:19-25;

(d) a polynucleotide encoding an DMI3 phosphomimic having a nucleotide sequence of SEQ ID NO:26, or SEQ ID NO:27;

(e) a polynucleotide encoding an isoflavone synthase (IFS) having a nucleotide sequence of any one of SEQ ID NOs:37-45;

(f) a polynucleotide encoding a flavone synthase 1 (FS1) having a nucleotide sequence of any one of SEQ ID NOs: 55-61; and/or (g) a polynucleotide encoding a flavone synthase 2 (FS2) having a nucleotide sequence of any one of SEQ ID NOs: 69-79;

(h) a polynucleotide having at least 70% identity to any one of the polynucleotides of (a)-(g);

(i) a polynucleotide that is complementary to any one of the polynucleotides of (a) to (h) above;

(j) a polynucleotide that hybridizes to any one of the polynucleotides of (a) to (i) above under stringent hybridization conditions;

(k) a functional fragment of any one of the polynucleotides of (a) to (j) above; or (l) any combination of the polynucleotides of (a) to (k) above.

In some embodiments, the present invention provides a recombinant nucleic acid molecule comprising at least one of the following polynucleotides:

(a) a polynucleotide encoding an IPD3 (DMI3-interacting protein IPD3/CYCLOPS) having an amino acid sequence of any one of SEQ ID NOs:10-14;

(b) a polynucleotide encoding an IPD3 phosphomimic having an amino acid sequence of SEQ ID NOs:15-18;

(c) a polynucleotide encoding a DMI3 (Doesn't Make Infections 3) polypeptide having an amino acid sequence of any one of SEQ ID NOs:28-34;

(d) a polynucleotide encoding an DMI3 phosphomimic having an amino acid sequence of SEQ ID NO:35 or SEQ ID NO:36;

(e) a polynucleotide encoding an isoflavone synthase (IFS) having an amino acid sequence of any one of SEQ ID NOs:46-54;

(f) a polynucleotide encoding a FS1 flavone synthase 1 having an amino acid sequence of any one of SEQ ID NO:62-68; and/or (g) a polynucleotide encoding a FS2 flavone synthase having an amino acid sequence of any one of SEQ ID NO:80-90;

(h) a polynucleotide having at least 70% identity to any one of the polynucleotides of (a)-(g);

(i) a polynucleotide that is complementary to any one of the polynucleotides of (a) to (h) above;

(j) a polynucleotide that hybridizes to any one of the polynucleotides of (a) to (i) above under stringent hybridization conditions;

(k) a functional fragment of any one of the polynucleotides of (a) to (j) above; or (l) any combination of the polynucleotides of (a) to (k) above.

A recombinant nucleic acid molecule of the invention may be comprised in an expression cassette. An expression cassette comprising a recombinant nucleic acid molecule may be chimeric, meaning that at least one of its components is heterologous with respect to at least one of its other components. An expression cassette may also be one that is naturally occurring but has been obtained in a recombinant form useful for heterologous expression.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of plants and other organisms are well known in the art. Non-limiting examples of general classes of vectors include, but are not limited to, a viral vector, a plasmid vector, a phage vector, a phagemid vector, a cosmid, a fosmid, a bacteriophage, or an artificial chromosome. The selection of a vector will depend upon the preferred transformation technique and the target species for transformation. Accordingly, in further embodiments, a recombinant nucleic acid molecule of the invention can be comprised within a recombinant vector. The size of a vector can vary considerably depending on whether the vector comprises one or multiple expression cassettes (e.g., for molecular stacking). Thus, a vector size can range from about 3 kb to about 30 kb. Thus, in some embodiments, a vector is about 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 40 kb, 50 kb, 60 kb, and the like or any range therein, in size. In some particular embodiments, a vector can be about 3 kb to about 10 kb in size.

Additionally, shuttle vectors are included, which are DNA vehicles capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, a polynucleotide of this invention and/or expression cassettes comprising polynucleotides of this invention can be comprised in vectors as described herein and as known in the art.

In some embodiments, heterologous polynucleotides encoding an IPD3, IPD3 phosphomimic, DMI3, DMI3 phosphomimic, IFS, FS1 and/or FS2 polypeptide can be comprised in a single expression cassette. The expression cassette can be operably linked to a promoter that drives expression of all of the polynucleotides comprised in the expression cassette and/or the expression cassette can comprise one or more promoters operably linked to one or more of the heterologous polynucleotides for driving the expression of said heterologous polynucleotides. In some embodiments, the heterologous polynucleotides encoding IPD3, IPD3 phosphomimic, DMI3, DMI3 phosphomimic, IFS, and/or FS1 and FS2 polypeptides can be comprised in one or more expression cassettes, in any combination.

When the heterologous polynucleotides are comprised within more than one expression cassette, said heterologous polynucleotides can be introduced into plants singly or more than one at a time using co-transformation methods as known in the art. In addition to transformation technology, traditional breeding methods as known in the art can be used to assist in introducing into a single plant each of the polynucleotides encoding the polypeptides of the invention as described herein and/or any other polynucleotides of interest to produce a plant, plant part, and/or plant cell comprising and expressing each of the introduced heterologous polynucleotides.

Any promoter useful for initiation of transcription in a cell of a plant can be used in the expression cassettes/vectors of the present invention. A "promoter," as used herein, is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of a recombinant nucleic acid molecule of the invention, i.e., "chimeric genes" or "chimeric polynucleotides." A promoter can be identified in and isolated from an organism to be transformed and then inserted into the nucleic acid construct to be used in transformation of the organism.

The choice of promoter will vary depending on the temporal and spatial requirements for expression, and also depending on the host cell in which gene expression is desired. Promoters useful with the invention include, but are not limited to, those that drive expression of a nucleotide sequence constitutively, those that drive expression when induced, and those that drive expression in a tissue- or developmentally-specific manner. These various types of promoters are known in the art. Promoters can be identified in and isolated from the plant to be transformed and then inserted into the expression cassette to be used in transformation of the plant.

In any of the embodiments described herein, a heterologous polynucleotide and/or recombinant nucleic acid molecule of the invention can be operatively associated with a variety of promoters and other regulatory elements for expression in cells of various organisms. In embodiments described herein, one or more of the polynucleotides and nucleic acids of the invention may be operably associated with a promoter as well as a terminator, and/or other regulatory elements for expression in plant cell. Any promoter, terminator or other regulatory element that is functional in a plant cell may be used with the nucleic acids of this invention. In some embodiments, a regulatory element (e.g., promoter, terminator, and the like) that is useful with this invention may be a native or heterologous regulatory element. In some embodiments, a promoter may be a heterologous promoter or it may be a native promoter (e.g., native to the introduced nucleic acid, and/or native to the plant being transformed). Thus, in some embodiments, a promoter useful with this invention may be a native IPD3, DMI3, IFS, FS1 and/or FS2 promoter.

In some embodiments, a promoter may be from *Medicago* spp. (e.g., *Medicago truncatula*), *Lotus* spp. (e.g., *Lotus japonicus*), *Zea* spp. (e.g., *Zea mays*), *Oryza* spp. (e.g., *Oryza sativa*), *Triticum* spp. (e.g., *Triticum aestivum*), *Lycopersicon* spp. (e.g., *Lycopersicon esculentum*), *Cucumis* spp. (e.g., *Cucumis sativus*), *Tropaeolum* spp. (e.g., *Tropaeolum majus*), *Carica* spp. (e.g., *Carica papaya*), or *Moringa* spp. (e.g., *Moringa oleifera*). In some embodiments, a promoter useful with the invention may be a native IPD3, DMI3, IFS, FS1 and/or FS2 promoter from *Medicago* spp. (e.g., *Medicago truncatula*) (e.g., SEQ ID NO:91)), *Lotus* spp. (e.g., *Lotus japonicus*), *Zea* spp. (e.g., *Zea mays*), *Oryza* spp. (e.g., *Oryza sativa*), *Triticum* spp. (e.g., *Triticum aestivum*), *Lycopersicon* spp. (e.g., *Lycopersicon esculentum*), *Cucumis* spp. (e.g., *Cucumis sativus*), *Tropaeolum* spp. (e.g., *Tropaeolum majus*), *Carica* spp. (e.g., *Carica papaya*), or *Moringa* spp. (e.g., *Moringa oleifera*).

While expression of the heterologous polynucleotide encoding the polypeptides IPD3, IPD3 phosphomimic, DMI3, DMI3 phosphomimic, IFS, and/or FS1 and FS2 polypeptides as described herein may be designed to occur anywhere in a plant in an induced or developmentally regulated manner, it may be useful to express the polynucleotides in roots and root cortex cells and/or root epidermis cells where mycorrhizal colonization takes place using tissue-specific or tissue preferred promoter(s) (e.g., a root specific/preferred promoter(s)) Example root specific/root-preferred promoters include, but are not limited to, those described by de Framond (FEBS 290:103-106 (1991); EP 0 452 269 to Ciba-Geigy), the root hair-specific cis-elements (RHES) (Kim et al. *The Plant Cell* 18:2958-2970 (2006)), and the root-specific promoters RCc3 (Jeong et al. *Plant Physiol.* 153:185-197 (2010)) and RB7 (U.S. Pat. No. 5,459, 252). In some embodiments, a root specific promoter useful with the invention may include, but is not limited to, a promoter from the *Arabidopsis thaliana* Pht1;2 gene(s), the *Arabidopsis thaliana* Pyk10 gene, the *Sorghum bicolor* RCc3 gene, the *Avena strigose* Sad1 gene or the *Lotus japonicus* Cbp1 gene.

An expression cassette of the invention may include a terminator sequence. In some embodiments, a terminator sequence useful with this invention may be a native or heterologous terminator sequence. In some embodiments, a terminator sequence may be a terminator sequence from a gene from *Medicago* spp. In some embodiments, a terminator sequence may include, but is not limited to, a terminator sequence from an IPD3 gene of *Medicago trunculata* (e.g., SEQ ID NO:92).

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to a plant, plant part and/or plant cell expressing the marker and thus allows such a transformed plant, plant part, and/or plant cell to be distinguished from that which does not have the marker. Such a nucleotide sequence may encode either a selectable or screenable marker, depending on whether the marker confers a trait that can be selected for by chemical means, such as by using a selective agent (e.g., an antibiotic, herbicide, or the like), or whether the marker is simply a trait that one can identify through observation or testing, such as by screening. Of course, many examples of suitable selectable markers are known in the art and can be used in the expression cassettes described herein.

Examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aphA6 (i.e., kanamycin resistance), a nucleotide sequence encoding nptII (i.e., kanamycin resistance), a nucleotide sequence encoding bar (i.e., phosphinothricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp (i.e., green fluorescent protein), a nucleotide sequence encoding luc (i.e., luciferase), a nucleotide sequence encoding mCherry (i.e. a red fluorescent protein), a nucleotide sequence encoding ble (bleomycin resistance), a nucleotide sequence encoding ereA (erythromycin resistance), and any combination thereof.

Further examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts*, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci.* USA 75:3737-3741); a nucleotide sequence encoding xylE that encodes a catechol dioxygenase (Zukowsky et al. (1983) *Proc. Natl. Acad. Sci.* USA 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding Bla that confers ampicillin resistance; or a nucleotide sequence encoding aequorin which may be employed in calcium-sensitive bioluminescence detection (Prasher et al. (1985) *Biochem. Biophys. Res. Comm.* 126:1259-1268), and/or any combination thereof. One of skill in the art is capable of choosing a suitable selectable marker for use in an expression cassette or recombinant nucleic acid construct of this invention.

The term "transformation" as used herein refers to the introduction of a heterologous polynucleotide into a cell. Transformation of a plant, plant part, plant cell, yeast cell and/or bacterial cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

The phrase "a stably transformed plant, plant part, and/or plant cell expressing said one or more polynucleotide sequences" and similar phrases used herein, means that the stably transformed plant, plant part, and/or plant cell comprises the one or more polynucleotide sequences and that said one or more polynucleotide sequences are functional in said stably transformed plant, plant part, and/or plant cell.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols that are well known in the art.

A heterologous polynucleotide encoding an IPD3, IPD3 phosphomimic, DMI3, DMI3 phosphomimic, IFS, and/or FS1 and FS2 polypeptide can be introduced into a cell of a plant by any method known to those of skill in the art. In some embodiments of the invention, transformation of a cell comprises nuclear transformation.

Procedures for transforming plants are well known and routine in the art and are described throughout the literature. Non-limiting examples of transformation methods include transformation via bacterial-mediated nucleic acid delivery (e.g., via *Agrobacteria*) (including floral dip), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)). General guides to the transformation of yeast include Guthrie and Fink (1991) (Guide to yeast genetics and molecular biology. In *Methods in Enzymology*, (Academic Press, San Diego) 194:1-932) and guides to methods related to the transformation of bacteria include Aune and Aachmann (*Appl. Microbiol Biotechnol* 85:1301-1313 (2010)).

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

In some embodiments, when a plant part or plant cell is stably transformed, it can then be used to regenerate a stably transformed plant comprising one or more heterologous polynucleotides encoding an IPD3 polypeptide, IPD3 phosphomimic polypeptide, DMI3 polypeptide, DMI3 phosphomimic polypeptide, IFS polypeptide, FS1 polypeptide and/or FS2 polypeptide, or any combination thereof, and/or any other polynucleotides of interest as described herein in its genome. Means for regeneration can vary from plant species to plant species, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

The particular conditions for transformation, selection and regeneration of a plant can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Further, the genetic properties engineered into the transgenic seeds and plants, plant parts, and/or plant cells of the present invention described herein can be passed on by sexual reproduction or vegetative growth and therefore can be maintained and propagated in progeny plants. Generally, maintenance and propagation make use of known agricultural methods developed to fit specific purposes such as harvesting, sowing or tilling.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Common Symbiosis Pathway

A common explanation for the lack of mycorrhizae, especially in the phylogenetic literature, is that functionally necessary CSP elements are genomically absent from the Brassicaceae. However, this account is contradicted by findings at the individual gene level that (1) mycorrhizal colonization proceeds in the face of knockouts of most CSP genes and (2) orthologs of genes that have been scored as absent in Brassicaceae by phylogenetic studies exist in *Arabidopsis* and are shown to retain their symbiotic function via rescue of *M. truncatula* knockouts.

In view of this apparent conflict in research findings, we revisited the bioinformatic analysis of 11 CSP genes identified by Delaux et al. (*Plos Genetics* 10(7) (2014)) as present in AM-positive plants but missing in AM-negative plants, using the now-available *Camelina* genome as well as *Arabidopsis* and *Brassica napus*. We also performed protein structure modeling with SWISS-MODEL and compared putative CSP orthologs in *Arabidopsis/Camelina/Brassica* to models of the template *M. truncatula* sequence using the RCSB PDF Protein Comparison Tool. Our results (shown in Table 1) indicate that consistent with the genetic rather than the phylogenetic literature, sequences are present in Brassicaceae genomes that may constitute functional orthologs of all but one of the CSP genes previously thought to be absent in this clade.

presymbiotic adaptation of the plant root, forming a positive feedback loop with the CSP. *Arabidopsis* and *Camelina* genomes are lacking isoflavone synthase (IFS), flavone synthase 1 (FS1) and flavone synthase 2 (FS2), the precise genes required for synthesis of these stimulatory metabolites, again suggesting that these missing genes may be part of the missing core of lost signaling in Brassicaceae.

While knockout experiments of flavonoid pathway genes in AM-positive plants mirror the pattern observed with most CSP genes in which symbiosis is not fully lost in the absence of these metabolites, in an AM-negative *Brassica* species, the addition of flavone and isoflavone molecules to plant roots apparently stimulated colonization by the fungus. In addition, tissue-specific transcriptomic research found that the immediate upstream enzyme in the flavonoid pathway, chalcone synthase (CHS) is highly expressed in the root cortex cells of *Arabidopsis*, indicating that the chemical substrate of IFS, FS1, and FS2 is already present in the right location. We therefore identify these three genes as possible additional candidates for insertion into naturally non-mycorrhizal plants such as those in the Brassicaceae family.

TABLE 1

Identification of proteins in *Lotus japonicus*, *Arabidopsis thaliana* and *Camelina sativa* with sequence and structure similarity to known AM symbiosis proteins of *Medicago trunculata*. E-values, % amino acid (aa) identity, and structure comparison Z-scores are shown for models of the highest scoring protein/translated nucleotide sequences identified through BLAST. *Lotus japonicus* serves as a positive control because it also establishes functional AM symbiosis.

| SPECIES CSP GENE | *Lotus japonicus* e-value/aa ident./Z | *Arabidopsis thaliana* e-value/aa ident./Z | *Camelina sativa* e-value/aa ident./Z | Functional Annotation |
|---|---|---|---|---|
| NFP | 0/71%/7.64 | 2e-65/32%/6.7 | 7e-70/28%/7.02 | Receptor kinase |
| DMI2 | 0/82%/7.34 | 1e-132/34%/7.34 | 7e-132/35%/7.34 | Receptor kinase |
| CASTOR | 0/81%/8.4 | 0/64%/7.64 | 0/64%/8.12 | $Ca^{2+}$ channel |
| DMI3 | 0/86%/7.34 | 9e-77/37%/7.64 | 1e-76/34%/7.44 | $Ca^{2+}$ dep. kinase |
| IPD3 | 0/78%/NA | no sequence | no sequence | Coiled coil |
| RAM1 | 0/81%/7.93 | 8e-97/44%/7.74 | 2e-96/41%/7.64 | GRAS-TF |
| RAM2 | 0/89%/3.07 | 0/55%/3.5 | 0/54%/6.92 | Cutin synthesis |
| VAPYRIN | 4e-17/33%/7.1 | 3e-19/32%/5.04 | 6e-21/29%/7.02 | Ankyrin domain |
| STR | 0/87%/7.02 | 1e-94/49%/7.34 | 1e-96/56%/7.24 | ABC transporter |
| STR2 | 0/44%/7.24 | 1e-126 /37%/7.13 | 5e-126/36%/6.92 | ABC transporter |
| PT4 | 0/87%/6.81 | 0/62%/6.35 | 0/60%/7.34 | $P_i$ transporter |

The only protein listed in Table 1 that was confirmed to be conclusively missing from the *Arabidopsis* and *Camelina* genomes was IPD3. IPD3 is a nuclear membrane localized protein that is phosphorylated by DMI3, leading to upregulation of RAM1, a transcription factor for RAM2, as well as upregulation of other genes. IPD3 is also one of the few CSP genes found by mutagenesis studies to completely disable mycorrhizal formation when knocked out of AM-positive plants, suggesting that its absence may indeed be at the center of the lost AM signaling in Brassicaceae.

Example 2. Flavonoid Synthesis Pathway

Rhizosphere signaling is the other historical area of focus in studies of the mycorrhizal relationship, in which signals produced by the plant diffuse into soil to recruit the symbiont. Flavonoid metabolites, particularly flavones and isoflavones, are well-documented stimulants of mycorrhizal fungus germination and growth. These metabolites also induce production of chitin oligomers by the fungi that stimulate Example 3. *Camelina* and *Arabidopsis*

The five identified transgenes will be introduced individually into separate lines of *Camelina* and *Arabidopsis* with phenotypic and transcriptomic screening over two transgenic generations. *Camelina* and *Arabidopsis* are selected as the primary study organism because they are mustard crops with direct applications and/or sufficient tools available for analysis. *Camelina* is readily transformed by floral dip with *Agrobacterium* and has a relatively short generation time (3-4 months). *Agrobacterium* stocks carrying vectors with the desired transgenes generated for *Camelina* can also be applied to *Arabidopsis, Brassica napus* or other related plants without modification. *Medicago truncatula*, a model system for mycorrhizae, will be used as a source of transgenes and promoters for insertion. A non-limiting example of a mycorrhizal fungus for use as a fungal stimulus in functional phenotyping includes *Rhizophagus irregularis* (*Glomus intraradices*), a model AM symbiont.

1) Production of Five Transgenic Lines

For each of the five transgenes, primers will be designed using the published *Medicago* genome. A stock of *Medicago*

*truncatula* A17 'Jemalong' template DNA is prepared. In order to confer expression patterns consistent with symbiosis, primers will amplify the native *Medicago* promoter and terminator sequences around the coding region. Coding regions or other portions or modified versions of the genes of interest may also be synthesized directly. Plasmids will be assembled with kanamycin resistance for bacterial selection and the fluorescent protein mCHERRY with a seed-specific promoter for plant selection. Plasmids amplified in *E. coli* will be transformed by electroporation into *Agrobacterium tumefaciens* GV3101. The helper plasmid pSOUP commonly used for this strain of *Agrobacterium* will be used to aid transformation. Successfully transformed *Agrobacterium* cultures will be used to transform *Camelina* germline cells via floral dip.

Flowering stems of *Camelina sativa* 'Calena' will be immersed in medium containing the appropriate *Agrobacterium* construct and infiltrated under vacuum. Plants will be allowed to set seed, and all mature seeds from the infiltrated stems will be collected for screening. We observe a high transformation rate of 10-80%, which allows to screen relatively small groups of progeny to obtain transformants. Five 'T0' parent plants will be transformed for each transgene.

Seed gathered for each construct will be screened by fluorescence until 30 putative transformants are obtained. These seeds will be grown in the NC State greenhouse as the T1 generation of each line. DNA will be extracted from all plants in this generation and assayed by PCR to confirm the presence of the expected transgene. Seeds of T1 plants will be collected and planted for segregation as the T2 generation and for preliminary phenotyping.

2) Fungal Phenotyping of Transgenic Lines

Transgenic seedlings will be grown on sterile agarose plates, then challenged with inoculum plugs containing spores and mycelium of *Rhizophagus*. *Rhizophagus* cultures for inoculation will be maintained on hairy root cultures of carrot or aseptically grown *M. truncatula*. Seedlings of transgenic plants will be allowed to grow for one week after inoculation, then stained with trypan blue and individually examined for evidence of fungal mycelium and arbuscules within the roots.

3) Transcriptional Profiling of Transgenic Lines

T2 siblings will also be assessed by a qPCR screen to detect changes induced by transgene expression beyond the qualitative presence of fungus within the plant tissue. Roots of control and fungus-inoculated seedlings from each line will be frozen and used for mRNA extraction. Primers for cDNA of IPD3 plus the 10 putative *Camelina* orthologs of CSP genes will be used to screen the IPD3 insertion line for upregulation of those orthologs in response to fungal signals when the transgene is present. Such upregulation will be considered as evidence for conserved CSP function of a particular ortholog. Conversely, failure to respond predictably to the knock-in of IPD3 will be an indication that the *Camelina* genes do not retain a symbiotic role and are candidates for insertion of additional transgenes. cDNA primers for IFS, FS1 and FS2 along with the native upstream enzymes CHS, F3H and F3'H will be used to examine the respective lines for correlated expression changes in native elements of the phenylpropanoid (flavonoid) pathway.

The foregoing is illustrative of the present invention, and is not to be construed as limiting thereof. The invention is defined by the following claims, with equivalents of the claims to be included therein.

APPENDIX OF SEQUENCES

```
Medicago truncatula IPD3
>XM_003612555.2 Medicago truncatula cyclops protein, putative mRNA
TTTCTAACCTTTGAAGATTAATTTTTAACATCACAATCTTTTCTCTTTCATTGTACACAAgACAAATG
AATGGTACATGGAATCTTTTGAGTATTTTTTTCACTCTTAGATGTCATAGCCACTGCTCTAATATTTAGT
ATTTATTAATTCTATTGACAAAAACAAAAATCAGAAAAATATTTACTATTAGTAAATGCCAAGTTCTAAG
ACAAAGTTTATTTATCTATATGCAAGATTTCTTTCAAGTTTCACGTGTAAATTGTTGTAGGAAGCTATTC
CTTTAACTGTTTCATGTTAATTAGTTACTACATGCTTTTGGAATAAAACAGTTCATAAAGTCTTTCTTTC
ATTTCCTTGGTTTTTGAGAAGAAAAAATAGTTGCTAGCTTAGGTTGAATTTTCATTGAGTATTCAAAATT
CTCTCCCTTGGTTTTTGAGAAGGGTATTGTGATGAATAAAGAATTCAGCTGAAAATTCATTTATGAAACC
TGAAAGATCTTAGCCAAAAACCTGTGTTGAAAATAAGTTCAAGCATCATTCAAGTGTTTCTTTATAATCA
AGCATCTTTAAAGTGTTGAA[protein sequence starts from here→]
ATGGAAGGGAGAGGATTTTCTGGTTTATACAAGAATTCAAGTGAGGAGTT
ATTCTTGAAGACAGTGATGGAGAGTCCTATTGGTATGCCGGTACCTACCATGGAGATGTTAGGATTCAAG
ACTGTTTCTCAAAGCTTTCGCACCGATAGTGAAGAGCTTTTCAAACGCTGGCTAACAAATGATCAAGAGG
GATACATTCATCAAGCATGGGACTTAACAGTCGTTTGTCGAAGAGAATATCAACTGAAATAGCTAATAT
GTCTAATCAACAACACATTGGTGTGGCTTCAGAAGGAAGAAACAATGATAAATCATGCTTACAAAATAAC
TTCTTGGCAAATGATGTTTCAAGTGATTTCAATTTTCCAATCAGAGATCCTGTTGATAGAGAATTGCAAT
CTAGTAACTTGTTTCTGGCCAAGGCCTGGTTTATTACCGATCAACGAATGACAAGAAGCCGGTCTTCTGA
ATTGCGGCGAAGGTATACTGAAATGCAAAATTCTCAAGCACCACAAGGATTGGATTCTATGTTCATGGTT
CCTGAGCATGATACTAACACTATAAAAGAAGAACTTGCAAATTTTAATGGGTTTGATTACCTTTCCATGT
GTGAGTTACCAAGCCAAAAGGGCACATTCATGTCTCCATCCAACTCATCTTCGTCTACCTTCAACACACA
TCAATTGGTTGATGTAGATAAAGTTTCATCTTGTGTAAGTATGCTAAAAGGTACATTACAGCGCAAGAAA
CTCGAATGCCAAGTCGAGAAAGAAGCTGCAGAAGATGGCTTGAATGAAATATTTTGCATTCGAGAACCTC
TTTTCCAATCAGCTTTTAATGAAGAAGAAAGTTGGAATCAACAAAAGCTAGTAAACGTTCAAGGAGATTT
TACCGATCAAGTTAACGATCCCGGAGTCATGCAAACCCTTGAAGGAACCACAAACTTTGTCTTAGATGGT
TTTGCAAATCAGACGAACCAAATACAAGGCAGAACAGCTTCTGGAGAACCGTCTCAAAGTGAATCTTCTG
CTGCTGCACCAGTAATCTCATCTGGCTTAGATGCATGTGAAGGTCCCAGCAATTCAAATCAAACTCTTGG
TGATAGCTCATGGAAACAAGTGGGAGAAAGCACTCAAAATAAAGTCAGAGGTGTCAGAGAACAGATAATG
GATAATCTGAAAGATGACAGAAAGAGGAAAAGTCTAGAAAGATATGGATCTGTAACATCAGCTGTTTCAG
ATGGCAAGATGGATAACACAAAAAAGCGGAGGGTGGAGCGCTCAAGAAAAATGGCTGAAGCAAAGGAAAG
AAATTTGACACCAACAATTCCCTCAGATATGCAAGCTATCTTGAAGCGATGCGAAAACCTTGAGAAGGAA
GTTCGATCACTAAAGCTTAATTTGTCCTTCATGAATAGGAAGGATTCTGAACAAACAAAGCAGATAGAGG
ACCTTCAGAAGCAGAATGAAGACTTGGCGGATGAAAAAGAGCGCCTCCTCGAAGAGATTGAAAGAATTCT
ATCAGAAACTGGAAAGATTTGATGTTTTGTTTCGCTGTTATATCCTTATCCTCGTCAGAAACAATGTAGT
ACTCAGACAAGCTAAAAATCTCACCACAGTTTACTTGTGGATGAAACAGCTTAGGTAAAAGTGAAAACAG
TGATTAATAGTGAACCTATGGAGTCTATTAGCAAAATATAAATGCATGGAATCTGAGATATTAGTAATGA
```

APPENDIX OF SEQUENCES

CATTATATATCTGGTAAAATCTAAGTGTTATTCAAAATTTGAGCCATATAAATGAATCCGGTAAATTTAA
ACATGGTCAAGTGTACCCACCAACCTCAATCATATGTAACAAACAAATATCTTCAATTTGTTTATGC SEQ ID
NO: 1

*Lotus japonicus* IPD3
>EF569221.1 *Lotus japonicus* CYCLOPS mRNA, complete cds
TTGTTGCTCTGTTGCATGTTAATTTCTGTGCTATTTGGATAAAACAGTTCATGAACTGATAATAGTAAAG
TCTTCTTTTCTTCTTTTTTTTATCAGGAATAATTGCTAGGTTGACATGATTAAAAAAATTGGGTTTTGGG
GTTGATTTTTAGAGTGTATATATGGTTTTGAAGAAGGGTATTATGATGATGGATGACAGAGAATTTAGAT
GAAAATTCTGTTCTGAAACCTGAAAGTGCTGTTGAGCCAAACTTGAGTTGAAAACAACAGCTTCAATTGG
AAATGGAAGGGAGGGGGTTTTCTGGTTTATATAGAAACTCAAGTGAAGAATTGTTCCTGAAGACAGTGAT
GGAGAGCCCTATTGGTATGCCAGTTCCTTCAATGGAGATGCTGGGTTTCAAGAATGTTTCTCAAGGCTTT
CGCGCAGATAGCGAGGAGCTTTTCAAACGCTGGCTAACAAATGGAGAGGGATACAATTCATCAAGCATAG
GGTTTAGCAGTCGATTATCAAAGAGGATATCCACTGAACTAGTTAATGGATCTAATCAGCTACAAGTTGG
TGTAGCCTCAGATGGAAGAAACAATGACAAACCATTCATACAAAATAACCTTTTGGCAAATGATGTTTCA
GGTGATTTCAATTTTCCAATCAGAGATCCTGTTGATAGAGAACTGCAACCTAGTAACTTGTTTCTAGCCA
AGGCCTGGTTTCTCAGTGATCAACGAATGACAAGAAGCCGGTCCTCTGAATTGCGGCGGCGATATTCTGA
AATGCAAATGGTCTAGCCACACAAGGAATAGAATCCATTTGCATGGATCCTCAGCATGGTGCTGAGGCA
ACAAAACAAGAAGTTGCAAATTTCAATGGTTACAATTATCTCTCTATGTGTGAGCTTCCAAGTCAAAAGG
GTTCATTCATGTCTCCGTCCAACTCATGTTCATCTAACTTCAACACACCTCAATTTGGCACATGGATAA
AGTTTCATCTTGTGTAAGTATGCTGAAAGGGACATTACAACGCCGGAGACTCAGCAGTCAACTTGAGAAA
GAAGCTGCAGAAGATGACTTAAATGGAATTTTTTATCCTCAAGAACCTCTTTTCCAAACTGGCTTTGATC
AAGGACAAGAAAACTGGAGTAATCAAACGCCAGTAAATGTTCAAGTAGACTCTATTGGTGAAGTTAAGGA
TCATGGAGTCCTGCAAACACTAGAAGGATCCACAAACCCTGTCGTTGATGGTTTTGCAAATCAGATAAAC
CAAATCTATGTCGGAACAGCTTCTGGAGAACCTTCTCAAAGTGAATCCTCTAATGCTGCACCAGTAATCT
CCTCTGGTTTAGACACATGCGAAGGTCCCATAAACTCGAATCAAACTCTCTGCGAAAGCTCATGGAAACA
AGTAGGAGTGAGTAAAAGTTCAGAAAATACTCAAAATAGAGTCAAAGGTTTCAGAGAACAGATCATGGAT
AATCTGAAAGATGATAAGAAGAGAAAAAGTCTAGAAAGATATGATCTATAACATCAGCTGTTTCAGATG
ACAAGGGAGACACCACTAAAAAGCGTAGGGTGGAACGCTCAAGGAAAATGGCTGAAGCTAAGGAAAGAAA
TTCGACACCATCAGTTCCCTCAGATATGCAAGCTGTCTTGAAGCGGTGCGAAAACCTTGAGAAGGAAGTT
CGATCGCTAAAACTCAACTTGTCTTCATGAATAGAAAGGATTCTGAACAAACAAAGCAGATAGAAGACC
TTCAGAAGCAGAATGAAGAGCTGGCAGATGAAAAAGAGCGCCTCCTGAAGAGATTGAAAGAATTCTATC
AGAAACTGAAAAAATGTAATGATATGAGAATCAATGTTGTGCTCAAACACGC SEQ ID NO: 2

*Pisum sativum* IPD3
>EF569222.1 *Pisum sativum* CYCLOPS mRNA, complete cds
TTGAGCTGAAAATCGGTTCAAGAAGCTTTTGAGTGCTGGTTGAAATGGAAGGGAGAGGATTTTCTGGTTT
ATACAAGAATTCAAGTGAAGAGTTGTTCTTGAAGACAGTGATGGAGAGTCCTATTGGTATGCCAGTACCT
ACCATGGAGATGTTAGGATTCAAGACCGTTTCTCAAAGCTTTCGCGCCGATAGCGAGGAGCTTTTCAAGC
GCTGGCTGACAAATGAAGAGGGATACAATTCAACGAGCATGGGACTTAACAGTCGATTATCGAAGAGAAT
CTCCACTGAACTAGTTAATGTGTCTAATCAGCAACATGTTGGTGTGGCTTCAGAAGGAAGAAACAATGAT
AAATCATGCTTACAAAATAGCTTTTTGACAAATGATGTTTCGGGCGATTTCAATTTTCCAATCAGAGAAC
CTGTTGATAGAGAATTGCAATCTGGTAACTTGTTTCTGGCCAAGGCATGGTTTCTTACCGATCAAAGAAT
GACAAGAAGCCGGTCTTCTGAATTGCGGCGAAGGTATACCGAAATGCAAAATACTCAAGCACCACAAGGA
TTGGATTCAATGTTCATGGCTCCTAAGCATGATGCTAACATTATAAAAGAAGAACTTGCACATTTCAATG
GTTTTGATTACCTTTCAATGTGCGAAATACCAAGTCAAAAGGGCTCATTCATGTCTCCATCGAACTCATC
TTCGTCTACCTTCAACACACAACAATTGGTTGATGTAGATAAAGTTTCATCTTGCGTAAGTATGCTAAAA
GGTACGTTACAACGCAAGAGACTCGAATGCCAAGTCGAGAAAGATGCTGCAGAAGACGGTTTAAACGAAA
TTTTTGGTATTCGAGAGCCTCTTTTCCAATCTGGTTTTAATGAAGGACAAGAAAATTGGAAATCATCAAAA
GCTAGTAAATGTTCAAGGAGATTTTACCGATCAAGTTAAGGATACTGGAGTCATTGAAACATTTGAAGGA
GCCGCAAACTTTGTCTTAGAGGGTTTTGCAAATCAAACGAGCCAAATACACGGTGGAACGGCTTCCGGTG
AACCTTCTCAAAGTGAGTCTTCTGCTGCTGCACCAGTAATCTCATCTGGTTTAGATGCTTGTGAAGGACC
TAGCAATTCAAGTCAAACTCTTTGTGATAGCTCATGGAAACAATAGTAGGAGAAGCACTCAAAATGCAGCC
AAAGGTGTCAGAGAACAGATAATGGATAATCTGAAAGACGACAGGAAGAGGAAAAGACTAGAGAGATATG
GATCAGTAACATCAGCTGTTTCAGATGACAAGGTGGACACAACAAAAAAGCGAAGGGTGGAACGATCAAG
AAAAATGGCTGAGGCAAAGGAAAGAAATTTGACACCAACAATTCCCTCAGATATGCAAGCTGTCATGAAG
CGATGCGAAAACCTTGAGAAGGAAGTTCGATCGCTAAAGCTTAATTTGTCCTTCATGAATAGGAAGGATT
CTGAACAAACAAAGCAGATAGAGGATCTTCAGAAGCAGAATGAAGAGCTTGGCAGATGAAAAAGAGCGCCT
ACTCGAAGAGATCGAAAGACTTTTATCAGAAACTGGAAAGATTTAATGTTTTGTTGTTTTCTTATCATGT
CC SEQ ID NO: 3

*Solanum lycopersicum* IPD3
>NM_001282316.1 *Solanum lycopersicum* CYCLOPS/IPD3-like protein (Rmc), mRNA
ATGGAAATGGAGGGAAGAGGTTATTCAGATTTCTATAGAAACACAAGTGAAGAATTGTTCATAAGAACTA
TGATGGACAACTCAGTAGGAGGAGTGCCAGTTCCTACAATGGAGATGTTAGGTTTTAGAAACATCCCTCA
TTCTCTTCGAACCGACAGTGAGGAACTTTTCAAAAGCTGGCTCACAAGTGCAGAGAATAATGCAGTGAT
TCTACACCAATGGCTCGTGGTCGACAAGGATCACGAAGGATCTCCAGTGAACTTGCTGGTCTATCCAGTC
AGCAAAATGAGGGGATTCAGAAAAGAAAAATGGCCGATACTCAACAGCCACAGAATACATGTACTGCCAT
TGAATCATCTAGCAACCTTAATAAACATTCAACCAGGAACGCGACAGATAGGGAAATGCAAGCTAGTAAT
CTGTTTTTAGCCAAGACCTGGTTCCATAGCTCTCAGCCCATGACGGAAGCTGTTCATCTGAGTTAAGGA
GGAGGTATGCAGCCATGCAAAACTCACAGTCTTCACTAGCTCGTGAATCCTTGCAAAATATACCTGGAAA
TGCTGTTAATAGCTTCAAAGAAGAAGTTTCTCATCCCACTGGGTACACTGACATGTCAATGTGTGAAATG
ACCAACCAACCTAATACTTTTATGTCTCCATCAAATTCTTCTTCATCAACTTTTGAAGCACAGCAAGTGG
ATGGTGTGGATAATATTTCTTCTGTTGTAAGCATGCTAAAGGGGACCTTAGAGGAGAAGTCTTCAAGGA
CTATCATACTGCGAGGGAAGCCATTGAGGAGAATATGTTGGGTGTTATGGTAATCAAGAAATCTTTTGT
AACTCCGACATGAATCAACATCCAGGGAATCATATTTCTCTGAATCAAGGGACATATCAGGACACACCTG
TTGTTCAAGTCAGAGATACGGGGATCCCACAAACAGTTCAAGGGTCATTAGATGCCGTCTTAGAAAGTAT
TATGGCTCCCTCAAACCCAATCCAGATAGACATGGTAACACAGGAACCTTCTCAAAGTGGATCTTCTGTT

APPENDIX OF SEQUENCES

```
GCAGCACCAATACTTTCAATTGATTTTGATGCATATGATGGCCTGAGCAATGCAAGTCAAGCTTTAAATA
TGTACGAGGGCTGTAGAAATCAAGTCGGATATGGAAGGAGCTCAGAAAATGGTTCAACTGCTAGAGATAT
TAGAGAACGAATATATGACAACGTGAAGGACAACCAAAAGAAAGAAGGTTTAGTTCGAAATGGATCTTTA
ACATCTGTACAATCAGCGGAAAATGGAGATCCTAAGAAGAAGAGAAGGGTGGAGCGGTCTCGGAAAATGG
CAGAAGCCAAAGAGAGAAATTTAACACCAGCAATTCCTTCAGATATGCAATCCCTTGTGAAGCGCTGTGA
CAATCTGGAGAAGGAAGTTCGTTCACTTAAACTTAACCTGGCGTTTATGAACAGAAAGGATTCTGAACAG
ACTACACAAATTGAAGAGCTGCAGAAGCAGAATGAGGATTTGGTCAAGGAAAAAGAGCGCCTTCTTGGAG
AAATCGAGAGGATCATTTCAGAATCTGGAAAGTTTTAGATACTGTTACTCTTTAGCAGCTTCAGACGTGT
TT SEQ ID NO: 4
```

*Diphasiastrum digitatum* IPD3
>FJ913194.1 *Diphasiastrum digitatum* voucher Qiu 08001 cyclops (IPD3) mRNA, complete cds
```
ATGGTTGAGATTGCAGATAGGCGCATTACTAGAAGTGTGTCCTCCGAGCTTCAGGCCAGGCTTTCAACAC
AGCCTCAGACACAAGAAGGTGTGGAGGAGATAAGAGCTGTATCGGAGATATGGAGATATCGTGCTTTCA
AAGGAATTCAAGTGAGGAGATATTTTTGAGGAGTTTTATGGATGGTGCAATGGCGCCTGCCACTGAGGGC
ATGTCATTTTTGAGTCCGCCTCAGCCACCGCTTCGAGTAAACAGCGAGGAACTGTTTAACACTTGGCTCA
GCAATACGGATGCCCCGGGGCTTCCGCCATTATCTGGAGACTATCGAACCCTTCAAAATTCTTCAGAAT
GTCAAGTGAACTTGCTGGTAATCTTGGACAAGGAGCTGTCTCTCAACCATTTGATATTCCTGGAGAGAAT
GTGGCCCAAACAATTGGAGGACATCCTGATCCCAATGTCAGGGAAAGTAACATAGGGAAGCCAAGGAATC
ATGCTCCAAGCAAGGGATTGCCATTTCAAGATCATGCGTCTTGGCAGATGATCAACTGGTTTCAACAATC
TCAGCCGATGACACGAAGTCGCTCCTCTGAGCTTCGTCGTAAATACTTGGCAATGCAAGAAGGTCATAAA
CCTCCTCCCTCAGCCAACACCTTGCAATGGTTTGCAACACAAGGAACTGATGAATTGAATCGTGCTGTGG
CATCACTTGGGGCTTTCACACGTGCCCTTGCAAGCAAGAGACCAGATATATCCTCAACAGCATCTCCTCA
ACTTTCTCCCACCCCCATGTCCCATGTTAGTAAACTATCTCCCCAGAGGAATGGTGACTCTGTATCTGCT
GTTGTGAACATGCTTAAGGGAAGCTTAGAACGGAAGAAGCTTGCTGCAATGCAGCAACAGATGGATAAAC
CTGTTTCACCACCATATTGGAGATCCTTGGGACAGGACAAAGAGGATCCTCATAAGCCGATGATCGACTC
GCAACAGTGTATCTCTCCGCAAATTGAGTCTGAGCAACAACAAGAGAATCAAAAGGAAGCATTTTCGGCC
AGTCTTCAGATTACAAATGAGCAGTTCCAGGCTGGAGTGGTCACTCCACATGCCTTATCACCCAGCGATT
CATCTGGTAATGCACCTGGCCTGTCAGCTGGAGCAGCGACTAGTGAGGGGCCTTGCAACTCAAATCCTGC
TGTTTCCACTCAGAACAATTTCATCAAATGCTCTGGTCAGGGCAACTGGGCTGTAGATGAAACATTTCAG
CAAAACAACCTACCAAGCCCCACATCCAATGGGACAAGTAATGGAGAGATTCCTTACGAGGGTGTCTTGA
ATACAGACTACCAAAAGAGACAAGGCTACCTATCTCGTGCAGGCTCACTAACCTCTTCTTGTCGATCAGA
TCAAAGTATGCAAGTGTCTATTGGTGAGAGAACCCATAAGCTTGAAGGATCCACGGCAGATGCAGAAGAT
TCTACGAAGAAACGTCGAGTTGAACGGAAACGAATGATGGCTGAGGCAAAGGGGAGAAGTTATGTTCCTA
TGATGCCCTCTGATCTACAAGCAGCTACAAAACGATGTGATGCTTTGGAAAAGGAAGTAAGGTCCCTGAA
GCTGAACTTGTCTTTCATGAACAGAAAGGACTCTGAGCAGACCAAGCGAATAGAAGATCTTGAAAGCAG
AATGAGGAGTTACTTGCAGAGAAAGATCGACTAGTGGAGGAGGTCAGACGTTTTACCTCAGGAAAAAACT
TTGGTAGATCGTCTTAG SEQ ID NO: 5
``` nucleotide sequence of IPD3 phosphomimic 1 (modified from *Medicago truncatula*)
```
ATGGAAGGGAGAGGATTTTCTGGTTTATACAAGAATTCAAGTGAGGAGTTATTCTTGAAGACAGTGATGGAGAGT
CCTATTGGTATGCCGGTACCTACCATGGAGATGTTAGGATTCAAGACTGTTTCTCAAAGCTTTCGCACCGAT[GA
T]GAAGAGCTTTTCAAACGCTGGCTAACAAATGATCAAGAGGGATACAATTCATCAAGCATGGGACTTAACAGTC
GTTTGTCGAAGAGAATATCAACTGAAATAGCTAATATGTCTAATCAACAACACATTGGTGTGGCTTCAGAAGGAA
GAAACAATGATAAATCATGCTTACAAAATAACTTCTTGGCAAATGATGTTTCAAGTGATTTCAATTTTCCAATCA
GAGATCCTGTTGATAGAGAATTGCAATCTAGTAACTTGTTTCTGGCCAAGGCCTGGTTTATTACCGATCAACGAA
TGACAAGAAGCCGGTCTTCTGAATTGCGGCGAAGGTATACTGAAATGCAAAATTCTCAAGCACCACAAGGATTGG
ATTCTATGTTCATGGTTCCTGAGCATGATACTAACACTATAAAAGAAGAACTTGCAAATTTTAATGGGTTTGATT
ACCTTTCCATGTGTGAGTTACCAAGCCAAAAGGGCACATTCATGTCTCCATCCAACTCATCTTCGTCTACCTTCA
ACACACATCAATTGGTTGATGTAGATAAAGTTTCATCTTGTGTAAGTATGCTAAAAGGTACATTACAGCGCAAGA
AACTCGAATGCCAAGTCGAGAAAGAAGCTGCAGAAGATGGCTTGAATGAAATATTTTGCATTCGAGAACCTCTTT
TCCAATCAGCTTTTAATGAAGAAGAAAGTTGGAATCAACAAAAGCTAGTAAACGTTCAAGGAGATTTTACCGATC
AAGTTAACGATCCCGGAGTCATGCAAACCCTTGAAGGAACCACAAACTTTGTCTTAGATGGTTTTGCAAATCAGA
CGAACCAAATCAAGGCAGAACAGCTTCTGGAGAACCGTCTCAAAGTGAATCTTCTGCTGCTGCACCAGTAATCT
CATCTGGCTTAGATGCATGTGAAGGTCCCAGCAATTCAAATCAAACTCTTGGTGATAGCTCATGGAAACAAGTGG
GAGAAAGCACTCAAAATAAAGTCAGAGGTGTCAGAGAACAGATAATTGCAATAACTGAAGACTTGGCGGATGAAAAAGAGCGCCTCC
TCGAAGAGATTGAAAGAATTCTATCAGAAACTGGAAAGATTTGATGTTTTGTTTCGCTGTTATATCCTTATCCTC
GTCAGAAACAATGTAGTACTCAGACAAGCTAAAATCTCACCACAGTTTACTTGTGGATGAAACAGCTTAGGTAA
AAGTGAAAACAGTGATTAATAGTGAACCTATGGAGTCTATTAGCAAAATATAAATGCATGGAATCTGAGATATTA
GTAATGACATTATATATCTGGTAAAATCTAAGTGTTATTCAAAATTTGAGCCATATAAATGAATCCGGTAAATTT
AAACATGGTCAAGTGTACCCACCAACCTCAATCATATGTAACAAACAAATATCTTCAATTTGTTTATGC SEQ ID
NO: 6
``` nucleotide sequence of IPD3 phosphomimic 2 (modified from *Medicago truncatula*)
```
ATGGAAGGGAGAGGATTTTCTGGTTTATACAAGAATTCAAGTGAGGAGTTATTCTTGAAGACAGTGATGGAGAGT
CCTATTGGTATGCCGGTACCTACCATGGAGATGTTAGGATTCAAGACTGTT[GAG]CAAAGCTTTCGCACCGATA
GTGAAGAGCTTTTCAAACGCTGGCTAACAAATGATCAAGAGGGATACAATTCATCAAGCATGGGACTTAACAGTC
GTTTGTCGAAGAGAATATCAACTGAAATAGCTAATATGTCTAATCAACAACACATTGGTGTGGCTTCAGAAGGAA
GAAACAATGATAAATCATGCTTACAAAATAACTTCTTGGCAAATGATGTTTCAAGTGATTTCAATTTTCCAATCA
GAGATCCTGTTGATAGAGAATTGCAATCTAGTAACTTGTTTCTGGCCAAGGCCTGGTTTATTACCGATCAACGAA
TGACAAGAAGCCGGTCTTCTGAATTGCGGCGAAGGTATACTGAAATGCAAAATTCTCAAGCACCACAAGGATTGG
ATTCTATGTTCATGGTTCCTGAGCATGATACTAACACTATAAAAGAAGAACTTGCAAATTTTAATGGGTTTGATT
```

APPENDIX OF SEQUENCES

```
ACCTTTCCATGTGTGAGTTACCAAGCCAAAAGGGCACATTCATGTCTCCATCCAACTCATCTTCGTCTACCTTCA
ACACACATCAATTGGTTGATGTAGATAAAGTTTCATCTTGTGTAAGTATGCTAAAAGGTACATTACAGCGCAAGA
AACTCGAATGCCAAGTCGAGAAAGAAGCTGCAGAAGATGGCTTGAATGAAATATTTTGCATTCGAGAACCTCTTT
TCCAATCAGCTTTTAATGAAGAAGAAAGTTGGAATCAACAAAAGCTAGTAAACGTTCAAGGAGATTTTACCGATC
AAGTTAACGATCCCGGAGTCATGCAAACCCTTGAAGGAACCACAAACTTTGTCTTAGATGGTTTTGCAAATCAGA
CGAACCAAATACAAGGCAGAACAGCTTCTGGAGAACCGTCTCAAAGTGAATCTTCTGCTGCTGCACCAGTAATCT
CATCTGGCTTAGATGCATGTGAAGGTCCCAGCAATTCAAATCAAACTCTTGGTGATAGCTCATGGAAACAAGTGG
GAGAAAGCACTCAAAATAAAGTCAGAGGTGTCAGAGAACAGATAATGGATAATCTGAAAGATGACAGAAAGAGGA
AAAGTCTAGAAATATGGATCTGTAACATCAGCTGTTTCAGATGGCAAGATGGATAACACAAAAAAGCGGAGGG
TGGAGCGCTCAAGAAAATGGCTGAAGCAAAGGAAAGAAATTTGACACCAACAATTCCCTCAGATATGCAAGCTA
TCTTGAAGCGATGCGAAAACCTTGAGAAGGAAGTTCGATCACTAAAGCTTAATTTGTCCTTCATGAATAGGAAGG
ATTCTGAACAAACAAAGCAGATAGAGGACCTTCAGAAGCAGAATGAAGACTTGGCGGATGAAAAAGAGCGCCTCC
TCGAAGAGATTGAAAGAATTCTATCAGAAACTGGAAAGATTTGATGTTTTGTTTCGCTGTTATATCCTTATCCTC
GTCAGAAACAATGTAGTACTCAGACAAGCTAAAAATCTCACCACAGTTTACTTGTGGATGAAACAGCTTAGGTAA
AAGTGAAAACAGTGATTAATAGTGAACCTATGGAGTCTATTAGCAAAATATAATGCATGGAATCTGAGATATTA
GTAATGACATTATATATCTGGTAAAATCTAAGTGTTATTCAAAATTTGAGCCATATAAATGAATCCGGTAAATTT
AAACATGGTCAAGTGTACCCACCAACCTCAATCATATGTAACAAACAAATATCTTCAATTTGTTTATGC SEQ ID
NO: 7 nucleotide sequence of IPD3 phosphomimic 3 (modified from Lotus japonicus)
ATGGAAGGGAGGGGGTTTTCTGGTTTATATAGAAACTCAAGTGAAGAATTGTTCCTGAAGACAGTGATGGAGAGC
CCTATTGGTATGCCAGTTCCTTCAATGGAGATGCTGGGTTTCAAGAATGTTTCTCAAGGCTTTCGCGCAGATAGC
GAGGAGCTTTTCAAACGCTGGCTAACAAATGGAGAGGGATACAATTCATCAAGCATAGGGTTTAGCAGTCGATTA
TCAAAGAGGATATCCACTGAACTAGTTAATGGATCTAATCAGCTACAAGTTGGTGTAGCCTCAGATGGAAGAAAC
AATGACAAACCATTCATACAAAATAACCTTTTGGCAAATGATGTTTCAGGTGATTTCAATTTTCCAATCAGAGAT
CCTGTTGATAGAGAACTGCAACCTAGTAACTTGTTTCTAGCCAAGGCCTGGTTTCTCAGTGATCAACGAATGACA
AGAAGCCGG
[GAT]TCCTCTGAATTGCGGCGGCGATATTCTGAAATGCAAAATGGTCTAGCCACACAAGGAATAGAATCCATTT
GCATGGATCCTCAGCATGGTGCTGAGGCAACAAAACAAGAAGTTGCAAATTTCAATGGTTACAATTATCTCTCTA
TGTGTGAGCTTCCAAGTCAAAAGGGTTCATTCATGTCTCCGTCCAACTCATGTTCATCTAACTTCAACACACCTC
AATTTGGCGACATGGATAAAGTTTCATCTTGTGTAAGTATGCTGAAAGGGACATTACAACGCCGGAGACTCAGCA
GTCAACTTGAGAAAGAAGCTGCAGAAGATGACTTAAATGGAATTTTTTATCCTCAAGAACCTCTTTTCCAAACTG
GCTTTGATCAAGGACAAGAAAACTGGAGTAATCAAACGCCAGTAAATGTTCAAGTAGACTCTATTGGTGAAGTTA
AGGATCATGGAGTCCTGCAAACACTAGAAGGATCCACAAACCCTGTCGTTGATGGTTTTGCAAATCAGATAAACC
AAATCTATGTCGGAACAGCTTCTGGAGAACCTTCTCAAAGTGAATCCTCTAATGCTGCACCAGTAATCTCCTCTG
GTTTAGACACATGCGAAGGTCCCATAAACTCGAATCAAACTCTCTGCGAAAGCTCATGGAAACAAGTAGGAGTGA
GTAAAAGTTCAGAAAATACTCAAAATAGAGTCAAAGGTTTCAGAGAACAGATCATGGATAATCTGAAAGATGATA
AGAAGAGAAAAAGTCTAGAAAGATATGGATCTATAACATCAGCTGTTTCAGATGACAAGGGAGACACCACTAAAA
AGCGTAGGGTGGAACGCTCAAGGAAAATGGCTGAAGCTAAGGAAAGAAATTCGACACCATCAGTTCCCTCAGATA
TGCAAGCTGTCTTGAAGCGGTGCGAAAACCTTGAGAAGGAAGTTCGATCGCTAAAACTCAACTTGTCCTTCATGA
ATAGAAAGGATTCTGAACAAACAAAGCAGATAGAAGACCTTCAGAAGCAGAATGAAGAGCTGGCAGATGAAAAAG
AGCGCCTCCTCGAAGAGATTGAAAGAATTCTATCAGAAACTGAAAAAATGTAATGATATGAGAATCAATGTTGTG
CTCAAACACGC SEQ ID NO: 8

DNA sequence of IPD3 double phosphomimic (modified from Medicago truncatula)
ATGGAAGGGAGAGGATTTTCTGGTTTATACAAGAATTCAAGTGAGGAGTTATTCTTGAAGACAGTGATGGAGAGT
CCTATTGGTATGCCGGTACCTACCATGGAGATGTTAGGATTCAAGACTGTT[GAG]CAAAGCTTTCGCACCGAT[
GAT]GAAGAGCTTTTCAAACGCTGGCTAACAAATGATCAAGAGGGATACAATTCATCAAGCATGGGACTTAACAG
TCGTTTGTCGAAGAGAATATCAACTGAAATAGCTAATATGTCTAATCAACAACACATTGGTGTGGCTTCAGAAGG
AAGAAACAATGATAAATCATGCTTACAAAATAACTTCTTGGCAAATGATGTTTCAAGTGATTTCAATTTTCCAAT
CAGAGATCCTGTTGATAGAGAATTGCAATCTAGTAACTTGTTTCTGGCCAAGGCCTGGTTTATTACCGATCAACG
AATGACAAGAAGCCGGTCTTCTGAATTGCGGCGAAGGTATACTGAAATGCAAATTCTCAAGCACCACAAGGATT
GGATTCTATGTTCATGGTTCCTGAGCATGATACTAACACTATAAAAGAAGAACTTGCAAATTTTAATGGGTTTGA
TTACCTTTCCATGTGTGAGTTACCAAGCCAAAAGGGCACATTCATGTCTCCATCCAACTCATCTTCGTCTACCTT
CAACACACATCAATTGGTTGATGTAGATAAAGTTTCATCTTGTGTAAGTATGCTAAAAGGTACATTACAGCGCAA
GAAACTCGAATGCCAAGTCGAGAAAGAAGCTGCAGAAGATGGCTTGAATGAAATATTTTGCATTCGAGAACCTCT
TTTCCAATCAGCTTTTAATGAAGAAGAAAGTTGGAATCAACAAAAGCTAGTAAACGTTCAAGGAGATTTTACCGA
TCAAGTTAACGATCCCGGAGTCATGCAAACCCTTGAAGGAACCACAAACTTTGTCTTAGATGGTTTTGCAAATCA
GACGAACCAAATACAAGGCAGAACAGCTTCTGGAGAACCGTCTCAAAGTGAATCTTCTGCTGCTGCACCAGTAAT
CTCATCTGGCTTAGATGCATGTGAAGGTCCCAGCAATTCAAATCAAACTCTTGGTGATAGCTCATGGAAACAAGT
GGGAGAAAAGCACTCAAAATAAAGTCAGAGGTGTCAGAGAACAGATAATGGATAATCTGAAAGATGACAGAAAGAG
GAAAAGTCTAGAAATATGGATCTGTAACATCAGCTGTTTCAGATGGCAAGATGGATAACACAAAAAAGCGGAG
GGTGGAGCGCTCAAGAAAATGGCTGAAGCAAAGGAAAGAAATTTGACACCAACAATTCCCTCAGATATGCAAGC
TATCTTGAAGCGATGCGAAAACCTTGAGAAGGAAGTTCGATCACTAAAGCTTAATTTGTCCTTCATGAATAGGAA
GGATTCTGAACAAACAAAGCAGATAGAGGACCTTCAGAAGCAGAATGAAGACTTGGCGGATGAAAAAGAGCGCCT
CCTCGAAGAGATTGAAAGAATTCTATCAGAAACTGGAAAGATTTGATGTTTTGTTTCGCTGTTATATCCTTATCC
TCGTCAGAAACAATGTAGTACTCAGACAAGCTAAAAATCTCACCACAGTTTACTTGTGGATGAAACAGCTTAGGT
AAAAGTGAAAACAGTGATTAATAGTGAACCTATGGAGTCTATTAGCAAAATATAATGCATGGAATCTGAGATAT
TAGTAATGACATTATATATCTGGTAAAATCTAAGTGTTATTCAAAATTTGAGCCATATAAATGAATCCGGTAAAT
TTAAACATGGTCAAGTGTACCCACCAACCTCAATCATATGTAACAAACAAATATCTTCAATTTGTTTATGC SEQ
ID NO: 9

Medicago truncatula IPD3
>ABN45743.1 interacting protein of DMI3 [Medicago truncatula]
MEGRGFSGLYKNSSEELFLKTVMESPIGMPVPTMEMLGFKTVSQSFRTDSEELFKRWLTNDQEGYNSSSM
GLNSRLSKRISTEIANMSNQQHIGVASEGRNNDKSCLQNNFLANDVSSDFNPIRDPVDRELQSSNLFLA
KAWFITDQRMTRSRSSELRRRYTEMQNSQAPQGLDSMFMVPEHDTNTIKEELANENGFDYLSMCELPSQK
```

APPENDIX OF SEQUENCES

```
GTFMSPSNSSSSTFNTHQLVDVDKVSSCVSMLKGTLQRKKLECQVEKEAAEDGLNEIFCIREPLFQSAFN
EEESWNQQKLVNVQGDFTDQVNDPGVMQTLEGTTNFVLDGFANQTNQIQGRTASGEPSQSESSAAAPVIS
SGLDACEGPSNSNQTLGDSSWKQVGESTQNKVRGVREQIMDNLKDDRKRKSLERYGSVTSAVSDGKMDNT
KKRRVERSRKMAEAKERNLTPTIPSDMQAILKRCENLEKEVRSLKLNLSFMNRKDSEQTKQIEDLQKQNE
DLADEKERLLEEIERILSETGKI SEQ ID NO: 10
```

*Lotus japonicus* IPD3
>ABU63668.1 CYCLOPS [*Lotus japonicus*]
```
MEGRGFSGLYRNSSEELFLKTVMESPIGMPVPSMEMLGFKNVSQGFRADSEELFKRWLTNGEGYNSSSIG
FSSRLSKRISTELVNGSNQLQVGVASDGRNNDKPFIQNNLLANDVSGDFNFPIRDPVDRELQPSNLFLAK
AWFLSDQRMTRSRSSELRRRYSEMQNGLATQGIESICMDPQHGAEATKQEVANFNGYNYLSMCELPSQKG
SFMSPSNSCSSNFNTPQFGDMDKVSSCVSMLKGTLQRRLSSQLEKEAAEDDLNGIFYPQEPLFQTGFDQ
GQENWSNQTPVNVQVDSIGEVKDHGVLQTLEGSTNPVVDGFANQINQIYVGTASGEPSQSESSNAAPVIS
SGLDTCEGPINSNQTLCESSWKQVGVSKSSENTQNRVKGFREQIMDNLKDDKKRKSLERYGSITSAVSDD
KGDTTKKRRVERSRKMAEAKERNSTPSVPSDMQAVLKRCENLEKEVRSLKLNLSFMNRKDSEQTKQIEDL
QKQNEELADEKERLLEEIERILSETEKM SEQ ID NO: 11
```

*Pisum sativum* IPD3
>ABU63669.1 CYCLOPS [*Pisum sativum*]
```
MEGRGFSGLYKNSSEELFLKTVMESPIGMPVPTMEMLGFKTVSQSFRADSEELFKRWLTNEEGYNSTSMG
LNSRLSKRISTELVNVSNQQHVGVASEGRNNDKSCLQNSFLTNDVSGDFNFPIREPVDRELQSGNLFLAK
AWFLTDQRMTRSRSSELRRRYTEMQNTQAPQGLDSMFMAPKHDANIIKEELAHFNGFDYLSMCEIPSQKG
SFMSPSNSSSSTFNTQQLVDVDKVSSCVSMLKGTLQRKRLECQVEKDAAEDGLNEIFGIREPLFQSGFNE
GQENWNHQKLVNVQGDFTDQVKDTGVIETLEGAANFVLEGFANQTSQIHGGTASGEPSQSESSAAAPVIS
SGLDACEGPSNSSQTLCDSSWKQVGESTQNRAKGVREQIMDNLKDDRKRKRLERYGSVTSAVSDDKVDTT
KKRRVERSRKMAEAKERNLTPTIPSDMQAVMKRCENLEKEVRSLKLNLSFMNRKDSEQTKQIEDLQKQNE
ELADEKERLLEEIERLLSETGKI SEQ ID NO: 12
```

*Solanum lycopersicum* IPD3
>NP_001269245.1 CYCLOPS/IPD3-like protein [*Solanum lycopersicum*]
```
MEMEGRGYSDFYRNTSEELFIRTMMDNSVGGVPVPTMEMLGFRNIPHSLRTDSEELFKSWLTSAENNGSD
STPMARGRQGSRRISSELAGLSSQQNEGIQKRKMADTQQPQNTCTAIESSNLNKHSTRNATDREMQASN
LFLAKTWFHSSQPMTRSRSSELRRRYAAMQNSQSSLARESLQNIPGNAVNSFKEEVSHPTGYTDMSMCEM
TNQPNTFMSPSNSSSSTFEAQQVDGVDNISSVVSMLKGTLERKKLTNYHTAREAIEENMLGCYGNQEIFC
NSDMNQHPGNHISLNQGTYQDTPVVQVRDTGIPQTVQGSLDAVLESIMAPSNPIQIDMVTQEPSQSGSSV
AAPILSIDFDAYDGLSNASQALNMYEGCRNQVGYGRSSENGSTARDIRERIYDNVKDNQKKEGLVRNGSL
TSVQSAENGDPKKKRRVERSRKMAEAKERNLTPAIPSDMQSLVKRCDNLEKEVRSLKLNLAFMNRKDSEQ
TTQIEELQKQNEDLVKEKERLLGEIERIISESGKF SEQ ID NO: 13
```

*Diphasiastrum digitatum* IPD3
>ADV78033.1 cyclops [*Diphasiastrum digitatum*]
```
MVEIADRRITRSVSSELQARLSTQPQTQEGVEEIRAVSGDMEISCFQRNSSEEIFLRSFMDGAMAPATEG
MSFLSPPQPPLRVNSEELFNTWLSNTDAPGLPPLSGDYRTLQNSCRMSSELAGNLGQGAVSQPFDIPGEN
VAQTIGGHPDPNVRESNIGKPRNHAPSKGLPFQDHASWQMINWFQQSQPMTRSRSSELRRKYLAMQEGHK
PPPSANTLQWFATQGTDELNRAVASLGAFTRALASKRPDISSTASPQLSPTPMSHVSKLSPQRNGDSVSA
VVNMLKGSLERKKLAAMQQQMDKPVSPPYWRSLGQDKEDPHKPMIDSQQCISPQIESEQQQENQKEAFSA
SLQITNEQFQAGVVTPHALSPSDSSGNAPGLSAGAATSEGPCNSNPAVSTQNNFIKCSGQGNWAVDETFQ
QNNLPSPTSNGTSNGEIPYEGVLNTDYQKRQGYLSRAGSLTSSCRSDQSMQVSIGERTHKLEGSTADAED
STKKRRVERKRMMAEAKGRSYVPMMPSDLQAATKRCDALEKEVRSLKLNLSFMNRKDSEQTKRIEDLEKQ
NEELLAEKDRLVEEVRRFTSGKNFGRSS SEQ ID NO: 14
``` amino acid sequence of IPD3 phosphomimic 1 (modified from *Medicago truncatula*)
```
MEGRGESGLYKNSSEELFLKTVMESPIGMPVPTMEMLGFKTVSQSFRTD[D]EELFKRWLTNDQEGYNSSSM
GLNSRLSKRISTEIANMSNQQHIGVASEGRNNDKSCLQNNFLANDVSSDFNFPIRDPVDRELQSSNLFLA
KAWFITDQRMTRSRSSELRRRYTEMQNSQAPQGLDSMFMVPEHDTNTIKEELANFNGFDYLSMCELPSQK
GTFMSPSNSSSSTFNTHQLVDVDKVSSCVSMLKGTLQRKKLECQVEKEAAEDGLNEIFCIREPLFQSAFN
EEESWNQQKLVNVQGDFTDQVNDPGVMQTLEGTTNFVLDGFANQTNQIQGRTASGEPSQSESSAAAPVIS
SGLDACEGPSNSNQTLGDSSWKQVGESTQNKVRGVREQIMDNLKDDRKRKSLERYGSVTSAVSDGKMDNT
KKRRVERSRKMAEAKERNLTPTIPSDMQAILKRCENLEKEVRSLKLNLSFMNRKDSEQTKQIEDLQKQNE
DLADEKERLLEEIERILSETGKI SEQ ID NO: 15
``` amino acid sequence of IPD3 phosphomimic 2 (modified from *Medicago truncatula*)
```
MEGRGFSGLYKNSSEELFLKTVMESPIGMPVPTMEMLGFKTV[E]QSFRTDSEELFKRWLTNDQEGYNSSSM
GLNSRLSKRISTEIANMSNQQHIGVASEGRNNDKSCLQNNFLANDVSSDFNFPIRDPVDRELQSSNLFLA
KAWFITDQRMTRSRSSELRRRYTEMQNSQAPQGLDSMFMVPEHDTNTIKEELANFNGFDYLSMCELPSQK
GTFMSPSNSSSSTFNTHQLVDVDKVSSCVSMLKGTLQRKKLECQVEKEAAEDGLNEIFCIREPLFQSAFN
EEESWNQQKLVNVQGDFTDQVNDPGVMQTLEGTTNFVLDGFANQTNQIQGRTASGEPSQSESSAAAPVIS
SGLDACEGPSNSNQTLGDSSWKQVGESTQNKVRGVREQIMDNLKDDRKRKSLERYGSVTSAVSDGKMDNT
KKRRVERSRKMAEAKERNLTPTIPSDMQAILKRCENLEKEVRSLKLNLSFMNRKDSEQTKQIEDLQKQNE
DLADEKERLLEEIERILSETGKI SEQ ID NO: 16
``` amino acid sequence of IPD3 phosphomimic 3 (modified from *Lotus japonicus*)
```
MEGRGFSGLYRNSSEELFLKTVMESPIGMPVPSMEMLGFKNVSQGFRADSEELFKRWLTNGEGYNSSSIG
FSSRLSKRISTELVNGSNQLQVGVASDGRNNDKPFIQNNLLANDVSGDFNFPIRDPVDRELQPSNLFLAK
AWFLSDQRMTRSR[D]SELRRRYSEMQNGLATQGIESICMDPQHGAEATKQEVANFNGYNYLSMCELPSQKG
SFMSPSNSCSSNFNTPQFGDMDKVSSCVSMLKGTLQRRLSSQLEKEAAEDDLNGIFYPQEPLFQTGFDQ
GQENWSNQTPVNVQVDSIGEVKDHGVLQTLEGSTNPVVDGFANQINQIYVGTASGEPSQSESSNAAPVIS
```

APPENDIX OF SEQUENCES

```
SGLDTCEGPINSNQTLCESSWKQVGVSKSSENTQNRVKGFREQIMDNLKDDKKRKSLERYGSITSAVSDD
KGDTTKKRRVERSRKMAEAKERNSTPSVPSDMQAVLKRCENLEKEVRSLKLNLSFMNRKDSEQTKQIEDL
QKQNEELADEKERLLEEIERILSETEKM SEQ ID NO: 17
``` amino acid sequence of IPD3 double phosphomimic (modified from *Medicago truncatula*)
```
MEGRGFSGLYKNSSEELFLKTVMESPIGMPVPTMEMLGFKTV[E]QSFRTD[D]EELFKRWLTNDQEGYNSSSM
GLNSRLSKRISTEIANMSNQQHIGVASEGRNNDKSCLQNNFLANDVSSDFNFPIRDPVDRELQSSNLFLA
KAWFITDQRMTRSRSSELRRRYTEMQNSQAPQGLDSMFMVPEHDTNTIKEELANFNGFDYLSMCELPSQK
GTFMSPSNSSSSTFNTHQLVDVDKVSSCVSMLKGTLQRKKLECQVEKEAAEDGLNEIFCIREPLFQSAFN
EEESWNQQKLVNVQGDFTDQVNDPGVMQTLEGTTNFVLDGFANQTNQIQGRTASGEPSQSESSAAAPVIS
SGLDACEGPSNSNQTLGDSSWKQVGESTQNKVRGVREQIMDNLKDDRKRKSLERYGSVTSAVSDGKMDNT
KKRRVERSRKMAEAKERNLTPTIPSDMQAILKRCENLEKEVRSLKLNLSFMNRKDSEQTKQIEDLQKQNE
DLADEKERLLEEIERILSETGKI SEQ ID NO: 18
```

*Medicago truncatula* DMI3
>AY496049.1 *Medicago truncatula* calcium-dependent protein kinase (DMI3) mRNA, DMI3-1 allele, complete cds
```
ATGGGATATGGAACAAGAAAACTCTCAGATGAATATGAAGTTTCAGAAATTCTAGGTAGAGGTGGATTTT
CTGTTGTTAGAAAAGGTACAAAAAAATCAAGCATTGAAGAAGAAAATCACAATCACAAGTAGCAATCAA
AACCCTAAGAAGGTTAGGTGCTTCAAATAACCCTAGTGGATTCCAAGAAAAAAAGATATTGGAGAAAA
AGCACAATAGGGTTCCCTACAATGAGACAAGTTTCAGTTTCAGATACATTACTAACAAATGAGATACTTG
TAATGAGACGAATAGTCGAAAACGTTTCGCCACATCCAAATGTGATTGATCTTTATGATGTATATGAGGA
CACAAATGGTGTTCATCTTGTTCTTGAGCTTTGTTCCGGTGGTGAACTTTTCGATAGGATTGTTGCACAA
GATAAGTATAGTGAGACTGAAGCTGCAACTGTGGTTCATCAAATAGCTTCAGGGTTAGAAGCTGTTCATA
GAGCTAATATAGTTCATAGAGATTTGAAACCTGAAAATTGTCTTTTTTTAGATGTTAGGAAAGATTCTCC
TCTTAAGATTATGGATTTTGGGTTGAGTTCTGTTGAAGAGTTTACTGATCCTGTTGTTGGTTTGTTTGGA
TCTATTGATTATGTTTCACCTGAGGCTCTTTCTCAAGGAAAGATTACTACTAAGAGTGATATGTGGTCTC
TTGGGGTTATTCTATATATCTTACTTTCAGGGTATCCACCTTTCATTGCCCAAAATAATCGCCAAAAACA
ACAAATGATAATGAATGGGAATTTTAGTTTTTATGAGAAGACTTGGAAGGGAATTTCACAACCAGCAAAG
AATTTGATTTCAAGTCTTTTAACCGTTGATCCTAGCAAGAGACCTAGTGCTCTTGAGCTTCTAAGTGATC
CATGGGTCAAAGGTGAGAAAGCCAAAGATGTTCAAATGGACCCTGAGATTGTCTCAAGGCTACAAAGCTT
TAATGCAAGACGTAAACTTCGTGCAGCTGCAATTGCTAGTGTTTGGAGCTCCACAATCTTCCTTAGAACA
AAAAAATTGAAATCATTGGTTGGATCCTATGATCTTAAAGAAGAGGAAATTGAAAATCTCAGGATGCATT
TCAAGAAGATATGTGCAGATAGAGACAATGCAACTCTGTCAGAGTTTGAGGAGGTGTTAAAAGCAATGAA
TATGTTATCATTGATCCCTTTTGCTTCTCGTATATTTGATTTGTTTGACAACAACCGTGATGGAACAGTT
GACATGCGTGAGATACTTTGTGGATTTTCCAGTCTCAAGAATTCCAAAGGAGAGGATGCTCTTCGTTTGT
GCTTCCAGATGTATGATACAGATAGATCAGGCTGCATCAGCAAAGAGGAAGTAGCATCCATGCTCAGGGC
TTTGCCATATGATTGTCTTCCAACTGATATCACTGAACCTGGAAAATTGGATGAGATTTTTGACTTAATG
GATGCTAATAATGATGGAAAAGTTACATTTGATGAATTCAAAGCTGCTATGCAAAGAGATAGCTCTCTTC
AAGATGTAGTTCTCTCTTCTATTCGTCCATAA SEQ ID NO: 19
```

*Lotus japonicus* DMI3
>AM230793.1 *Lotus japonicus* mRNA for calcium calmodulin-dependent protein kinase (ccamk gene), ecotype Gifu
```
AAAGATTCCAATATTTTCAAACACTCTGCCATGGGATATGATCAAACCAGAAAGCTCTCTGATGAGTATG
AGATTTCAGAGATTCTAGGAAGAGGTGGATTCTCTGTTGTCAGAAAAGGAACCAAAAAATCAGGCAATGA
GAAAACCCAAGTAGCCATCAAAACACTCAGAAGGTTAGGTAGTTCTCCCTCTGGGACAGGTGGTGGACAG
AAGAGCACAGCAACTGTGATGGGGTTCCCTTCTTTGAGACAGGTTTCAGTCTCAGATGCTTTGCTCACCA
ATGAGATTCTTGTGATGAGGAGGATAGTGGAAAACGTTTCGCCACATCCAAACGTGATTGATCTCTATGA
TGTGTGTGAGGACTCAAATGGGGTGCATCTTGTGCTGGAGCTTTGTTCTGGTGGGAGCTGTTTGATAGG
ATTGTTGCACAGGATAAGTATGCTGAGACGGAAGCTGCCGCGGTGGTTCGCCAGATTGCGGCGGGGCTAG
AGGCGGTTCACAAGGCTGACATTGTTCACAGGGATTTGAAGCCTGAGAATTGCCTTTTCTTGGATTCCAG
GAAGGACTCTCCTCTCAAGATCATGGACTTTGGGTTGAGCTCTGTTGAGGAGTTCACTGACCCTGTTGTT
GGGTTGTTTGGATCCATTGATTATGTTTCACCAGAGGCTCTTTCTCAAGGGAAGATCACTGCCAAGAGTG
ACATGTGGTCTCTGGGAGTGATTCTATATATCTTGCTCTCTGGGTATCCGCCTTTCATTGCACAAAATAA
TCGCCAAAAACAACAAATGATAATCAATGGGAATTTCAGTTTCTATGAGAAGACTTGGAAGGGCATTACC
CAATCAGCGAAGCAATTGATTTCAAGTCTTTTGACTGTTGATCCAAGTAAGAGGCCTAGTGCTCAAGAGC
TCTTGAGTCATCCATGGGTCAGAGGTGACAAAGCCAAAGATGAGCAAATGGACCCTGAGATTGTCTCAAG
GCTGCAGAGCTTTAATGCAAGACGCAAACTCCGCGCAGCTGCAATTGCTAGTGTTTGGAGCAGCACAATC
TTCCTGAGAACCAAAAAGCTGAGATCCTTGGTAGGAACTTATGATCTCAAAGAAGAGGAAATTGAAAGTC
TCAGGATACACTTTAAGAAGATATGTGGAAATGGAGACAATGCAACTCTGTCTGAGTTTGTGGAGGTGCT
GAAAGCAATGAAGATGCCCTCATTGATCCCTCTAGCACCGCGTATATTTGACTTGTTTGACAACAACCGT
GATGGAACAATTGACATGAGAGAGATACTATGTGGGTTTTCTAGCCTCAAGAACTCCAAAGGAGATGATG
CTCTCCGTTTGTGCTTCCAGATGTATGACACAGATAGATCAGGGTGCATCACCAAGGAAGAAGTAGCATC
CATGCTCTGTGCTTTGCCAGAGGAATGTCTTCCAGCTGATATCACTGAACCTGGGAAATTGGATGAGATA
TTTGACTTAATGGATGCCAACAGTGATGGAAAAGTTACATTTGATGAAGTTCAAAGCTGCTATGCAGAGAG
ATAGCTCTCTCCAAGACATGCTCCTCTCTTCTCTTCGTCCATCATAGTTTTTTTTTTTTCCATTCATGG
TGTTATGGTCTTTCAAACTTTGATATTGACTACACCTTTTACGTTTCTTTTAATCTCTTTTGGGGCTATC
CTTCTCTTTGAGGTATTCATACTACATGGAAAAAGGGTGGTAAAGAGGGTGAAATTGTGTCATCTAACTT
TTGCTATGACAACTAGGAACTTTTGCAAAAAAA SEQ ID NO: 20
```

*Glycine max* DMI3
>XM_006597983.2 PREDICTED: *Glycine max* calcium and calcium/calmodulin-dependent serine/threonine-protein kinase (LOC732616), mRNA
```
TATAATGCCAGCAGTTGACTCTCTCTTTGTCCCTTCCAGAACAGCTCCTACCAGCCATATTGTTTTTTCT
CTTGTACCTATCCCAATTTGTTTCATATTTTATGTCATAAACTAATCCACAAACTCTTACAACAGGCTAA
TGTCACTCTCAACCGTTTCAACACGCGTTTTGAAAGCCCCTATCATTGAATTAAAGTTAACATTTTTTA
```

APPENDIX OF SEQUENCES

```
CATACCAATTCCCTTCCCACTGCACATTTTCTGAGTCTTCAAGATTCCATAATTTCAAAGACTTTGTGTG
CACCACACCACCATGGGGAATGAAACCAGAAAACTCTCAGATGAGTATGAAGTTTCAGAAGTCCTAGGAA
GAGGTGGATTTTCTGTTGTCAGAAAAGGCACCAAAAAATCAAGCAGTGACACCAAAACACATGTAGCCAT
CAAAACCCTGAGAAGGGTAGGCACTGCCTCAAACTCCAACAACCCTTCTGGATTTCCAAGACCAAAGGGT
GGAGAGAAGAAGAGCACAGCAGCTATGATGGGATTCCCCACATGGAGACAAGTCTCAGTCTCAGATGCCT
TGCTCACAAATGAGATTCTTGTGATGAGGAGAATAGTGGAAAATGTTTCACCACACCCTAATGTGATTGA
CCTCTATGATGTGTATGAGGACTCAAATGGGGTGCACCTTGTGTTGGAGCTGTGTTCTGGTGGAGAACTG
TTTGATAGGATTGTGGCACAAGATAGGTACTCAGAGACTGAAGCTGCAGGTGTGGTTCGCCAGATAGCTT
CAGGATTAGAGGCTATTCATAGAGCTAACATTGTCCACAGAGATTTGAAGCCTGAGAATTGCCTTTTCTT
GGATGTGAGGAGGGACTCTCCTCTTAAGATCATGGACTTTGGGTTGAGTTCTGTTGAGGAATTCACTGAC
CCAGTTGTTGGTTTGTTTGGATCCATTGATTACGTTTCACCAGAGGCTCTTTCTCAAGGGAAGATAACTA
CCAAGAGTGACATGTGGTCTCTGGGGGTGATTCTATATATCTTGCTCTCAGGGTATCCACCTTTCATTGC
TCAAAATAATCGCCAGAAACAACAAATGATAATGAATGGGAATTTCAGTTTCTATGAGAAGACATGGAAG
GGCATTACCCGTTCAGCGAAGCAACTGATTTCAGATCTTTTGATTGTTGATCCTAGTAGAAGACCTAGTG
CTCAAGATCTTCTGAGTCATCCATGGGTGGTAGGTGACAAGGCCAAAGATGATGCAATGGACCCTGAGAT
TGTCTCAAGATTGCAGAGCTTCAACGCTAGGCGCAAACTGCGTGCAGTTGCAATTGCAAGTATTTGGAGC
ACCACAATCTTCCTCAGAACCAAAAAACTGAAATCCTTGGTGGGAACACATGATCTCACAGAAGAGGAAA
TTGAAAATCTCAGGATGAGTTTTAAGAAGATATGTGTGAGTGGGGACAATGCCACTCTATCTGAGTTTGA
GGAGGTGCTGAAAGCAATGAACATGCCATCACTGATCCCTCTAGCACCGCGAATATTTGACTTATTTGAC
GACAACCGAGATGGAACAGTTGACATGAGAGAGATACTATGTGGTTTTTCCAGCTTCAAAAACTCCAAAG
GGGATGATGCTCTCCGTTTGTGCTTCCAGATGTATGACACAGATCGATCCGGGTGCATCACCAAGGAAGA
AGTAGCATCCATGCTCAGAGCTTTGCCAGAAGACTGTCTCCCAACTGACATCACTGAACCTGGCAAATTG
GATGAGATATTTGACCTAATGGATGCCAACAGTGATGGAAAAGTTACCTTTGATGAATTCAAAGCTGCTA
TGCAGAGAGATAGCTCTCTCCAAGACGTAGTTCTCTCTTCTCTTCGCCCACAATAGTTCTCCTAATTTTC
ATTAATTTATTGTATTATTAACTATGGTATTTTAAAATGGAGTAGTACTAGTGTTGTCCTTTTCTTTTTC
TTCTTCCTGGCCTGGGCCATTCTTTTTGCTGACTTATTGATACTATAGGAAGAAAAAGGATTGGATTACT
ATATAGTGAATTTTTGCTTTTGACAGTTATCTATGAACTTCTGCGTTCTCATGTTGTTCGTCAA   SEQ ID NO: 21
```

*Phaseolus vulgaris* DMI3
>XM_007133469.1 *Phaseolus vulgaris* hypothetical protein (PHAVU_011G186900g) mRNA, complete cds

```
TCTCAACCGTTTCAACACGCGTTTTGAAGGCTCCTCCTATCATTTTTTTAACAAACAAATTCCTTTGTCC
CTGCAAATTTTCTGAGTCTTCAAGATTCCTTAGTTTCCAAGACTCTGTGTGCAGCACACCACCATGGGGT
ATGAAACCAGAATACTCTCAGATGAGTATGAAGTCTCAGAGGTTCTAGGAAGAGGTGGATTTTCTGTTGT
CAGAAAAGGCACAAGAAATCAAGTAGTGACACCAAAAGCCTTGTAGCCATCAAAACCCTGAGAAGGTCA
GGAACTGCCTCAAGCCCCAGCTACCCTTCTGGGTTTCCAAGACCAAAGGGTGGAGAGAAGAGCACAGCAG
CTATGATGGGGTTCCCCTCAGGGAGACAAGTCTCAGTCTCAGATGCCTTGCTCACCAATGAGATTCTTGT
GATGAGGAGAATAGTGGAAAACGTTTCACCACACCCTAATGTGATTGACCTTTATGATGTGTATGAGGAC
TCCAATGGAGTGCACCTTGTGTTGGAGCTGTGCTCTGGTGGGGAATTGTTTGATAGGATTGTAGCACAAG
ATAGGTACTCAGAGACTGAAGCTGCAGGTGTGGTTCGCCAGATAGCTTCAGGATTAGAGGCTATTCATAG
AGCTAACATTGTGCACAGGGACTTGAAGCCTGAGAATTGTCTTTTCTTGGATGTGAGGAGGGACTCCCCT
CTTAAGATCATGGACTTTGGATTGAGTTCTGTTGAAGAATTCACTGACCCAGTTGTTGGTTTGTTTGGAT
CCATTGATTATGTTTCACCAGAGGCTCTTTCTCAAGGGAAGATAACTACCAAGAGTGACATGTGGTCTCT
TGGAGTGATTCTATACATCTTACTCTCTGGGTATCCACCTTTCATTGCTCAGACCAATCGCCAGAAACAA
CAAATGATAATGAATGGGAATTTCAGTTTCTATGAAGACATGGAAGGGCATTACTCAATCAGCAAAAC
AGCTAATTTCAGATCTTCTGACTATAGATCCTAGCAGGAGACCTAGTGCTCAAGATCTTCTGAGTCATCC
ATGGGTGGTAGGTGACAAAGCCAAGGATGATGCAATGGACCCTGAGATTGTCTCAAGATTGCAGAGCTTC
AACGCAAGACGCAAATTGCGTGCAGCTGCAATTGCTAGTGTTTGGAGCTCCACAATCTTCCTCAGAACCA
AAAAGCTGAAATCCTTGGTGGGAACACATGATCTCACAGCAGAGGAAATTGAAAACCTCAGGATAAATTT
TAAGAAAATATGTGTGAATGGAGACAATGCCACTCTCTCTGAGTTTGAAGGGTGCTGAAAGCAATGAAT
ATGCCATCACTGATCCCTCTAGCACCACGAATATTTGACTTGTTTGACAACAACCGTGATGGAACAGTTG
ACATGAGAGAGATACTTTGTGGCTTTTCCAGCTTCAAAAACTCCAAAGGAGATGATGCTCTCCGTTTGTG
CTTCCAGATGTATGACACAGATCGATCAGGGTGCATCACCAAGGAAGAAGTAGCATCCATGCTCAGAGCT
TTACCGAAGAGTGTCTACCTGCTGATATCACTGAACCTGGGAAACTGGATGAGATATTTGACAGAATGG
ATGCCAACAGTGATGGAAAAGTTACCTTTGATGAATTCAAAGCTGCCATGCAGAGAGATAGCTCTTTGCA
AGACCTTCTTCTCTCTTCTAAGACCACAATCTTAACTCTTCAAATTTCCATTGATCTATATGCTATTG
TTATCAACCATGCACAACTATTTTTGTCCTTTTTGTCCCTTCACACTGTAGGAAAAAACACTATTCCAGG
ACTATACACTGATGTTGTTCCATCTAACTTTTGCTTAGACTCATGTTAATTAAGTATG   SEQ ID NO: 22
```

*Arachis hypogea* DMI3
>EU395429.1 *Arachis hypogaea* calcium calmodulin-dependent protein kinase (CCaMK) mRNA, partial cds

```
ATGGGATATGAAACCAGAAAGCTCTCTGATGAGTATGAAGTTTCAGAATTCTAGGAAGAGGTGGATTCT
CTGTTGTCAGGAAAGGCATAAAAAAATCAAGCAGTGATGAGAAAACTCATGTTGCCATAAAGACACTAAG
AAGAGTAAGTGTCTTCTCTACAACCCCTGGTTGTTTACCAAGAGAGAGGAGCAACATGGGGTTTCCCACA
TGGAGACAGGTTTCAGTATCAGATGCTCTTCTCACCAATGAGATCCTTGTGATGAGGAGAATAGTCGAAA
ATGTGTCGCCACATCCGAATGTGGTTGACCTCTATGATGTTTATGAGGACTCGAATGGTGTTCATCTTGT
TTTGGAGCTGTGTTCTGGCGGTGAGCTGTTTGATCGCATTGTGGCACAGGATAGGTACTCAGAGACTGAG
GCTGCGACAGTTATCGCCAGATTGCGGCGGGCTTAGAGGCTATTCATAAAGCAAACATTGTCCATAGAG
ACTTGAAGCCTGAGAATTGCTTGTTCTTGACAAGAGGAAGGATTCTCCTCTAAAGATCATGGATTTCGG
TTTGAGCTCTGTTGAAGAGTTTACTGATCCAGTTGTTGGTTTGTTTGGTTCCATTGATTATGTTTCACCG
GAGGCTCTTTCTCAAGGAAAGATTACTACTAAGAGTGACATGTGGTCTCTAGGGGGTAATTTTGTACATCT
TATTATCTGGATATCCGCCTTTCATTGCTCAGTCTAATCGCAAAAACAACAATGATAATGAATGGGAA
CTTCAGCTTCTATGAGAAGACATGGAAGGGCATTTCTCAATCAGCAAAGCAATTGATTTCGAGTCTTCTG
ACAGTTGATCCTAGTAGGAGACCTAGTGCGCAGGAGCTCCTGAGTCATCCATGGGTCATAGGTGATGTAG
CCAAAGATGTTCAAATGGACCCTGAGATTGTCTCAAGGTTGCAAAGCTTCAATGCTCGTCGCAAGCTCCG
GGCAGCTGCAATTGCAAGCGTATGGAGCACCACAGTGTTCTTGAGAACCAAGAAACTGAAATCCTTGATA
```

APPENDIX OF SEQUENCES

```
GGATCCTATGATCTTACAGAAGAGGAAATTGAAAGTCTCAGGATACACTTCAAGAAGATATGTGGAAATG
GGGACAATGCCACGCTCTCTAAGTTTGAGGAGGTACTGAAAGCAATAAATATGCCATCACTAATTCCTCT
AGCACCACGCATATTTGACTTGTTCGACAACAACCGTGATGGAACGGTTGACATGCGAGAGATTTTATGT
GGGCTTTCCAGCCTCAAGAATTCCAAAGGAGATGATGCCCTCCGTTTGTGCTTCCAGATGTATGATGCAG
ATCGATCCGGGTGTATCACAAAGGAAGAAGTAGCATCCATGCTTAGAGCTTTGCCGGATGACTGTCTTCC
CGTTGATATCACGGAACCTGGCAAATTGGACGAGATTTTCGACAGAATGGATGCCAACAGTGATGGAAAA
GTCACCTTTGAGGAATTCAAAGCTGCTATGCAAAGAGATAGCTCTCTCCAAGACGTAGTCCTCTCTTCTC
TTCGTCCA SEQ ID NO: 23

Petunia x hybrida DMI3
>EF592572.1 Petunia x hybrida CCaMK mRNA, complete cds
GCGGGGAGTGCTTTGATGGGACAAAAGGAAGATACAAGAAGTCTAAGTGATGAATATGAAGTAACAGACA
TACTTGGAAGAGGTGGCTTTTCAGTAGTAAGGAGAGGAAGAACACGTAGCAGTGAAGAAGTTGCCATTAA
GACACTCCGGCGATTCGGACCGCCGGAGAAGAAAGAATTTAGTAGGTCTACTACTCATGTTAATTCTCGA
CCAGCTGCACAGGCTTTAATATCTGAAACTTTGTTGACAAATGAGCTGTTAGTTATGAGGAAGATTGTGG
AAGATGTTTCACCTCATCCTAATGTTATACATCTGTATGACGTTTGTGAGGATTCTTCAGGTGTTCATCT
CATCTTGGAGCTTTGTTGTGGTGGGGAGCTCTTTGATCGGATTGTTGGGCAAGCAAGGTATAACGAGGCA
GGCGCAGCTGCAGTGGTGAGACAGATAGCTAAGGGTCTTGAGGCACTACATGGGCAAGTATAGTTCATA
GGGACTTGAAACCAGAGAACTGTCTATTCTTGAACAAGGATGAGAATTCACCACTGAAATCATGGACTT
TGGACTCAGCTCTATTGAGGATTTTGCCAATCCAGTGGTTGGTTTATTTGGTTCCATAGATTATGTTTCA
CCAGAAGCACTTTCAAGGGGAAACATCACTAGCAAAAGTGATATTTGGTCACTTGGAGTAATCCTTTACA
TTCTCCTATCCGGGTACCCACCTTTCTTCGCACCGTCCAATCGGCAAAAGCAACAATGATATTAAACGG
GGAGTTCAGTTTTGATGAGAAAACATGGAAAAATATTTCGTCATCCGCAAAACAGCTAATATCCAGTCTT
TTGAAAGTTGATCCTAACATGAGACCTACTGCTCAAGAGATACTTGAACACCCATGGGTGACAGGAGACT
TGGCAAAGCAAGAACAGATGGATGCCGAAATTGTATCTCGCCTGCAAAGCTTCAATGCTCGGCGCAAGTT
CAGGGCGGCAGCTATGGCTAGTGTGTTAAGCAGTAGTTTCTCCTTGAGAACTAAGAATTGAAGAAGTTG
GTTGGTTCCTATGACCTCAAGCCTGAAGAATTGGAAAACCTCAGCCACAACTTCAAGAAAATATGCAAAA
ATGGAGAAAATGCAACTTTATTGGAATTTGAAGAGGTCCTGAAAGCTATGGAAATGTCATCTTTAGTCCC
TTTAGCTCCTCGGATATTCGATCTATTTGACAACAATCGTGATGGAACAGTAGATATGAGAGAGATCATA
GGTGGCTTCTCTAGCCTCAAGTATTCCCAAGGGGATGATGCACTTCGTCTTTGTTTCCAGATGTATGATA
CAGATCGGTCAGGCTGCATTAGCAAGGAAGAGGTCGCATCCATGTTAAGAGCACTTCCTGAAGACTGCCT
TCCAATGGATATAACAGAACCTGGAAAACTTGATGAGATATTTGATTTAATGGATGCAAATAGTGATGGT
AAAGTCACTTTTGATGAGTTCAGAGCTGCCATGCAAAGAGATAGCTCTCTTCAAGATGTAGTTCTCTCCT
CTCTTCGTCCCACTTTAATTCCTTTATTATTTAATTTTCCTTTTAGCATACTAGTTGTATTAATCTCTAA
CCTTCTATGACAATGATTTATTTTTTATTCGCAACTGAGAAAAAGGGCATGGAATTAATTTGAAAGCTT
TATCGAACGCT SEQ ID NO: 24

Sesbania rostrata DMI3
>EU622875.1 Sesbania rostrata Ca2+ and calmodulin-dependent protein kinase
(CCaMK) mRNA, complete cds
GGGAATTCAAAGACTTGATTTTTTTGTTTTGTTTTGTGCACCACCATGGGATATGAAACCAGAAGGCTCT
CAGATGAGTATGAGGTTTCAGATGTTCTAGGAAGAGGTGGATTTTCTGTTGTCAGAAAAGGTACCAAAAA
ATCAAGCAGTGAGAAAACCTTAGTAGCCATCAAAACACTGAGAAGGTTAGGTGCCTCTAATAACAACCCT
TCTGGTTTACCAAAAACAAAAGGTGGAGAGAAAAGCATAGCAACTATGATGGGGTTCCCCACATGGAGAC
AAGTTTCAGTCTCAGATGCCTTGTTGACCAATGAGATTCTTGTCATGAGGAGGATAGTGGAAAATGTTTC
ACCTCACCCCAATGTGATTGACCTCTATGATGTGTATGAGGACTCAAATGGGGTTCATCTTGTGCTTGAG
CTTTGTTCTGGTGGGAATTGTTTGATAGGATTGTGGCACAAGATAGGTACTCAGAGACTGAAGCTGCAG
CTGTGGTTCGCCAGATAGCAGCAGGATTAGAGGCTATTCATAAAGCTAACATTGTTCATAGGGACTTGAA
GCCTGAGAATTGCCTTTTTTTGGATACCAGGAAGGACTCTCCTCTCAAGATCATGGACTTTGGGTTGAGT
TCTGTTGAAGAATTTACTGACCCTGTTGTTGGTTTGTTTGGATCCATTGATTATGTTTCACCAGAGGCTC
TTTCTCAAGGAAAGATAACTACTAAGAGTGACATGTGGTCTCTAGGAGTAATTCTATATATCTTACTCTC
TGGGTATCCACCTTTCATTGCTCCGTCTAATCGCCAAAAACAACAAATGATAGTGAACGGGAATTTCAGT
TTCTATGAGAAGACTTGGAAGGGCATTTCCCAATCAGCAAAGCAATTGATTTCAAGTCTTCTGACTGTTG
ATCCTAGCAAGAGACCCAGTGCTCAACAGCTTCTGAGTCATCCATGGGTTATAGGTGAGAAAGCCAAAGA
TGATCAAATGGACCCTGAAATTGTCTCAAGGCTGCAGAGCTTTAATGCAAGACGCAAACTGCGTGCAGCT
GCAATTGCTAGTGTTTGGAGCTCCACAGTCTTCCTCAGAACCAAAAAACTGAGATCCTTGGTAGGAACCC
ATGATCTCAAAGAAGAGGAAATTGAAAACCTCAGGATACATTTCAAGAAGATATGTGCAAATGGAGACAA
TGCCACTCTCTCTGAGTTTGAGGAGGTGCTGAAAGCAATGAATATGCCATCATTGATCCCTCTAGCACCT
CGTATATTTGACTTGTTTGACAACAACCGTGATGAACAGTTGACATGCGAGAGATACTATGTGGGTTTT
CTAGTCTCAAGAACTCCAAGGAGATGATGCTCTCCGTTTGTGCTTCCAGATGTATGACACAGATCGATC
CGGGTGCATCACAAAGGAAGAAGTAGCATCTATGCTGAGAGCTTTGCCAGATGATTGTCTTCCAGCTGAT
ATCACTGAACCTGGCAAATTGGATGAGATATTTGATTTAATGGATGCAAATAGTGATGGAAAAGTTACCT
TTGATGAATTCAAAGCTGCTATGCAGAGAGATAGCTCTCTTCAAGATGTAGTCCTCTCTTCTTCGCCC
ATAATCCTTTTATTATGACATAATATTCACACTACAAGGAAAAGTGTAATGCAGTACTAAACAGGGTGAA
ACTGTGCCATCTAACTTCTGCTATGACAATTAGGAACTTTTGCATTTTCATGTTATACAAGCTAGCTAGC
TACCTACCTGAGTCTTGAAACTGCAATTGAGTAGCAGAAAGCTAACATGTTCATCTTGAATCGAACAAAT
TCTTCCAAATTTAGTTTTTATTGCATC SEQ ID NO: 25 nucleotide sequence of DMI3 phosphomimic 1
ATGGGATATGGAACAAGAAAACTCTCAGATGAATATGAAGTTTCAGAAATTCTAGGTAGAGGTGGATTTT
CTGTTGTTAGAAAAGGTACAAAAAAATCAAGCATTGAAGAAGAAAATCACAATCACAAGTAGCAATCAA
AACCCTAAGAAGGTTAGGTGCTTCAAATAACCCTAGTGGATTACCAAGAAAAAAAGATATTGGAGAAAAA
AGCACAATAGGGTTCCCTACAATGAGACAAGTTTCAGTTTCAGATACATTACTAACAAATGAGATACTTG
TAATGAGACGAATAGTCGAAAACGTTTCGCCACATCCAAATGTGATTGATCTTTATGATGTATATGAGGA
CACAAATGGTGTTCATCTTGTTCTTGAGCTTTGTTCCGGTGGTGAACTTTTCGATAGGATTGTTGCACAA
GATAAGTATAGTGAGACTGAAGCTGCAACTGTGGTTCATCAAATAGCTTCAGGGTTAGAAGCTGTTCATA
GAGCTAATATAGTTCATAGAGATTTGAAACCTGAAAATTGTCTTTTTTAGATGTTAGGAAAGATTCTCC
```

APPENDIX OF SEQUENCES

```
TCTTAAGATTATGGATTTTGGGTTGAGTTCTGTTGAAGAGTTTACTGATCCTGTTGTTGGTTTGTTTGGA
TCTATTGATTATGTTTCACCTGAGGCTCTTTCTCAAGGAAAGATTACTACTAAGAGTGATATGTGGTCTC
TTGGGGTTATTCTATATATCTTACTTTCAGGGTATCCACCTTTCATTGCCCAAAATAATCGCCAAAAACA
ACAAATGATAATGAATGGAATTTTAGTTTTTATGAGAAG[GAT]TGGAAGGGAATTTCACAACCAGCAAAG
AATTTGATTTCAAGTCTTTTAACCGTTGATCCTAGCAAGAGACCTAGTGCTCTTGAGCTTCTAAGTGATC
CATGGGTCAAAGGTGAGAAAGCCAAAGATGTTCAAATGGACCCTGAGATTGTCTCAAGGCTACAAAGCTT
TAATGCAAGACGTAAACTTCGTGCAGCTGCAATTGCTAGTGTTTGGAGCTCCACAATCTTCCTTAGAACA
AAAAAATTGAAATCATTGGTTGGATCCTATGATCTTAAAGAAGAGGAAATTGAAAATCTCAGGATGCATT
TCAAGAAGATATGTGCAGATAGAGACAATGCAACTCTGTCAGAGTTTGAGGAGGTGTTAAAAGCAATGAA
TATGTTATCATTGATCCCTTTTGCTTCTCGTATATTTGATTTGTTTGACAACAACCGTGATGGAACAGTT
GACATGCGTGAGATACTTTGTGGATTTTCCAGTCTCAAGAATTCCAAAGGAGGAGGATGCTCTTCGTTTGT
GCTTCCAGATGTATGATACAGATAGATCAGGCTGCATCAGCAAAGAGGAAGTAGCATCCATGCTCAGGGC
TTTGCCACATGATTGTCTTCCAACTGATATCACTGAACCTGGAAAATTGGATGAGATTTTTGACTTAATG
GATGCTAATAATGATGGAAAAGTTACATTTGATGAATTCAAAGCTGCTATGCAAAGAGATAGCTCTCTTC
AAGATGTAGTTCTCTCTTCTATTCGTCCATAA SEQ ID NO: 26 nucleotide sequence of DMI3 phosphomimic 2
ATGGGATATGGAACAAGAAAACTCTCAGATGAATATGAAGTTTCAGAAATTCTAGGTAGAGGTGGATTTT
CTGTTGTTAGAAAAGGTACAAAAAAATCAAGCATTGAAGAAGAAAATCACAATCACAAGTAGCAATCAA
AACCCTAAGAAGGTTAGGTGCTTCAAATAACCCTAGTGGATTACCAGAGAAAAAAGATATTGGAGAAAA
AGCACAATAGGGTTCCCTACAATGAGACAAGTTTCAGTTTCAGATACATTACTAACAAATGAGATACTTG
TAATGAGACGAATAGTCGAAACGTTTCGCCACATCCAAATGTGATTGATCTTTATGATGTATATGAGGA
CACAAATGGTGTTCATCTTGTTCTTGAGCTTTGTTCCGGTGGTGAACTTTTCGATAGGATTGTTGCACAA
GATAAGTATAGTGAGACTGAAGCTGCAACTGTGGTTCATCAAATAGCTTCAGGGTTAGAAGCTGTTCATA
GAGCTAATATAGTTCATAGAGATTTGAAACCTGAAAATTGTCTTTTTTTAGATGTTAGGAAAGATTCTCC
TCTTAAGATTATGGATTTTGGGTTGAGTTCTGTTGAAGAGTTTACTGATCCTGTTGTTGGTTTGTTTGGA
TCTATTGATTATGTTTCACCTGAGGCTCTTTCTCAAGGAAAGATTACTACTAAGAGTGATATGTGGTCTC
TTGGGGTTATTCTATATATCTTACTTTCAGGGTATCCACCTTTCATTGCCCAAAATAATCGCCAAAAACA
ACAAATGATAATGAATGGAATTTTAGTTTTTATGAGAAG[ATT]TGGAAGGGAATTTCACAACCAGCAAAG
AATTTGATTTCAAGTCTTTTAACCGTTGATCCTAGCAAGAGACCTAGTGCTCTTGAGCTTCTAAGTGATC
CATGGGTCAAAGGTGAGAAAGCCAAAGATGTTCAAATGGACCCTGAGATTGTCTCAAGGCTACAAAGCTT
TAATGCAAGACGTAAACTTCGTGCAGCTGCAATTGCTAGTGTTTGGAGCTCCACAATCTTCCTTAGAACA
AAAAAATTGAAATCATTGGTTGGATCCTATGATCTTAAAGAAGAGGAAATTGAAAATCTCAGGATGCATT
TCAAGAAGATATGTGCAGATAGAGACAATGCAACTCTGTCAGAGTTTGAGGAGGTGTTAAAAGCAATGAA
TATGTTATCATTGATCCCTTTTGCTTCTCGTATATTTGATTTGTTTGACAACAACCGTGATGGAACAGTT
GACATGCGTGAGATACTTTGTGGATTTTCCAGTCTCAAGAATTCCAAAGGAGGAGGATGCTCTTCGTTTGT
GCTTCCAGATGTATGATACAGATAGATCAGGCTGCATCAGCAAAGAGGAAGTAGCATCCATGCTCAGGGC
TTTGCCACATGATTGTCTTCCAACTGATATCACTGAACCTGGAAAATTGGATGAGATTTTTGACTTAATG
GATGCTAATAATGATGGAAAAGTTACATTTGATGAATTCAAAGCTGCTATGCAAAGAGATAGCTCTCTTC
AAGATGTAGTTCTCTCTTCTATTCGTCCATAA SEQ ID NO: 27
```

Medicago truncatula DMI3
>sp|Q6RET7.1|CCAMK_MEDTR RecName: Full = Calcium and calcium/calmodulin-dependent serine/threonine-protein kinase DMI-3; AltName: Full = CCaMK DMI3; AltName: Full = Does not make infections protein 3; AltName: Full = MtCCaMK

```
MGYGTRKLSDEYEVSEILGRGGFSVVRKGTKKSSIEEEKSQSQVAIKTLRRLGASNNPSGLPRKKDIGEK
STIGEPTMRQVSVSDTLLTNEILVMRRIVENVSPHPNVIDLYDVYEDTNGVHLVLELCSGGELFDRIVAQ
DKYSETEAATVVHQIASGLEAVHRANIVHRDLKPENCLFLDVRKDSPLKIMDFGLSSVEEFTDPVVGLFG
SIDYVSPEALSQGKITTKSDMWSLGVILYILLSGYPPFIAQNNRQKQQMIMNGNFSFYEKTWKGISQPAK
NLISSLLTVDPSKRPSALELLSDPWVKGEKAKDVQMDPEIVSRLQSFNARRKLRAAAIASVWSSTIFLRT
KKLKSLVGSYDLKEEEIENLRMHFKKICADRDNATLSEFEEVLKAMNMLSLIPFASRIFDLEDNNRDGTV
DMREILCGFSSLKNSKGEDALRLCFQMYDTDRSGCISKEEVASMLRALPYDCLPTDITEPGKLDEIFDLM
DANNDGKVTFDEFKAAMQRDSSLQDVVLSSIRP SEQ ID NO: 28
```

*Lotus japonicus* DMI3
>CAJ76700.1 calcium calmodulin-dependent protein kinase [*Lotus japonicus*]

```
MGYDQTRKLSDEYEISEILGRGGFSVVRKGTKKSGNEKTQVAIKTLRRLGSSPSGTGGGQKSTATVMGFP
SLRQVSVSDALLTNEILVMRRIVENVSPHPNVIDLYDVCEDSNGVHLVLELCSGGELFDRIVAQDKYAET
EAAAVVRQIAAGLEAVHKADIVHRDLKPENCLFLDSRKDSPLKIMDFGLSSVEEFTDPVVGLFGSIDYVS
PEALSQGKITAKSDMWSLGVILYILLSGYPPFIAQNNRQKQQMIINGNFSFYEKTWKGITQSAKQLISSL
LTVDPSKRPSAQELLSHPWVRGDKAKDEQMDPEIVSRLQSFNARRKLRAAAIASVWSSTIFLRTKKLRSL
VGTYDLKEEEIESLRIHFKKICGNGDNATLSEFVEVLKAMKMPSLIPLAPRIFDLFDNNRDGTIDMREIL
CGFSSLKNSKGDDALRLCFQMYDTDRSGCITKEEVASMLCALPEECLPADITEPGKLDEIFDLMDANSDG
KVTFEEFKAAMQRDSSLQDMLLSSLRPS SEQ ID NO: 29
```

Glycine max DMI3
>XP_006598046.1 PREDICTED: calcium and calcium/calmodulin-dependent serine/threonine-protein kinase [Glycine max]

```
MGNETRKLSDEYEVSEVLGRGGFSVVRKGTKKSSSDTKTHVAIKTLRRVGTASNSNNPSGFPRPKGGEKK
STAAMMGFPTWRQVSVSDALLTNEILVMRRIVENVSPHPNVIDLYDVYEDSNGVHLVLELCSGGELFDRI
VAQDRYSETEAAGVVRQIASGLEAIHRANIVHRDLKPENCLFLDVRRDSPLKIMDFGLSSVEEFTDPVVG
LFGSIDYVSPEALSQGKITTKSDMWSLGVILYILLSGYPPFIAQNNRQKQQMIMNGNFSFYEKTWKGITR
SAKQLISDLLIVDPSRRPSAQDLLSHPWVVGDKAKDDAMDPEIVSRLQSFNARRKLRAVAIASIWSTTIF
LRTKKLKSLVGTHDLTEEEIENLRMSPKKICVSGDNATLSEFEEVLKAMNMPSLIPLAPRIFDLFDDNRD
GTVDMREILCGFSSFKNSKGDDALRLCFQMYDTDRSGCITKEEVASMLRALPEDCLPTDITEPGKLDEIF
DLMDANSDGKVTFDEFKAAMQRDSSLQDVVLSSLRPQ SEQ ID NO: 30
```

APPENDIX OF SEQUENCES

*Phaseolus vulgaris* DMI3
>XP_007133531.1 hypothetical protein PHAVU_011G186900g [*Phaseolus vulgaris*]
MGYETRILSDEYEVSEVLGRGGFSVVRKGTRKSSSDTKSLVAYKTLRRSGTASSPSYPSGFPRPKGGEKS
TAAMMGFPSGRQVSVSDALLTNEILVMRRIVENVSPHPNVIDLYDVYEDSNGVHLVLELCSGGELFDRIV
AQDRYSETEAAGVVRQIASGLEAIHRANIVHRDLKPENCLFLDVRRDSPLKIMDFGLSSVEEFTDPVVGL
FGSIDYVSPEALSQGKITTKSDMWSLGVILYILLSGYPPFIAQTNRQKQQMIMNGNFSFYEKTWKGITQS
AKQLISDLLTIDPSRRPSAQDLLSHPWVVGDKAKDDAMDPEIVSRLQSFNARRKLRAAAIASVWSSTIFL
RTKKLKSLVGTHDLTAEEIENLRINFKKICVNGDNATLSEFEEVLKAMNMPSLIPLAPRIFDLFDNNRDG
TVDMREILCGFSSFKNSKGDDALRLCFQMYDTDRSGCITKEEVASMLRALPEECLPADITEPGKLDEIFD
RMDANSDGKVTFDEFKAAMQRDSSLQDLLLSSLRPQS SEQ ID NO: 31

*Arachis hypogea* DMI3
>ACB46142.1 calcium calmodulin-dependent protein kinase, partial [*Arachis hypogaea*]
MGYETRKLSDEYEVSEILGRGGFSVVRKGIKKSSSDEKTHVAIKTLRRVSVFSTTPGCLPRERSNMGFPT
WRQVSVSDALLTNEILVMRKIVENVSPHPNVVDLYDVYEDSNGVHLVLELCSGGELFDRIVAQDRYSETE
AATVIRQIAAGLEAIHKANIVHRDLKPENCLFLDKRKDSPLKIMDFGLSSVEEFTDPVVGLFGSIDYVSP
EALSQGKITTKSDMWSLGVILYILLSGYPPFIAQSNRQKQQMIMNGNFSFYEKTWKGISQSAKQLISSLL
TVDPSRRPSAQELLSHPWVIGDVAKDVQMDPEIVSRLQSFNARRKLRAAAIASVWSSTTVFLRTKKLKSLI
GSYDLTEEEIESLRIHFKKICNGDNATLSKFEEVLKAINMPSLIPLAPRIFDLFDNNRDGTVDMREILC
GLSSLKNSKGDDALRLCFQMYDADRSGCITKEEVASMLRALPDDCLPVDITEPGKLDEIFDRMDANSDGK
VTFEEFKAAMQRDSSLQDVVLSSLRP SEQ ID NO: 32

*Petunia x hybrida* DMI3
>ABQ95545.1 CCaMK [*Petunia x hybrida*]
MGQKEDTRSLSDEYEVTDILGRGGFSVVRRGRTRSSEEVAIKTLRRFGPPEKKEFSRSTTHVNSRPAAQA
LISETLLTNELLVMRKIVEDVSPHPNVIHLYDVCEDSSGVHLILELCCGGELFDRIVGQARYNEAGAAAV
VRQIAKGLEALHGASIVHRDLKPENCLFLNKDENSPLKIMDFGLSSIEDFANPVVGLFGSIDYVSPEALS
RGNITSKSDIWSLGVILYILLSGYPPFFAPSNRQKQQMILNGEFSFDEKTWKNISSSAKQLISSLLKVDP
NMRPTAQEILEHPWVTGDLAKQEQMDAEIVSRLQSFNARRKFRAAAMASVLSSSFSLRTKKLKKLVGSYD
LKPEELENLSHNFKKICKNGENATLLEFEEVLKAMEMSSLVPLAPRIFDLFDNNRDGTVDMREIIGGFSS
LKYSQGDDALRLCFQMYDTDRSGCISKEEVASMLRALPEDCLPMDITEPGKLDEIFDLMDANSDGKVTFD
EFRAAMQRDSSLQDVVLSSLRPTLIPLLFNFPFSILVVLISNLL SEQ ID NO: 33

*Sesbania rostrata* DMI3
>ACC94267.1 Ca2+ and calmodulin-dependent protein kinase [*Sesbania rostrata*]
MGYETRRLSDEYEVSDVLGRGGFSVVRKGTKKSSSEKTLVAIKTLRRLGASNNNPSGLPKTKGGEKSIAT
MMGFPTWRQVSVSDALLTNEILVMRRIVENVSPHPNVIDLYDVYEDSNGVHLVLELCSGGELFDRIVAQD
RYSETEAAAVVRQIAAGLEAIHKANIVHRDLKPENCLFLDTRKDSPLKIMDFGLSSVEEFTDPVVGLFGS
IDYVSPEALSQGKITTKSDMWSLGVILYILLSGYPPFIAPSNRQKQQMIVNGNFSFYEKTWKGISQSAKQ
LISSLLTVDPSKRPSAQQLLSHPWVIGEKAKDDQMDPEIVSRLQSFNARRKLRAAAIASVWSSTVFLRTK
KLRSLVGTHDLKEEEIENLRIHFKKICANGDNATLSEFEEVLKAMNMPSLIPLAPRIFDLFDNNRDGTVD
MREILCGFSSLKNSKGDDALRLCFQMYDTDRSGCITKEEVASMLRALPDDCLPADITEPGKLDEIFDLMD
ANSDGKVTFDEFKAAMQRDSSLQDVVLSSLRP SEQ ID NO: 34 amino acid sequence of DMI3 phosphomimic 1
MGYGTRKLSDEYEVSEILGRGGFSVVRKGTKKSSIEEEKSQSQVAIKTLRRLGASNNPSGLPRKKDIGEK
STIGFPTMRQVSVSDTLLTNEILVMRRIVENVSPHPNVIDLYDVYEDTNGVHLVLELCSGGELFDRIVAQ
DKYSETEAATVVHQIASGLEAVHRANIVHRDLKPENCLFLDVRKDSPLKIMDFGLSSVEEFTDPVVGLFG
SIDYVSPEALSQGKITIKSDMWSLGVILYILLSGYPPFIAQNNRQKQQMIMNGNFSFYEK[D]WKGISQPAK
NLISSLLTVDPSKRPSALELLSDPWVKGEKAKDVQMDPEIVSRLQSFNARRKLRAAAIASVWSSTIFLRT
KKLKSLVGSYDLKEEEIENLRMHFKKICADRDNATLSEFEEVLKAMNMSLIPFASRIFDLFDNNRDGTV
DMREILCGFSSLKNSKGEDALRLCFQMYDTDRSGCISKEEVASMLRALPYDCLPTDITEPGKLDEIFDLM
DANNDGKVTFDEFKAAMQRDSSLQDVVLSSIRP SEQ ID NO: 35 amino acid sequence of DMI3 phosphomimic 2
MGYGTRKLSDEYEVSEILGRGGFSVVRKGTKKSSIEEEKSQSQVAIKTLRRLGASNNPSGLPRKKDIGEK
STIGFPTMRQVSVSDTLLTNEILVMRRIVENVSPHPNVIDLYDVYEDTNGVHLVLELCSGGELFDRIVAQ
DKYSETEAATVVHQIASGLEAVHRANIVHRDLKPENCLFLDVRKDSPLKIMDFGLSSVEEFTDPVVGLFG
SIDYVSPEALSQGKITTKSDMWSLGVILYILLSGYPPFIAQNNRQKQQMIMNGNFSFYEK[I]WKGISQPAK
NLISSLLTVDPSKRPSALELLSDPWVKGEKAKDVQMDPEIVSRLQSFNARRKLRAAAIASVWSSTIFLRT
KKLKSLVGSYDLKEEEIENLRMHFKKICADRDNATLSEFEEVLKAMNMLSLIPFASRIFDLFDNNRDGTV
DMREILCGFSSLKNSKGEDALRLCFQMYDTDRSGCISKEEVASMLRALPYDCLPTDITEPGKLDEIFDLM
DANNDGKVTFDEFKAAMQRDSSLQDVVLSSIRP SEQ ID NO: 36

*Medicago truncatula* IFS
>AY939826.1 *Medicago truncatula* isoflavone synthase 1 mRNA, complete cds
ATGTTGGTGGAACTTGCAGTTACTCTATTGCTCATTGCTCTCTTCTTACACTTGCGTCCAACACCTACTG
CAAAATCAAAGGCTCTTCGCCACCTTCCAAATCCACCAAGCCCTAAACCACGTCTTCCATTCATAGGTCA
TCTTCACCTTTTGGATAACCCACTTCTTCACCACACTCTTATCAAGTTAGGAAAGCGTTATGGCCCTTTG
TACACTCTTTACTTTGGTTCCATGCCTACCGTTGTTGCATCCACTCCTGACTTGTTTAAACTTTTCCTTC
AAACCCATGAAGCTACTTCCTTTAACACAAGATTCCAAACCTCTGCTATTAGTCGTCTTACCTATGACAA
CTCTGTTGCTATGGTTCCATTTGCACCTTATTGGAAGTTTATTAGAAAGCTTATCATGAACGACTTGCTC
AACGCCACCACTGTTAACAAATTGAGGCCATTGAGGAGCCGAGAAATCCTTAAGGTTCTTAAGGTCATGG
CTAATAGTGCTGAAACTCAACAGCCACTTGATGTCACTGAGGAGCTTCTCAAGTGGACAAACAGCACAAT
CTCTACCATGATGTTGGGTGAGGCCGAAGAGGTTAGAGATATTGCTCGTGATGTTCTTAAGATCTTTGGA

APPENDIX OF SEQUENCES

```
GAATATAGTGTTACAAACTTTATTTGGCCTTTGAACAAGTTTAAGTTTGGAAACTATGATAAGAGAACTG
AGGAGATTTTCAATAAGTATGATCCTATCATTGAAAAGGTTATCAAGAAACGACAAGAGATTGTGAACAA
AAGAAAAAATGGAGAAATCGTAGAAGGCGAGCAGAATGTTGTTTTTCTTGACACTTTGCTTGAATTTGCA
CAAGATGAGACCATGGAGATCAAAATTACAAAGGAACAAATCAAGGGTCTTGTTGTGGATTTTTTCTCTG
CAGGAACAGACTCCACCGCCGTGTCTACAGAATGGACTTTATCAGAGCTCATCAATAATCCTAGAGTGTT
GAAGAAAGCTCGAGAGGAGATTGACTCTGTTGTGGGAAAAGATAGACTGGTTGATGAATCAGATGTTCAG
AATCTTCCTTACATTAAAGCCATCGTAAAAGAAGCATTTCGCTTGCACCCACCACTACCTGTAGTCAAAA
GAAAATGTACACAAGAATGTGAGATCGACGGGTATGTGGTTCCAGAAGGAGCACTAATACTTTTCAATGT
CTGGGCAGTGGGAAGAGACCCAAATATTGGGTAAAGCCATTGGAATTTCGTCCAGAGAGGTTCATAGAA
AATGTTGGTGAAGGTGAAGCAGCTTCAATTGATCTTAGGGGTCAACATTTCACACTTCTACCATTTGGGT
CTGGAAGAAGGATGTGTCCTGGAGTCAATTTGGCTACTGCAGGAATGGCCACAATGATTGCATCTATTAT
CCAATGCTTCGATCTCCAAGTACCTGGTCAACATGGAGAAATATTGAATGGTGATTATGCTAAGGTTAGC
ATGGAAGAGAGACCTGGTCTCACAGTTCCAAGGGCACATAATCTCATGTGTGTTCCTCTTGCAAGAGCTG
GTGTCGCAGATAAACTTCTTTCCTCCTAA    SEQ ID NO: 37
```

*Lotus japonicus IFS*
>AB279984.1 *Lotus japonicus* IFS2 mRNA for 2-hydroxyisoflavanone synthase, complete cds

```
ATGTTGGTGGAACTTGCATTAGCATTACTGGCCATAGCTCTGTTCTTACATTTACGTCCCACACCAACTG
CCAAATCCAAGGCCCTTCGTCACCTTCCAAACCCTCCAAGTCCCAAGCCTCGTCTTCATTCGTTGGACA
CCTTCACCTTTTGGACCAACCACTTCTCCACCACTCCCTCATCAAACTCGGCGAGCGATATGGGCCTTTG
TACTCTCTCTATTTTGGATCCATGCCCACCGTTGTTGCCTCAACCCCTGAACTCTTCAAACTCTTCCTTC
AGACCCATGAGGCCTCTTCCTTCAACACAAGGTTCCAAACCTCTGCCATTAGGCGCCTCACCTATGACAA
CTCTGTTGCCATGGTCCCTTTTGCTCCTTATTGGAAGTTCATCAGGAAGATCATCATGAACGACCTCCTC
AACGCCACCACCGTCAACAAGTTGAGGCCTTTGAGGAGCCAAGAGATTCGTAAGGTTCTGAAGGCTATGG
CACATAGTGCGGAATCTCAACAACCCCTTAATGTCACTGAGGAGCTTCTCAAGTGGACAAACAACACCAT
CTCTCGAATGATGTTGGGGAGGCTGAAGAGGTCAGAGATATTGCTCGTGAGGTGCTTAAGATCTTCGGG
GAATATAGTCTCACAGACTTCATTTGGCCATTGAAGAAGCTCAAGGTTGGACAGTATGAAAAGAGAATAG
ATGAGATATTTAACAAATTCGACCCCGTCATTGAGAAGGTCATCAAGAAACGCCAAGAGATAATAAAGAG
GAGAAAAGAGAGATGGAGAACTTGAGGAGGGTGAGCAAAGTGTAGTTTTCCTCGATACTTTGCTTGAA
TTTGCTGAAGATGAGACCATGGAAATCAAAATCACAAAGGAACAAATTAAGGGTCTTGTAGTGGATTTCT
TCTCTGCAGGGACAGATTCGACAGCTGTGGCAACAGACTGGGCTCTATCAGAGCTCATCAACAACCCGAG
GGTGCTGAAGAAAGCAAGAGAGGAAGTTGAAAGTGTTGTTGGAAAAGATAGACTTGTTGATGAAGCAGAT
ATTCAAAATCTTCCATACATTAGAGCCATCGTGAAGGAGACATTCCGCATGCATCCTCCACTCCCTGTTG
TTAAGAGAAAGTGTGTACAAGAATGTGAGCTCAACGGTTACGTGATCCCAGAGGGAGCACTGATACTCTT
CAACGTGTGGGCCGTGCAAAGAGATCCCAAATACTGGGAGGGCCCATCCGAATTCCGTCCTGAGAGGTTT
TTAACTGCTGAAGGGGGAGCAACCTCCATTGATCTTAGAGGCCAGAATTTCGAGCTTCTCCCATTTGGGT
CTGGAAGGAGGATGTGTCCAGGTGTGAATTTGGCAACTGCAGGAATGGCCACATTGCTTGCATCTGTTAT
CCAATGCTTTGATTTACAGGTTGTGGGTCAAAAGGGCAAATTATTGAAAGGAAGTGATGCCAAAGTTAGC
ATGGAAGAGAGTCCTGGTCTCACTGTTCCAAGGGCACATAATCTGATGTGCGTTCCACTTGCAAGAACCA
ACGTCACATCTGAACTCCTTTCCTCATAA    SEQ ID NO: 38
```

Glycine max IFS
>EU391490.1 Glycine max isolate C_HC24IFS1 isoflavone synthase 1 (ifs1) gene, complete cds

```
ATGTGTTTCTGGGGTTATTGCCTCTTGAGTTCAATTGCAACTTGTTAAGCAAATCAGCCGGCTTAAGACC
TAAGCAACACAAGCAAGGGCTTTAGGTTTCAAAAAAAGGTTTCAATTTTTTTTAATATTAATATATCTCA
AAAAAATTATTGTAAAATTATATTTGAAAATAAGTTTTAATTAAAATATTATAACTAACCGTTAATCTTT
TTATTGGTATTATAAATAATCAATGAGCAACAATTCTTCACCGACATCATATCTTTGTTTTAAAAAA
ATAATAATTTTAATAAATTATTTGATGAATAAATAAAAGATTTTATTCTTAAATTTATTTTAAATCTCTT
TGCGTCCTTGAAAAGTCCATGATACAGGATGAGATATTTGACTATTTGACTAGAAACGTAGTAGGTGATA
TATGGACATTTCCTGGTTTATTTTATATTCTTAAAAAATAACAATTCAATCGAATGTAGTTGCCAAATTT
TAATAAATAAATAAAAAGAAGCATTCATCGAATTCTTCGTCTTTTATGAGTGTAAAACAAAACATTGAAT
TAGGAACAATTATTATCACGTTACTTAAAATAAAATATACTAAAACCGTTAATGAAATCTTCATATTTG
ATAAGTGTAGGTAGACCCACAACACAAACATTGAATAGAATAAATTTCCCCGTACAGTGTCGTCCACTAT
GTGGCTATAAAATGGAAGCATTGAAGGTTGTTTCCTCAGGCCAAGATCTTGGATAGTAATTAACCTCACT
CAAACTCGGGATCACAGAAACCAACAACAGTTCTTGCACTGAGGTTTCACGATGTTGCTGGAACTTGCAC
TTGGTTTGTTTGTGTTAGCTTTGTTTCTGCACTTGCGTCCCACACCAAGTGCAAAATCAAAAGCACTTCG
CCACCTCCCAAACCCTCCAAGCCCAAAGCCTCGTCTTCCCTTCATTGGCCACCTTCACCTCTTAAAGAT
AAACTTCTCCACTATGCACTCATCGATCTCTCCAAAAAGCATGGCCCCTTATTCTCTCTCCTTCGGCT
CCATGCCAACCGTCGTTGCCTCCACCCCTGAGTTGTTCAAGCTCTTCCTCCAAACCCACGAGGCAACTTC
CTTCAACACAAGGTTCCAAACCTCTGCCATAAGACGCCTCACTTACGACAACTCTGTGGCCATGGTTCCA
TTCGGACCTTACTGGAAGTTCGTGAGGAAGCTCATCATGAACGACCTTCTCAACGCCACCACCGTCAACA
AGCTCAGGCCTTTGAGGACCCAACAGATCCGCAAGTTCCTTAGGGTTATGGCCCAAAGCGCAGAGGCCCA
GAAGCCCCTTGACGTCACCGAGGAGCTTCTCAAATGGACCAACAGCACCATCTCCATGATGATGCTCGGC
GAGGCTGAGGAGATCAGAGACATCGCTCGCGAGGTTCTTAAGATCTTCGGCGAATACAGCCTCACTGAT
TCATCTGGCCTTTGAAGTATCTCAAGGTTGGAAAGTATGAGAAGAGGATTGATGACATCTTGAACAAGTT
CGACCCTGTCGTTGAAAGGGTCATCAAGAAGCGCCGTGAGATCGTCAGAAGGAGAAAGAACGGAGAAGTT
GTTGAGGGCGAGGCCAGCGGCGTCTTCCTCGACACTTTGCTTGAATTCGCTGAGGACGAGACCATGGAGA
TCAAAATTACCAAGGAGCAAATCAAGGGCCTTGTTGTCGTAAGTTTCCTTCTTCTCTCCTACTTTATTAC
TTTCTTTCATTCATCATATGTATTGGCATTAAATAGTATACTATATGAGAAAATATGTTACGCACTCACG
GTGTAAAGATATGTGGTGTTTTTAAAAAGAGATACAGAAGTTGCTTTTATGCATGTATGTTAACGTAT
ATTTACTCAAGTGGAAACTAATTAATTCTCAATTTTGGGTATGTAGGACTTTTTCTCTGCAGGGACAGAT
TCCACTGCGGTGGCAACAGAGTGGGCATTGGCAGAGCTCATCAACAATCCCAGGGTGTTGCAAAAGGCTC
GTGAGGAGGTCTACAGTGTTGTGGGCAAAGATAGACTCGTTGACGAAGTTGACACTCAAAACCTTCCTTA
CATTAGGGCCATTGTGAAGGAGACATTCCGAATGCACCCACCACTCCCAGTGGTCAAAAGAAAGTGCACA
GAAGAGTGTGAGATTAATGGGTATGTGATCCCAGAGGGAGCATTGGTTCTTTTCAATGTTTGGCAAGTAG
```

APPENDIX OF SEQUENCES

GAAGGGACCCCAAATACTGGGACAGACCATCAGAATTCCGTCCCGAGAGGTTCTTAGAAACTGGTGCTGA
AGGGGAAGCAGGGCCTCTTGATCTTAGGGGCCAGCATTTCCAACTCCTCCCATTTGGGTCTGGGAGGAGA
ATGTGCCCTGGTGTCAATTTGGCTACTTCAGGAATGGCAACACTTCTTGCATCTCTTATCCAATGCTTTG
ACCTGCAAGTGCTGGGCCCTCAAGGACAAATATTGAAAGGTGATGATGCCAAAGTTAGCATGGAAGAGAG
AGCTGGCCTCACGGTTCCAAGGGCACATAGTCTCGTTTGTGTTCCACTTGCAAGGATCGGCGTTGCATCT
AAACTCCTTTCTTAATTAAGATAATCATCATATACAATAGTAGTGTCTTGCCATCGCAGTTGCTTTTTAT
GTATTCATAATCATCATTTCAATAAGGTGTGACTGGTACTTAATCAAGTAATTAAGGTTACAT SEQ ID NO: 39

*Trifolium pratense* IFS
>AF195811.1 *Trifolium pratense* isoflavone synthase 2 (ifs2) mRNA, complete
cds
ATGTTGCTGGAACTTGCACTTGGTTTATTGGTTTTGGCTCTGTTTCTGCACTTGCTCCCACACCCACTG
CAAAATCAAAAGCACTTCGCCATCTCCCAAACCCACCAAGCCCAAAGCCTCGTCTTCCCTTCATAGGACA
CCCTTCATCTCTTAAAAGACAAACTTCTCCACTACGCACTCATCGACCTCTCCAAAAAACATGGTCCCTTA
TTCTCTCTCTACTTTGGCTCCATGCCAACCGTTGTTGCCTCCACACCAGAATTGTTCAAGCTCTTCCTCC
AAACGCACGAGGCAACTTCCTTCAACACAAGGTTCCAAACCTCAGCCATAAGACGCCTCACCTATGATAG
CTCAGTGGCCATGGTTCCCTTCGGACCTTACTGGAAGTTCGTGAGGAAGCTCATCATGAACGACCTTCTC
AACGCCACCACTGTAAACAAGTTGAGGCCTTTGAGGACCCAACAGATCCGCAAGTTCCTTAGGGTTATGG
CCCAAGGCGCAGAGGCACAGAAGCCCCTTGACTTGACCGAGGAGCTTCTGAAATGGACCAACAGCACCAT
CTCCATGATGATGCTCGGCGAGGCTGAGGAGATCAGAGACATCGCTCGCGAGGTTCTTAAGATCTTTGGC
GAATACAGCCTCACTGACTTCATCTGGCCATTGAAGCATCTCAAGGTTGGAAAGTATGAGAAGAGGATCG
ACGACATCTTGAACAAGTTCGACCCTGTCGTTGAAAGAGTCATCAAGAAGCGCCGTGAGATCGTGAGGAG
GAGAAAGAACGGAGAGGTTGTTGAGGGTGAGGTCAGCGGGGTTTTCCTTGACACTTTGCTTGAATTCGCT
GAGGATGAGACCACGGAGATCAAAATCACCAAGGACCACATCAAGGGTCTTGTTGTCGACTTTTTCTCGG
CAGGAACAGACTCCACAGCGGTGGCAACAGAGTGGGCATTGGCAGAACTCATCAACAATCCTAAGGTGTT
GGAAAAGGCTCGTGAGGAGGTCTACAGTGTTGTGGGAAAGGACAGACTTGTGGACGAAGTTGACACTCAA
AACCTTCCTTACATTAGAGCAATCGTGAAGGAGACATTCCGCATGCACCCGCCACTCCCAGTGGTCAAA
GAAAGTGCACAGAAGAGTGTGAGATTAATGGATATGTGATCCCAGAGGGAGCATTGATTCTCTTCAATGT
ATGGCAAGTAGGAAGAGACCCCAAATACTGGGACAGACCATCGGAGTTCCGTCCTGAGAGGTTCCTAGAG
ACAGGGGCTGAAGGGGAAGCAAGGCCTCTTGATCTTAGGGGACAACATTTTCAACTTCTCCCATTTGGGT
CTGGGAGGAGAATGTGCCCTGGAGTCAATCTGGCTACTTCGGGAATGGCAACACTTCTTGCATCTCTTAT
TCAGTGCTTTGACTTGCAAGTGCTGGGTCCACAAGGACAGATATTGAAGGGTGGTGACGCCAAAGTTAGC
ATGGAAGAGAGGGCCGGCCTCACTGTTCCAAGGGCACATAGTCTTGTCTGTGTTCCACTTGCAAGGATCG
GCGTTGCATCTAAACTCCTTTCTTAA SEQ ID NO: 40

*Pisum sativum* IFS
>AF195812.1 *Pisum sativum* isoflavone synthase 1 (ifs1) mRNA, partial cds
ATGTTGCTGGAACTTGCACTTGGTTTGTTTGTGTTAGCTTTGTTTCTGCACTTGCTCCCACACCAAGCG
CAAAATCAAAAGCACTTCGCCACCTCCCAAACCCTCCAAGCCCAAAGCCTCGTCTTCCCTTCATTGGCCA
CCCTTCACCTCTTAAAAGATAAACTTCTCCACTATGCACTCATCGATCTCTCAAAAAGCATGGCCCCTTA
TTCTCTCTCCTTCGGCTCCATGCCAACCGTCGTTGCCTCCACCCGTGAGTTGTTCAAGCTCTTCCTCC
AAGCCCACGAGGCAACTTCCTTCAGCACAAGGTTCCAAACCTCTGCCGTAAGACGCCTCACTTACGACAA
CTCTGTGGCCATGGTTCCATTCGGACCTTACTGGAAGTTCGTGAGGAAGCTCATCATGAACGACCTTCTC
AACGCCACCACCGTCAACGAGCTCAGGCCTTTGAGGACCCAACAGATCCGCAAGTTCCTTAGGGTTATGG
CCCAAAGCGCAGAGGCCCAGAAGCCCCTTGACGTCACCGAGGAGCTTCTCAAATGGACCAACAGCACCAT
CTCCATGATGATGCTCGGCGAGGCTGAGGAGATCAGAGACATCGCTCGCGAGGTCCTTAAGATCTTCGGC
GAATACAGCCTCACTGACTTCATCTGGCCTTTGAAGTATCTCAAGGTTGGAAAGTATGAGAAGAGGATTG
ATGACATCTTGAACAAGTTCGACCCTGTCGTTGAAAGGGTCATCAAGAAGCGCCGTGAGATCGTCAGAAG
GAGAAAGAACGGAGAAGTTGTTGAGGGCGAGGCCAGCGGCGTCTTCCTCGACACTTTGCTTGAATTCGCT
GAGGACGAGACCATGGAGATCAAAATTACCAAGGAGCAAATCAAGGGCCTTGTTGTCGACTTTTTCTCTG
CAGGGACAGATTCCACAGCGGTGGCAACAGAGTGGGCATTGGCAGAGCTCATCAACAATCCCAGGGTGTT
GCAAAAGGCTCGTGAGGAGGTCTACAGTGTTGTGGGCAAAGATAGACTCGTTGACGAAGTCGACACTCAA
AACCTTCCTTACATTAGGGCCATTGTGAAGGAGACATTCCGAATGCACCCACCACTCCCAGTGGTCAAAA
GAAAGTGCACAGAAGAGTGTGAGATTAATGGGTATGTGATCCCAGAGGGAGCATTGGTTCTTTTCAATGT
TTGGCAAGTAGGAAGGACCCCAAATACTGGGACAGACCATCAGAATTCCGTCCCGAGAGGTTCTTAGAA
ACTGGCGCTGAAGGGGAAGCAGGGCCTCTTGATCTTAGGGGCCAGCATTTCCAACTCCTCCCATTTGGGT
CTGGGAGGAGAATGTGCCCTGGTGTCAATTTGGCTACTTCAGGAATGGCAACACTTCTTGCATCTCTTAT
CCAATGCTTTGACCTGCAAGTGCTGGGCCCTCAAGGACAAATATTGAAAGGTGACGATGCCAAAGTTAGC
ATGGAAGAGAGCTGGCCTCACCGTTCCAAGGGCACATAGTCTCGTTTGTGTTCCACTTGCAAGGATCG
GCGTTGCATCTAAACTCCTTTCT SEQ ID NO: 41

*Beta vulgaris* IFS
>AF195816.1 *Beta vulgaris* isoflavone synthase 1 (ifs1) mRNA, partial cds
TCTGCACTTGCGTCCCACACCCACTGCAAAATCAAAAGCACTTCGCCATCTCCCAAACCCACCAAGCCCA
AAGCCTCGTCTTCCCTTCATAGGACACCTTCATCTCTTAAAAGACAAACTTCTCCACTACGCACTCATCG
ACCTCTCCAAAAAACATGGTCCCTTATTCTCTCACTACTTTGGCTCCATGCCAACCGTTGTTGCCTCCAC
ACCAGAATTGTTCAAGCTCTTCCTCCAAACGAACGAGGCAACTTCCTTCAACACAAGGTTCCAAACCTCA
GCCATAAGACGCCTCACCTATGATAGCTCAGTGGCCATGGTTCCCTTCGGACCTTACTGGAAGTTCGTGA
GGAAGCTCATCATGAACGACCTTCTCAACGCCACCACTGTAAACAAGTTGAGGCCTTTGAGGACCCAACA
GATCCGCAAGTTCCTTAGGGCTATGGCCCAAGGCGCAGAGGCACGGAAGCCCCTTGACTTGACCGAGGAG
CTTCTGAAATGGGCCAACAGCACCATCTCCATGATGATGCTCGGCGAGGCTGAGGAGATCAGAGACATCG
CTCGCGAGGTTCTTAAGATCTTTGGCGAATACAGCCTCACTGACTTCATCTGGCCATTGAAGCATCTCAA
GGTTGGAAAGTATGAGAAGAGGATCGACGACATCTTGAACAAGTTCGACCCTGTCGTTGAAAGAGTCATC
AAGAAGCGCCGTGAGATCGTGAGGAGGAGAAAGAACGGAGAGGTTGTTGAGGGTGAGGTCAGCGGGGTTT
TCCTTGACACTTTGCTTGAATTCGCTGAGGATGAGACCATGGAGATCAAAATCACCAAGGACCACACCAA
GGGTCTTGTTGTCGACTTCTTCTCGGCAGGAACAGACTCCACAGCGGTGGCAACAGAGTGGGCATTGGCA
GAACTCATCAACAATCCTAAGGTGTTGGAAAAGGCTCGTGAGGAGGTCTACAGTGTTGTGGGAAAGGACA

| APPENDIX OF SEQUENCES |
| --- |

GACTTGTGGACGAAGTTGACACTCAAAACCTTCCTTACATTAGAGCAATCGTGAAGGAGACATTCCGCAT
GCACCCGCCACTCCCAGTGGTCAAAAGAAAGTGCACAGAAGAGTGTGAGATTAATGGATATGTGATCCCA
GAGGGAGCATTGATTCCCTTCAATGTATGGCAAGTAGGAAGGACCCCAAATACTGGGACAGACCATCGG
AGTTCCGTCCTGAGAGGTTCCTAGAGACAGGGGCTGAAGGGGAAGCAAGGCCTCTTGATCTTAGGGGACA
ACATTTTCAACTTCTCCCATTTGGGTCTGGGAGGAGAATGTGCCCTGGAGTCAATCTGGCTACTTCGGGA
ACGGCAACACTTCTTGCATCTCTTATTCAGTGCTTTGACTTGCAAGTGCTGGGTCCACAGGGACAGATAT
TGAAGGGTGGTGACGCCAAAGTTAGCATGGAAGAGAGAGCCGGCCTCACTGTTCCAAGGGCACATAGTCT
TGTCTGTGTTCCACTTGCAAGGATCGG SEQ ID NO: 42

*Vicia villosa* IFS
>AF195803.1 *Vicia villosa* isoflavone synthase 1 (ifs1) mRNA, partial cds
TGTTTCTGCACTTGCGTCCCACACCCACTGCAAAATCAAAAGCACTTCGCCATCTCCCAAACCCACCAAG
CCCAAAGCCTCGTCTTCCCTTCATAGGACACCTTCATCTCTTAAAAGACAAACTTCTCCACTACGCACTC
ATCGACCTCTCCAAAAAACATGGTCCCTTATTCTCTCTACTTTGGCTCCATGCCAACCGTTGTTGCCT
CCACACCAGAATTGTTCAAGCTCTTCCTCCAAACGCACGAGGCAACTTCCTTCAACACAAGGTTCCAAAC
CTCAGCCATAAGACGCCTCACCTATGATAGCTTAGTGGCCATGGTTCCCTTCGGACCTTACTGGAAGTTC
GTGAGGAAGCTCATCATGAACGACCTTCTCAACGCCACCACTGTAAACAAGTTGAGGCCTTTGAGGACCC
AACAGATCCGCAAGTTCCTTAGGGTTATGGCCCAAGGCGCAGAGGCACAGAAGCCCCTTGACTTGACCGA
GGAGCTTCTGAAATGGACCAACAGCACCATCTCTATGATGATGCTCGGCGAGGCTGAGGAGATCAGAGAC
ATCGCTCGCGAGGTTCTTAAGATCTATGGCGAATACAGCCTCACTGACTTCATCTGGCCATTGAAGCATC
TCAAGGTTGGAAAGTATGAGAAGAGGATCGACGCACATCTTGAACAAGTTCGACCCTGTCGTTGAAAGAGT
CATCAAGAAGCGCCGTGAGATCGTGAGGAGGAGAAAGAACGGAGAGGTTGTTGAGGGTGAGGTCAGCGGG
GTTTTCCTTGACACTTTGCTTGAATTCGCTGAGGATGAGACCACGGAGATCAAAATCACCAAGGACCACA
TCAAGGGTCTTGTTGTCGACTTTTTCTCGGCAGGAATAGACTCCACAGCGGTGGCAACAGAGTGGGCATT
GGCAGAACTCATCAACAATCCTAAGGTGTTGAAAAGGCTCGTGAGGAGGTCTACAGTGTTGTGGGAAAG
GACAGACTTGTGGACGAAGTTGACACTCAAAACCTTCCTTACATTAGAGCAATCGTGAAGGAGACATTCC
GCATGCACCCGCCACTCCCAGTGGTCAAAAGAAAGTGCACAGAAGAGTGTGAGATTAATGGATATGTGAT
CCCAGAGGGAGCATTGATTCTCTTCAATGTATGGCAAGTAGGAAGGACCCCAAATACTGGGACAGACCA
TCGGAGTTCCGTCCTGAGAGGTTCCTAGAGACAGGGGCTGAAGGGGAAGCAAGGCCTCTTGATCTTAGGG
GACAACATTTTCAACTTCTCCCATTTGGGTCTGGGAGGGAATGTGCCCTGGAGTCAATCTGGCTACTTC
GGGAATGGCAACACTTCTTGCATCTCTTATTCAGTGCTTTGACTTGCAAGTGCTGGGTCCACAAGGACAG
ATATTGAAGGGTGGTGACGCCAAAGTTAGCATGGAAGAGAGGGCCGGCCTCACTGTTCCAAGGGCACATA
GTCTTGTCTGTGTTCCACTTGCAAGGATCGG SEQ ID NO: 43

*Caragana arborescens* IFS
>JF912331.1 *Caragana arborescens* isoflavone synthase (IFS) mRNA, complete cds
AAGATCAAAGAAACACAAAACAAACACCATGTTGGTGGAACTAGCAATTACTCTATTAGTGATAGCTCTG
TTCCTACACCTTCGTCCCACACCTTCTGCAAAATCAAAAGCCCTTCGCCACCTTCCAAACCCACCGAGTC
CAAAACCTCGTCTTCCCTTTCATAGGTCACCTTCACCTTTTAGACAAACCTCTTCTCCACCAGTCCCTCAT
CCGTCTCAGCGAACGCTATGGCCCCTTATACTCTCTACTTTGGTTCCATGCCTACCGTTGTTGCCTCC
ACCCCTGAATTGTTCAAACTCTTCCTTCAAACCCACGAGGCTTCTTCCTTCAACACCAGGTTCCAAACCT
CTGCCATCAGACGCCTTACCTACGATAACTCCGTTGCCATGGTTCCCTTTGGACCTTACTGGAAGTTCAT
CAGAAAGCTCATCATGAACGACCTTCTAAACGCCACAACCGTCAACAAGTTGAGACCCTTGAGGAGCCAG
GAAATCCGTAAGCTTCTTAAGGTGATGGCACAGAGCGCGGAAACTCAACAGCCACTTAATGTCACCAAGG
AGCTTCTCAAGTGGACCAACAGCACCATCTCTAGGATGATGTTGGGTGAGGCTGAAGAGATTAGAGACAT
TGCTCGTGATGTGCTTAAGATCTTTGGAGAGTATAGTCTTACGGATTTCATTTGGCCATTGAGAAACTC
AAGGTTGGACAGTATGAGAAGAGAATAGATGATATTTTCAACAGGTTTGACCCTGTCATTGAAAAGGTCA
TCAAGAAACGCCAGGAGATTAGGAAGAGAAGAAAGGGAGAAGATTGGTGAACTTGAAGAGGGTGAGCAGAG
TGTTGTTTTTCTTGATACTTTGCTTGATTTTGCTGAGGAYGAGACCATGGAGATCAAAATTACCAAGGAA
CAAATCAAGGGTCTTATTGTGGATTCTTCTCAGCAGGGACAGATTCAACGGCAGTGGCAACAGACTATG
CTTTGTCAGAGCTAATCAACAACCCCAGGGTGTTGCAAAAAGCGCGAGAGGAAGTCGATAGTGTTGTGGG
AAAAGATAGACTGGTTGACGAATCAGATGTTCAAAACCTTCCTTTCATTAGAGCAATCGTGAAGGAGACA
TTCCGTATGCACCCGCCACTACCCGTTGTGAAAAGAAATGTACACAAGAGTGTGAGATAGACGGTTTTG
TGATCCCAGAGGGAGCATTGATACTTTTCAATGTTTGGGCTGTTGGAAGAGACCCAAAGTACTGGGAAAG
GCCCTCGGAATTTCGTCCTGAGAGGTTCTTACAAAATGCTGGTGAAGGGGAAGTAGGTTCAATTGATCTT
AGGGGCCAACATTTCCAACTTTTTGCCATTTGGGTCTGGTAGGAGCATTGTGCCTGGAGTCAATTTGGCTA
CTGCAGGAATGGCTACACTTCTTGCATCTGTTATTCAGTGCTTTGACCTGCAAGTACCGGGCCCACAAGG
AGAACTATTGAAAGGTGATGATGCCAAGGTTAGCATGGAAGAGAGACCTGGTCTTACAGTTCCAAGGGCG
AATAATCTCATGTGTGTTCCTCTTGCTAGAGCAGGTGTTGCAGCTAAACTTCTTTCCTCCTAAAAACACA
GTACAACACAGCACAACCACAAGAATGTTGCTATGGATGGTGTTTTTTTATATTTGTAGTAATAATCATT
TTCAATAAGGTATCATTGAGAGACAATGAGTCCAAGTTCCCCCGGCACATGGGCTGCTGGAAGAGTCACA
TATATATTTATCGTCTCAATTAAACTCTCTTTGATGTAATTTTCATCTTTGTTTTTCTTTTTCCTTTTT
GTCACCGAAGAGTGTTGTACTTGTAACAGCTTATATCTATAATTTTTACGAAAAAAAAAAAAAAAAAA
AAAAAAAA SEQ ID NO: 44

*Vigna unguiculata* IFS
>EU616499.1 *Vigna unguiculata* isoflavone synthase 1 mRNA, complete cds
AGGCCAAAATCTTGGTGTCACATAGCCTCAAGCTCGGGATCTCACAAAAACAAAGGTCAAGCAAACACAT
ACACAACCATGTTGCTCGAAATTACAATTGGTTTGTTGGTGCTGGCTTTGTTTTGCACTTGCGTCCCAC
ACCCACTGCTAAATCAAAGGCCCTTCGCCACCTTCCAAACCCTCCTAGTCCAAAACCTCGTCTTCCATTC
ATTGGTCACCTTCACCTTCTAAAAGACAAACTTCTCCACTATGCCCTCATAGATTTATCCAAAACCTATG
GCCCTTTGTACTCTCTCTACTTTGGGTCTATGCCAACCGTTGTTGCCTCCTCCCCTGAGTTGTTCAAACT
CTTCCTTCAAACCCACGAGGCTGCTTCCTTCAACACAAGGTTCCAAACCTCTGCCATTAGGCGCCTCACT
TATGACAACTCAGTGGCCATGGTTCCCTTTGGACCTTACTGGAAGTTCATCAGGAAGCTCATCATGAACG
ACCTCCTCAACGCCACCACCGTCAACAAGTTGAGGCCCCTCAGGACCCAACAGATCCGCAAGTTCCTCAA
GGTCATGGCCCAAAGCGCACAGGCTCAGCAGCCCCTTAACGTCACCGAGGAGCTTCTCAAGTGGACCAAC

APPENDIX OF SEQUENCES

```
AGCACTATCTCCATGATGATGTTGGGTGAGGCTGAAGAGATTAGAGATATCGCTCGTGAGGTGCTTAAGA
TTTTCGGGGAGTACAGTCTCACTGACTTCATCTGGCCCTTGAAGAAGCTTAAGTTTGGACAGTACGAGAA
GAGGATCGATGAAATATTCAACAAGTTCGACCCTGTCATCGAGAGGGTTATTAAGAAGCGCCAGAGATC
ATGAGAAGGAGAAAGAACGGAGAAGCCGTTGAGGAAGAGCAGAGCGGAGTCTTCCTCGACACTTTGCTTC
AATTCGCTGAGGACGAGACCATGGAGATCAAAATTACCAAGGAGCAGATCAAGGGTCTTGTTGTCGACTT
CTTCTCAGCAGGAACAGATTCCACAGCCGTGGCAACTGAGTGGGCTTTGGCAGAGCTGATCAACAACCCT
AGGGTGTTGCAGAAGGCTCGGGAGGAGGTGTACAGTGTTGTGGGGAAAGATAGACTGGTTGATGAAGTTG
ATACTCAAAACCTTCCTTACATCAGGGCGATTGTGAAGGAGACATTCCGCATGCACCCACCACTCCCAGT
GGTGAAGAGAAAGTGTGTGGAGGAGTGTGAGATTGAGGGTATGTGATCCCAGAGGGAGCATTGATACTT
TTCAATGTGTGGGCTGTAGGAAGAGACCCTAAATACTGGGACAGACCATTGGAGTTTCGTCCTGAGAGAT
TCCTAGAAACTGGAGCTGAAGGAGAAGCTGGGCCTCTTGATCTTAGGGGCCAACATTTCACTCTTCTCCC
ATTTGGGTCAGGTAGAAGAATGTGCCCTGGAGTGAATTTGGCTACTTCAGGTATGGCAACACTTCTTGCA
TCTGTTATCCAGTGCTTTGACCTTCAAGTGGTGGGCCCACAAGGACAAATATTGAAAGGCAATGACGCCA
AAGTGAGCATGGAAGAGAGAGCTGGACTCACGGTTCCGAGGGCACATAATCTGGAGTGTGTTCCAGTTGC
AAGGACAAGCGTTGCAGCTAAACTCCTTTCCTAGTTCACAACATATATACAACAACAGTGTCTTGCCACT
CATGCTTTTGCTTTTGTGTGTTAATAATAATCGTTTCAATAAGGTGTCTTTGATAACGAAGTCAGACACA
TTCACATGTAAAAAAAAAAA SEQ ID NO: 45
```

*Medicago truncatula* IFS
>AAY18206.1 isoflavone synthase 1 [*Medicago truncatula*]
```
MLVELAVTLLLIALFLHLRPTPTAKSKALRHLPNPPSPKPRLPFIGHLHLLDNPLLHHTLIKLGKRYGPL
YTLYFGSMPTVVASTPDLFKLFLQTHEATSFNTRFQTSAISRLTYDNSVAMVPFAPYWKFIRKLIMNDLL
NATTVNKLRPLRSREILKVLKVMANSAETQQPLDVTEELLKWTNSTISTMMLGEAEEVRDIARDVLKIFG
EYSVTNPIWPLNKFKFGNYDKRTEEIFNKYDPIIEKVIKKRQEIVNRRKNGEIVEGEQNVVFLDTLLEFA
QDETMEIKITKEQIKGLVVDFFSAGTDSTAVSTEWTLSELINNPRVLKKAREEIDSVVGKDRLVDESDVQ
NLPYIKAIVKEAFRLHPPLPVVKRKCTQECEIDGYVVPEGALILFNVWAVGRDPKYWVKPLEFRPERFIE
NVGEGEAASIDLRGQHFTLLPFGSGRRMCPGVNLATAGMATMIASITQCFDLQVPGQHGEILNGDYAKVS
MEERPGLTVPRAHNLMCVPLARAGVADKLLSS SEQ ID NO: 46
```

*Lotus japonicus* IFS
>BAF64284.1 2-hydroxyisoflavanone synthase [*Lotus japonicus*]
```
MLVELALALLAIALFLHLRPTPTAKSKALRHLPNPPSPKPRLPFVGHLHLLDQPLLHHLSLIKLGERYGPL
YSLYFGSMPTVVASTPELFKLFLQTHEASSENTRFQTSAIRRLTYDNSVAMVPFAPYWKFIRKIIMNDLL
NATTVNKLRPLRSQEIRKVLKAMHSAESQQPLNVTEELLKWTNNTISRMMLGEAEEVRDIAREVLKIFG
EYSLTDFIWPLKKLKVGQYEKRIDEIFNKFDPVIEKVIKKRQEIIKRRKERDGELEEGEQSVVFLDTLLE
FAEDETMEIKITKEQIKGLVVDFFSAGTDSTAVATDWALSELINNPRVLKKAREEVESVVGKDRLVDEAD
IQNLPYIRAIVKETFRMHPPLPVVKRKCVQECELNGYVIPEGALILFNVWAVQRDPKYWEGPSEFRPERF
LTAEGGATSIDLRGQNFELLPFGSGRRMCPGVNLATAGMATLLASVIQCFDLQVVGQKGKLLKGSDAKVS
MEESPGLTVPRAHNLMCVPLARTNVTSELLSS SEQ ID NO: 47
```

*Glycine max* IFS
>ACA81489.1 isoflavone synthase 1 [*Glycine max*]
```
MLLELALGLFVLALFLHLRPTPSAKSKALRHLPNPPSPKPRLPFIGHLHLLDKLLHYALIDLSKKHGPL
FSLSFGSMPTVVASTPELFKLFLQTHEATSFNTRFQTSAIRRLTYDNSVAMVPFGPYWKFVRKLIMNDLL
NATTVNKLRPLRTQQIRKFLRVMAQSAEAQKPLDVTEELLKWTNSTISMMMLGEAEEIRDIAREVLKIFG
EYSLTDFIWPLKYLKVGKYEKRIDDILNKFDPVVERVIKKRREIVRRRKNGEVVEGEASGVFLDTLLEFA
EDETMEIKITKEQIKGLVVDFFSAGTDSTAVATEWALAELINNPRVLQKAREEVYSVVGKDRLVDEVDTQ
NLPYIRAIVKETFRMHPPLPVVKRKCTEECEINGYVIPEGALVLFNVWQVGRDPKYWDRPSEFRPERFLE
TGAEGEAGPLDLRGQHFQLLPFGSGRRMCPGVNLATSGMATLLASLIQCFDLQVLGPQGQILKGDDAKVS
MEERAGLTVPRAHSLVCVPLARIGVASKLLS SEQ ID NO: 48
```

*Trifolium pratense* IFS
>AAF34532.1 isoflavone synthase 2 [*Trifolium pratense*]
```
MLLELALGLLVLALFLHLRPTPTAKSKALRHLPNPPSPKPRLPFIGHLHLLDKLLHYALIDLSKKHGPL
FSLYFGSMPTVVASTPELFKLFLQTHEATSFNTRFQTSAIRRLTYDSSVAMVPFGPYWKFVRKLIMNDLL
NATTVNKLRPLRTQQIRKFLRVMAQGAEAQKPLDLTEELLKWTNSTISMMMLGEAEEIRDIAREVLKIFG
EYSLTDFIWPLKHLKVGKYEKRIDDILNKFDPVVERVIKKRREIVRRRKNGEVVEGEASGVFLDTLLEFA
EDETTEIKITKDHIKGLVVDFFSAGTDSTAVATEWALAELINNPKVLEKAREEVYSVVGKDRLVDEVDTQ
NLPYIRAIVKETFRMHPPLPVVKRKCTEECEINGYVIPEGALILFNVWQVGRDPKYWDRPSEFRPERFLE
TGAEGEARPLDLRGQHFQLLPFGSGRRMCPGVNLATSGMATLLASLIQCFDLQVLGPQGQILKGGDAKVS
MEERAGLTVPRAHSLVCVPLARIGVASKLLS SEQ ID NO: 49
```

*Pisum sativum* IFS
>AAF34533.1 isoflavone synthase 1, partial [*Pisum sativum*]
```
MLLELALGLFVLALFLHLRPTPSAKSKALRHLPNPPSPKPRLPFIGHLHLLDKLLHYALIDLSKKHGPL
FSLSFGSMPTVVASTPELFKLFLQAHEATSFSTRFQTSAVRRLTYDNSVAMVPFGPYWKFVRKLIMNDLL
NATTVNELRPLRTQQIRKFLRVMAQSAEAQKPLDVTEELLKWTNSTISMMMLGEAEEIRDIAREVLKIFG
EYSLTDFIWPLKYLKVGKYEKRIDDILNKFDPVVERVIKKRREIVRRRKNGEVVEGEASGVFLDTLLEFA
EDETMEIKITKEQIKGLVVDFFSAGTDSTAVATEWALAELINNPRVLQKAREEVYSVVGKDRLVDEVDTQ
NLPYIRAIVKETFRMHPPLPVVKRKCTEECEINGYVIPEGALVLFNVWQVGKDPKYWDRPSEFRPERFLE
TGAEGEAGPLDLRGQHFQLLPFGSGRRMCPGVNLATSGMATLLASLIQCFDLQVLGPQGQILKGDDAKVS
MEERAGLTVPRAHSLVCVPLARIGVASKLLS SEQ ID NO: 50
```

*Beta vulgaris* IFS
>AAF34537.1 isoflavone synthase 1, partial [*Beta vulgaris*]
```
LHLRPTPTAKSKALRHLPNPPSPKPRLPFIGHLHLLDKLLHYALIDLSKKHGPLFSHYFGSMPTVVAST
PELFKLFLQTNEATSFNTRFQTSAIRRLTYDSSVAMVPFGPYWKFVRKLIMNDLLNATTVNKLRPLRTQQ
```

APPENDIX OF SEQUENCES

```
IRKFLRAMAQGAEARKPLDLTEELLKWANSTISMMMLGEAEEIRDIAREVLKIFGEYSLTDFIWPLKHLK
VGKYEKRIDDILNKFDPVVERVIKKRREIVRRRKNGEVVEGEVSGVFLDTLLEFAEDETMEIKITKDHTK
GLVVDFFSAGTDSTAVATEWALAELINNPKVLEKAREEVYSVVGKDRLVDEVDTQNLPYIRAIVKETFRM
HPPLPVVKRKCTEECEINGYVIPEGALIPFNVWQVGRDPKYWDRPSEFRPERFLETGAEGEARPLDLRGQ
HFQLLPFGSGRRMCPGVNLATSGTATLLASLIQCFDLQVLGPQGQILKGGDAKVSMEERAGLTVPRAHSL
VCVPLARIG SEQ ID NO: 51
```

*Vicia villosa* IFS
>AAF34524.1 isoflavone synthase 1, partial [*Vicia villosa*]
```
FLHLRPTPTAKSKALRHLPNPPSPKPRLPFIGHLHLLKDKLLHYALIDLSKKHGPLFSLYFGSMPTVVAS
TPELFKLFLQTHEATSFNTRFQTSAIRRLTYDSLVAMVPFGPYWKFVRKLIMNDLLNATTVNKLRPLRTQ
QIRKFLRVMAQGAEAQKPLDLTEELLKWTNSTISMMMLGEAEEIRDIAREVLKIYGEYSLTDFIWPLKHL
KVGKYEKRIDDILNKFDPVVERVIKKRREIVRRRKNGEVVEGEVSGVFLDTLLEFAEDETTEIKITKDHI
KGLVVDFFSAGIDSTAVATEWALAELINNPKVLEKAREEVYSVVGKDRLVDEVDTQNLPYIRAIVKETFR
MHPPLPVVKRKCTEECEINGYVIPEGALILFNVWQVGRDPKYWDRPSEFRPERFLETGAEGEARPLDLRG
QHFQLLPFGSGRGMCPGVNLATSGMATLLASLIQCFDLQVLGPQGQILKGGDAKVSMEERAGLTVPRAHS
LVCVPLARIG SEQ ID NO: 52
```

*Caragana arborescens* IFS
>AEQ39026.1 isoflavone synthase [*Caragana arborescens*]
```
MLVELAITLLVIALFLHLRPTPSAKSKALRHLPNPPSPKPRLPFIGHLHLLDKPLLHQSLIRLSERYGPL
YSLYFGSMPTVVASTPELFKLFLQTHEASSFNTRFQTSAIRRLTYDNSVAMVPFGPYWKFIRKLIMNDLL
NATTVNKLRPLRSQEIRKVLKVMAQSAETQQPLNVTEELLKWTNSTISRMMLGEAEEIRDIARDVLKIFG
EYSLTDFIWPLKKLKVGQYEKRIDDIFNRFDPVIEKVIKKRQEIRKRKERNGELEEGEQSVVFLDTLLD
FAEDETMEIKTKEQIKGLIVDFFSAGTDSTAVATDYALSELINNPRVLQKAREEVDSVVGKDRLVDESD
VQNLPFIRAIVKETFRMHPPLPVVKRKCTQECEIDGFVIPEGALILFNVWAVGRDPKYWERPSEFRPERF
LQNAGEGEVGSIDLRGQHFQLLPFGSGRRMCPGVNLATAGMATLLASVIQCFDLQVPGPQGELLKGDDAK
VSMEERPGLTVPRANNLMCVPLARAGVAAKLLSS SEQ ID NO: 53
```

*Vigna unguiculata* IFS
>ACC77196.1 isoflavone synthase 1 [*Vigna unguiculata*]
```
MLLEITIGLLVLALFLHLRPTPTAKSKALRHLPNPPSPKPRLPFIGHLHLLKDKLLHYALIDLSKTYGPL
YSLYFGSMPTVVASSPELFKLFLQTHEAASFNTRFQTSAIRRLTYDNSVAMVPFGPYWKFIRKLIMNDLL
NATTVNKLRPLRTQQIRKFLKVMAQSAQAQQPLNVTEELLKWTNSTISMMMLGEAEEIRDIAREVLKIFG
EYSLTDFIWPLKKLKFGQYEKRIDEIFNKFDPVIERVIKKRREIMRRRKNGEAVEEEQSGVFLDTLLQFA
EDETMEIKITKEQIKGLVVDFFSAGTDSTAVATEWALAELINNPRVLQKAREEVYSVVGKDRLVDEVDTQ
NLPYIRAIVKETFRMHPPLPVVKRKCVEECEIEGYVIPEGALIFNVWAVGRDPKYWDRPLEFRPERFLE
TGAEGEAGPLDLRGQHFTLLPFGSGRRMCPGVNLATSGMATLLASVIQCFDLQVVGPQGQILKGNDAKVS
MEERAGLTVPRAHNLECVPVARTSVAAKLLS SEQ ID NO: 54
```

*Petroselinum crispum* FS1
>AY230247.1 *Petroselinum crispum* flavone synthase I mRNA, complete cds
```
CTCGCCCTTCAATGGCTCCTACAACAATAACCGCATTAGCCAAGGAGAAAACACTAAACTTGGACTTTGT
GAGGGATGAAGACGAGCGTCCCAAAGTTGCTTACAATCAATTCAGCAATGAAATTCCCATTATTTCTTTA
GCCGGTTTGGATGACGATTCTGATGGCAGGAGACCCGAGATATGTCGCAAATAGTTAAGGCTTGGAAG
ACTGGGGAATTTTCCAAGTGGTTGATCATGGTATTGACAGCGGCTTGATTTCCGAGATGACTCGTCTTTC
TCGTGAATTCTTTGCTTTGCCTGCTGAGGAAAACTTGAGTATGATACAACTGGGGAAAGAGAGGCGGC
TTTACTATATCCACTGTTCTTCAGGGTGACGACGCTATGGATTGGCGTGAGTTCGTTACTTACTTTTCGT
ACCCAATCAATGCTCGGGACTACTCAAGATGGCCTAAAAAGCCCGAAGGATGGAGATCAACCACGGAGGT
TTATAGCGAGAAGTTAATGGTGCTAGGTGCCAAGTTACTGGAAGTGTTATCAGAGGCCATGGGGCTTGAG
AAAGGGGATCTTACTAAGGCTTGTGTGGATATGGAACAGAAAGTGTTAATTAATTACTATCCCACGTGCC
CCCAACCCGACTTGACACTTGGAGTCAGAAGGCATACGGATCCAGGTACTATTACCATTCTACTTCAGGA
CATGGTTGGTGGGTTACAAGCCACCAGGGACGGTGGCAAAACTTGGATTACTGTTCAGCCTGTGGAGGGA
GCTTTTGTTGTCAATTTGGGCGATCATGGTCATTATTTGAGCAATGGAAGGTTCAGGAATGCTGACCACC
AAGCAGTAGTGAATTCAACCTCTAGGAGATTGTCAATTGCAACTTTCCAGAACCCGGCTCAGAATGCGAT
AGTATATCCATTAAAGATCAGGGAGGGAGAGAAGGCAATTCTGGATGAGGCCATCACCTACGCTGAAATG
TATAAGAAATGCATGACTAAACATATTGAGGTGGCTACTCGGAAGAATGGGAGGTCAGTTACAGAGGTTTATAGTGAGA
TATAAGAAATGCATGACTAAACATATTGAGGTGGCTACTCGGAAGGATGGGTCAAGGAGAAAAGGTTGC
AAGACGAGAAAGCCAAGCTGGAGATGAAATCCAAGAGTGCAGATGAAAATTTAGCTTAGGCTTTGTGCAC
TCTACCATCTACATTATGTTTTGCGAGTTTGTGCTCCCTGCATTAGTGAATGATGTCATTTGCGAGTTTG
TGCTCTCTGCATTAGTGAATAATGTCATTGTTCAATTCCATGTCTAAACGCTGAATACTATGGAGTCATG
GTACTCTTTGGTTAGAAATTCTTACAATGTCGTTCTTTTAGAGTCCTTAATAATAATAATTCTCGGAGTG
TTTAATTATGTTTATTATGTGCTATAATCAATGGTGTGTGTTATTGGCAGAAG SEQ ID NO: 55
```

*Cuminum cyminum* FS1
>DQ683349.1 *Cuminum cyminum* flavone synthase I mRNA, complete cds
```
ATGGCTCCAACAACAATTACTGCATTGGCCCAAGAGAAAACACTTAACTCTGATTTTGTCCGGGATGAAG
ATGAGCGCCCCAAAGTTGCCTACAATCAGTTCAGCACTGAGATTCCCATCATTTCTTTAGCTGGCATCGA
TGATGATTCCAAAGGCAGGAGGCCTGAGGTGTGTAGAAAATAGTTGAGGCCTTTGAAGACTGGGGCATT
TTTCAGGTGGTTGATCACGGTGTTGACAGCGCTTTGATCTCCGAAATGTCTCGTCTGTCTCGTGAATTCT
TCGCTTTGCCTGCTGAGGAAAAACTCCGGTATGATACCACTGGTGGAAAGAGAGGCGGCTTCACTATCTC
CACTCATCAACAGGGTGACGACGTGCGGGACTGGCGTGAGTTGTTACTTATTTTTCGTACCCAGTGGAT
GCTCGGGACTACTCAAGATGGCCTGAGAAGCCAGAGGGATGGAGGTCAGTTACAGAGGTTTATAGTGAGA
AGTTGATGGTTCTAGGTGCCAAGTTACTGGAAGTGTTATCAGAGGCCATGGGGCTTGACAAAGGGGCTCT
TACAAAGGCTTGTGTGAATATGGAACAGAAAGTGCTAATTAATTACTATCCCACATGCCCCGAGCCAGAC
TTGACACTTGGAGTCAGAAGGCATACGGATCCAGGTACTATTACCATTTGCTTCAGGACATGGTTGGTG
GGTTACAGGCCACGAGGGATGGCGGCAAAACCTGGATCACTGTTCAGCCTGTGGAGGGAGTTTTTGTCGT
CAATTTGGGTGATCATGGTCATTATTTGAGCAATGGGAGGTTCAAGAACGCGGACCACCAGGCAGTAGTG
```

APPENDIX OF SEQUENCES

AATTCAACCTCAAGCAGATTGTCAATCGCAACTTTCCAGAACCCGGCTCAGAACGCTATAGTGTATCCAT
TAAAGATCAGGGAGGGTGAGAAGCCAATTCTGGAGGAGGCCATCACGTACGCGGAGATGTATAAGAAAAA
CATGACTAAACATATTGAGGTGGCTACACAGAAGAAATTGGCCAAGGAGAAAAGATTGCAAGAAGAGAAG
GCCAAGCTGGAGACGAAAACCAAGAGCGCAGATGGAATTTTAGCTTAG SEQ ID NO: 56

*Aethusa cynapium* FS1
>DQ683350.1 *Aethusa cynapium* flavone synthase I mRNA, complete cds
ATGGCTCCTACAACCATAACTGCATTATCCCAGGAGAAATCACTAAACTTAGACTTTGTCAGGGATGAAG
ACGAGCGTCCCAAAGTTGCTTACAATCAGTTCAGCAATGAAATTCCCATCATTTCTCTAGCTGGTATGGA
TGATGATTCTAATGGCAGGAGACCCGAGATATGTCGTAAAATAGTCGAGGCATTCGAAGACTGGGGAATT
TTCCAGGTGGTTGATCACGGTATTGACAAAGGTTTGATTTCTCAGATGTCTCGTCTCTCTCGTGAATTCT
TTGCTTTGCCTGCTGAGGAAAAACTCCGGTATGATACAACTGGTGGAAAGAGAGGTGGCTTTACTATCTC
CACTCATCTTCAGGGTGACGATGTTAAGGATTGGCGTGAGTTCGTTACTTACTTTTCGTACCCAATCGAA
GATCGGGACTACTCAAGATGGCCTGAAAAGCCAGAGGGATGGAGGTCAACCACTGAGGTTTATAGTGAGA
AGTTAATGGTGCTAGGTGCCAAGTTACTGGAAGTGTTGTCAGAGGCCATGGGCCTTGAGAAAGAGGCTCT
TACAAAGGCTTGTGTGAATATGGAACAGAAAGTGTTAATCAATTACTATCCCACATGCCCCGAACCCGAC
TTGACACTTGGAGTCAGAAGGCATACGGATCCAGGTACTATTACCATTCTGCTTCAGGACATGGTTGGTG
GATTACAGGCTACTAGGGATGGCGGCAAAACATGGATCACTGTTCAGCCTGTGGAGGGAGCTTTTGTGGT
CAATTTGGGTGACCATGGTCATTATTTGAGCAATGGAAGGTTCAAGAATGCTGACCACCAAGCAGTAGTG
AATTCAACTTCTAGCAGATTGTCTATTGCAACTTTCCAGAACCCGGCCAGAATGCGATAGTGTATCCCT
TAAAAATCAGGGAGGGAGAAAAGGCAATTCTTGATGAGGCCATCACCTACGCTGAAATGTATAAGAAAA
CATGACTAAACATATTGAGGTGGCTGCCCTGAAGAAATTGGCCAAGGAGAAAAGGCTGCAAGATGAGAAG
GCCAAGCTGGAGATGTAATCCAAGAGTGCAGATGAAAATTTAGCTTAG SEQ ID NO: 57

*Angelica archangelica* FS1
>DQ683352.1 *Angelica archangelica* flavone synthase I mRNA, complete cds
ATGGCTCCAACAACTATAACTGCATTAGCCCAGGAGAAAACACTAAATTTAGCCTTTGTCAGGGATGAAG
ACGAGCGTCCCAAAGTTGCCTACAATCAGTTCAGCAATGAAATTCCCATCATTTCTTTAGCTGGTATGGA
TGACGATACTGGCAGGAGACCCCAGATATGTCGTAAAATAGTTGAGGCATTTGAAGACTGGGGAATTTTC
CAGGTGGTTGATCACGGCATTGACGGCACTTTGATTTCTGAGATGACTCGTCTTTCTCGTGAATTCTTTG
CTTTGCCTGCTGAGGAAAAACTTCGGTATGATACAACTGGTGGAAAGAGAGGCGGCTTTACCATCTCCAC
TCATCTTCAGGGTGACGATGTTAAGGATTGGCGTGAGTTCGTTACTTACTTTTCGTACCCAATCGATGAT
CGGGACTACTCAAGATGGCCTGATAAGCCCCAGGGATGGAGGTCAACCACGGAGGTTTATAGTGAGAAGT
TAATGGTGCTAGGTGCCAAGTTACTTGAAGTGTTATCAGAGGCCATGGGCCTTGAGAAAGAGGCTCTTAC
AAAGGCTTGTGTGAATATGGAACAAAAAGTGTTAATCAATTACTATCCCACGTGCCCCGAACCGGACTTG
ACACTTGGAGTCAGAAGGCATACGGATCCAGGTACTATTACCATTCTGCTTCAGGACATGGTTGGTGGGT
TACAGGCTACTAGGGATGGTGGCAAAACTTGGATTACTGTTCAGCCTGTGGAGGGAGCTTTTGTGGTCAA
TTTGGGTGACCATGGTCATTATTTGAGCAATGGGAGGTTCAAGAATGCTGACCACCAAGCAGTAGTGAAT
TCAACCTCTAGCAGATTGTCTATTGCAACTTTCCAGAACCCGGCCCAGAATGCGATAGTGTATCCCTTGA
GGATCAGGGAGGGAGAGAAGGCAGTTCTTGATGAGGCCATCACCTACGCTGAAATGTATAAGAAAACAT
GACTAAACATATTGAGGTGGCTACCCTGAAGAAATTGGCCAAGGAGAAAAGGTTGCAAGAGGAAAAGGCC
AAGCTGGAACGGAATCCAAGAGTGCAGATGGAATTTCAGCTTAG SEQ ID NO: 58

*Apium graveolens* FS1
>AY817676.1 *Apium graveolens* flavone synthase I mRNA, complete cds
AAAAATGGCTCCATCAACTATAACTGCACTGTCTCAAGAGAAGACACTGAACTTAGACTTTGTGAGGGAT
GAAGATGAGCGTCCCAAAGTTGCTTACAATCAATTCAGCAATGAAGTTCCCATCATTTCTTTAGCTGGTT
TGGATGACGATTCTAATGGCAGGAGAGCTGAGATATGTCGTAAAATAGTTGAGGCTTTCGAAGAATGGGG
AATTTTCCAAGTTGTTGATCACGGTATTGATAGCGGTTTGATTTCTGAGATGAGTCGTCTTTCTCGTGAA
TTCTTCGCTTTGCCTGCTGAGGAAAAACTTGTGTATGATACCACTGGTGAAAAGAAAGGCGGCTTTACTA
TCTCCACTCATCTTCAGGGAGATGATGTTCGGGATTGGCGTGAGTTTGTTACTTACTTTTCGTATCCAAT
CAGTGCTCGGGACTACTCAAGATGGCCTAAAAAGCCCGAGGGGTGGAGATCAACCACGGAGGTTTATAGT
GAGAAGTTAATGGTGCTAGGTGCCAAGTTACTGGAGGTGTTATCCAGGGCAATGGGGCTTGAGAAAGAGG
CTCTTACAAAGGCTTGTGTGGAAATGGAACAGAAAGTGTTAATTAATTACTATCCCACATGCCCCGAACC
CGACTTGACGCTAGGTGTCAGAAGGCATACGGATCCAGGTACTATTACCATTCTGCTTCAGGACATGGTT
GGTGGTTTACAGGCTACTAGGGATGGCGGCAAAACTTGGATTACTGTTCAGCCTGTGGAGGGAGCTTTTG
TTGTCAATTTGGGTGATCATGGTCATTATTTGAGCAATGCAACCTTCAGGAATGCTGACCATCAAGCAGT
AGTGAATTCAACTTCCACCAGATTGTCAATTGCAACTTTCCAGAACCCGGCTCAGAATGCGATAGTATAT
CCGTTAAAGATCAGGGAGGGAGAGAAGGCAATTCTGGATGAGGCCATCACCTACGCTGAAATGTATAAGA
AAACATGACTAAACATATTGCGGTGGCTACCCAGAAGAAATTGGCCAAGGAGAAAAGGTTGCAAGATGA
GAAGGCCAAGATGAAGATATGATCGGAGATTGCCAGGGCAGGTGGAATTTAAGCTCAGCCTTTGTCCACC
ATACCATCTATGTTTCACGAAGTTTGTGCTCGCTGCGTTAGTGAACTATTGGGCCGTTGGTCAATTTCCA
TGTCTAAATGTCATGGTCTCTTTTGGTCAGAAATTCGAAATGTCGTCTTTTTAGGGACTTTATAATAATT
CTAAGTTTGGGAGGGGTC SEQ ID NO: 59

*Conium maculatum* FS1
>AY817677.1 *Conium maculatum* flavone synthase I mRNA, complete cds
AAATGGCTCCTACAACTATAACCGCATTAGCCCAGGAGAAAACACTAAACTTAGCCTTTGTGAGGGATGA
AGACGAGCGTCCCAAAGTTGCCTACAATGAATTCAGCAATGAAATTCCCATAATTTCTCTAGCTGGTTTG
GAAAATGACTCTGATGGGAGGAGACCCGAGATATGTCGTAAAATAGTCGAGGCTTTTGAAAACTGGGGAA
TTTTCCAAGTGGCTGATCATGGTATTGACAGTGCTTTGATTTCTGAGATGTCTCGTCTTTCTCGTGAATT
CTTTGCTTTGCCTGCTGAGGAAAAACTTCGGTATGATACCACTGGTGGAAAGAGAGGCGGCTTTACTATC
TCCACTCATCTTCAGGGTGATGACGTTCGGGATTGGCGTGAATTCGTTACTTACTTTTCGTACCCAATAG
ATGCTCGGGACTGCTCGAGATGGCCTGATAAGCCCGAGGGATGGAGGTCAATACGGAGGTTTACAGTGA
GAGGTTAATGGTGCTAGGTGCCAAGTTACTGGAAGTGTTATCAGAGGCCATGGGCCTTGAGAAAGAGGCT
CTTACAAAGGCTTGTGTGAATATGGAACAGAAAGTGTTAATTAATTACTATCCCACGTGCCCCGAGCCCG
ACTTGACACTTGGAGTCAGAAGGCATACGGATCCAGGTACTATTACTGTTCTGCTTCAGGACATGGTTGG

APPENDIX OF SEQUENCES

```
TGGGTTACAGGCTACTAGGGATGGTGGCAAAACTTGGATTACTGTTCAGCCTGTGGAGGGAGCTTTTGTT
GTCAATTTGGGTGATCATGGTCATTATCTGAGCAATGGAAGGTTCAAGAATGCTGACCACCAAGCGGTAG
TAAATTCAAGCTCTAGCAGATTGTCAATTGCGACATTCCAGAACCCGGCTCAGAATGCGATAGTTTATCC
ATTAAAGATCAGGGAGGGAGAGAAGGCAATTCTTGATGAGGCCATCACCTACGCCGAAATGTATAAGAAA
AACATGACTAAACATATTGAGGTGGCTACCCTCAAGAAATTGGCCAAGGAGAAAAGGTTGCAAGATGAGA
AGGCCAACATGGAGAAGAAATCCAAGAGTGCACATGGAATTTCAGCTTAGGTGCATGATGGCATCTAAAT
AATGTTTCTGGATTTTGTAGGTGAATAATATCATTGTTAAATTCTGTCCAAACGCTGCGTACGATGTAGT
CATGGCCCTCTTTGGCCGGAAAATCGGACAGTCTCAATCTTTCTGAGTACTCAATAACAGTAATTCTAAA
ATTTTGAAGTGTTTGATG SEQ ID NO: 60
```

*Daucus carota sativa* FS1
>AY817675.1 *Daucus carota* flavone synthase I mRNA, complete cds
```
GGACTTAAAATGGCTCCAACAACTATTACTGCATTGGCCAAGGAAAAAACACTTAACTCTGATTTTGTCC
GGGATGAGGATGAGCGTCCCAAAGTTGCCTACAATCAATTCAGCACTGAAATTCCCATTATTTCTTTAGC
TGGTATCGATGATGATTCCAATGGCAGGAGACCTGAGGTGTGTCGTAAAATAGTGGAGGCCTTCGAAGAC
TGGGGGATTTTCCAGGTAGTTGATCACGGTATTGACAGCGGTTTGATCGCGGAAATGTCTCGTCTGTCTC
GTGAATTCTTTGCTTTGCCTGCCGAGGAGAAACTTCGGTATGATACTACTGGTGGAAAGAGAGGCGGCTT
CACTATCTCCACTCATCTTCAGGGTGACGATGTGAAGGATTGGCGTGAGTTTGTTGTTTATTTTTCGTAC
CCAGTCGATGCTCGGGACTACTCGAGATGCCCTGATAAGCCCGAGGGATGGAGGTCAGTTACAGAGGTTT
ATAGTGAGAAGTTGATGGCGCTAGGTGCCAAGTTACTGGAAGTGCTATCAGAGGCCATGGGGCTTGAAAA
AGAGGCTCTTACAGAGGCTTGTGTGAATATGGAACAGAAAGTGTTGATCAATTACTATCCTACATGTCCC
CAACCGGACTTGACACTTGGAGTCAGAAGGCACACGGATCCGGGTACGATTACCATTTTGCTTCAGGACA
TGGTTGGGGGTTACAGGCTACCAGGGATGGCGGCAAAACTTGGATTACTGTTCAGCCTGTCGAGGGAGC
TTTTGTCGTCAATTTGGGTGATCATGGTCATTATTTGAGCAATGGAAGGTTCAAGAATGCCGATCACCAA
GCAGTAGTGAATTCAACCTCTAGCAGATTGTCCATCGCAACTTTCCAGAACCCAGCTCAGAATGCTATAG
TGTATCCTTTAAAGATCAGGGAGGGCGAGAAGCCAATTCTTGAGGAGGCCATGACATACGCCGAGATGTA
TAAGAAAAACATGACTAAACATATTGAGGTGGCTACTCAGAAGAAATTGGCCAAGGAGAAAGATTGCAG
AACGAGAAGGCCAAGCTGGAGACGAAATTTTAGCTTAGGCTTTGTCCATTATAGTATCTATATTATGTTT
TCCGAGTTTGTGTTATCTACAATAATACAGTAGTKAATWAGGCCATTTTTGTTAATGTCTAAATKCTGCG
TACTGTGGTCAGAGTWCTGTKTTAAGAAATTCATACAATATCGTTCTTAATCCTAAACTTTCGTGTGTTT
GATTTTGTTCATTCTATACAATAATTTAATAGTTCATTCTATTACAGTTATGCGAAAWAAAAAAAAAA SEQ ID NO: 61
```

*Petroselinum crispum* FS1
>Q7XZQ8.1 RecName: Full = Flavone synthase; AltName: Full = Flavone synthase I
```
MAPTTITALAKEKTLNLDFVRDEDERPKVAYNQFSNEIPIISLAGLDDDSDGRRPEICRKIVKACEDWGI
FQVVDHGIDSGLISEMTRLSREFFALPAEEKLEYDTTGGKRGGFTISTVLQGDDAMDWREFVTYFSYPIN
ARDYSRWPKKPEGWRSTTEVYSEKLMVLGAKLLEVLSEAMGLEKGDLTKACVDMEQKVLINYYPTCPQPD
LTLGVRRHTDPGTITILLQDMVGGLQATRDGGKTWITVQPVEGAFVVNLGDHGHYLSNGRFRNADHQAVV
NSTSSRLSIATFQNPAQNAIVYPLKIREGEKAILDEAITYAEMYKKCMTKHIEVATRKKLAKEKRLQDEK
AKLEMKSKSADENLA SEQ ID NO: 62
```

*Cuminum cyminum* FS1
>ABG78790.1 flavone synthase I [*Cuminum cyminum*]
```
MAPTTITALAQEKTLNSDFVRDEDERPKVAYNQFSTEIPIISLAGLDDDSKGRRPEVCRKIVEAFEDWGI
FQVVDHGVDSALISEMSRLSREFFALPAEEKLRYDTTGGKRGGFTISTHQQGDDVRDWREFVTYFSYPVD
ARDYSRWPEKPEGWRSVTEVYSEKLMVLGAKLLEVLSEAMGLDKGALTKACVNMEQKVLINYYPTCPEPD
LTLGVRRHTDPGTITILLQDMVGGLQATRDGGKTWITVQPVEGVFVVNLGDHGHYLSNGRFKNADHQAVV
NSTSSRLSIATFQNPAQNAIVYPLKIREGEKPILEEAITYAEMYKKNMTKHIEVATQKKLAKEKRLQEEK
AKLETKTKSADGILA SEQ ID NO: 63
```

*Aethusa cynapium* FS1
>ABG78791.1 flavone synthase I [*Aethusa cynapium*]
```
MAPTTITALSQEKSLNLDFVRDEDERPKVAYNQFSNEIPIISLAGMDDDSNGRRPEICRKIVEAFEDWGI
FQVVDHGIDKGLISQMSRLSREFFALPAEEKLRYDTTGGKRGGFTISTHLQGDDVKDWREFVTYFSYPIE
DRDYSRWPEKPEGWRSTTEVYSEKLMVLGAKLLEVLSEAMGLEKEALTKACVNMEQKVLINYYPTCPEPD
LTLGVRRHTDPGTITILLQDMVGGLQATRDGGKTWITVQPVEGAFVVNLGDHGHYLSNGRFKNADHQAVV
NSTSSRLSIATFQNPAQNAIVYPLKIREGEKAILDEAITYAEMYKKNMTKHIEVAALKKLAKEKRLQDEK
AKLEM SEQ ID NO: 64
```

*Angelica archangelica* FS1
>ABG78793.1 flavone synthase I [*Angelica archangelica*]
```
MAPTTITALAQEKTLNLAFVRDEDERPKVAYNQFSNEIPIISLAGMDDDTGRRPQICRKIVEAFEDWGIF
QVVDHGIDGTLISEMTRLSREFFALPAEEKLRYDTTGGKRGGFTISTHLQGDDVKDWREFVTYFSYPIDD
RDYSRWPDKPQGWRSTTEVYSEKLMVLGAKLLEVLSEAMGLEKEALTKACVNMEQKVLINYYPTCPEPDL
TLGVRRHTDPGTITILLQDMVGGLQATRDGGKTWITVQPVEGAFVVNLGDHGHYLSNGRFKNADHQAVVN
STSSRLSIATFQNPAQNAIVYPLRIREGEKAVLDEAITYAEMYKKNMTKHIEVATLKKLAKEKRLQEEKA
KLETESKSADGISA SEQ ID NO: 65
```

*Apium graveolens* FS1
>AAX21537.1 flavone synthase I [*Apium graveolens*]
```
MAPSTITALSQEKTLNLDFVRDEDERPKVAYNQFSNEVPIISLAGLDDDSNGRRAEICRKIVEAFEEWGI
FQVVDHGIDSGLISEMSRLSREFFALPAEEKLVYDTTGEKKGGFTISTHLQGDDVRDWREFVTYFSYPIS
ARDYSRWPKKPEGWRSTTEVYSEKLMVLGAKLLEVLSEAMGLEKEALTKACVEMEQKVLINYYPTCPEPD
LTLGVRRHTDPGTITILLQDMVGGLQATRDGGKTWITVQPVEGAFVVNLGDHGHYLSNGRERNADHQAVV
NSTSTRLSIATFQNPAQNAIVYPLKIREGEKAILDEAITYAEMYKKNMTKHIAVATQKKLAKEKRLQDEK
AKMKI SEQ ID NO: 66
```

-continued

APPENDIX OF SEQUENCES

*Conium maculatum* FS1
>AAX21538.1 flavone synthase I [*Conium maculatum*]
MAPTTITALAQEKTLNLAFVRDEDERPKVAYNEFSNEIPIISLAGLENDSDGRRPEICRKIVEAFENWGI
FQVADHGIDSALISEMSRLSREFFALPAEEKLRYDTTGGKRGGFTISTHLQGDDVRDWREFVTYFSYPID
ARDCSRWPDKPEGWRSITEVYSERLMVLGAKLLEVLSEAMGLEKEALTKACVNMEQKVLINYYPTCPEPD
LTLGVRRHTDPGTITVLLQDMVGGLQATRDGGKTWITVQPVEGAFVVNLGDHGHYLSNGRFKNADHQAVV
NSSSSRLSIATFQNPAQNAIVYPLKIREGEKAILDEAITYAEMYKKNMTKHIEVATLKKLAKEKRLQDEK
ANMEKKSKSAHGISA SEQ ID NO: 67

*Daucus carota* sativa FS1
>AAX21536.1 flavone synthase I [*Daucus carota* subsp. *sativus*]
MAPTTITALAKEKTLNSDFVRDEDERPKVAYNQFSTEIPIISLAGIDDDSNGRRPEVCRKIVEAFEDWGI
FQVVDHGIDSGLIAEMSRLSREFFALPAEEKLRYDTTGGKRGGFTISTHLQGDDVKDWREFVVYFSYPVD
ARDYSRCPDKPEGWRSVTEVYSEKLMALGAKLLEVLSEAMGLEKEALTEACVNMEQKVLINYYPTCPQPD
LTLGVRRHTDPGTITILLQDMVGGLQATRDGGKTWITVQPVEGAFVVNLGDHGHYLSNGRFKNADHQAVV
NSTSSRLSIATFQNPAQNAIVYPLKIREGEKPILEEAMTYAEMYKKNMTKHIEVATQKKLAKEKRLQNEK
AKLETKF SEQ ID NO: 68

*Medicago truncatula* FS2
>XM_013600611.1 *Medicago truncatula* cytochrome P450 family flavone synthase
mRNA
CTCTAGAGATGGTTTCATTAGTGTAACGTATACACTATAAAATGCTCAAGGAGGTAATCCAAATCCCACA
ATCATTTCTCAACTATTCTCATGAGTTTTCATTTCCAATATAAAGACAATAACCAAGATGATTTCTCAGC
CAATCTTATTAGCTTTGATTCTATTCCTCCTCTTCCTTCTCCAACTCTTTTTGTTTAAGAGAAACAACAG
AGCAAAGGAGCACTTACCTTACCCTCCAAGTCCACTAGCAATACCAATAATTGGTCATCTTCATCTCCTC
AAACCCCTCGTTCATCAAGCCTTTCGCGACCTCTCTGATCGATATGGACCCCTTATATCCCTTCGACTTG
GTTCTGTTCCATTTATCGTTGTTAGTTCCCCATCACTCGCAAAAGAGTTTCTCAAAACAAACGAGCTTGT
TTATTCTTCCCGTAAAATGAACATTGCCATCAACACAGTTGTCTACGATGATGCTACTTTTGCTTTTGCC
CCTTATGGGCATATTGGAAATTCATCAAAAAGCTTAGTACCTTTGAGCTCTTAGGCAACCGGACTATTG
GACAATTCTTACCAATTCGAACTCGAGAACTCAACGAGTTCATTCAAACTTTGGAAAATAAATCCAAGGT
TGAAGAAAGCGTGAACCTCACTCAAGCTTTGTTGAAGCTTTCCAACAACATAATATCACGGATGATGTTG
AGCATTGAGAGCTCAGGAACGGATAGTCAGGCTGAACAGGCGAGGACGTTGGTTCGAGATGTGACCCAAA
TTTTCGGGGAATTTAACATTTCGGATTTTATAGGATTTTGCAAGAACTTGGACTTTCAAGGTCTCAAAAA
GAGGGCATTGGATATACATAAGAGGTATGATGCTTTTCTGGAGAAGTTAATTTGTGATCGTGAGGAATCA
CGAAGGAAAGCCAAGGTTGAGGGTGGTTGTGAGGATAGAGACGAAAAGTGAAGGATTTTCTTGATATGT
TGCTTGATGTTTTCGAGGCCAAAGAATGTGAGGTCGACTTTACTAGGAACCATATCAAATCGTTGATCTT
GGATTACTTCACAGCAGCTACAGATACAACTGCCATTTCATTGGAATGGACAATAGCAGAACTGTTCAAC
AATCCAATAGTACTGAAGAAAGCACAAGAAGAGGTGGAGAGAATAATAGGGAAGGAAAGACTAGTATGTG
AAGCAGACATTCCAAACCTTCCTTATATACAAGCCATTATAAAAGAAACATTGAGGCTTCACCCACCACT
ACCGATGATTGCTAGGAAAGGAACAAAAGATTGTGTGGTCGATGGGAAAATGATCAAAAAAGGCTCAATA
GTTTGTGTGAACATTTGGGCTATTGGAAGGGACTCAAAGACTTGGAAAAACCCACTAGAGTTTAGGCCTG
AAAGGTTTTTAGAATCTGGAAAAGAGAGTGAGATAGATATCAAAGGGCATGACTTTGAGTTGTTGCCATT
TGGTTCTGGAAGGAGAGGTTGCCCGGGGATGCCTTTGGCCATGCGCGAATTGCCGACTGTGATTGGAGCT
TTAGTACAATGCTTTGAGTGGAAGATGCTTGACTCTGAAGGTAAATTATTAGATCAAGGCAAAACAATCG
ATATGGATGAACGGCCTGGATTGACTGCTCCTAGAGCCAATGATCTTTTTTGCATTCCAGTTGCAAGATT
GAATTTGATTCCTTTGGTTCAATTGTAGTGTAAAGCAATTGCGATAAGGTATTATGAAAATTTCTTTCAA
ATTGTTTTTCTGGGCCAAGGGCCTAATATAAGATAACTTTATTTATTGTATGTTTATTTTAATTTAATAC
TCACTCCGTCCCAAATTGTACGACGTTTTGAGCATTTAACATATATTAAGAAATATAATTAATA SEQ ID NO: 69

*Lotus japonicus* FS2
>AB279984.1 *Lotus japonicus* IFS2 mRNA for 2-hydroxyisoflavanone synthase,
complete cds
ATGTTGGTGGAACTTGCATTAGCATTACTGGCCATAGCTCTGTTCTTACATTTACGTCCCACACCAACTG
CCAAATCCAAGGCCCTTCGTCACCTTCCAAACCCTCCAAGTCCCAAGCCTCGTCTTCCATTCGTTGGACA
CCTTCACCTTTTGGACCAACCACTTCTCCACCACTCCCTCATCAAACTCGGCGAGCGATATGGGCCTTTG
TACTCTCTCTATTTTGGATCCATGCCCACCGTTGTTGCCTCAACCCTGAACTCTTCAAACTCTTCCTTC
AGACCCATGAGGCCTCTTCCTTCAACACAAGGTTCCAAACCTCTGCCATTAGGCGCCTCACCTATGACAA
CTCTGTTGCCATGGTCCCTTTTGCTCCTTATTGGAAGTTCATCAGGAAGATCATCATGAACGACCTCCTC
AACGCCACCACCGTCAACAAGTTGAGGCCTTTGAGGAGCCAAGAGATTCGTAAGGTTCTGAAGGCTATGG
CACATAGTGCGGAATCTCAACAACCCCTTAATGTCACTGAGGAGCTTCTCAAGTGGCAAACAACACCAT
CTCTCGAATGATGTTGGGGGAGGCTGAAGAGGTCAGAGATATTGCTCGTGAGGTGCTTAAGATCTTCGGG
GAATATAGTCTCACAGACTTCATTTGGCCATTGAAGAAGCTCAAGGTTGGACAGTATGAAAAGAGAATAG
ATGAGATATTTAACAAATTCGACCCCGTCATTGAGAAGGTCATCAAGAAACGCCAAGAGATAATAAAGAG
GAGAAAAGAGAGATGGAGAACTTGAGGAGGGTGAGCAAAGTGTAGTTTTCCTCGATACTTTGCTTGAA
TTTGCTGAAGATGAGACCATGGAAATCAAAATCACAAAGGAACAAATTAAGGGTCTTGTAGTGGATTTCT
TCTCTGCAGGGACAGATTCGACAGCTGTGGCAACAGACTGGGCTCTATCAGAGCTCATCAACAACCCGAG
GGTGCTGAAGAAAGCAAGAGAGGAAGTTGAAAGTGTTGTGAAAAGATAGACTTGTTGATGAAGCAGAT
ATTCAAAATCTTCCATACATTAGAGCCATCGTGAAGGAGACATTCCGCATGCATCCTCCACTCCCTGTTG
TTAAGAGAAAGTGTGTACAAGAATGTGAGCTCAACGGTTACGTGATCCCAGAGGGAGCACTGATACTCTT
CAACGTGTGGGCCGTGCAAAGAGATCCCAAATACTGGGAGGGCCCATCCGAATTCCGTCCTGAGAGGTTT
TTAACTGCTGAAGGGGGAGCAACCTCCATTGATCTTAGAGGCCAGAATTTCGAGCTTCTCCCATTTGGGT
CTGGAAGGAGGATGTGTCCAGGTGTGAATTTGGCAACTGCAGGAATGGCCACATTGCTTGCATCTGTTAT
CCAATGCTTTGATTTACAGGTTGTGGGTCAAAAGGGCAAATTATTGAAGGAAGTGATGCCAAAGTTAGC
ATGGAAGAGAGTCCTGGTCTCACTGTTCCAAGGGCACATAATCTGATGTGCGTTCCACTTGCAAGAACCA
ACGTCACATCTGAACTCCTTTCCTCATAA SEQ ID NO: 70

APPENDIX OF SEQUENCES

Glycine max FS2
>FJ767774.1 Glycine max cultivar Harosoy 63 flavone synthase II (CYP93B16)
mRNA, complete cds
GATGGTCATTTTCCTAATTAATCAAACCAACCACCAACAAGATGATTTCTGAGTCCCTCTTGGTAGTATT
CCTCATTGTCTTCATTTCTGCTTCCCTTCTCAAACTCTTGTTTGTGAGAGAAAACAAACCAAGGCCCAC
TTGAAGAACCCACCAAGCCCACCTGCAATACCCATAATAGGTCATCTCCACCTCCTTAAACCCCTCATCC
ATCACTCATTCCGAGACCTCTCTCTCCGATATGGGCCCCTCCTAAGCCTTCGAATTGGTTCCGTTAAGTT
CATAGTTGCAAGCACCCCATCACTCGCCCAAGAGTTTCTCAAGACCAACGAGCTCACATACTCTTCCCGC
AAAATGAACATGGCCATCAACATGGTCACTTACCACAACGCCACGTTTGCGTTTGCACCTTACGACACTT
ACTGGAAGTTCATGAAAAAACTAAGCACCACTGAGCTCTTGGGAAACAAAACCCTCGGACACTTCCTACC
TATTCGGACGAGGGAAGTTCATGACATCATTCAATTTTTGTTCCATAAATCAAAGGCCCAAGAGAGCGTG
AACCTCACCGAAGCGCTTTTGAGTCTTTCCAACAACGTAATATCGCAGATGATGTTGAGCATTAAGAGCT
CCGGTACAGACAGCCAGGCAGAGCAGGCACGGACTTTGGTTCGTGAAGTGACGCAGATTTTCGGGGAGTT
TAACGTGTCGGATTTCTTAGGTTTCTGCAAAAACTTGGACTTGCAAGGTTTCAGGAAGAGGGCATTGGAC
ATACATAAGAGGTACGATGCTCTGCTAGAGAAGATCATCTCTGATCGTGAGGAGTTGAGAAGGAAATCAA
AGGTAGACGGCTGCGAAGATGGAGATGATGAGAAAGTGAAGGATTTTCTTGACATTTTGTTGGATGTTGC
TGAGCAGAAAGAATGCGAGGTCCAGTTAACTCGGAACCATGTCAATCATTGATCTTGGATTATTTTACG
GCAGCTACTGACACAACTGCCATATCAGTGGAATGGACAATAGCAGAACTATTTAACAATCAAAGGTGT
TAAAGAAAGCGCAAGAGGAAGTTGATAGAGTCACCGGAAACACGCAATTAGTGTGTGAAGCAGACATTCC
AAACCTTCCTTATATTCATGCCATCATAAAAGAAACAATGAGACTTCACCCGCCAATACCAATGATTATG
AGGAAAGGAATCGAAGACTGCGTGGTTAATGGAAACATGATTCCAAAAGGTTCAATAGTTTGTGTAAACA
TTTGGGCTATGGGAAGGGACCCAAATATCTGGAAGAACCCTTTAGAATTCAAGCCAGAGAGGTTTCTAGA
AGGTGAAGGAAGTGCTATAGATACCAAAGGGCATCATTTGAGTTGTTGCCATTTGGCAGTGGAAGGAGA
GGGTGTCCTGGAATGCCTTTGGCCATGCGTGAATTGCCCACCATCATTGGACACTCATACAATGCTTTG
AGTGGAAGATGTTAGGTTCACAAGGTGAAATCTTAGATCATGGAAGAAGCTTAATCAGTATGGATGAACG
GCCAGGATTGACTGCCCCAAGGGCCAATGATCTTATTGGCATTCCTGTTGCACGATTGAATCCCACTCCT
TTTCGTCAAATGTAGTTTATTGTCAAGGGAATTTGTGACAACAAAGAGTTATACGTGCCAACTAATAAGT
ATTTCCATGAAAAAATAGAGTCAGTATTATTTCCATGATAAACTCAGTTTGATATTATGGTAGGTG
TATGAGTTGAAAAATGTTCTTTCAAATCGTATTTGTGGTGTAATATATCTAAGATATTATGATTATGATG
AGTGTAGGAGCTGGAAAATGTTCCTTCTATGTATTTTTTTAATTCAAATAAAGACGAAATTGAATAAAAA
TTATCTTGTTGCAAAAAAAAAAAAAAAAA SEQ ID NO: 71

*Perilla frutescens* crispa FS2
>AB045592.1 *Perilla frutescens* var. crispa PFSII3 mRNA for flavone synthase
II, complete cds
TGTCGACGGAGCAAGTGGAAATGGCACTGTACGCCGCCCTCTTCCTCCTGTCCGCCGCCGTGGTCCGCTC
CGTTCTGGATCGAAAACGCGGGCGGCCGCCCTACCCTCCCGGGCCGTTCCCTCTTCCCATCATCGGCCAC
TTACACCTCCTCGGGCCGAGACTCCACCAAACCTTCCACGATCTGTCCCAACGGTACGGGCCCTTAATGC
AGCTCCGCCTCGGGTCCATCCGCTGCGTCATTGCTGCCTCGCCGGAGCTCGCCAAGGAATGCCTCAAGAC
ACACGAGCTCGTCTTCTCCTCCCGCAAACACTCCACCGGCCATTGATATCGTCACCTACGATTCATCCTTC
GCTTTCTCTCCCTACGGGCCTTACTGGAAATTCATCAAGAAATTTATGCACCTACGGAGCTGCTCGGGCC
GAAATCTCGCCCACTTTCAGCCCATCAGGACTCTCGAAGTCAAGTCTTTCCTCCAAATTCTTATGCGCAA
GGGTGAATCGGGGGAGAGCTTCAACGTGACTGAGGAGCTCGTGAAGCTGACGAGCAACGTCATATCGCAT
ATGATGCTGAGCATACGGTGTTCAGAGACGGAGTCGGAGGCGGAGGCGGCGAGGACGGTGATTCGGGAGG
TCACGCAGATATTTGGGGAGTTCGACGTCTCCGACATCATATGGCTTTGTAAGAACTTCGATTTCCAAGG
TATAAGGAAGCGGTCCGAGGATATCCAGAGGAGATATGATGCTCTGCTGGAGAAGATCATCACCGACAGA
GAGAAGCAGAGGCGGACCCACGGCGGCGGTGGCGGCGGCGGGGAAGCCAAGGATTTTCTTGACATGTTCC
TCGACATAATGGAGAGCGGGAAAGCCGAAGTTAAATTCACGAGGGAGCATCTCAAAGCTTTGATTCTGGA
TTTCTTCACCGCCGGCACCGACACGACGGCGATCGTGTGTGAATGGGCACTACCCGACGGCGTTCAGCCGGAGA
GGTTTCTGGAGAAGGAAAAGGCCGCCATCGATGTTAAAGGGCAGCATTTTGAGCTGCTACCGTTCGGAAC
GGGCAGGAGAGGCTGCCCAGGGATGCTTTTAGCCATTCAGGAGGTGGTCATCATAATTGGGACGATGATT
CAATGCTTCGATTGGAAGCTGCCCGACGGCTCCGGCCATGTTGATATGGCAGAACGGCCAGGGCTCACGG
CACCGCGAGAGACCGATTTGTTTTGCCGTGTGGTGCCGCGAGTTGATCCGTTGGTTGTTTCCACCCAGTG
ATCACCCCCTTTAAATTTATTAATGATATATTTTTATTTTGAGAAAAAATAAAAATGCTAATTGTTTTGT
TTCATGATGTAATTGTTAATTAGTTTCTATTGTGCGCTGTCGCGTGTCGCGTGGCTTAAGATAAGATTGT
ATCATTGGTACCTAGGATGTATTTTCATTTTCAATAAATTATTTTGTGCTGTGTATATTAAAAAAAAAAA
AGAAAAAAAAAAAAAAAAAA SEQ ID NO: 72

*Gerbera* x *hybrida* FS2
>AF156976.1 Gerbera hybrida flavone synthase II (CYP93B2) mRNA, complete
cds
ATGTCCTAACACAACCCAACACCATGAATACACTCCAACTCATCTTCCTCCTCTTCTTCTTCCCAACCTT
ACTCTTCCTCTACTGTCTCCCCTACAAAAGAAACCAAAACCACCGCCGTCTTCCGCCGTCCCCGCCATCT
TTTCCGATCATCGGCCACCTCCACCATCTCGGCCCACTCATCCACCAATCCTTCCACGCTCTCTCCACTC
GCTACGGCTCTCTAATCCACCTCCGTCTCGGCTCAGTCCCATGCGTCGTCGTTTCAACCCCCAGACCTCGC
CAAAGACTTCCTCAAAACAAACGAACTCGCGTTCTCATCAAGAAAACACTCCTTAGCCATCGACCACATC
ACCTATGGCGTAGCATTTGCATTCGCACCATATGGAACTTACTGGAGTTCATCAAGAAACTCTTCACAG
TGGAGCTTTTGGGCACCCAGAATCTCAGCCATTTCCTACCCATTCGAACCCATGAAATTCGCGAGCTTCT
TCGAACGTTAATGGTGAAATCTAGGGCAAGGAGAGAGTAAACTTGACGGAAGAGTTGTTGAAGTTGACC
AACAATGTGATAAGTCAAATGATGATGAGCATTAGGTGTTCGGGGACGAATAGTGAGGCTGATGAAGCAA
AGAATCTTGTTCGGAAGTGACCAAAATTTTTGGACAGTTTAATGTTTCAGATTTCATATGGTTTTGTAA
GAACATAGATTTGCAAGGGTTTAAGAAGAGGTACGAGGGTACACATAGAAGATATGATGCTTTGCTTGAA
AGGATTATAATGGGGAGGGAAGAAAATAGAAGAAGAGGGAAGATAAAAGATGGTGAAGGGAAAGATTTTC

APPENDIX OF SEQUENCES

TTGATATGTTACTTGATGTTTTGGAGGATGGTAAGGCAGAGATTAAAATTACTAGAGACCACATCAAAGC
CTTGATTTTGGACTTTCTTACAGCTGGGACGGATACCACCGCGATTGCAATTGAATGGGCACTAGTCGAA
TTGATAAACAACCCGAACGCTCTCGAGAAAGCAAGACAAGAGATTGATCAGGTCATCGGTGATGAGAGGC
TAGTTCAAGAATCAGACACGCCTAACCTCCCTTATATCCAAGCTATCATAAAGGAAGCCCTACGACTTCA
CCCACCAATCCCAATGTTGATTCGCAAGTCAACAGAAAATGTAATTGTTCAGGGGTATGACATCCCAGCC
GGCACCTTGTTGTTTGTCAATATTTGGTCCATTGGAAGAAACCCTCAATGTTGGGAAACCCCTTTAGAGT
TCAAGCCTCATCGGTTTTTGGATGGTGGTGACCTTAAAAGCTCTTTAGATATTAAAGGCCACAATTTTCA
ACTATTGCCTTTTGGGACGGGGAGGAGAGGGTGTCCTGGTGTTAATTTGGCCATGAGAGAACTCTCAGTG
GTGATTGCAAACCTCATACAATGCTTTGATTGGGATGTTGTAGGTAACGACTATTGAATACAGATGAAC
GTGCTGGATTGACGGCTCCAAGGGCGGTAGATTTTGTGTGTGTTCCATTGGAACGAGGAAACACTTTGAA
GATTCTTGGTTCAAACTAAATTTATTTGTTGTTGCTTTCTTGATGGCAGTCGGTCTATCTATAGGTCATA
ATACCTTGGGACTCACGTGTTTGAATCTTAATACGCTTTTAGTACATTGCTTATCGTATATCTTGGGTAT
GCATGAAAAAAAAAAAA SEQ ID NO: 73

*Gentiana triflora* FS2
>AB193314.1 *Gentiana triflora* GtFSII mRNA for flavone synthase II, complete cds
ACCTCACAGTATATCATAATGATGCTTCTTGACTTTTTTTACTCTGCTTCCATTTTCGTCCTCTCAATCC
TCCTCTTCCGTGCAATCTACACCACCAAAAACCGCCGTCTCCGCCTCCCGCCGAGCCCATTCGGGTTACC
AATCATCGGCCATCTCCACCTCCTCGGCCCCAAAATCCACCATTCTTTCCACAACCTCTACAAACGCTAC
GGCCCAATATTCCATCTTCGTCTCGGATCTAATCGTTGTATTGTAGTCTCCACCCCTGAACTAGCTAAAG
AATTCCTCAAAACCCATGAACTCGATTTCGCTTACCGGAAAAACAGCTCCGCCATTAGTCTTTTAACTTA
CCATGTTTCTTTCGCTTTTGCACCTTATGGTCCCTACTGGAAATACATCAAGAAAATCACTACTTACCAG
CTACTGGGTAACCGGAATCTCACCCATTTCGAACCAATTCGAAGACTGGAAACGAATCGGGTTCTTTACG
ATTTGATGGTGAGTTCTAAACATGGCAAATCAGTGAATTTAACAGAGGAGATGATAAAATTGACGAGCA
CATCATTTCACAGATGATGTTAAGTATCCGATGTTCAGATACAGAGTCCGGAGCTACGAATGTACGGAAC
GTTATCCGGGATGTGACTGAACTGTTCGGAGAGTTCGATGTTTCGGATATAATATGGTTTTGTAAGAACA
CTGATTTGCAAGGGATTAAAAAGAGGGCTAACGGTATACATGAAAGGTACGATGCTTTGTTGGAGAAGAT
CATTTCGGACAGAGAAAGAACCAGAATTGTTGAGAAGAAGAACAGCGGTGCTGGCGGTGGAAGCGGCGAC
GGTGAGAGGAATGATTTTCTTGATATTCTGATGGATGCAATGGAAGATGACACGTCGGAAGTCAAGTTAT
CCAGAAATCATATCAAAGCTATAATCTTGGACTTCCTAACAGCTGCAACAGATACAACAGCCATATCACT
AGAATGGGCATTGTCTGAGCTCATTAACAATCCAAGGGTCCTAAAGAAAGCACAAGAAGAAATCAACAAT
GTGGTTGGAAATCAACGGCTAGTAAAAGAGTTAGACACTCCTAATTTCCCCTACATTAAGGCAATAATTA
AAGAAACATTTCGTCTTCACCCACCCATCCCGATGGTCATTCGAAAATCAGCTAACGACATCCAAGTGGC
TGGATATGACGTACCAAAAAATACGATGCTTTTCGTGAACATTTGGTCTATTGGAAGGAATCCCAGTTAC
TGGGAGAAGGCGTCGGAGTTTTCCCCGGAGAGATTTTTGGCTGATACAGATGGTGGCGGTTTGAGTCACA
TGGATATAAACGGGCAGTATTTCGAGCTTATGCCGTTTGGTACTGGAAGGAGAGGTTGTCCTGGGATGCC
GTTAGCCATGCAAGAATTACCAACTGTTCTTTCGCTTATGATACAATGTTTCGATTATATTCCGCTTGAT
TTCAAGGGAGAAAAGGCTGAAAGGGTTATGGACATGAGTGAACGGCCAGGACTGACTGCTCCGAGGGCGA
ATGAGTTGATGTGTTGCTTAAACCGCGAATTGATCTTCCAAATCTCCTTGGTAATGTAAAGGGTGAGTA
GATGACATTTGTGAGGATGTGTTTTTAACTAGTCGATAATTATTTATCGACTAATAATGTGATTTAAGAG
AAGTATGGGGACCAACTTTTAGTTGTTTCAATTTGTCCAAGGGTGTGAATGTAATAAGATATAAGTTGCA
TGTTCATCTTTCTTGTATCCGAGTTATTTTGATCTTAATGAATTCTCTATTTAATTATAAAAAPAAAPd
AAAAAAAAAAAAAAAA SEQ ID NO: 74

*Antirrhinum majus* FS2
>AB028151.1 *Antirrhinum majus* AFNS2 mRNA for cytochrome P450, complete cds
GCTTTACACACACACACACACACACACACAAACAAAAATGTCTACACTTGTCTACAGCACACTCTTCA
TCCTCTCAACCCTCCTCCTCACCCCTCCTAACCCGCACCCGCCGCAAGACCCGCCCGCCCGGCCCATTAGC
CCTCCCCTTAATAGGCCACTTACACCTCCTCGGCCCAAAGCTCCACCACACCTTCCACCAATTCTCCCAA
CGCTACGGCCCGCTCATCCAGCTCTACCTCGGCTCCGTCCCATGCGTCGTCGCTTCCACGCCCGAACTCG
CCCGCGAATTCCTCAAGACGCACGAACTCGACTTCTCGTCCCGCAAGCACTCCACCGCCATCGACATCGT
CACGTACGACTCCTCGTTCGCCTTCGCGCCGTACGGGCCGTACTGGAAATTCATCAAGAAATTATGTACT
TACGAGCTACTGGGTGCCCGGAACTTGAGCCATTTCCAGCCCATTAGAGCTTTGGAGGTCAACAGTTTCT
TGAGAATTTTGTACGAGAAAACAGAGCAGAAACAGAGTGTTAATGTGACTGAGGAGCTTGTGAAGCTGAC
GAGTAATGTGATCAGTAACATGATGTTGGGGATCAGGTGTTCGGGGACGGAAGGGGAGGCGGAGGTGGCG
AGGACGGTGATAAGGGAGGTGACGCAGATATTTGGGGAGTTTGGATGTGTCGGAGATTGTTTGGTTTTGTA
AGAATTTGGATCTGCAGGGGATTAGGAAGAGGTCGGAGGATATTAGGAGGAGGTATGATGCTTTGTTGGA
GAAGATTATTAGTGATAGGGAGAGGTTGAGGTTGAGGGGGGGTGGTGGTGGAGGGGGTGGAGAGGTGAAG
GATTTTTTGGATATGTTGTTGGATGTGATGGAGAGTGAGAAATCGGAGGTGGAGTTTACGAGGGAGCATC
TCAAAGCTTTGATTCTGGATTTCTTCACTGCCGGTACAGACACAACAGCAATCACAACAGAATGGGCAAT
AGCAGAACTCATTAGCAATCCAAATGTACTCAAAAAAGCTCAAGAAGAGATGGACAAAGTCATAGGATCA
CAAAGGTTGTTGCAAGAATCCGACGCCCCTAACTTGCCTTACCTCAACGCGATCATAAAAGAAACGTTCC
GTCTCCACCCTCCAATCCCCATGCTCACTAGAAAATCAATTTCTGACGTTGTGGTCAACGGGTACACGAT
CCCTGCCAAAACGCTATTGTTTGTCAACCTTTGGTCCATGGGAAGGAATCCTAACTACTGGGAAAATCCG
ATGGAGTTCCGACCCGAGAGGTTTCTCGAGAAAGGGACCGGGTCGATAGACGTTAAAGGGCACGATTTCG
AGTTGCTGCCGTTTGGCACGGGCAGGCGGGCTGCCGGGGATGTTGTTAGGCATGCAGGAGTTGTTTAG
TATTATCGGGGCTATGGTGCAGTGCTTCGATTGGAAACTGCCCGATGGTGTGAAGTCGGTCGACATGACC
GAGCGGCCCGGGTTGACGGCTCCACGTGCCAATGATTTGGTGTGCCAATTGGTGCCACGGATTGACCCGG
TCGTTGTCTCCGGACCGTGAACCTTAAGGTAGTATCGATAATGTCTTTAATTAAATTGTTATTTGTTGTG
AGGATTTGATTTTTGTTATGTATGATTATGCGTGGATTAAGATAAGCCTGCAAGGACAAATTCCCTTTCT
TTGATTGATGTCAATGAGTTTGTGTC SEQ ID NO: 75

*Theobroma cacao* FS2
>XM_007020125.2 PREDICTED: *Theobroma cacao* licodione synthase (LOC18593084), mRNA
AATCCTGTGGGTTGAGAAAATTTGTCACCAAAACTCTCTCTTTCAGTCTGAGTTGAGGTAGCCATGTTGC
TTCAACTCCTGTCGTATTCCACCCTCTACATTGCTTCGTTTTTTCTTGTGAAAACAATATTAATCTCCAT

APPENDIX OF SEQUENCES

```
CAACAACCGTCCCAAGCTTCCCCCAGGCCCCATTGCCTTACCAGTCATCGGCCACCTCCACCTCCTTGGC
CCCTTCATTCATCAAACTTTCCACAAGTTCTCCTCCCGCTATGGTCCCTTAATGTATCTCCGTCTTGGCT
CTATTGGGTGCGTCGTGGCCTCTAACCCAGAGCTTGCAAAAGAGCTTCTCAAAACTTACGAGCTGGCATT
CGCCGCCCGCATGCACACCGCTGCCATTACCCACCTTACATACGACTCTTCCTTTGCCTTTGCACCCTAC
GGACCTTACTGGAAATTCATAAAAAAGTTTAGCACCTATGAGCTCCTAGGTAACCGAACTCTTAGCCAGT
TTCTTCCCGTTCGGACCAAGGAATTGCACTGTTTCATTAAGTTTCTTCTTGACAGGTCTAAAGCAGGCGA
AAGCGTGAATGTAACTCAAGAGCTGTTGAAATTAACCAACAACACAATATCACAGATGATGCTGAGCATG
AGGTGCTCGGGGAGTGGAAACCCCGCCGATGGGGTTCGAGCTCTAGTGAGGGAGGTGACTGAGATCTTCG
GAGAGTTCAACATCTCAGACAGTATATGGTTTTGCAAAAACTGGGATCTGCAGGGATTCCGAAGGAGATT
TGAGGACATACATAGAAGGTATGACGCTTTGTTGGAGAGAATCATAAGAGATCGCGAGGAAGTAAGAAAA
AGCAAGGAAAGAGTGTGACCAACGAGACAATGGAAATGAGGTCAAGGATTTTCTGGACATGATGCTTGATG
TATTGGAAAATGATAACTCGGAGATCCAATTAACCAGAAATCACATTAAGGCCTTGGTTTTGGATTTCTT
GACAGCCGGTACGGATACAACAGCAATTGTACTTGAATGGGCACTGGCAGAGCTCATCAACAACCCGGAA
GTGCTAAAACTAGCTCAAAAGAGATTGATCAAGTTGTGGGAACAAGCAGGTTGGTAGAAGAATCGGACA
GTCCTCGTCTCCAATACATCCAAGCCATCATTAAGGAAACTTTTCGGCTCCACCCACCGGTCCCGATGAT
CAGCAGAAAATCAATCCAATCATGCAAAATTAAGGGATACACCATCCCTGCCGACTGTTTGGTGTTCGTA
AACATTTGGGCTATAGGAAGGGATCCCACGGTCTGGGCAGATCCATTGAGGTTTCAGCCTGAGAGGTTCC
TGAAATCCTATGAGGGAGATCATAGTTCAGGGCCTATAGATGTTAGAGGCCTCCATTATCAGCTGTTGCC
TTTCGGTACAGGGAGGAGGGGCTGCCCTGGTGCTTCTTTAGCAATGCAGGAGCTGCCCACCACTCTGGCA
GCCATGATTCAGTGCTTTGACTGGAAGCCTGCGGCTACTTCAAAGACTGGAGATGGTGTTGACATGTCTG
AACGGCCTGGACTTACGGCTCCCAGGGCAAAGGATCTGGAGTGTGTTCCAGTTGCACGCTTCACACCCAG
TCTTTGCAACTTAAGCAGGTGACCACTTACGTATGATGTGATGAGCAATCGAGCATCAGTCTCCCCCGTT
CTCCCGATTTCCTAGGCTCTGTGTCTTTAGCGTGTTACGAGTGATGTGACTGTGATGGCATGCATTTAGG
TAGAAATAAATGCAATTATATTGCATATTTGCTTGCCAAAAACAAAATAAAAAAAATGTATTAATAGTTT
ATGAATTTTTCTGTTTGGTTTATTTC  SEQ ID NO: 76
```

*Camellia sinensis* FS2
>KF750635.1 *Camellia sinensis* flavone synthase II (FNSII) mRNA, complete cds
```
TTTTCCTTTCCTAGTTTCTATTTAAAGCAACATATAATTTCTCGAATGCATAATTTCTCTTGAAATCAAG
CCAAGATGTTTGACTTAATCTCCATTGCCACCTTATTCTTTGTTATTATCTCCACCACCATCCTCCTCCT
CTCCATAAACCACTTCAAAAAACCACCACATCTCCGCCGCCGTCTCAGCCTCCCACCAACCCCCTTCGCC
CTGCCAATCATCGGCCACCTCCACCTCCTCGGCCCCATCATCCACCGCTCCTTCCATGACCTCTCCTCCC
GCTACGGCCCCTTGTTTCACCTCCGCCTCGGCTCAGTCCATGCTTCGTGGTCTCCACTCCAGAGCTCGC
AAAAGAGTTCCTCTTGACACATGAGCTCAAGTTCTCATCTCGCAGGGATTCCATCGCCATCCAACGCCTC
ACCTATGACTCTGCATTCGCCTTCGCCCCTTACGGTCCCTACTGGAAATTCCTAAAGAAGCTTTGTACTT
GTGATCTTCTCGGCGCTCGTAGTATCAATCATTTTCTTCCCACACGGACCCGTGAACTACACTGCTTTGT
TCGACTTCTCATCGACAAGGCCGTGGCTTGTGAACCTGTCAACATCACTAAAGAGCTTTCAACGCTCGCC
AACAATATCATCTCTCAAATGATGATTGGTGTAAGGTGTTCGGGGACGACAGGAGAGGCTGAGGAGGCTA
CAACTCTTGCCCGCGAGGTGACGAAGATATTCGGAGAGTTTAATGTGTCGGATTTTATGTGGGTTATCAG
GAACTTTGATTTGCAGGGGTTTAGGAAGAGAGTTGAGGATATATACACAAGGTATGATGCGTTGCTGGAA
AGGATTATCACAAACAGGGAAGAAGTCAGAGAAAAGAACGTACAAGAAAGAAAATTGGGTGTTGGAGAAG
GTCATCACGTCAAGGATTTTCTTGATCTATTGCTTGATGTTTTGGAAGAGGACCATTCGGAGATTAACTT
CAGTAGAGATAACATTAAGGGCTTGATTTTGGATTTCTTCACCGCAGGAACAGATACATCATCTATTGCA
ATTGAATGGGCATTAGCAGAGCTGATCAACAATCCAAGAGTGCTCCAAAAAGCACAAGAGGAGATTGATA
ATGTGGTTGGGAAACATCGGTTAGTAAGCGAATCACACGGTCCAAATCTTCCATACATCCAAGCCATCAT
AAGGGAAGCACTTCGGCTTCACCCTCCAGTCCCCTTGATCACAAGAAATCAATAGAGGACTGCATGATC
CAAGGATACAACATCCCAGCCAACTCCATGCTATTTGTGAATGTTTGGTCTCTTGCTAGAAATCCCAAGT
ATTGGGATAGCCCACTGGACTTCTTGCCTGAGCGATTCTTAAGGCCCGAAAAGGGTGGCCCAGTGGGCCC
AACAGATGTTAAGGGCCAACATTTCCAGCTATTACCCTTTGGTACTGGGAGGAGAGGCTGCCCTGGTACT
TCTTTGGCCATGCAAGAGCTGCCTGCTATGCTAGCAGCAATGATTCAGTGTTTCGAGTGGAAGGTTGTGA
ATCAGAGTGGGGATGTGATGAACGGTGATGGAGCGCTTGATATGACTGAACAACCCGGGATGACAGCTCC
GAGGGCCCATGATCTTGTGTGCATGCCGATACCACGAATCGATCAACTTTATGCCCTTCTTGATCCATAG
TTTATGCTAAGGCAAGGATTCTCAGTAGTTAAAATTTTTGTGCCCAATAAATTTCTAATCGCATGATTTT
GTCGTCAATAAAAGTTGTGAAATACAATCATACGATTAAGAAGGCAATATGAATAAGGGATAAAGATTTT
GGAATAGAGGATCTGTACCTTTGTGCTATGATTTGCCCAATATTGCTCTCTTTAACCTATTTTTAGAAAA
AAAAAAAAAAAAAAAA  SEQ ID NO: 77
```

*Plectranthus barbatus* FS2
>KF606861.1 *Plectranthus barbatus* voucher RRLH: 22176 clone 2L flavone synthase (FNS) mRNA, complete cds
```
ATGGACCATGTCGAAGCCGCTCTCTTCGCCGCCATCTTCCTCCTCTCCGCCGCCCTCCTCAACCACCTTC
TCACCGGAAAACGCCGCCAGAACGCTTACCCTCCCGGCCCGTTCCCTCTTCCCATCATCGGCCACTTACA
CCTTCTCGGGCCGAGACTCCACCACACCTTCCACGATCTGACCCAACGGTATGGGCCCTTGATGCAGGTC
CGCCTCGGCTCCATCCGCTGTGTCATCGCCGCCACGCCGGAGCTGGCAAAGGAATTCCTCAAGACGAGCG
AGCTCGTCTTCTCCGCTCGGAAGCACTCAACCGCCATTGATATCGTCACCTACGAATCCTCCTTCGCTTT
CTCCCCCTACGCCCCTACTGGAAATACATCAAGAAATTATGCACCTACGAGCTGCTCGGGGCCAGGAAT
CTCAACCACTTTCTCCCGATTCGAACGATTGAAGTCAAGACTTTCTTAGAAGCTCTCATGCAAAAGGGTA
AAACGGGGGAGAGGTTGAACGTGACGGAGGAGCTGGTGAAGCTGACGAGCAACGTGATATCGCAGATGAT
GCTGAGCATACGGTGCTCGGGGACGGAGGGGGAGACGGAGGCGGTGAAGAACTGTGATTCGGGAGGTGACG
CAGATATTTGGGGAGTTCGACGTTGCAGACATTATTTGGTTTTGCAAGAACTTCGATTTCCAAGGGATAA
GGAAGAGGTCGGAGGATATACAGAGGAGGTATGATGCTTTGCTGGAAGATCATCACCGACCGGGAGAA
GCAGCGGCGGACGCAGCACGGCGGCGAGGCCAAGGATTTTCTGGACATGTTTCTGGATATAATGAAGAGT
GGGAAAGCTGAAGTCAATTTCACCAGGGACCATCTCAAGGCTCTCATTCTGGATTTCTTCACCGCCGGCA
CCGACACTACGGCCATTGTCGTCGGATGGGCGATAGCAGAGCTCATCAACAACCCTAATGTGCTGAAGAA
AGCTCAAGCCGAGATCGATAAAGTCGTCGGACTCCACAGAATCCTGCAAGAATCCGACGGTCCAAATCTG
```

```
CCCTACCTTAACGCCGTCATCAAAGAAACATTCCGGCTTCATCCTCCCATCCCCATGCTGTCGAGGAAAT
CAATCTCCGACTGCGTGATCGACGGCTACACGATACCGGCCAACACACTGCTGTTCGTCAACATCTGGTC
CATGGGGCGGAACCCTAAAATCTGGGACAACCCGATGGCGTTCCGGCCGGAGAGGTTTCTGGAGAAGGAA
AAAACCGGCATCGACATTAAAGGGCAGCATTTCGAGCTTCTGCCGTTTGGCACGGGCAGGAGGGGCTGCC
CCGGGATGCTGCTCGCCATTCGGGAGGTGGTCGTTATAATTGGGACCGTGATTCAGTGCTTTGACTGGAA
GCTTCCCGTCGACGATGTCTCCGGCCTTGTGGACATGACGGAGCGGCCGGGGCTCACGGCGCCGAGAGCT
GACGATTTGATTTGTCGTGGTGCCGCGAGTTGATCCTTTGGTTGTTTCCGGCCATTGA SEQ ID NO: 78

Lonicera japonica FS2
>KU127576.1 Lonicera japonica flavone synthase II (FNSII-1.1) mRNA,
complete cds
ATGTGGATCTTTGACCTCACAATCTCGTTCACCACACTCCTCTTCCTCATCTTCACCACCGCCCTCCTAC
TCCTCCTCAAGGTTTTCAAGAAAAACCACAAACTCCGACCGCCGCCTAGCCCCTTCACCCTACCGATAAT
CGGCCACCTCCACCTCCTCGGCCCCCTCATCCACCAGTCCTTCCATCGCCTCTCCACCCTCTATGGCCCC
TTAATCCAGCTCAAAATCGGCTACATCCCATGCGTTGTTGCCTCAACTCCCGAGCTAGCAAAAGAATTTT
TAAAAACACACGAACTCGCGTTCTCCTCGCGTAAACACTCCGCTGCCATTAAACTCCTCACCTACGATGT
ATCATTTGCTTTTTCACCCTACGGTCCCTATTGGAAATTCATCAAAAAAACATGCACCTTTGAACTTTTG
GGCACACGTAACATGAACCACTTTCTCCCCATTAGGACCAACGAGATTCGTCGTTTCTTACAAGTGATGT
TAGAAAAAGCCAAGGCTAGTGAGGGGGTGAACGTGACTGAAGAGTTGATCAAGCTCACGAACAACGTTAT
CTCTCAAATGATGTTTAGTACTCGGAGCTCGGGGACCGAGGGGGAGATGAGGACATTGGTA
CGTGAGGTGACTCAAATATTCGGAGAATTTAATGTTTCGGATTTTATAAAGTTGTGTAAGAACATTGATA
TTGGAGGGTTTAAGAAGAGAAGTAAGGATATACAAAAAAGGTATGATGCTTTGTTGGAGAAGATAATAAG
TGAGAGGGAGAGTGAAAGAGCAAGAAGGGGTAAAAATAGAGAGACTTTAGGGGAGGAAGGAGGGAAAGAT
TTTCTTGATATGATGCTTGATACTATGGAGGATGGCAAGTGTGAAGTTGAGATAACAAGAGATCACATTA
AGGCCTTGGTTTTGGATTTCTTAACTGCGGCCACGGATACAACTGCGATTGCTGTTGAATGGACATTAGC
CGAGCTTATCAGCAACCCGGAAGTGTTCGATAAAGCTCGAGAGGAGATCGATAAAGTCGTAGGGAAGCAC
AGGCTAGTCACAGAATTGGACACGCCAAATCTTCCCTACATCCACGCGATCATAAAGGAAAGTTTTCGGC
TTCACCCGCCAATTCCTCTGCTCATAAGAAAATCAGTCCAAGATTGCACGGTAGGTGGCTACCACATCTC
GGCTAACACCATACTTTTTGTCAATATTTGGGCCATCGGGCGAAATCCCAAGTATTGGGAAAGCCCAATG
AAGTTCTGGCCCGAAAGATTTCTTGAATCCAATGGGCCAGGTCCAGTGGGCTCTATGGATATTAAGGGCC
ATCATTATGAGCTTTTGCCTTTTGGGAGTGGGAGAAGGGGTTGCCCCGGGATGGCTTTAGCCATGCAAGA
ACTGCCCGTGGTGCTCGCCGCCATGATACAATGCTTTAATTGGAAGCCGGTGACATTGGACGGAGAGGAA
CTGGATATGAGTGAGCGGCCTGGTCTAACTGCTCCAAGAGCCCACGATCTTGTATGCGTTCCCTCCGCTC
GAATTAATTCTTTCGATAATTTTTAA SEQ ID NO: 79

Medicago truncatula FS2
>XP_013456065.1 cytochrome P450 family flavone synthase [Medicago
truncatula]
MISQPILLALILFLLFLLQLFLFKRNNRAKEHLPYPPSPLAIPIIGHLHLLKPLVHQAFRDLSDRYGPLI
SLRLGSVPFIVVSSPSLAKEFLKTNELVYSSRKMNIAINTVVYDDATFAFAPYGAYWKFIKKLSTFELLG
NRTIGQFLPIRTRELNEFIQTLENKSKVEESVNLTQALLKLSNNIISRMMLSIESSGTDSQAEQARTLV
DVTQIFGEFNISDFIGFCKNLDFQGLKKRALDIHKRYDAFLEKLICDREESRRKAKVEGGCEDRDEKVKD
FLDMLLDVFEAKECEVDFTRNHIKSLILDYFTAATDTTAISLEWTIAELFNNPIVLKKAQEEVERIIGKE
RLVCEADIPNLPYIQAIIKETLRLHPPLPMIARKGTKDCVVDGKMIKKGSIVCVNIWAIGRDSKTWKNPL
EFRPERFLESGKESEIDIKGHDFELLPFGSGRRGCPGMPLAMRELPTVIGALVQCFEWKMLDSEGKLLDQ
GKTIDMDERPGLTAPRANDLFCIPVARLNLIPLVQL SEQ ID NO: 80

Lotus japonicus FS2
>BAF64284.1 2-hydroxyisoflavanone synthase [Lotus japonicus]
MLVELALALLLAIALFLHLRPTPTAKSKALRHLPNPPSPKPRLPFVGHLHLLDDQPLLHHSLIKLGERYGPL
YSLYFGSMPTVVASTPELFKLFLQTHEASSFNTRFQTSAIRRLTYDNSVAMVPFAPYWKFIRKIIMNDLL
NATTVNKLRPLRSQEIRKVLKAMAHSAESQQPLNVTEELLKWTNNTISRMMLGEAEEVRDIAREVLKIFG
EYSLTDFIWPLKKLKVGQYEKRIDEIFNKFDPVIEKVIKKRQEIIKRRKERDGELEEGEQSVVFLDTLLE
FAEDETMEIKITKEQIKGLVVDFFSAGTDSTAVATDWALSELINNPRVLKKAREEVESVVGKDRLVDEAD
IQNLPYIRAIVKETFRMHPPLPVVKRKCVQECELNGYVIPEGALILFNVWAVQRDPKYWEGPSEFRPERF
LTAEGGATSIDLRGQNFELLPFGSGRRMCPGVNLATAGMATLLASVIQCFDLQVVGQKGKLLKGSDAKVS
MEESPGLTVPRAHNLMCVPLARTNVTSELLSS SEQ ID NO: 81

Glycine max FS2
>ACV65037.1 flavone synthase II [Glycine max]
MISESLLVVFLIVFISASLLKLLFVRENKPKAHLKNPPSPPAIPIIGHLHLLKPLIHRSFRDLSLRYGPL
LSLRIGSVKFIVASTPSLAQEFLKTNELTYSSRKMNMAINMVTYHNATFAFAPYDTYWKFMKKLSTTELL
GNKTLGHFLPIRTREVHDIIQFLFHKSKAQESVNLTEALLSLSNNVISQMMLSIKSSGTDSQAEQARTLV
REVTQIFGEFNVSDFLGFCKNLDLQGFRKRALDIHKRYDALLEKIISDREELRRKSKVDGCEDGDDEKVK
DPLDILLDVAEQKECEVQLTRNHVKSLILDYFTAATDTTAISVEWTIAELFNNPKVLKKAQEEVDRVTGN
TQLVCEADIPNLPYIHAIIKETMRLHPPIPMIMRKGIEDCVVNGNMIPKGSIVCVNIWAMGRDPNIWKNP
LEFKPERFLEGEGSAIDTKGHHFELLPFGSGRRGCPGMPLAMRELPTIIGALIQCFEWKMLGSQGEILDH
GRSLISMDERPGLTAPRANDLIGIPVARLNPTPFRQM SEQ ID NO: 82

Perilla frutescens crispa FS2
>BAB59004.1 flavone synthase II [Perilla frutescens var. crispa]
MALYAALFLLSAAVVRSVLDRKRGRPPYPPGPFPLPIIGHLHLLGPRLHQTFHDLSQRYGPLMQLRLGSI
RCVIAASPELAKECLKTHELVFSSRKHSTAIDIVTYDSSFAFSPYGPYWKFIKKLCTYELLGARNLAHFQ
PIRTLEVKSFLQILMRKGESGESFNVTEELVKLTSNVISHMMLSIRCSETESEAEAARTVIREVTQIFGE
FDVSDIIWLCKNFDFQGIRKRSEDIQRRYDALLEKIITDREKQRRTHGGGGGGGEAKDFLDMFLDIMESG
KAEVKFTREHLKALILDFFTAGTDTTAIVCEWAIAEVINNPNVLKKAQEEIANIVGFDRILQESDAPNLP
```

APPENDIX OF SEQUENCES

YLQALIKETFRLEPPIPMLARKSISDCVIDGYMIPANTLLFVNLWSMGRNPKIWDYPTAFQPERFLEKEK
AAIDVKGQHFELLPFGTGRRGCPGMLLAIQEVVIIIGTMIQCFDWKLPDGSGHVDMAERPGLTAPRETDL
FCRVVPRVDPLVVSTQ  SEQ ID NO: 83

Gerbera x hybrida FS2
>AAD39549.1 flavone synthase II [Gerbera hybrid cultivar]
MNTLQLIFLLFFFPTLLFLYCLPYKRNQNHRRLPPSPPSFPIIGHLHHLGPLIHQSFHALSTRYGSLIHL
RLGSVPCVVVSTPDLAKDFLKTNELAFSSRKHSLAIDHITYGVAFAFAPYGTYWKFIKKLFTVELLGTQN
LSHFLPIRTHEIRELLRTLMVKSRAKERVNLTEELLKLTNNVISQMMMSIRCSGTNSEADEAKNLVREVT
KIFGQFNVSDFIWFCKNIDLQGFKKRYEGTHRRYDALLERIIMGREENRRRGKIKDGEGKDFLDMLLDVL
EDGKAEIKITRDHIKALILDFLTAGTDTTAIAIEWALVELINNPNALEKARQEIDQVIGDERLVQESDTP
NLPYIQAIIKEALRLHPPIPMLIRKSTENVIVQGYDIPAGTLLFVNIWSIGRNPQCWETPLEFKPHRFLD
GGDLKSSLDIKGHNFQLLPFGTGRRGCPGVNLAMRELSVVIANLIQCFDWDVVGERLLNTDERAGLTAPR
AVDFVCVPLERGNTLKILGSN  SEQ ID NO: 84

Gentiana triflora FS2
>BAD91809.1 flavone synthase II [Gentiana triflora]
MMLLDFFYSASIFVLSILLFRAIYTTKNRRLRLPPSPFGLPIIGHLHLLGPKIHHSFHNLYKRYGPIFHL
RLGSNRCIVVSTPELAKEFLKTHELDFAYRKNSSAISLLTYHVSFAFAPYGPYWKYIKKITTYQLLGNRN
LTHFEPIRRLETNRVLYDLMVSSKHGKSVNLTEEMIKLTSNIISQMMLSIRCSDTESGATNVRNVIRDVT
ELFGEFDVSDIIWFCKNIDLQGIKKRANGIHERYDALLEKIISDRERTRIVEKKNSGAGGGSGDGERNDF
LDILMDAMEDDTSEVKLSRNHIKAIILDFLTAAIDTTAISLEWALSELINNPRVLKKAQEEINNVVGNQR
LVKELDTPNFPYIKAIIKETFRLHPPIPMVIRKSANDIQVAGYDVPKNTMLFVNIWSIGRNPSYWEKASE
FSPERFLADTDGGGLSHMDINGQYFELMPFGTGRRGCPGMPLAMQELPTVLSLMIQCFDYIPLDFKGEKA
ERVMDMSERPGLTAPRANELMCLLKPRIDLPNLLGNVKGE  SEQ ID NO: 85

Antirrhinum majus FS2
>BAA84071.1 cytochrome P450 [Antirrhinum majus]
MSTLVYSTLFILSTLLLTLLTRTRRKTRPPGPLALPLIGHLHLLGPKLHHTFHQFSQRYGPLIQLYLGSV
PCVVASTPELAREFLKTHELDFSSRKHSTAIDIVTYDSSFAFAPYGPYWKFIKKLCTYELLGARNLSHFQ
PIRALEVNSFLRILYEKTEQKQSVNVTEELVKLISNVISNMMLGIRCSGTEGEAEVARTVIREVTQIFGE
FDVSEIVWFCKNLDLQGIRKRSEDIRRRYDALLEKIISDRERLRLRGGGGGGGGEVKFLDMLLDVMESE
KSEVEFTREHLKALILDFFTAGTDTTAITTEWAIAELISNPNVLKKAQEEMDKVIGSQRLLQESDAPNLP
YLNAIIKETFRLHPPIPMLIRKSISDVVVNGYTIPAKTLLFVNLWSMGRNPNYWENPMEFRPERFLEKGT
GSIDVKGQHFELLPFGTGRRGCPGMLLGMQELFSIIGAMVQCFDWKLPDGVKSVDMTERPGLTAPRANDL
VCQLVPRIDPVVVSGP  SEQ ID NO: 86

Theobroma cacao FS2
>EOY17412.1 Flavone synthase II, putative [Theobroma cacao]
MMLLQLLSYSTLYIASFFLVKTILISINNRPKLPPGPIALPVIGHLLHLLGPFIHQTFHKFSSRYGPLMYLR
LGSIGCVVASNPELAKELLKTYELAFAARMHTAAITHLTYDSSFAFAPYGPYWKFIKKFSTYELLGNRTL
SQFLPVRTKELHRFIKFLLDRSKAGESVNVTQELLKLINNTISQMMLSMRCSGSGNPADGVRALVREVTE
IFGEFNISDSIWFCKSWDLQGFRRRFEDIHRRYDALLERIIRDREEVRKSKKECDQRDNGNEVKDFLDMM
LDVLENDNSEMQLTRNHIKALVLDFLTAGTDTTAIVLEWALAELINNPEVLKLAQKEIDQVVGTSRLVEE
SDSPRLQYIQAIIKETFRLHPPVPMISRKSIQSCKIKGYTIPADCLVFVNIWAIGRDPTVWADPLRFQPE
RFLKSYEGDHSSGPIDVRGLHYQLLPFGTGRRGCPGASLAMQELPTTLAAMIQCFDWKPAATSKTGDGVD
MSERPGLTAPRAKDLECVPVARFTPTVFAT  SEQ ID NO: 87

Camellia sinensis FS2
>AHB32110.1 flavone synthase II [Camellia sinensis]
MFDLISIATLFFVIISTTILLLSINHFKKPPHLRRRLSLPPTPFALPIIGHLHLLGPIIHRSFHDLSSRY
GPLFHLRLGSVPCFVVSTPELAKEFLLTHELKFSSRRDSIAIQRLTYDSAFAFAPYGPYWKFLKKLCTCD
LLGARSINHFLPTRTRELHCFVRLLIDKAVACEPVNITKELSTLANNIISQMMIGVRCSGTTGEAEEATT
LAREVIKIFGEFNVSDFMWVIRNFDLQGFRKRVEDIYTRYDALLERIITNREEVREKNVQERKLGVGEGH
HVKDFLDLLLDVLEEDHSEINFSRDNIKGLILDFFTAGTDTSSIAIEWALAELINNPRVLQKAQEEIDNV
VGKHRLVSESHGPNLPYIQAIIREALRLHPPVPLITRKSIEDCMIQGYNIPANSMLFVNVWSLARNPKYW
DSPLDFLPERFLRPEKGGPVGPTDVKGQHFQLLPFGTGRRGCPGTSLAMQELPAMLAAMIQCFEWKVVNQ
SGDVMNGDGALDMTEQPGMTAPRAHDLVCMPIPRIDQLYALLDP  SEQ ID NO: 88

Plectranthus barbatus FS2
>AHJ89438.1 flavone synthase [Plectranthus barbatus]
MDHVEAALFAAIFLLSAALLNHLLTGKRRQNAYPPGPFPLPIIGHLHLLGPRLHHTFHDLTQRYGPLMQV
RLGSIRCVIAATPELAKEFLKTSELVFSARKHSTAIDIVTYESSFAFSPYGPYWKYIKKLCTYELLGARN
LNHFLPIRTIEVKTFLEALMQKGKTGERLNVTEELVKLTSNVISQMMLSIRCSGTEGETEAVRTVIREVT
QIFGEFDVADIIWFCKNFDFQGIRKRSEDIQRRYDALLEKIITDREKQRRIQHGGEAKDFLDMFLDIMKS
GKAEVNFTRDHLKALILDFFTAGTDTTAIVVGWAIAELINNPVLKKAQAEIDKVVGLHRILQESDGPNL
PYLNAVIKETFRLHPPIPMLSRKSISDCVIDGYTIPANTLLFVNIWSMGRNPKIWDNPMAFRPERFLEKE
KTGIDIKGQHFELLPFGTGRRGCPGMLLAIREVVVIIGTVIQCFDWKLPVDDVSGLVDMTERPGLTAPRA
DDLICRVVPRVDPLVVSGH  SEQ ID NO: 89

Lonicera japonica FS2
>AMQ91109.1 flavone synthase II [Lonicera japonica]
MWIFDLTISFTTLLFLIFTTALLLLLKVFKKNHKLRPPPSPFTLPIIGHLHLLGPLIHQSFHRLSTLYGP
LIQEKIGYIPCVVASTPELAKEFLKTHELAFSSRKHSAAIKLLTYDVSFAFSPYGPYWKFIKKICTFELL
GTRNMNHFLPIRTNEIRRFLQVMLEKAKASEGVNVTEELIKLTNNVISQMMFSTRSSGTEGEAEEMRTLV
REVTQIFGEFNVSDFIKLCKNIDIGGFKKRSKDIQKRYDALLEKIISERESERARRGKNRETLGEEGGKD
FLDMMLDTMEDGKCEVEITRDHIKALVLDFLTAATDTTAIAVEWTLAELISNPEVFDKAREEIDKVVGKH

APPENDIX OF SEQUENCES

RLVTELDTPNLPYIHAIIKESFRLHPPIPLLIRKSVQDCTVGGYHISANTILFVNIWAIGRNPKYWESPM
KFWPERFLESNGPGPVGSMDIKGHHYELLPFGSGRRGCPGMALAMQELPVVLAAMIQCFNWKPVTLDGEE
LDMSERPGLTAPRAHDLVCVPSARINSFDNF SEQ ID NO: 90

Promoter sequence for *Medicago truncatula* IPD3
CCTTTAATGACGGATAGTGGTACGGTATATCATTGAATACTTAAGATTCATCCCCTTGCGGGGCTTGCAGTATA
CTGCATTTTAGGCAAAAAAAAAATGATGTTGTAACAAACTCTGAAAATTTCAGGCTTATTGTGTGTAGGATGC
CGCGGCATTTTTATTTGTCTTTCAACTGTGATCCAGTAACGGAGAAATTTGTTGATTATTGTTATATTGATTGTT
CCTTTCTTATGTCTTAACTACTACAGAGTCTTTTTTTTAGTCGCACGACATTTGAACCTCAACTTTTCCAAGTA
GAGCCTGGTGTATCTGTATTAGGGGCATTACAATTGTCTTAGGATACGTTTGGATTGGTGGAGTGAAAAGTCG
CAAAAGCTGTGAAGTTTGACATGATGTCATAGCACCTATTGAGGAGTTAAACATCTCGAATTAAGTTGTGCCG
TCGGAAAACGCTCTTAGCGCAATATCTTCATTTCACTGTGAATGCACTAGCAGGTCGGAAAACGCTCTTAGCG
CAATATCTTCATTTCACTGTGAATGCACTAGCAGATGGCACGATGAACAACCTCTCATGAAGTCTCTGTTGGG
ATCTACTCATTGGGTAGAAATTCGAAATCAAAGCCATTGCTATAGTCCAGCAGAAACATATCAAATAGAGTTT
AAATAAGCTTAAAGATTCTGAGTGCATTTTGTTTCAGCTTTAAAAAAAATAGATTTTGAGTTAAAAAATCTCTA
GAGATTTTAAAAAAAATCTAAAGCTATTTCTATTTGTTTACTATCATAAAAAATCATTTTTCTAAGATTTAAAG
CTCTTACACTTGAGTTCTTTATGTTTAGAAAAAAAATAGATTTTGGAAAAGCTACTTGAAATAGCTTTTCATTT
TAAAGCTAAAAATGATTTTTTTAATAAAATGGATTTTTTTAAAATCTAAAACAAATACTAAAAAAATAAAAAA
AGTGATTTTTTTAGATCAAAAATAGATTTTTTTCAAAAAAATCCAAAACAATCGGGCCCTCTATGAAAACATG
AGAATTTAAGCTAACCAGAACTTAAACTTCGTTTAAAATTGTTGAAAATACTGATTATAAAAGAGATAAGGGA
TATAAATATTACACACAATAATTTATGTCCTCACCCCTATATTATTAAACATAAAATGTCAATAATGATAGGCA
CTGTTTTGTAGGTCAATCTTTGACTTGTCACCAAGAAATGAAATGCTGCCGACTCATCAAAGAAGGAGCCTTT
AATTTATTTGTTTTTTACTATAATATTGGGACACTACCGCTTAATAGTAGTAACTAATCTTAGTTGGAGAATTT
GAAAAACAAATAAGATGTGCTCTTCAATTTCAACCAAAAATTTTCTATATGCATGAGACAGAAATTAAAACTC
CGACCATATGTTTAAAAAGCCTAAATCTCTTGTCTGTTCAACCAATATATTTTTGATGGAGCCTCTAATTACTA
ATTAGTGATTAATCAAATATTAATTTTGAAACTCAACTCTCAGCCTATGTCACAGTGTGAAAAAAGCTAAAAA
GAGTAGCCTTGTCTTTTTTGTTGAAAATTTGGGAAACTTATTGCCGGATGAACCGAATATACCCTTTGAATGAT
AACGCCATTTCATGTTTTGACTCTAATATTCAAAACTCAAAAGTCCAAACTAATACATGTATTTTTTTATTAAA
AAAATAATATTAGCAATCAAAGTCTATTTCTTGTACTCCCTCCGGTCATATTTATAATCAAAAAATAATTTTTT
AGATACATTGAATAATTAACTAATGTATCTAACATATAAATGTGACCGGAAATATTAATTATTCGATGAACTT
AAAAAATTATTTTTTACTTATAAATGTGACCAGAATGTGTACTAATTATGCCTGCAATGATGCACATGTGAAG
ACATTATTATTAATGCTACTACTACTATTGTCATGATTTTTGAAAATATTTCTACAATCGTAGATGACCATTA
GCTTAAATAAATAAAGGTCCAGTTTATTTAGACTGGATTTTGTATGAGTTTTTTTTTTATCTAATAATTAGCCTA
ATTCTTTACTTCTAAAAATATTCTTATAAATATTTACAGGGAAATTAAAAATTAAATTAATCTTTTTTATGAAA
GAAAATTAAATTAATCATAAAATTCAAATATGTAGATTAATTTTGATTTACGCTAAAACCATTATATAAAGA
TACATAATCATTTCAAGTAAAAAAAGATACATAATCATATGGAGATTATCTTAATCATTTTTTTAAATACTTTT
CACCTCTACCTCAACGAGCAGCAGTTAAAACAGGGAAACTACTAATAAACTATCGTAATGATGTGACATGCAA
GATTTGTTTTAGCTGTTGGTTCAACTAGAAGCCAAGCCTTAAATCTTTTTTGCTTATTTAAATGCTACCTTATT
GTAATTGATATTAAAGGATACAAGTAGTTTTTATTTTTATTTTTTAAATATCATATCATTCACTTCAAAGTTAAA
AATTATTCTTTTGAAATATGAAGATCCGTTTAAAAAGCTAACATTTCTCAACAGACGCTCTTTCATATGTACCA
ACTCGATTAGATATCATACTTGTATAGTTACGAGATATAGTTATTTATAAACCGTATCGTGTCATATTATATTG
GTAGATGAAATAATATAATATACTGTATAATTTGTCTAACAAGACTAGTTGCATGATTAGGAGACGTGCCTAA
TCATGTCCTTATCTTTTTGTCCTTAAAGTAACCAAAAATAGAGTTGCAAAGGTGTTATATCTACTTGTTTTAATA
TGTTTAATTCTGCAAATGATACATCACAAATTATATATATATAATAGATTAAGTGTGTAGGTACATGTATCTTC
TATAGCAACCATAGACTCATTTAGAGGATCACTTTAATATCTACACTGTAATCACACTAACTAGTTGAATAAGT
TGCATTGTCAAGAAAAAATAATTAGTTCAATAGGTTAAACCAATGTGATTATAATTAGATCAGATCAGCTTTTT
GAATCGGAATAGGGGTCTGATCTGGCTCATGCAGTCCATGAGAAACTACCATAATGTGATTATTTACTCGATG
GCATATTAACCAATTTGATTCTAAGACTTTCACCCAAAACATTGCTCTCAATTCAAGTAGATTGTGATATGTAA
TGGCCGGAGTTTGAACTCTAAATTTCTTATGCGTTTGATTTGTTAAAAAATAAGGATAGGATATGACAACTTCA
ATTGTAAGGTGTTTAATTTGTAAAATTGTTTTTGGAACATGACAAACATAGAGGTCAGAGATTGGACGAAAACT
GAAATTCTTGACCCTCACTAAGCCACGACACAACTTTTTGTCTCACGTACACGTTGTCTAAAATATCAAAAAGT
TTTTTGTCCATAAAAATTTGTATAATACCAAAATAGTTTTTTTTTCATAAAAAGTTGTCATGTGTTGTTCTGCTT
TGTGTTATGATGTTATGTTCAATACTTTTGGTTTAACATATCAAACGCACCCTTAAAGATGAATTTCTAGTAAT
TATGTTACGTGACCGGAAAAAAAAAACTTTCACCCAAAATATTGCTATCAATTCATATGTTGATTATAGATTAT
GTCAGGTTCTTAATTAGTATACGTTTTTTGAGAGGAGGTTGTTGATATTTTTTTTTGAAAGACTTGTATATAAA
TACGACTCACTTAACATTATGATTGTGCGCATTGAAGAAGAAAATGCAAAATCCTCTCTTAATTATTAATTAA
AAGGACATTAATGATAATTTTACAATCTTTTTTTTTTTGAGAGCAATGATAATTTTACAATCATCTTCAATGT
GATTTCAATTATGTTCCTGAGGTTACAAAGTCGAACTCTTAATACCGAGATAACACCTCATCAACGTATACTTT
CAATTTTTTTCACTAGTTTGATTATTTTCATTAATAAATTTGAGCTAACTTTATCATATCATGTGAATGGAGTGAG
ATTAACAAAATAAGATTCACTTAAGAACAAATGGATCTGGATTATTCGAATATGAGTCATTACCAACTTTACT
TGACCTCTTTTCACTAAAAAAGATGGTTAAGACATAAAAATAAAGTTTAGAAAATACATAAAACTGTTTGAA
AAAGATCAATTTATTATTCATAATTAAAGAGTAAATAAGATAGGTTAGACACCTTCATCCGAATTCAAACCCA
AGACCTTGTAGTATGTGAGTTCTTTTACATAATTTTTTTACCTTTACAAAAAAGGTAAAAAAAAATAGTATAAA
AAAAAAAAAGATACATAAATTTTTTTATACATGTCTAATGATACTTCTTTTATTGATCAAAACATCATTTAAAC
AAAATCTTTAAAAGAACTAATTTCAGTAATCATAAAATCTTTAAATCTAAAATTCATCTTGTAGGGCTTCTTTT
TGGTAACTTTCATTTTCATTTCTTTTTTGGTTTTAGACTTTTGAAGTATTTGCCCCATTCTTTCCCAACACCTCT
ACTTCTTCGAGATTTCCACATATCCGTGTGATTATGTTAAGAAAGTCAACTCTTATGTCACCTTAAAAGTTGAT
TCTAATACAGTTTTGTCATCTATGACCACAATAAGACACTATATAATTAATATCAATGATCAATAAGGTGACA
AATATTGGGATATAAGATTAGGTGTACTTCCTCTAAAAAAAATTAGGTCCTTAGTTAGTTTGTAAAATAGTATT
AGAGATTTAGTGTATATTGTTGTAATATAAGTATATAACCACCTCATTATAGAGGCACTCTTTATGATTTGTAA
CATACTTAAGGTTAAATATGTTTTTGGTCCCTGTAAATATGTCAACTTTTCGTTTTAGTTTCTCTAAAATTTCCT
TTCAACTTTTTAGTCCCTCAAAAAAATTTCATCTTCACTTTTGGTCCCTCCTTTAAAATAAACTCATATGTAGAAT
TCATATATTTGAATAAAATTTTGCAGAAAAATTCTTAATATTATAAGAATCTCTCCCAAAAAAATTTAGAATTT
TTTAACAAAACATGAATTTAATATGAATTTTTATATTTTGTGGTTAAAAATTTATATTAAATTTATGMTGTT
AAAAAATTCTAATTTTTTTTTGGAAAATATTTTTACAATATTCTACACATTTCTGCACAATTTCATTAAAAAAA
AAAATACTAAAATTAACTTTAAAATAGGAACCAAAAGTAGTGATTGAAAATTTTATAGGGACTAAAAGTTGA
AGGAAAATTTTAGAGGGACTAAAATGAAAAGATAATTAGGGACCAAAAACATATTTAACCCTACTTATTAATT

APPENDIX OF SEQUENCES

```
ACCATCAATACAACAATTATATTCTTCTTTCACTAAGTGGAGTCAAAAGAAATAGTTTATATGAAATAATAAT
ATCACAAGTCACCTACACATATAAATATTTGTATAAAGTGATGGAACACACATAAATTTCATTAGATAAAAA
ACGAATAACACTTGTACGTAACTAATAATTTATACGACATGACTAGACTTTAATGTTTTACATAACAGAATAA
ATTTTCACAGTCCTATAAAGAATTTATGGACGTGAGGTGAACAAACATTGCTGAAACATGCTTAGCAAACAAT
GAAAGCACCACCTTAACAGCTTCCTATTTTAATACAAAAAACAACCAATCAATGTTCCACAATATCCCTTTCAT
AACACCATCATCTAATTGCATCACCTACGGCATTTTATTTATTTAATAATATCAAAAGGTGACCAAAATTGTCA
TTAAATTAATCAAAATGACCCTCTTTGCTTGATTCAAAAGCTACAAATTTTTTTCATTTTTAAACCTGTCCATTA
AATTTCCACACACGGTTTTCTAACCTTTGAAGATTAATTTTTAACATCACAATCTTTTCTCTTTCATTGTACACA
AGAGACAAATGAATGGTACATGGAATCTTTTGAGTATTTTTTTCACTCTTAGATGTCATAGCCACTGCTCTAAT
ATTTAGTATTTATTAATTCTATTGACAAAAACAAAAATCAGAAAAATATTTACTATTAGTAAATGCCAAGTTCT
AAGACAAAGTTTATTTATCTATATGCAAGATTTCTTTCAAGTTTCACGTGTAAATTGTTGTAGGAAGCTATTCC
TTTAACTGTTTCATGTTAATTAGTTACTACATGCTTTTGGAATAAAACAGTTCATAAAGTCTTTCTTTCATTTCC
TTGGTTTTTGAGAAGAAAAATAGTTGCTAGCTTAGGTTGAATTTTCATTGAGTATTCAAAATTCTCTCCCTTG
GTTTTTGAGAAGGGTATTGTGATGAATAAAGAATTCAGCTGAAAATTCATTTATGAAACCTGAAAGATCTTAG
CCAAAAACCTGTGTTGAAAATAAGTTCAAGCATCATTCAAGTGTTTCTTTATAATCAAGCATCTTTAAAGTGTT
GAA SEQ ID NO: 91 terminator sequence for Medicago truncatula IPD3
TCACAACATTTTTATTTCTATAATAATAAATTTGTTATTTTCAGAATATTTTTTATTTAATAAAAATAACCAAACATTTTTTC
ATCATTACAACAGGTATCTTATCTATTCATTCAATTTAACTTTTACTATTTTTTGTTTTCATTATACTTAATAATCCTCAACA
TCAATTACTAAAACATCCTAAAAACTGAATTTTTTAATAAAAAAGGAATTTCACCCCTATGAAAGGATACTATCCTTTGAGCA
TGTGTGTGAAAAGATGGCTTTTCCTTTATAATGTTAACAATAACCTTCACACAAAATAATAATAATAAATCCTCTTAAGACAA
AGTTTAGTGATAATTTGTCACATCTAAGTTTATTATGAGCAAGTCAAAGATAACTATAACTTCATAAACATTTCTGTTGTGAC
ATCGTGCAACCATCACAAAGCTACGCCGTATGATGGGAGGTGGTCAACCACAGAAATAAAAATGAGCTTAATTAGACTCTGAT
AGAGTACACGTTTCTACTAAAATCATTCCATCAATCCAAACACGACCACAATGGCTTTTACAAAACTGTTAATTAAAGTGTGT
TTGTGACTCGTCATCGTTTGTAACGGGAACTTAGAGACATATTTGATGTAAGACAACTATGTAAACCACTATTAATGAACATA
ATATTTTAACCAAAAGATTGCATTTTTTTTTCTGAAGTAACAACAAGAACTCAGTAACTATTAGTACATTTTTCATTTTCAC
TCGAACTATACACGACTTCCTTATTGGTGTAGATGGGACAATAG SEQ ID NO: 92
```

That which is claimed is:

1. A method of increasing nitrogen uptake, phosphorus uptake, drought tolerance/resistance, resistance to fungal and/or bacterial pathogens, and/or growth rate, yield and/or biomass production of a naturally non-mycorrhizal plant, comprising:

introducing into a naturally non-mycorrhizal plant, or plant part or plant cell thereof, a heterologous polynucleotide encoding an IPD3 (Interacting Protein of DMI3) polypeptide or a heterologous polynucleotide encoding an IPD3 phosphomimic polypeptide to produce the modified naturally non-mycorrhizal plant, wherein the naturally non-mycorrhizal plant is a Brassicaceae plant, and contacting the modified naturally non-mycorrhizal plant with a mycorrhizal fungus to provide a modified and colonized naturally non-mycorrhizal plant that is colonized with the mycorrhizal fungus, wherein the modified and colonized naturally non-mycorrhizal plant has increased nitrogen uptake, phosphorus uptake, drought tolerance/resistance, resistance to fungal and/or bacterial pathogens, and/or growth rate, yield and/or biomass production.

2. The method of claim 1, further comprising:
introducing into the naturally non-mycorrhizal plant, or plant part or plant cell thereof, a heterologous polynucleotide encoding an DMI3 (Doesn't Make Infections 3) polypeptide or a heterologous polynucleotide encoding a DMI3 phosphomimic polypeptide.

3. The method of claim 1, comprising:
regenerating a plant from the plant cell or the plant part into which the heterologous polynucleotide was introduced.

4. The method of claim 1, wherein the Brassicaceae plant is Brassica napus, Brassica oleraceae, Brassica juncea, Brassica rapa, Camelina sativa, or Arabidopsis thaliana.

5. The method of claim 2, wherein the heterologous polynucleotide encoding an IPD3 comprises a nucleotide sequence having at least 70% identity to any one of SEQ ID NOs:1-5 and/or a nucleotide sequence having at least 70% identity to a polynucleotide encoding an amino acid sequence of any one of SEQ ID NOs:10-14, the heterologous polynucleotide encoding an IPD3 phosphomimic comprises a nucleotide sequence of any one of SEQ ID NOs:6-9, and/or a polynucleotide encoding an amino acid sequence of any one of SEQ ID NOs:15-18, the heterologous polynucleotide encoding an DMI3 comprises a nucleotide sequence having at least 70% identity to any one of SEQ ID NOs: 19-25 and/or a nucleotide sequence having at least 70% identity to a polynucleotide encoding an amino acid sequence of any one of SEQ ID NOs:28-34, the heterologous polynucleotide encoding an DMI3 phosphomimic comprises a nucleotide sequence of SEQ ID NO:26 or SEQ ID NO:27, and/or a polynucleotide encoding an amino acid sequence of SEQ ID NO: 35 or SEQ ID NO:36.

6. The method of claim 1, wherein the IPD3 polypeptide comprises a coiled coil domain and has at least 70% identity to SEQ ID NOs:10-14.

7. The method of claim 1, wherein the IPD3 phosphomimic polypeptide comprises a coiled coil domain and has at least 70% identity to SEQ ID NOs:15-18.

8. The method of claim 1, wherein the IPD3 polypeptide includes a functional fragment comprising a coiled coil domain and having at least 80% identity to about the last 100 consecutive residues from the C-terminal region of any one of SEQ ID NOs:10-14.

9. The method of claim 1, wherein the IPD3 phosphomimic polypeptide includes a functional fragment comprising a coiled coil domain and having at least 80% identity to about the last 100 consecutive residues from the C-terminal region of any one of SEQ ID NOs:15-18.

* * * * *

UNITED STATES PATENT AND TRADEMARK OFFICE
CERTIFICATE OF CORRECTION

PATENT NO. : 11,248,235 B2
APPLICATION NO. : 16/623962
DATED : February 15, 2022
INVENTOR(S) : Sederoff et al.

It is certified that error appears in the above-identified patent and that said Letters Patent is hereby corrected as shown below:

In the Specification

Column 28, Line 34: Please add a paragraph break between "element." and "In some"

Column 29, Line 3: Please correct "(RHES)" to read -- (RHEs) --

Signed and Sealed this
Seventeenth Day of May, 2022

Katherine Kelly Vidal
*Director of the United States Patent and Trademark Office*

SEQUENCE LISTING

```
<160> NUMBER OF SEQ ID NOS: 92

<210> SEQ ID NO 1
<211> LENGTH: 2445
<212> TYPE: DNA
<213> ORGANISM: Medicago truncatula

<400> SEQUENCE: 1
tttctaacct tgaagatta attttaaca tcacaatctt ttctctttca ttgtacacaa      60
gacaaatgaa tggtacatgg aatcttttga gtatttttt cactcttaga tgtcatagcc    120
actgctctaa tatttagtat ttattaattc tattgacaaa acaaaaatc agaaaaatat    180 ttactattag taaatgccaa gttctaagac aaagtttatt tatctatatg caagatttct    240
ttcaagtttc acgtgtaaat tgttgtagga agctattcct ttaactgttt catgttaatt    300
agttactaca tgcttttgga ataaaacagt tcataaagtc tttctttcat tccttggtt    360 tttgagaaga aaaatagtt gctagcttag gttgaatttt cattgagtat tcaaaattct    420
ctcccttggt ttttgagaag ggtattgtga tgaataaaga attcagctga aaattcattt    480
atgaaacctg aaagatctta gccaaaaacc tgtgttgaaa ataagttcaa gcatcattca    540
agtgtttctt tataatcaag catctttaaa gtgtttgaaat ggagggaga ggattttctg    600 gtttatacaa gaattcaagt gaggagttat tcttgaagac agtgatggag agtcctattg    660
gtatgccggt acctaccatg gagatgttag gattcaagac tgtttctcaa agctttcgca    720
ccgatagtga agagctttc aaacgctggc taacaaatga tcaagaggga tacaattcat    780
caagcatggg acttaacagt cgtttgtcga agagaatatc aactgaaata gctaatatgt    840
ctaatcaaca acacattggt gtggcttcag aaggaagaaa caatgataaa tcatgcttac    900
aaaataactt cttggcaaat gatgtttcaa gtgatttcaa ttttccaatc agagatcctg    960
ttgatagaga attgcaatct agtaacttgt ttctggccaa ggcctggttt attaccgatc   1020
```

```
aacgaatgac aagaagccgg tcttctgaat tgcggcgaag gtatactgaa atgcaaaatt    1080
ctcaagcacc acaaggattg gattctatgt tcatggttcc tgagcatgat actaacacta    1140
taaaagaaga acttgcaaat tttaatgggt ttgattacct ttccatgtgt gagttaccaa    1200
gccaaaaggg cacattcatg tctccatcca actcatcttc gtctaccttc aacacacatc    1260
aattggttga tgtagataaa gtttcatctt gtgtaagtat gctaaaaggt acattacagc    1320
gcaagaaact cgaatgccaa gtcgagaaag aagctgcaga agatggcttg aatgaaatat    1380
tttgcattcg agaacctctt ttccaatcag cttttaatga agaagaaagt tggaatcaac    1440
aaaagctagt aaacgttcaa ggagatttta ccgatcaagt taacgatccc ggagtcatgc    1500
aaacccttga aggaaccaca aactttgtct tagatggttt tgcaaatcag acgaaccaaa    1560
tacaaggcag aacagcttct ggagaaccgt ctcaaagtga atcttctgct gctgcaccag    1620
taatctcatc tggcttagat gcatgtgaag gtcccagcaa ttcaaatcaa actcttggtg    1680
atagctcatg gaaacaagtg ggagaaagca ctcaaaataa agtcagaggt gtcagagaac    1740
agataatgga taatctgaaa gatgacagaa agaggaaaag tctagaaaga tatggatctg    1800
taacatcagc tgtttcagat ggcaagatgg ataacacaaa aaagcggagg gtggagcgct    1860
caagaaaaat ggctgaagca aaggaaagaa atttgacacc aacaattccc tcagatatgc    1920
aagctatctt gaagcgatgc gaaaaccttg agaaggaagt tcgatcacta aagcttaatt    1980
tgtccttcat gaataggaag gattctgaac aaacaaagca gatagaggac cttcagaagc    2040
agaatgaaga cttggcggat gaaaagagc gcctcctcga agagattgaa agaattctat    2100
cagaaactgg aaagatttga tgttttgttt cgctgttata tccttatcct cgtcagaaac    2160
aatgtagtac tcagacaagc taaaaatctc accacagttt acttgtggat gaaacagctt    2220
aggtaaaagt gaaaacagtg attaatagtg aacctatgga gtctattagc aaaatataaa    2280
tgcatggaat ctgagatatt agtaatgaca ttatatatct ggtaaaatct aagtgttatt    2340
caaaatttga gccatataaa tgaatccggt aaatttaaac atggtcaagt gtacccacca    2400
acctcaatca tatgtaacaa acaaatatct tcaatttgtt tatgc                    2445
```

<210> SEQ ID NO 2
<211> LENGTH: 1872
<212> TYPE: DNA
<213> ORGANISM: Lotus japonicus

<400> SEQUENCE: 2

```
ttgttgctct gttgcatgtt aatttctgtg ctatttggat aaaacagttc atgaactgat      60
aatagtaaag tcttctttc ttcttttttt tatcaggaat aattgctagg ttgacatgat     120
taaaaaaatt gggttttggg gttgattttt tagagtgata tatggttttg aagaagggta     180
ttatgatgat ggatgacaga gaatttagat gaaaattctg ttctgaaacc tgaaagtgct     240
gttgagccaa acttgagttg aaaacaacag cttcaattgg aaatggaagg gaggggttt      300 tctggtttat atagaaactc aagtgaagaa ttgttcctga agacagtgat ggagagccct     360
attggtatgc cagttccttc aatggagatg ctgggtttca agaatgtttc tcaaggcttt     420
cgcgcagata gcgaggagct tttcaaacgc tggctaacaa atggagaggg atacaattca     480
tcaagcatag ggtttagcag tcgattatca aagaggatat ccactgaact agttaatgga     540
tctaatcagc tacaagttgg tgtagcctca gatggaagaa acaatgacaa accattcata     600
caaaataacc ttttggcaaa tgatgtttca ggtgatttca attttccaat cagagatcct     660
```

```
gttgatagag aactgcaacc tagtaacttg tttctagcca aggcctggtt tctcagtgat    720
caacgaatga caagaagccg gtcctctgaa ttgcggcggc gatattctga aatgcaaaat    780
ggtctagcca cacaaggaat agaatccatt tgcatggatc ctcagcatgg tgctgaggca    840
acaaaacaag aagttgcaaa tttcaatggt tacaattatc tctctatgtg tgagcttcca    900
agtcaaaagg gttcattcat gtctccgtcc aactcatgtt catctaactt caacacacct    960
caatttggcg acatggataa agtttcatct tgtgtaagta tgctgaaagg gacattacaa   1020
cgccggagac tcagcagtca acttgagaaa gaagctgcag aagatgactt aaatggaatt   1080
ttttatcctc aagaacctct tttccaaact ggctttgatc aaggacaaga aaactggagt   1140
aatcaaacgc cagtaaatgt tcaagtagac tctattggtg aagttaagga tcatggagtc   1200
ctgcaaacac tagaaggatc cacaaaccct gtcgttgatg gttttgcaaa tcagataaac   1260
caaatctatg tcggaacagc ttctggagaa ccttctcaaa gtgaatcctc taatgctgca   1320
ccagtaatct cctctggttt agacacatgc gaaggtccca taaactcgaa tcaaactctc   1380
tgcgaaagct catggaaaca gtaggagtg agtaaaagtt cagaaaatac tcaaaataga   1440
gtcaaaggtt tcagagaaca gatcatggat aatctgaaag atgataagaa gagaaaaagt   1500
ctagaaagat atggatctat aacatcagct gtttcagatg acaagggaga caccactaaa   1560
aagcgtaggg tggaacgctc aaggaaaatg gctgaagcta aggaaagaaa ttcgacacca   1620
tcagttccct cagatatgca agctgtcttg aagcggtgcg aaaaccttga aaggaagtt    1680 cgatcgctaa aactcaactt gtccttcatg aatagaaagg attctgaaca aacaaagcag   1740
atagaagacc ttcagaagca gaatgaagag ctggcagatg aaaaagagcg cctcctcgaa   1800
gagattgaaa gaattctatc agaaactgaa aaaatgtaat gatatgagaa tcaatgttgt   1860 gctcaaaacac gc                                                      1872

<210> SEQ ID NO 3
<211> LENGTH: 1612
<212> TYPE: DNA
<213> ORGANISM: Pisum sativum

<400> SEQUENCE: 3
ttgagctgaa aatcggttca agaagctttt gagtgctggt tgaaatggaa gggagaggat     60
tttctggttt atacaagaat tcaagtgaag agttgttctt gaagacagtg atggagagtc    120
ctattggtat gccagtacct accatggaga tgttaggatt caagaccgtt tctcaaagct    180
ttcgcgccga tagcgaggag cttttcaagc gctggctgac aaatgaagag ggatacaatt    240
caacgagcat gggacttaac agtcgattat cgaagagaat ctccactgaa ctagttaatg    300
tgtctaatca gcaacatgtt ggtgtggctt cagaaggaag aaacaatgat aaatcatgct    360
tacaaaatag ctttttgaca aatgatgttt cgggcgattt caattttcca atcagagaac    420
ctgttgatag agaattgcaa tctggtaact tgtttctggc caaggcatgg tttcttaccg    480
atcaaagaat gacaagaagc cggtcttctg aattgcggcg aaggtatacc gaaatgcaaa    540
atactcaagc accacaagga ttggattcaa tgttcatggc tcctaagcat gatgctaaca    600
ttataaaaga agaacttgca catttcaatg gttttgatta cctttcaatg tgcgaaatac    660
caagtcaaaa gggctcattc atgtctccat cgaactcatc ttcgtctacc ttcaacacac    720
aacaattggt tgatgtagat aaagtttcat cttgcgtaag tatgctaaaa ggtacgttac    780
aacgcaagag actcgaatgc caagtcgaga aagatgctgc agaagacggt ttaaacgaaa    840 ttttttggtat tcgagagcct cttttccaat ctggttttaa tgaaggacaa gaaaattgga    900
```

```
atcatcaaaa gctagtaaat gttcaaggag attttaccga tcaagttaag gatactggag      960
tcattgaaac acttgaagga gccgcaaact ttgtcttaga gggttttgca aatcaaacga     1020
gccaaataca cggtggaacg gcttccggtg aaccttctca aagtgagtct tctgctgctg     1080
caccagtaat ctcatctggt ttagatgctt gtgaaggacc tagcaattca agtcaaactc     1140
tttgtgatag ctcatggaaa caagtaggag aaagcactca aaatcgagcc aaaggtgtca     1200
gagaacagat aatggataat ctgaaagacg acaggaagag gaaagactca gagagatatg     1260
gatcagtaac atcagctgtt tcagatgaca aggtggacac aacaaaaaag cgaagggtgg     1320
aacgatcaag aaaaatggct gaggcaaagg aaagaaattt gacaccaaca attccctcag     1380
atatgcaagc tgtcatgaag cgatgcgaaa accttgagaa ggaagttcga tcgctaaagc     1440
ttaatttgtc cttcatgaat aggaaggatt ctgaacaaac aaagcagata gaggatcttc     1500
agaagcagaa tgaagagttg gcagatgaaa aagagcgcct actcgaagag atcgaaagac     1560
ttttatcaga aactggaaag atttaatgtt ttgttgtttt cttatcatgt cc             1612
```

<210> SEQ ID NO 4
<211> LENGTH: 1612
<212> TYPE: DNA
<213> ORGANISM: Solanum lycopersicum

<400> SEQUENCE: 4

```
atggaaatgg agggaagagg ttattcagat ttctatagaa acacaagtga agaattgttc       60
ataagaacta tgatggacaa ctcagtagga ggagtgccag ttcctacaat ggagatgtta      120
ggttttagaa acatccctca ttctcttcga accgacagtg aggaactttt caaaagctgg      180
ctcacaagtg cagagaataa tggcagtgat tctacaccaa tggctcgtgg tcgacaagga      240
tcacgaagga tctccagtga acttgctggt ctatccagtc agcaaaatga ggggattcag      300
aaaagaaaaa tggccgatac tcaacagcca cagaatacat gtactgccat tgaatcatct      360
agcaacctta ataaacattc aaccaggaac gcgacagata gggaaatgca agctagtaat      420 ctgttttttag ccaagacctg gttccatagc tctcagccca tgacgagaag tcgttcatct      480
gagttaagga ggaggtatgc agccatgcaa aactcacagt cttcactagc tcgtgaatcc      540
ttgcaaaata tacctggaaa tgctgttaat agcttcaaag aagaagtttc tcatcccact      600
gggtacactg acatgtcaat gtgtgaaatg accaaccaac ctaatacttt tatgtctcca      660
tcaaattctt cttcatcaac ttttgaagca cagcaagtgg atggtgtgga taatatttct      720
tctgttgtaa gcatgctaaa ggggaccttg agaggaagaa aattgacaaa ctatcatact      780
gcgagggaag ccattgagga gaatatgttg gggtgttatg gtaatcaaga aatcttttgt      840
aactccgaca tgaatcaaca tccagggaat catatttctc tgaatcaagg acatatcag      900 gacacacctg ttgttcaagt cagagatacg gggatcccac aaacagttca agggtcatta      960
gatgccgtct tagaaagtat tatggctccc tcaaacccaa tccagataga catggtaaca     1020
caggaacctt ctcaaagtgg atcttctgtt gcagcaccaa tactttcaat tgattttgat     1080
gcatatgatg gcctgagcaa tgcaagtcaa gctttaaata tgtacgaggg ctgtagaaat     1140
caagtcggat atgaaggag ctcagaaaat ggttcaactg ctagagatat tagagaacga     1200
atatatgaca acgtgaagga caaccaaaag aaagaaggtt tagttcgaaa tggatcttta     1260
acatctgtac aatcagcgga aaatggagat cctaagaaga agagaagggt ggagcggtct     1320
cggaaaatgg cagaagccaa agagagaaat ttaacaccag caattccttc agatatgcaa     1380
```

```
tcccttgtga agcgctgtga caatctggag aaggaagttc gttcacttaa acttaacctg    1440
gcgtttatga acagaaagga ttctgaacag actacacaaa ttgaagagct gcagaagcag    1500
aatgaggatt tggtcaagga aaaagagcgc cttcttggag aaatcgagag gatcatttca    1560
gaatctggaa agttttagat actgttactc tttagcagct tcagacgtgt tt            1612
```

<210> SEQ ID NO 5
<211> LENGTH: 1767
<212> TYPE: DNA
<213> ORGANISM: Diphasiastrum digitatum

<400> SEQUENCE: 5

```
atggttgaga ttgcagatag gcgcattact agaagtgtgt cctccgagct tcaggccagg      60 cttcaacac agcctcagac acagaaggt gtggaggaga taagagctgt atcgggagat       120
atggagatat cgtgctttca aaggaattca agtgaggaga tattttgag gagttttatg      180 gatggtgcaa tggcgcctgc cactgaggc atgtcatttt tgagtccgcc tcagccaccg     240
cttcgagtaa acagcgagga actgtttaac acttggctca gcaatacgga tgccccgggg   300
cttccgccat tatctggaga ctatcgaacc cttcaaaatt cttgcagaat gtcaagtgaa   360
cttgctggta atcttggaca aggagctgtc tctcaaccat ttgatattcc tggagagaat   420
gtggcccaaa caattggagg acatcctgat cccaatgtca gggaaagtaa catagggaag   480
ccaaggaatc atgctccaag caagggattg ccatttcaag atcatgcgtc ttggcagatg   540
atcaactggt ttcaacaatc tcagccgatg acacgaagtc gctcctctga gcttcgtcgt   600
aaatacttgg caatgcaaga aggtcataaa cctcctccct cagccaacac cttgcaatgg   660
tttgcaacac aaggaactga tgaattgaat cgtgctgtgg catcacttgg ggctttcaca   720
cgtgcccttg caagcaagag accagatata tcctcaacag catctcctca actttctccc   780
acccccatgt cccatgttag taaactatct ccccagagga atggtgactc tgtatctgct   840
gttgtgaaca tgcttaaggg aagcttagaa cggaagaagc ttgctgcaat gcagcaacag   900
atggataaac ctgtttcacc accatattgg agatccttgg acaggacaa agaggatcct   960 cataagccga tgatcgactc gcaacagtgt atctctccgc aaattgagtc tgagcaacaa   1020
caagagaatc aaaaggaagc attttcggcc agtcttcaga ttacaaatga gcagttccag   1080
gctggagtgg tcactccaca tgccttatca cccagcgatt catctggtaa tgcacctggc   1140
ctgtcagctg gagcagcgac tagtgagggg ccttgcaact caaatcctgc tgtttccact   1200
cagaacaatt tcatcaaatg ctctggtcag ggcaactggg ctgtagatga acatttcag   1260 caaaacaacc taccaagccc cacatccaat gggacaagta atggagagat tccttacgag   1320
ggtgtcttga atacgacta ccaaaagaga caaggctacc tatctcgtgc aggctcacta   1380
acctcttctt gtcgatcaga tcaaagtatg caagtgtcta ttggtgagag aacccataag   1440
cttgaaggat ccacggcaga tgcagaagat tctacgaaga acgtcgagt tgaacgaaa    1500 cgaatgatgg ctgaggcaaa ggggagaagt tatgttccta tgatgccctc tgatctacaa   1560
gcagctacaa aacgatgtga tgctttggaa aaggaagtaa ggtccctgaa gctgaacttg   1620
tctttcatga acgaaagga ctctgagcag accaagcgaa tagaagatct tgaaaagcag   1680
aatgaggagt tacttgcaga gaaagatcga ctagtggagg aggtcagacg ttttacctca   1740
ggaaaaaact tggtagatc gtcttag                                        1767
```

<210> SEQ ID NO 6
<211> LENGTH: 1867

```
<212> TYPE: DNA
<213> ORGANISM: Artificial
<220> FEATURE:
<223> OTHER INFORMATION: Modified IPD3 polynucleotide

<400> SEQUENCE: 6
atggaaggga gaggattttc tggtttatac aagaattcaa gtgaggagtt attcttgaag      60
acagtgatgg agagtcctat tggtatgccg gtacctacca tggagatgtt aggattcaag     120
actgtttctc aaagctttcg caccgatgat gaagagcttt tcaaacgctg gctaacaaat     180
gatcaagagg gatacaattc atcaagcatg ggacttaaca gtcgtttgtc gaagagaata     240
tcaactgaaa tagctaatat gtctaatcaa caacacattg gtgtggcttc agaaggaaga     300
aacaatgata aatcatgctt acaaaataac ttcttggcaa atgatgtttc aagtgatttc     360
aattttccaa tcagagatcc tgttgataga gaattgcaat ctagtaactt gtttctggcc     420
aaggcctggt ttattaccga tcaacgaatg acaagaagcc ggtcttctga attgcggcga     480
aggtatactg aaatgcaaaa ttctcaagca ccacaaggat tggattctat gttcatggtt     540
cctgagcatg atactaacac tataaaagaa gaacttgcaa attttaatgg gtttgattac     600
ctttccatgt gtgagttacc aagccaaaag ggcacattca tgtctccatc caactcatct     660
tcgtctacct tcaacacaca tcaattggtt gatgtagata agtttcatc ttgtgtaagt     720
atgctaaaag gtacattaca gcgcaagaaa ctcgaatgcc aagtcgagaa agaagctgca     780
gaagatggct tgaatgaaat attttgcatt cgagaacctc ttttccaatc agcttttaat     840
gaagaagaaa gttggaatca acaaaagcta gtaaacgttc aaggagattt taccgatcaa     900
gttaacgatc ccggagtcat gcaaacccctt gaaggaacca caaactttgt cttagatggt     960
tttgcaaatc agacgaacca aatacaaggc agaacagctt ctggagaacc gtctcaaagt    1020
gaatcttctg ctgctgcacc agtaatctca tctggcttag atgcatgtga aggtcccagc    1080
aattcaaatc aaactcttgg tgatagctca tggaaacaag tgggagaaag cactcaaaat    1140
aaagtcagag gtgtcagaga acagataatg gataatctga aagatgacag aaagaggaaa    1200
agtctagaaa gatatggatc tgtaacatca gctgtttcag atgcaagat ggataacaca    1260
aaaaagcgga gggtggagcg ctcaagaaaa atggctgaag caaaggaaag aaatttgaca    1320
ccaacaattc cctcagatat gcaagctatc ttgaagcgat gcgaaaacct tgagaaggaa    1380
gttcgatcac taaagcttaa tttgtccttc atgaatagga aggattctga acaaacaaag    1440
cagatagagg accttcagaa gcagaatgaa gacttggcgg atgaaaaaga gcgcctcctc    1500
gaagagattg aaagaattct atcagaaact ggaaagattt gatgttttgt ttcgctgtta    1560
tatccttatc ctcgtcagaa acaatgtagt actcagacaa gctaaaaatc tcaccacagt    1620
ttacttgtgg atgaaacagc ttaggtaaaa gtgaaacag tgattaatag tgaacctatg    1680
gagtctatta gcaaaatata aatgcatgga atctgagata ttagtaatga cattatatat    1740
ctggtaaaat ctaagtgtta ttcaaaattt gagccatata aatgaatccg gtaaatttaa    1800
acatggtcaa gtgtacccac caacctcaat catatgtaac aaacaaatat cttcaatttg    1860
tttatgc                                                              1867
```

<210> SEQ ID NO 7
<211> LENGTH: 1867
<212> TYPE: DNA
<213> ORGANISM: Artificial
<220> FEATURE:
<223> OTHER INFORMATION: Modified IPD3 polynucleotide

<400> SEQUENCE: 7

```
atggaaggga gaggattttc tggtttatac aagaattcaa gtgaggagtt attcttgaag      60
acagtgatgg agagtcctat tggtatgccg gtacctacca tggagatgtt aggattcaag     120
actgttgagc aaagctttcg caccgatagt gaagagcttt tcaaacgctg gctaacaaat     180
gatcaagagg gatacaattc atcaagcatg ggacttaaca gtcgtttgtc gaagagaata     240
tcaactgaaa tagctaatat gtctaatcaa caacacattg gtgtggcttc agaaggaaga     300
aacaatgata aatcatgctt acaaaataac ttcttggcaa atgatgtttc aagtgatttc     360
aattttccaa tcagagatcc tgttgataga gaattgcaat ctagtaactt gtttctggcc     420
aaggcctggt ttattaccga tcaacgaatg acaagaagcc ggtcttctga attgcggcga     480
aggtatactg aaatgcaaaa ttctcaagca ccacaaggat tggattctat gttcatggtt     540
cctgagcatg atactaacac tataaaagaa gaacttgcaa attttaatgg gtttgattac     600
ctttccatgt gtgagttacc aagccaaaag ggcacattca tgtctccatc caactcatct     660
tcgtctacct tcaacacaca tcaattggtt gatgtagata agtttcatc ttgtgtaagt      720
atgctaaaag gtacattaca gcgcaagaaa ctcgaatgcc aagtcgagaa agaagctgca     780
gaagatggct tgaatgaaat attttgcatt cgagaacctc ttttccaatc agcttttaat     840
gaagaagaaa gttggaatca acaaaagcta gtaaacgttc aaggagattt taccgatcaa     900
gttaacgatc ccgagtcat gcaaacccctt gaaggaacca caactttgt cttagatggt       960
tttgcaaatc agacgaacca atacaaggc agaacagctt ctggagaacc gtctcaaagt     1020
gaatcttctg ctgctgcacc agtaatctca tctggcttag atgcatgtga aggtcccagc     1080
aattcaaatc aaactcttgg tgatagctca tggaacaag tgggagaaag cactcaaaat      1140
aaagtcagag gtgtcagaga acagataatg gataatctga agatgacag aaagaggaaa      1200
agtctagaaa gatatggatc tgtaacatca gctgtttcag atggcaagat ggataacaca     1260
aaaaagcgga gggtggagcg ctcaagaaaa atggctgaag caaggaaag aaatttgaca      1320
ccaacaattc cctcagatat gcaagctatc ttgaagcgat gcgaaaacct tgagaaggaa     1380
gttcgatcac taaagcttaa tttgtccttc atgaatagga aggattctga acaaacaaag     1440
cagatagagg accttcagaa gcagaatgaa gacttggcgg atgaaaaaga gcgcctcctc     1500
gaagagattg aaagaattct atcagaaact ggaaagattt gatgtttgt ttcgctgtta       1560
tatccttatc ctcgtcagaa acaatgtagt actcagacaa gctaaaaatc tcaccacagt     1620
ttacttgtgg atgaaacagc ttaggtaaaa gtgaaaacag tgattaatag tgaacctatg     1680
gagtctatta gcaaaatata aatgcatgga atctgagata ttagtaatga cattatatat     1740
ctggtaaaat ctaagtgtta ttcaaaattt gagccatata aatgaatccg gtaaattaa      1800
acatggtcaa gtgtacccac caacctcaat catatgtaac aaacaaatat cttcaatttg     1860
tttatgc                                                               1867
```

<210> SEQ ID NO 8
<211> LENGTH: 1593
<212> TYPE: DNA
<213> ORGANISM: Artificial
<220> FEATURE:
<223> OTHER INFORMATION: Modified IPD3 polynucleotide

<400> SEQUENCE: 8

```
atggaaggga gggggttttc tggtttatat agaaactcaa gtgaagaatt gttcctgaag       60
acagtgatgg agagccctat tggtatgcca gttccttcaa tggagatgct gggtttcaag      120
```

```
aatgtttctc aaggctttcg cgcagatagc gaggagcttt tcaaacgctg gctaacaaat      180
ggagagggat acaattcatc aagcataggg tttagcagtc gattatcaaa gaggatatcc      240
actgaactag ttaatggatc taatcagcta caagttggtg tagcctcaga tggaagaaac      300
aatgacaaac cattcataca aaataacctt ttggcaaatg atgtttcagg tgatttcaat      360
tttccaatca gagatcctgt tgatagagaa ctgcaaccta gtaacttgtt tctagccaag      420
gcctggtttc tcagtgatca acgaatgaca agaagccggg attcctctga attgcggcgg      480
cgatattctg aaatgcaaaa tggtctagcc acacaaggaa tagaatccat ttgcatggat      540
cctcagcatg tgctgaggc aacaaaacaa gaagttgcaa atttcaatgg ttacaattat       600
ctctctatgt gtgagcttcc aagtcaaaag ggttcattca tgtctccgtc caactcatgt      660
tcatctaact tcaacacacc tcaatttggc gacatggata agtttcatc ttgtgtaagt       720 atgctgaaag ggacattaca acgccggaga ctcagcagtc aacttgagaa agaagctgca      780
gaagatgact taaatggaat ttttatcct caagaacctc ttttccaaac tggctttgat       840
caaggacaag aaaactggag taatcaaacg ccagtaaatg ttcaagtaga ctctattggt      900
gaagttaagg atcatggagt cctgcaaaca ctagaaggat ccacaaaccc tgtcgttgat      960
ggttttgcaa atcagataaa ccaaatctat gtcggaacag cttctggaga accttctcaa      1020
agtgaatcct ctaatgctgc accagtaatc tcctctggtt tagacacatg cgaaggtccc     1080
ataaactcga atcaaactct ctgcgaaagc tcatggaaac aagtaggagt gagtaaaagt     1140
tcagaaaata ctcaaaatag agtcaaaggt ttcagaaac agatcatgga taatctgaaa       1200
gatgataaga agagaaaaag tctagaaaga tatggatcta acatcagc tgtttcagat       1260 gacaagggag acaccactaa aaagcgtagg gtggaacgct caaggaaaat ggctgaagct     1320
aaggaaagaa attcgacacc atcagttccc tcagatatgc aagctgtctt gaagcggtgc     1380
gaaaaccttg agaaggaagt tcgatcgcta aaactcaact tgtccttcat gaatagaaag     1440
gattctgaac aaacaaagca gatagaagac cttcagaagc agaatgaaga gctggcagat     1500 gaaaagagc gcctcctcga agagattgaa agaattctat cagaaactga aaaaatgtaa     1560
tgatatgaga atcaatgttg tgctcaaaca cgc                                   1593
```

<210> SEQ ID NO 9
<211> LENGTH: 1867
<212> TYPE: DNA
<213> ORGANISM: Artificial
<220> FEATURE:
<223> OTHER INFORMATION: Modified IPD3 polynucleotide

<400> SEQUENCE: 9

```
atggaaggga gaggattttc tggtttatac aagaattcaa gtgaggagtt attcttgaag       60
acagtgatgg agagtcctat tggtatgccg gtacctacca tggagatgtt aggattcaag      120
actgttgagc aaagctttcg caccgatgat gaagagcttt tcaaacgctg gctaacaaat      180
gatcaagagg gatacaattc atcaagcatg ggacttaaca gtcgtttgtc gaagagaata      240
tcaactgaaa tagctaatat gtctaatcaa caacacattg gtgtggcttc agaaggaaga      300
aacaatgata aatcatgctt acaaaataac ttccttggcaa atgatgtttc aagtgatttc     360 aatttttccaa tcagagatcc tgttgataga gaattgcaat ctagtaactt gtttctggcc    420
aaggcctggt ttattaccga tcaacgaatg acaagaagcc ggtcttctga attgcggcga     480
aggtatactg aaatgcaaaa ttctcaagca ccacaaggat tggattctat gttcatggtt     540
```

```
cctgagcatg atactaacac tataaaagaa gaacttgcaa attttaatgg gtttgattac      600 cttccatgt gtgagttacc aagccaaaag ggcacattca tgtctccatc caactcatct      660
tcgtctacct tcaacacaca tcaattggtt gatgtagata aagtttcatc ttgtgtaagt      720
atgctaaaag gtacattaca gcgcaagaaa ctcgaatgcc aagtcgagaa agaagctgca      780
gaagatggct tgaatgaaat attttgcatt cgagaacctc ttttccaatc agcttttaat      840
gaagaagaaa gttggaatca acaaaagcta gtaaacgttc aaggagattt taccgatcaa      900
gttaacgatc ccggagtcat gcaaacccctt gaaggaacca caaactttgt cttagatggt      960
tttgcaaatc agacgaacca aatacaaggc agaacagctt ctggagaacc gtctcaaagt     1020
gaatcttctg ctgctgcacc agtaatctca tctggcttag atgcatgtga aggtcccagc     1080
aattcaaatc aaactcttgg tgatagctca tggaaacaag tgggagaaag cactcaaaat     1140
aaagtcagag gtgtcagaga acagataatg gataatctga aagatgacag aaagaggaaa     1200
agtctagaaa gatatggatc tgtaacatca gctgtttcag atgcaagat ggataacaca      1260 aaaaagcgga gggtggagcg ctcaagaaaa atggctgaag caaaggaaag aaatttgaca     1320
ccaacaattc cctcagatat gcaagctatc ttgaagcgat gcgaaaacct tgagaaggaa     1380
gttcgatcac taaagcttaa tttgtccttc atgaatagga aggattctga acaaacaaag     1440
cagatagagg accttcagaa gcagaatgaa gacttggcgg atgaaaaaga gcgcctcctc     1500
gaagagattg aaagaattct atcagaaact ggaaagattt gatgtttgt ttcgctgtta     1560 tatccttatc ctcgtcagaa acaatgtagt actcagacaa gctaaaaatc tcaccacagt     1620
ttacttgtgg atgaaacagc ttaggtaaaa gtgaaacag tgattaatag tgaacctatg     1680
gagtctatta gcaaaatata aatgcatgga atctgagata ttagtaatga cattatatat     1740
ctggtaaaat ctaagtgtta ttcaaaattt gagccatata aatgaatccg gtaaatttaa     1800
acatggtcaa gtgtacccac caacctcaat catatgtaac aaacaaatat cttcaatttg     1860
tttatgc                                                              1867
```

<210> SEQ ID NO 10
<211> LENGTH: 513
<212> TYPE: PRT
<213> ORGANISM: Medicago truncatula

<400> SEQUENCE: 10

```
Met Glu Gly Arg Gly Phe Ser Gly Leu Tyr Lys Asn Ser Ser Glu Glu
1               5                   10                  15

Leu Phe Leu Lys Thr Val Met Glu Ser Pro Ile Gly Met Pro Val Pro
                20                  25                  30

Thr Met Glu Met Leu Gly Phe Lys Thr Val Ser Gln Ser Phe Arg Thr
            35                  40                  45

Asp Ser Glu Glu Leu Phe Lys Arg Trp Leu Thr Asn Asp Gln Glu Gly
        50                  55                  60

Tyr Asn Ser Ser Ser Met Gly Leu Asn Ser Arg Leu Ser Lys Arg Ile
65                  70                  75                  80

Ser Thr Glu Ile Ala Asn Met Ser Asn Gln Gln His Ile Gly Val Ala
                85                  90                  95

Ser Glu Gly Arg Asn Asn Asp Lys Ser Cys Leu Gln Asn Asn Phe Leu
            100                 105                 110

Ala Asn Asp Val Ser Ser Asp Phe Asn Phe Pro Ile Arg Asp Pro Val
        115                 120                 125

Asp Arg Glu Leu Gln Ser Ser Asn Leu Phe Leu Ala Lys Ala Trp Phe
```

```
            130                 135                 140
Ile Thr Asp Gln Arg Met Thr Arg Ser Arg Ser Ser Glu Leu Arg Arg
145                 150                 155                 160

Arg Tyr Thr Glu Met Gln Asn Ser Gln Ala Pro Gln Gly Leu Asp Ser
                165                 170                 175

Met Phe Met Val Pro Glu His Asp Thr Asn Thr Ile Lys Glu Glu Leu
            180                 185                 190

Ala Asn Phe Asn Gly Phe Asp Tyr Leu Ser Met Cys Glu Leu Pro Ser
        195                 200                 205

Gln Lys Gly Thr Phe Met Ser Pro Ser Asn Ser Ser Ser Thr Phe
    210                 215                 220

Asn Thr His Gln Leu Val Asp Val Asp Lys Val Ser Ser Cys Val Ser
225                 230                 235                 240

Met Leu Lys Gly Thr Leu Gln Arg Lys Lys Leu Glu Cys Gln Val Glu
                245                 250                 255

Lys Glu Ala Ala Glu Asp Gly Leu Asn Glu Ile Phe Cys Ile Arg Glu
                260                 265                 270

Pro Leu Phe Gln Ser Ala Phe Asn Glu Glu Ser Trp Asn Gln Gln
    275                 280                 285

Lys Leu Val Asn Val Gln Gly Asp Phe Thr Asp Gln Val Asn Asp Pro
    290                 295                 300

Gly Val Met Gln Thr Leu Glu Gly Thr Thr Asn Phe Val Leu Asp Gly
305                 310                 315                 320

Phe Ala Asn Gln Thr Asn Gln Ile Gln Gly Arg Thr Ala Ser Gly Glu
                325                 330                 335

Pro Ser Gln Ser Glu Ser Ser Ala Ala Ala Pro Val Ile Ser Ser Gly
                340                 345                 350

Leu Asp Ala Cys Glu Gly Pro Ser Asn Ser Asn Gln Thr Leu Gly Asp
            355                 360                 365

Ser Ser Trp Lys Gln Val Gly Glu Ser Thr Gln Asn Lys Val Arg Gly
        370                 375                 380

Val Arg Glu Gln Ile Met Asp Asn Leu Lys Asp Asp Arg Lys Arg Lys
385                 390                 395                 400

Ser Leu Glu Arg Tyr Gly Ser Val Thr Ser Ala Val Ser Asp Gly Lys
                405                 410                 415

Met Asp Asn Thr Lys Lys Arg Arg Val Glu Arg Ser Lys Met Ala
            420                 425                 430

Glu Ala Lys Glu Arg Asn Leu Thr Pro Thr Ile Pro Ser Asp Met Gln
        435                 440                 445

Ala Ile Leu Lys Arg Cys Glu Asn Leu Glu Lys Glu Val Arg Ser Leu
    450                 455                 460

Lys Leu Asn Leu Ser Phe Met Asn Arg Lys Ser Glu Gln Thr Lys
465                 470                 475                 480

Gln Ile Glu Asp Leu Gln Lys Gln Asn Glu Asp Leu Ala Asp Glu Lys
                485                 490                 495

Glu Arg Leu Leu Glu Glu Ile Glu Arg Ile Leu Ser Glu Thr Gly Lys
            500                 505                 510

Ile
```

<210> SEQ ID NO 11
<211> LENGTH: 518
<212> TYPE: PRT
<213> ORGANISM: Lotus japonicus

<400> SEQUENCE: 11

```
Met Glu Gly Arg Gly Phe Ser Gly Leu Tyr Arg Asn Ser Ser Glu Glu
1               5                   10                  15

Leu Phe Leu Lys Thr Val Met Glu Ser Pro Ile Gly Met Pro Val Pro
            20                  25                  30

Ser Met Glu Met Leu Gly Phe Lys Asn Val Ser Gln Gly Phe Arg Ala
        35                  40                  45

Asp Ser Glu Glu Leu Phe Lys Arg Trp Leu Thr Asn Gly Glu Gly Tyr
    50                  55                  60

Asn Ser Ser Ser Ile Gly Phe Ser Ser Arg Leu Ser Lys Arg Ile Ser
65                  70                  75                  80

Thr Glu Leu Val Asn Gly Ser Asn Gln Leu Gln Val Gly Val Ala Ser
                85                  90                  95

Asp Gly Arg Asn Asn Asp Lys Pro Phe Ile Gln Asn Asn Leu Leu Ala
            100                 105                 110

Asn Asp Val Ser Gly Asp Phe Asn Phe Pro Ile Arg Asp Pro Val Asp
        115                 120                 125

Arg Glu Leu Gln Pro Ser Asn Leu Phe Leu Ala Lys Ala Trp Phe Leu
    130                 135                 140

Ser Asp Gln Arg Met Thr Arg Ser Arg Ser Ser Glu Leu Arg Arg Arg
145                 150                 155                 160

Tyr Ser Glu Met Gln Asn Gly Leu Ala Thr Gln Gly Ile Glu Ser Ile
                165                 170                 175

Cys Met Asp Pro Gln His Gly Ala Glu Ala Thr Lys Gln Glu Val Ala
            180                 185                 190

Asn Phe Asn Gly Tyr Asn Tyr Leu Ser Met Cys Glu Leu Pro Ser Gln
        195                 200                 205

Lys Gly Ser Phe Met Ser Pro Ser Asn Ser Cys Ser Ser Asn Phe Asn
    210                 215                 220

Thr Pro Gln Phe Gly Asp Met Asp Lys Val Ser Ser Cys Val Ser Met
225                 230                 235                 240

Leu Lys Gly Thr Leu Gln Arg Arg Leu Ser Ser Gln Leu Glu Lys
                245                 250                 255

Glu Ala Ala Glu Asp Asp Leu Asn Gly Ile Phe Tyr Pro Gln Glu Pro
            260                 265                 270

Leu Phe Gln Thr Gly Phe Asp Gln Gly Gln Glu Asn Trp Ser Asn Gln
        275                 280                 285

Thr Pro Val Asn Val Gln Val Asp Ser Ile Gly Glu Val Lys Asp His
    290                 295                 300

Gly Val Leu Gln Thr Leu Glu Gly Ser Thr Asn Pro Val Val Asp Gly
305                 310                 315                 320

Phe Ala Asn Gln Ile Asn Gln Ile Tyr Val Gly Thr Ala Ser Gly Glu
                325                 330                 335

Pro Ser Gln Ser Glu Ser Ser Asn Ala Ala Pro Val Ile Ser Ser Gly
            340                 345                 350

Leu Asp Thr Cys Glu Gly Pro Ile Asn Ser Asn Gln Thr Leu Cys Glu
        355                 360                 365

Ser Ser Trp Lys Gln Val Gly Val Ser Lys Ser Glu Asn Thr Gln
    370                 375                 380

Asn Arg Val Lys Gly Phe Arg Glu Gln Ile Met Asp Asn Leu Lys Asp
385                 390                 395                 400

Asp Lys Lys Arg Lys Ser Leu Glu Arg Tyr Gly Ser Ile Thr Ser Ala
                405                 410                 415
```

-continued

```
Val Ser Asp Asp Lys Gly Asp Thr Thr Lys Lys Arg Arg Val Glu Arg
            420                 425                 430

Ser Arg Lys Met Ala Glu Ala Lys Glu Arg Asn Ser Thr Pro Ser Val
        435                 440                 445

Pro Ser Asp Met Gln Ala Val Leu Lys Arg Cys Glu Asn Leu Glu Lys
        450                 455                 460

Glu Val Arg Ser Leu Lys Leu Asn Leu Ser Phe Met Asn Arg Lys Asp
465                 470                 475                 480

Ser Glu Gln Thr Lys Gln Ile Glu Asp Leu Gln Lys Gln Asn Glu Glu
                485                 490                 495

Leu Ala Asp Glu Lys Glu Arg Leu Leu Glu Glu Ile Glu Arg Ile Leu
            500                 505                 510

Ser Glu Thr Glu Lys Met
        515

<210> SEQ ID NO 12
<211> LENGTH: 513
<212> TYPE: PRT
<213> ORGANISM: Pisum sativum

<400> SEQUENCE: 12

Met Glu Gly Arg Gly Phe Ser Gly Leu Tyr Lys Asn Ser Ser Glu Glu
1               5                   10                  15

Leu Phe Leu Lys Thr Val Met Glu Ser Pro Ile Gly Met Pro Val Pro
                20                  25                  30

Thr Met Glu Met Leu Gly Phe Lys Thr Val Ser Gln Ser Phe Arg Ala
            35                  40                  45

Asp Ser Glu Glu Leu Phe Lys Arg Trp Leu Thr Asn Glu Glu Gly Tyr
        50                  55                  60

Asn Ser Thr Ser Met Gly Leu Asn Ser Arg Leu Ser Lys Arg Ile Ser
65                  70                  75                  80

Thr Glu Leu Val Asn Val Ser Asn Gln Gln His Val Gly Val Ala Ser
                85                  90                  95

Glu Gly Arg Asn Asn Asp Lys Ser Cys Leu Gln Asn Ser Phe Leu Thr
            100                 105                 110

Asn Asp Val Ser Gly Asp Phe Asn Phe Pro Ile Arg Glu Pro Val Asp
        115                 120                 125

Arg Glu Leu Gln Ser Gly Asn Leu Phe Leu Ala Lys Ala Trp Phe Leu
130                 135                 140

Thr Asp Gln Arg Met Thr Arg Ser Arg Ser Glu Leu Arg Arg Arg
145                 150                 155                 160

Tyr Thr Glu Met Gln Asn Thr Gln Ala Pro Gln Gly Leu Asp Ser Met
                165                 170                 175

Phe Met Ala Pro Lys His Asp Ala Asn Ile Ile Lys Glu Glu Leu Ala
            180                 185                 190

His Phe Asn Gly Phe Asp Tyr Leu Ser Met Cys Glu Ile Pro Ser Gln
        195                 200                 205

Lys Gly Ser Phe Met Ser Pro Ser Asn Ser Ser Ser Thr Phe Asn
    210                 215                 220

Thr Gln Gln Leu Val Asp Val Asp Lys Val Ser Ser Cys Val Ser Met
225                 230                 235                 240

Leu Lys Gly Thr Leu Gln Arg Lys Arg Leu Glu Cys Gln Val Glu Lys
                245                 250                 255

Asp Ala Ala Glu Asp Gly Leu Asn Glu Ile Phe Gly Ile Arg Glu Pro
```

```
            260                 265                 270
Leu Phe Gln Ser Gly Phe Asn Glu Gly Gln Glu Asn Trp Asn His Gln
        275                 280                 285

Lys Leu Val Asn Val Gln Gly Asp Phe Thr Asp Gln Val Lys Asp Thr
290                 295                 300

Gly Val Ile Glu Thr Leu Gly Ala Ala Asn Phe Val Leu Glu Gly
305                 310                 315                 320

Phe Ala Asn Gln Thr Ser Gln Ile His Gly Gly Thr Ala Ser Gly Glu
                325                 330                 335

Pro Ser Gln Ser Glu Ser Ser Ala Ala Pro Val Ile Ser Ser Gly
            340                 345                 350

Leu Asp Ala Cys Glu Gly Pro Ser Asn Ser Ser Gln Thr Leu Cys Asp
        355                 360                 365

Ser Ser Trp Lys Gln Val Gly Glu Ser Thr Gln Asn Arg Ala Lys Gly
        370                 375                 380

Val Arg Glu Gln Ile Met Asp Asn Leu Lys Asp Asp Arg Lys Arg Lys
385                 390                 395                 400

Arg Leu Glu Arg Tyr Gly Ser Val Thr Ser Ala Val Ser Asp Asp Lys
                405                 410                 415

Val Asp Thr Thr Lys Lys Arg Arg Val Glu Arg Ser Arg Lys Met Ala
            420                 425                 430

Glu Ala Lys Glu Arg Asn Leu Thr Pro Thr Ile Pro Ser Asp Met Gln
        435                 440                 445

Ala Val Met Lys Arg Cys Glu Asn Leu Glu Lys Glu Val Arg Ser Leu
    450                 455                 460

Lys Leu Asn Leu Ser Phe Met Asn Arg Lys Asp Ser Glu Gln Thr Lys
465                 470                 475                 480

Gln Ile Glu Asp Leu Gln Lys Gln Asn Glu Glu Leu Ala Asp Glu Lys
                485                 490                 495

Glu Arg Leu Leu Glu Glu Ile Glu Arg Leu Ser Glu Thr Gly Lys
            500                 505                 510

Ile
```

<210> SEQ ID NO 13
<211> LENGTH: 525
<212> TYPE: PRT
<213> ORGANISM: Solanum lycopersicum

<400> SEQUENCE: 13

```
Met Glu Met Glu Gly Arg Gly Tyr Ser Asp Phe Tyr Arg Asn Thr Ser
1               5                   10                  15

Glu Glu Leu Phe Ile Arg Thr Met Met Asp Asn Ser Val Gly Gly Val
            20                  25                  30

Pro Val Pro Thr Met Glu Met Leu Gly Phe Arg Asn Ile Pro His Ser
        35                  40                  45

Leu Arg Thr Asp Ser Glu Glu Leu Phe Lys Ser Trp Leu Thr Ser Ala
    50                  55                  60

Glu Asn Asn Gly Ser Asp Ser Thr Pro Met Ala Arg Gly Arg Gln Gly
65                  70                  75                  80

Ser Arg Arg Ile Ser Ser Glu Leu Ala Gly Leu Ser Ser Gln Gln Asn
                85                  90                  95

Glu Gly Ile Gln Lys Arg Lys Met Ala Asp Thr Gln Gln Pro Gln Asn
            100                 105                 110

Thr Cys Thr Ala Ile Glu Ser Ser Ser Asn Leu Asn Lys His Ser Thr
```

```
            115                 120                 125
Arg Asn Ala Thr Asp Arg Glu Met Gln Ala Ser Asn Leu Phe Leu Ala
130                 135                 140

Lys Thr Trp Phe His Ser Ser Gln Pro Met Thr Arg Ser Arg Ser Ser
145                 150                 155                 160

Glu Leu Arg Arg Arg Tyr Ala Ala Met Gln Asn Ser Gln Ser Ser Leu
                165                 170                 175

Ala Arg Glu Ser Leu Gln Asn Ile Pro Gly Asn Ala Val Asn Ser Phe
            180                 185                 190

Lys Glu Glu Val Ser His Pro Thr Gly Tyr Thr Asp Met Ser Met Cys
        195                 200                 205

Glu Met Thr Asn Gln Pro Asn Thr Phe Met Ser Pro Ser Asn Ser Ser
210                 215                 220

Ser Ser Thr Phe Glu Ala Gln Gln Val Asp Gly Val Asp Asn Ile Ser
225                 230                 235                 240

Ser Val Val Ser Met Leu Lys Gly Thr Leu Glu Arg Lys Lys Leu Thr
                245                 250                 255

Asn Tyr His Thr Ala Arg Glu Ala Ile Glu Glu Asn Met Leu Gly Cys
            260                 265                 270

Tyr Gly Asn Gln Glu Ile Phe Cys Asn Ser Asp Met Asn Gln His Pro
        275                 280                 285

Gly Asn His Ile Ser Leu Asn Gln Gly Thr Tyr Gln Asp Thr Pro Val
    290                 295                 300

Val Gln Val Arg Asp Thr Gly Ile Pro Gln Thr Val Gln Gly Ser Leu
305                 310                 315                 320

Asp Ala Val Leu Glu Ser Ile Met Ala Pro Ser Asn Pro Ile Gln Ile
                325                 330                 335

Asp Met Val Thr Gln Glu Pro Ser Gln Ser Gly Ser Ser Val Ala Ala
            340                 345                 350

Pro Ile Leu Ser Ile Asp Phe Asp Ala Tyr Asp Gly Leu Ser Asn Ala
        355                 360                 365

Ser Gln Ala Leu Asn Met Tyr Glu Gly Cys Arg Asn Gln Val Gly Tyr
    370                 375                 380

Gly Arg Ser Ser Glu Asn Gly Ser Thr Ala Arg Asp Ile Arg Glu Arg
385                 390                 395                 400

Ile Tyr Asp Asn Val Lys Asp Asn Gln Lys Lys Glu Gly Leu Val Arg
                405                 410                 415

Asn Gly Ser Leu Thr Ser Val Gln Ser Ala Glu Asn Gly Asp Pro Lys
            420                 425                 430

Lys Lys Arg Arg Val Glu Arg Ser Arg Lys Met Ala Glu Ala Lys Glu
        435                 440                 445

Arg Asn Leu Thr Pro Ala Ile Pro Ser Asp Met Gln Ser Leu Val Lys
    450                 455                 460

Arg Cys Asp Asn Leu Glu Lys Glu Val Arg Ser Leu Lys Leu Asn Leu
465                 470                 475                 480

Ala Phe Met Asn Arg Lys Asp Ser Glu Gln Thr Thr Gln Ile Glu Glu
                485                 490                 495

Leu Gln Lys Gln Asn Glu Asp Leu Val Lys Glu Lys Arg Leu Leu
            500                 505                 510

Gly Glu Ile Glu Arg Ile Ile Ser Glu Ser Gly Lys Phe
        515                 520                 525

<210> SEQ ID NO 14
```

```
<211> LENGTH: 588
<212> TYPE: PRT
<213> ORGANISM: Diphasiastrum digitatum

<400> SEQUENCE: 14
```

| | | | | | | | | | | | | | | |
|---|---|---|---|---|---|---|---|---|---|---|---|---|---|---|
| Met | Val | Glu | Ile | Ala | Asp | Arg | Arg | Ile | Thr | Arg | Ser | Val | Ser | Glu |
| 1 | | | | 5 | | | | | 10 | | | | | 15 |
| Leu | Gln | Ala | Arg | Leu | Ser | Thr | Gln | Pro | Gln | Thr | Gln | Glu | Gly | Val | Glu |
| | | | 20 | | | | | 25 | | | | | 30 | | |
| Glu | Ile | Arg | Ala | Val | Ser | Gly | Asp | Met | Glu | Ile | Ser | Cys | Phe | Gln | Arg |
| | | 35 | | | | | 40 | | | | | 45 | | | |
| Asn | Ser | Ser | Glu | Glu | Ile | Phe | Leu | Arg | Ser | Phe | Met | Asp | Gly | Ala | Met |
| | 50 | | | | | 55 | | | | | 60 | | | | |
| Ala | Pro | Ala | Thr | Glu | Gly | Met | Ser | Phe | Leu | Ser | Pro | Gln | Pro | Pro |
| 65 | | | | | 70 | | | | | 75 | | | | | 80 |
| Leu | Arg | Val | Asn | Ser | Glu | Glu | Leu | Phe | Asn | Thr | Trp | Leu | Ser | Asn | Thr |
| | | | | 85 | | | | | 90 | | | | | 95 | |
| Asp | Ala | Pro | Gly | Leu | Pro | Pro | Leu | Ser | Gly | Asp | Tyr | Arg | Thr | Leu | Gln |
| | | | 100 | | | | | 105 | | | | | 110 | | |
| Asn | Ser | Cys | Arg | Met | Ser | Ser | Glu | Leu | Ala | Gly | Asn | Leu | Gly | Gln | Gly |
| | | 115 | | | | | 120 | | | | | 125 | | | |
| Ala | Val | Ser | Gln | Pro | Phe | Asp | Ile | Pro | Gly | Glu | Asn | Val | Ala | Gln | Thr |
| | 130 | | | | | 135 | | | | | 140 | | | | |
| Ile | Gly | Gly | His | Pro | Asp | Pro | Asn | Val | Arg | Glu | Ser | Asn | Ile | Gly | Lys |
| 145 | | | | | 150 | | | | | 155 | | | | | 160 |
| Pro | Arg | Asn | His | Ala | Pro | Ser | Lys | Gly | Leu | Pro | Phe | Gln | Asp | His | Ala |
| | | | | 165 | | | | | 170 | | | | | 175 | |
| Ser | Trp | Gln | Met | Ile | Asn | Trp | Phe | Gln | Gln | Ser | Gln | Pro | Met | Thr | Arg |
| | | | 180 | | | | | 185 | | | | | 190 | | |
| Ser | Arg | Ser | Ser | Glu | Leu | Arg | Arg | Lys | Tyr | Leu | Ala | Met | Gln | Glu | Gly |
| | | 195 | | | | | 200 | | | | | 205 | | | |
| His | Lys | Pro | Pro | Pro | Ser | Ala | Asn | Thr | Leu | Gln | Trp | Phe | Ala | Thr | Gln |
| | 210 | | | | | 215 | | | | | 220 | | | | |
| Gly | Thr | Asp | Glu | Leu | Asn | Arg | Ala | Val | Ala | Ser | Leu | Gly | Ala | Phe | Thr |
| 225 | | | | | 230 | | | | | 235 | | | | | 240 |
| Arg | Ala | Leu | Ala | Ser | Lys | Arg | Pro | Asp | Ile | Ser | Ser | Thr | Ala | Ser | Pro |
| | | | | 245 | | | | | 250 | | | | | 255 | |
| Gln | Leu | Ser | Pro | Thr | Pro | Met | Ser | His | Val | Ser | Lys | Leu | Ser | Pro | Gln |
| | | | 260 | | | | | 265 | | | | | 270 | | |
| Arg | Asn | Gly | Asp | Ser | Val | Ser | Ala | Val | Val | Asn | Met | Leu | Lys | Gly | Ser |
| | | 275 | | | | | 280 | | | | | 285 | | | |
| Leu | Glu | Arg | Lys | Lys | Leu | Ala | Ala | Met | Gln | Gln | Gln | Met | Asp | Lys | Pro |
| | 290 | | | | | 295 | | | | | 300 | | | | |
| Val | Ser | Pro | Pro | Tyr | Trp | Arg | Ser | Leu | Gly | Gln | Asp | Lys | Glu | Asp | Pro |
| 305 | | | | | 310 | | | | | 315 | | | | | 320 |
| His | Lys | Pro | Met | Ile | Asp | Ser | Gln | Gln | Cys | Ile | Ser | Pro | Gln | Ile | Glu |
| | | | | 325 | | | | | 330 | | | | | 335 | |
| Ser | Glu | Gln | Gln | Gln | Glu | Asn | Gln | Lys | Glu | Ala | Phe | Ser | Ala | Ser | Leu |
| | | | 340 | | | | | 345 | | | | | 350 | | |
| Gln | Ile | Thr | Asn | Glu | Gln | Phe | Gln | Ala | Gly | Val | Val | Thr | Pro | His | Ala |
| | | 355 | | | | | 360 | | | | | 365 | | | |
| Leu | Ser | Pro | Ser | Asp | Ser | Ser | Gly | Asn | Ala | Pro | Gly | Leu | Ser | Ala | Gly |
| | 370 | | | | | 375 | | | | | 380 | | | | |
| Ala | Ala | Thr | Ser | Glu | Gly | Pro | Cys | Asn | Ser | Asn | Pro | Ala | Val | Ser | Thr |

```
385                 390                 395                 400
    Gln Asn Asn Phe Ile Lys Cys Ser Gly Gln Gly Asn Trp Ala Val Asp
                    405                 410                 415

Glu Thr Phe Gln Gln Asn Asn Leu Pro Ser Pro Thr Ser Asn Gly Thr
                    420                 425                 430

Ser Asn Gly Glu Ile Pro Tyr Glu Gly Val Leu Asn Thr Asp Tyr Gln
                    435                 440                 445

Lys Arg Gln Gly Tyr Leu Ser Arg Ala Gly Ser Leu Thr Ser Ser Cys
                    450                 455                 460

Arg Ser Asp Gln Ser Met Gln Val Ser Ile Gly Glu Arg Thr His Lys
    465                 470                 475                 480

Leu Glu Gly Ser Thr Ala Asp Ala Glu Asp Ser Thr Lys Lys Arg Arg
                    485                 490                 495

Val Glu Arg Lys Arg Met Met Ala Glu Ala Lys Gly Arg Ser Tyr Val
                    500                 505                 510

Pro Met Met Pro Ser Asp Leu Gln Ala Ala Thr Lys Arg Cys Asp Ala
                    515                 520                 525

Leu Glu Lys Glu Val Arg Ser Leu Lys Leu Asn Leu Ser Phe Met Asn
                    530                 535                 540

Arg Lys Asp Ser Glu Gln Thr Lys Arg Ile Glu Asp Leu Glu Lys Gln
    545                 550                 555                 560

Asn Glu Glu Leu Leu Ala Glu Lys Asp Arg Leu Val Glu Glu Val Arg
                    565                 570                 575

Arg Phe Thr Ser Gly Lys Asn Phe Gly Arg Ser Ser
                    580                 585

<210> SEQ ID NO 15
<211> LENGTH: 513
<212> TYPE: PRT
<213> ORGANISM: Artificial
<220> FEATURE:
<223> OTHER INFORMATION: Modified IPD3 polypeptide

<400> SEQUENCE: 15

Met Glu Gly Arg Gly Phe Ser Gly Leu Tyr Lys Asn Ser Ser Glu Glu
1               5                   10                  15

Leu Phe Leu Lys Thr Val Met Glu Ser Pro Ile Gly Met Pro Val Pro
                20                  25                  30

Thr Met Glu Met Leu Gly Phe Lys Thr Val Ser Gln Ser Phe Arg Thr
            35                  40                  45

Asp Asp Glu Glu Leu Phe Lys Arg Trp Leu Thr Asn Asp Gln Glu Gly
        50                  55                  60

Tyr Asn Ser Ser Met Gly Leu Asn Ser Arg Leu Ser Lys Arg Ile
65                  70                  75                  80

Ser Thr Glu Ile Ala Asn Met Ser Asn Gln Gln His Ile Gly Val Ala
                85                  90                  95

Ser Glu Gly Arg Asn Asn Asp Lys Ser Cys Leu Gln Asn Asn Phe Leu
            100                 105                 110

Ala Asn Asp Val Ser Ser Asp Phe Asn Phe Pro Ile Arg Asp Pro Val
        115                 120                 125

Asp Arg Glu Leu Gln Ser Ser Asn Leu Phe Leu Ala Lys Ala Trp Phe
    130                 135                 140

Ile Thr Asp Gln Arg Met Thr Arg Ser Arg Ser Ser Glu Leu Arg Arg
145                 150                 155                 160

Arg Tyr Thr Glu Met Gln Asn Ser Gln Ala Pro Gln Gly Leu Asp Ser
```

```
                165                 170                 175
Met Phe Met Val Pro Glu His Asp Thr Asn Thr Ile Lys Glu Glu Leu
            180                 185                 190

Ala Asn Phe Asn Gly Phe Asp Tyr Leu Ser Met Cys Glu Leu Pro Ser
        195                 200                 205

Gln Lys Gly Thr Phe Met Ser Pro Ser Asn Ser Ser Ser Thr Phe
    210                 215                 220

Asn Thr His Gln Leu Val Asp Val Asp Lys Val Ser Ser Cys Val Ser
225                 230                 235                 240

Met Leu Lys Gly Thr Leu Gln Arg Lys Lys Leu Glu Cys Gln Val Glu
            245                 250                 255

Lys Glu Ala Ala Glu Asp Gly Leu Asn Glu Ile Phe Cys Ile Arg Glu
        260                 265                 270

Pro Leu Phe Gln Ser Ala Phe Asn Glu Glu Ser Trp Asn Gln Gln
    275                 280                 285

Lys Leu Val Asn Val Gln Gly Asp Phe Thr Asp Gln Val Asn Asp Pro
        290                 295                 300

Gly Val Met Gln Thr Leu Glu Gly Thr Thr Asn Phe Val Leu Asp Gly
305                 310                 315                 320

Phe Ala Asn Gln Thr Asn Gln Ile Gln Gly Arg Thr Ala Ser Gly Glu
            325                 330                 335

Pro Ser Gln Ser Glu Ser Ser Ala Ala Ala Pro Val Ile Ser Ser Gly
        340                 345                 350

Leu Asp Ala Cys Glu Gly Pro Ser Asn Ser Asn Gln Thr Leu Gly Asp
        355                 360                 365

Ser Ser Trp Lys Gln Val Gly Glu Ser Thr Gln Asn Lys Val Arg Gly
    370                 375                 380

Val Arg Glu Gln Ile Met Asp Asn Leu Lys Asp Asp Arg Lys Arg Lys
385                 390                 395                 400

Ser Leu Glu Arg Tyr Gly Ser Val Thr Ser Ala Val Ser Asp Gly Lys
            405                 410                 415

Met Asp Asn Thr Lys Lys Arg Arg Val Glu Arg Ser Arg Lys Met Ala
        420                 425                 430

Glu Ala Lys Glu Arg Asn Leu Thr Pro Thr Ile Pro Ser Asp Met Gln
    435                 440                 445

Ala Ile Leu Lys Arg Cys Glu Asn Leu Glu Lys Glu Val Arg Ser Leu
        450                 455                 460

Lys Leu Asn Leu Ser Phe Met Asn Arg Lys Asp Ser Glu Gln Thr Lys
465                 470                 475                 480

Gln Ile Glu Asp Leu Gln Lys Gln Asn Glu Asp Leu Ala Asp Glu Lys
            485                 490                 495

Glu Arg Leu Leu Glu Glu Ile Glu Arg Ile Leu Ser Glu Thr Gly Lys
        500                 505                 510

Ile

<210> SEQ ID NO 16
<211> LENGTH: 513
<212> TYPE: PRT
<213> ORGANISM: Artificial
<220> FEATURE:
<223> OTHER INFORMATION: Modified IPD3 polypeptide

<400> SEQUENCE: 16

Met Glu Gly Arg Gly Phe Ser Gly Leu Tyr Lys Asn Ser Ser Glu Glu
1               5                   10                  15
```

```
Leu Phe Leu Lys Thr Val Met Glu Ser Pro Ile Gly Met Pro Val Pro
            20                  25                  30

Thr Met Glu Met Leu Gly Phe Lys Thr Val Glu Gln Ser Phe Arg Thr
        35                  40                  45

Asp Ser Glu Glu Leu Phe Lys Arg Trp Leu Thr Asn Asp Gln Glu Gly
 50                  55                  60

Tyr Asn Ser Ser Ser Met Gly Leu Asn Ser Arg Leu Ser Lys Arg Ile
 65                  70                  75                  80

Ser Thr Glu Ile Ala Asn Met Ser Asn Gln Gln His Ile Gly Val Ala
                85                  90                  95

Ser Glu Gly Arg Asn Asn Asp Lys Ser Cys Leu Gln Asn Asn Phe Leu
            100                 105                 110

Ala Asn Asp Val Ser Ser Asp Phe Asn Phe Pro Ile Arg Asp Pro Val
        115                 120                 125

Asp Arg Glu Leu Gln Ser Ser Asn Leu Phe Leu Ala Lys Ala Trp Phe
130                 135                 140

Ile Thr Asp Gln Arg Met Thr Arg Ser Arg Ser Glu Leu Arg Arg
145                 150                 155                 160

Arg Tyr Thr Glu Met Gln Asn Ser Gln Ala Pro Gln Gly Leu Asp Ser
                165                 170                 175

Met Phe Met Val Pro Glu His Asp Thr Asn Thr Ile Lys Glu Glu Leu
            180                 185                 190

Ala Asn Phe Asn Gly Phe Asp Tyr Leu Ser Met Cys Glu Leu Pro Ser
        195                 200                 205

Gln Lys Gly Thr Phe Met Ser Pro Ser Asn Ser Ser Ser Thr Phe
210                 215                 220

Asn Thr His Gln Leu Val Asp Val Asp Lys Val Ser Ser Cys Val Ser
225                 230                 235                 240

Met Leu Lys Gly Thr Leu Gln Arg Lys Lys Leu Glu Cys Gln Val Glu
                245                 250                 255

Lys Glu Ala Ala Glu Asp Gly Leu Asn Glu Ile Phe Cys Ile Arg Glu
            260                 265                 270

Pro Leu Phe Gln Ser Ala Phe Asn Glu Glu Ser Trp Asn Gln Gln
        275                 280                 285

Lys Leu Val Asn Val Gln Gly Asp Phe Thr Asp Gln Val Asn Asp Pro
290                 295                 300

Gly Val Met Gln Thr Leu Glu Gly Thr Thr Asn Phe Val Leu Asp Gly
305                 310                 315                 320

Phe Ala Asn Gln Thr Asn Gln Ile Gln Gly Arg Thr Ala Ser Gly Glu
                325                 330                 335

Pro Ser Gln Ser Glu Ser Ser Ala Ala Ala Pro Val Ile Ser Ser Gly
            340                 345                 350

Leu Asp Ala Cys Glu Gly Pro Ser Asn Ser Asn Gln Thr Leu Gly Asp
        355                 360                 365

Ser Ser Trp Lys Gln Val Gly Glu Ser Thr Gln Asn Lys Val Arg Gly
370                 375                 380

Val Arg Glu Gln Ile Met Asp Asn Leu Lys Asp Asp Arg Lys Arg Lys
385                 390                 395                 400

Ser Leu Glu Arg Tyr Gly Ser Val Thr Ser Ala Val Ser Asp Gly Lys
                405                 410                 415

Met Asp Asn Thr Lys Lys Arg Arg Val Glu Arg Ser Arg Lys Met Ala
            420                 425                 430
```

```
Glu Ala Lys Glu Arg Asn Leu Thr Pro Thr Ile Pro Ser Asp Met Gln
            435                 440                 445

Ala Ile Leu Lys Arg Cys Glu Asn Leu Glu Lys Glu Val Arg Ser Leu
450                 455                 460

Lys Leu Asn Leu Ser Phe Met Asn Arg Lys Asp Ser Glu Gln Thr Lys
465                 470                 475                 480

Gln Ile Glu Asp Leu Gln Lys Gln Asn Glu Asp Leu Ala Asp Glu Lys
                485                 490                 495

Glu Arg Leu Leu Glu Glu Ile Glu Arg Ile Leu Ser Glu Thr Gly Lys
            500                 505                 510

Ile
```

<210> SEQ ID NO 17
<211> LENGTH: 518
<212> TYPE: PRT
<213> ORGANISM: Artificial
<220> FEATURE:
<223> OTHER INFORMATION: Modified IPD3 polypeptide

<400> SEQUENCE: 17

```
Met Glu Gly Arg Gly Phe Ser Gly Leu Tyr Arg Asn Ser Ser Glu Glu
1               5                   10                  15

Leu Phe Leu Lys Thr Val Met Glu Ser Pro Ile Gly Met Pro Val Pro
            20                  25                  30

Ser Met Glu Met Leu Gly Phe Lys Asn Val Ser Gln Gly Phe Arg Ala
        35                  40                  45

Asp Ser Glu Glu Leu Phe Lys Arg Trp Leu Thr Asn Gly Glu Gly Tyr
    50                  55                  60

Asn Ser Ser Ser Ile Gly Phe Ser Ser Arg Leu Ser Lys Arg Ile Ser
65                  70                  75                  80

Thr Glu Leu Val Asn Gly Ser Asn Gln Leu Gln Val Gly Val Ala Ser
                85                  90                  95

Asp Gly Arg Asn Asn Asp Lys Pro Phe Ile Gln Asn Asn Leu Leu Ala
            100                 105                 110

Asn Asp Val Ser Gly Asp Phe Asn Phe Pro Ile Arg Asp Pro Val Asp
        115                 120                 125

Arg Glu Leu Gln Pro Ser Asn Leu Phe Leu Ala Lys Ala Trp Phe Leu
    130                 135                 140

Ser Asp Gln Arg Met Thr Arg Ser Arg Asp Ser Glu Leu Arg Arg Arg
145                 150                 155                 160

Tyr Ser Glu Met Gln Asn Gly Leu Ala Thr Gln Gly Ile Glu Ser Ile
                165                 170                 175

Cys Met Asp Pro Gln His Gly Ala Glu Ala Thr Lys Gln Glu Val Ala
            180                 185                 190

Asn Phe Asn Gly Tyr Asn Tyr Leu Ser Met Cys Glu Leu Pro Ser Gln
        195                 200                 205

Lys Gly Ser Phe Met Ser Pro Ser Asn Ser Cys Ser Asn Phe Asn
    210                 215                 220

Thr Pro Gln Phe Gly Asp Met Asp Lys Val Ser Ser Cys Val Ser Met
225                 230                 235                 240

Leu Lys Gly Thr Leu Gln Arg Arg Leu Ser Ser Gln Leu Glu Lys
                245                 250                 255

Glu Ala Ala Glu Asp Asp Leu Asn Gly Ile Phe Tyr Pro Gln Glu Pro
            260                 265                 270

Leu Phe Gln Thr Gly Phe Asp Gln Gly Gln Glu Asn Trp Ser Asn Gln
```

```
                 275                 280                 285
        Thr Pro Val Asn Val Gln Val Asp Ser Ile Gly Glu Val Lys Asp His
        290                 295                 300

Gly Val Leu Gln Thr Leu Glu Gly Ser Thr Asn Pro Val Val Asp Gly
    305                 310                 315                 320

Phe Ala Asn Gln Ile Asn Gln Ile Tyr Val Gly Thr Ala Ser Gly Glu
                        325                 330                 335

Pro Ser Gln Ser Glu Ser Ser Asn Ala Ala Pro Val Ile Ser Ser Gly
                        340                 345                 350

Leu Asp Thr Cys Glu Gly Pro Ile Asn Ser Asn Gln Thr Leu Cys Glu
                        355                 360                 365

Ser Ser Trp Lys Gln Val Gly Val Ser Lys Ser Glu Asn Thr Gln
                        370                 375                 380

Asn Arg Val Lys Gly Phe Arg Glu Gln Ile Met Asp Asn Leu Lys Asp
    385                 390                 395                 400

Asp Lys Lys Arg Lys Ser Leu Glu Arg Tyr Gly Ser Ile Thr Ser Ala
                        405                 410                 415

Val Ser Asp Asp Lys Gly Asp Thr Thr Lys Arg Arg Val Glu Arg
                        420                 425                 430

Ser Arg Lys Met Ala Glu Ala Lys Glu Arg Asn Ser Thr Pro Ser Val
                        435                 440                 445

Pro Ser Asp Met Gln Ala Val Leu Lys Arg Cys Glu Asn Leu Glu Lys
        450                 455                 460

Glu Val Arg Ser Leu Lys Leu Asn Leu Ser Phe Met Asn Arg Lys Asp
    465                 470                 475                 480

Ser Glu Gln Thr Lys Gln Ile Glu Asp Leu Gln Lys Gln Asn Glu Glu
                        485                 490                 495

Leu Ala Asp Glu Lys Glu Arg Leu Leu Glu Glu Ile Glu Arg Ile Leu
                        500                 505                 510

Ser Glu Thr Glu Lys Met
                        515

<210> SEQ ID NO 18
<211> LENGTH: 513
<212> TYPE: PRT
<213> ORGANISM: Artificial
<220> FEATURE:
<223> OTHER INFORMATION: Modified IPD3 polypeptide

<400> SEQUENCE: 18

Met Glu Gly Arg Gly Phe Ser Gly Leu Tyr Lys Asn Ser Ser Glu Glu
    1                   5                   10                  15

Leu Phe Leu Lys Thr Val Met Glu Ser Pro Ile Gly Met Pro Val Pro
                        20                  25                  30

Thr Met Glu Met Leu Gly Phe Lys Thr Val Glu Gln Ser Phe Arg Thr
                        35                  40                  45

Asp Asp Glu Glu Leu Phe Lys Arg Trp Leu Thr Asn Asp Gln Glu Gly
        50                  55                  60

Tyr Asn Ser Ser Met Gly Leu Asn Ser Arg Leu Ser Lys Arg Ile
    65                  70                  75                  80

Ser Thr Glu Ile Ala Asn Met Ser Asn Gln Gln His Ile Gly Val Ala
                        85                  90                  95

Ser Glu Gly Arg Asn Asn Asp Lys Ser Cys Leu Gln Asn Asn Phe Leu
                        100                 105                 110

Ala Asn Asp Val Ser Ser Asp Phe Asn Phe Pro Ile Arg Asp Pro Val
```

```
            115                 120                 125
Asp Arg Glu Leu Gln Ser Ser Asn Leu Phe Leu Ala Lys Ala Trp Phe
    130                 135                 140

Ile Thr Asp Gln Arg Met Thr Arg Ser Arg Ser Ser Glu Leu Arg Arg
145                 150                 155                 160

Arg Tyr Thr Glu Met Gln Asn Ser Gln Ala Pro Gln Gly Leu Asp Ser
                165                 170                 175

Met Phe Met Val Pro Glu His Asp Thr Asn Thr Ile Lys Glu Glu Leu
            180                 185                 190

Ala Asn Phe Asn Gly Phe Asp Tyr Leu Ser Met Cys Glu Leu Pro Ser
        195                 200                 205

Gln Lys Gly Thr Phe Met Ser Pro Ser Asn Ser Ser Ser Thr Phe
    210                 215                 220

Asn Thr His Gln Leu Val Asp Val Asp Lys Val Ser Ser Cys Val Ser
225                 230                 235                 240

Met Leu Lys Gly Thr Leu Gln Arg Lys Lys Leu Glu Cys Gln Val Glu
                245                 250                 255

Lys Glu Ala Ala Glu Asp Gly Leu Asn Glu Ile Phe Cys Ile Arg Glu
                260                 265                 270

Pro Leu Phe Gln Ser Ala Phe Asn Glu Glu Ser Trp Asn Gln Gln
            275                 280                 285

Lys Leu Val Asn Val Gln Gly Asp Phe Thr Asp Gln Val Asn Asp Pro
    290                 295                 300

Gly Val Met Gln Thr Leu Glu Gly Thr Thr Asn Phe Val Leu Asp Gly
305                 310                 315                 320

Phe Ala Asn Gln Thr Asn Gln Ile Gln Gly Arg Thr Ala Ser Gly Glu
                325                 330                 335

Pro Ser Gln Ser Glu Ser Ser Ala Ala Pro Val Ile Ser Ser Gly
            340                 345                 350

Leu Asp Ala Cys Glu Gly Pro Ser Asn Ser Asn Gln Thr Leu Gly Asp
        355                 360                 365

Ser Ser Trp Lys Gln Val Gly Glu Ser Thr Gln Asn Lys Val Arg Gly
    370                 375                 380

Val Arg Glu Gln Ile Met Asp Asn Leu Lys Asp Asp Arg Lys Arg Lys
385                 390                 395                 400

Ser Leu Glu Arg Tyr Gly Ser Val Thr Ser Ala Val Ser Asp Gly Lys
                405                 410                 415

Met Asp Asn Thr Lys Lys Arg Val Glu Arg Ser Arg Lys Met Ala
            420                 425                 430

Glu Ala Lys Glu Arg Asn Leu Thr Pro Thr Ile Pro Ser Asp Met Gln
        435                 440                 445

Ala Ile Leu Lys Arg Cys Glu Asn Leu Glu Lys Glu Val Arg Ser Leu
    450                 455                 460

Lys Leu Asn Leu Ser Phe Met Asn Arg Lys Asp Ser Glu Gln Thr Lys
465                 470                 475                 480

Gln Ile Glu Asp Leu Gln Lys Gln Asn Glu Asp Leu Ala Asp Glu Lys
                485                 490                 495

Glu Arg Leu Leu Glu Glu Ile Glu Arg Ile Leu Ser Gly Thr Gly Lys
            500                 505                 510

Ile
```

<210> SEQ ID NO 19
<211> LENGTH: 1572

```
<212> TYPE: DNA
<213> ORGANISM: Medicago truncatula

<400> SEQUENCE: 19
atgggatatg gaacaagaaa actctcagat gaatatgaag tttcagaaat tctaggtaga      60
ggtggatttt ctgttgttag aaaaggtaca aaaaaatcaa gcattgaaga agaaaaatca     120
caatcacaag tagcaatcaa aaccctaaga aggttaggtg cttcaaataa ccctagtgga     180
ttaccaagaa aaaagatat tggagaaaaa agcacaatag ggttccctac aatgagacaa      240
gtttcagttt cagatacatt actaacaaat gagatacttg taatgagacg aatagtcgaa     300
aacgtttcgc cacatccaaa tgtgattgat ctttatgatg tatatgagga cacaaatggt     360
gttcatcttg ttcttgagct ttgttccggt ggtgaacttt tcgataggat tgttgcacaa     420
gataagtata gtgagactga agctgcaact gtggttcatc aaatagcttc agggttagaa     480
gctgttcata gagctaatat agttcataga gatttgaaac ctgaaaattg tcttttttta     540
gatgttagga aagattctcc tcttaagatt atggattttg ggttgagttc tgttgaagag     600
tttactgatc ctgttgttgg tttgtttgga tctattgatt atgtttcacc tgaggctctt     660
tctcaaggaa agattactac taagagtgat atgtggtctc ttgggggttat tctatatatc     720
ttactttcag ggtatccacc tttcattgcc caaaataatc gccaaaaaca acaaatgata     780
atgaatggga atttagtttt ttatgagaag acttggaagg gaatttcaca accagcaaag     840
aatttgattt caagtctttt aaccgttgat cctagcaaga gacctagtgc tcttgagctt     900
ctaagtgatc catgggtcaa aggtgagaaa gccaaagatg ttcaaatgga ccctgagatt     960
gtctcaaggc tacaaagctt taatgcaaga cgtaaacttc gtgcagctgc aattgctagt    1020
gtttggagct ccacaatctt ccttagaaca aaaaaattga atcattggt tggatcctat     1080
gatcttaaag aagaggaaat tgaaaatctc aggatgcatt tcaagaagat atgtgcagat    1140
agagacaatg caactctgtc agagtttgag gaggtgttaa aagcaatgaa tatgttatca    1200
ttgatcccctt ttgcttctcg tatatttgat ttgtttgaca acaaccgtga tggaacagtt    1260
gacatgcgtg agatactttg tggatttttcc agtctcaaga attccaaagg agaggatgct    1320
cttcgtttgt gcttccagat gtatgataca gatagatcag gctgcatcag caaagaggaa    1380
gtagcatcca tgctcagggc tttgccatat gattgtcttc caactgatat cactgaacct    1440
ggaaaattgg atgagatttt tgacttaatg gatgctaata atgatggaaa agttacattt    1500
gatgaattca agctgctat gcaaagagat agctctcttc aagatgtagt tctctcttct    1560
attcgtccat aa                                                         1572

<210> SEQ ID NO 20
<211> LENGTH: 1783
<212> TYPE: DNA
<213> ORGANISM: Lotus japonicus

<400> SEQUENCE: 20
aaagattcca atattttcaa acactctgcc atgggatatg atcaaaccag aaagctctct      60
gatgagtatg agatttcaga gattctagga agaggtggat tctctgttgt cagaaaagga     120
accaaaaaat caggcaatga gaaacccaa gtagccatca aaacactcag aaggttaggt     180
agttctccct ctgggacagg tggtggacag aagagcacag caactgtgat ggggttccct     240
tctttgagac aggtttcagt ctcagatgct tgctcacca atgagattct tgtgatgagg     300
aggatagtgg aaaacgtttc gccacatcca aacgtgattg atctctatga tgtgtgtgag    360
```

```
gactcaaatg gggtgcatct tgtgctggag ctttgttctg gtggggagct gtttgatagg      420
attgttgcac aggataagta tgctgagacg gaagctgccg cggtggttcg ccagattgcg      480
gcggggctag aggcggttca caaggctgac attgttcaca gggatttgaa gcctgagaat      540
tgccttttct tggattccag gaaggactct cctctcaaga tcatggactt tggggttgagc    600 tctgttgagg agttcactga ccctgttgtt gggttgtttg gatccattga ttatgtttca      660
ccagaggctc tttctcaagg gaagatcact gccaagagtg acatgtggtc tctgggagtg     720
attctatata tcttgctctc tgggtatccg cctttcattg cacaaaataa tcgccaaaaa      780
caacaaatga taatcaatgg gaatttcagt ttctatgaga agacttggaa gggcattacc     840
caatcagcga agcaattgat ttcaagtctt ttgactgttg atccaagtaa gaggcctagt    900
gctcaagagc tcttgagtca tccatgggtc agaggtgaca aagccaaaga tgagcaaatg    960
gaccctgaga ttgtctcaag gctgcagagc tttaatgcaa gacgcaaact ccgcgcagct  1020
gcaattgcta gtgtttggag cagcacaatc ttcctgagaa ccaaaaagct gagatccttg   1080
gtaggaactt atgatctcaa agaagaggaa attgaaagtc tcaggataca ctttaagaag  1140
atatgtggaa atggagacaa tgcaactctg tctgagtttg tggaggtgct gaaagcaatg   1200
aagatgccct cattgatccc tctagcaccg cgtatatttg acttgtttga caacaaccgt   1260
gatggaacaa ttgacatgag agagatacta tgtgggtttt ctagcctcaa gaactccaaa  1320
ggagatgatg ctctccgttt gtgcttccag atgtatgaca cagatagatc agggtgcatc    1380
accaaggaag aagtagcatc catgctctgt gctttgccag aggaatgtct tccagctgat   1440
atcactgaac ctgggaaatt ggatgagata tttgacttaa tggatgccaa cagtgatgga  1500
aaagttacat ttgaagaatt caaagctgct atgcagagag atagctctct ccaagacatg   1560
ctcctctctt ctcttcgtcc atcatagttt ttttttttt ccattcatgg tgttatggtc      1620
tttcaaactt tgatattgac tacaccttttt acgtttcttt taatctcttt tggggctatc     1680
cttctctttg aggtattcat actacatgga aaaagggtgg taaagagggt gaaattgtgt   1740
catctaactt ttgctatgac aactaggaac ttttgcaaaa aaa                       1783

<210> SEQ ID NO 21
<211> LENGTH: 2094
<212> TYPE: DNA
<213> ORGANISM: Glycine max

<400> SEQUENCE: 21
tataatgcca gcagttgact ctctctttgt cccttccaga acagctccta ccagccatat       60
tgttttttct cttgtaccta tcccaatttg tttcatattt tatgtcataa actaatccac       120
aaactcttac aacaggctaa tgtcactctc aaccgtttca cacgcgtttt tgaaagcccc       180
tatcattgaa ttaaagttaa catttttta cataccaatt cccttcccac tgcacatttt        240
ctgagtcttc aagattccat aatttcaaag actttgtgtg caccacacca ccatggggaa     300
tgaaaccaga aaactctcag atgagtatga agtttcagaa gtcctaggaa gaggtggatt     360
ttctgttgtc agaaaaggca ccaaaaaatc aagcagtgac accaaaacac atgtagccat     420
caaaaccctg agaagggtag gcactgcctc aaactccaac aaccccttctg gatttccaag   480 accaaagggt ggagagaaga agagcacagc agctatgatg ggattcccca catggagaca  540
agtctcagtc tcagatgcct tgctcacaaa tgagattctt gtgatgagga gaatagtgga     600
aaatgtttca ccacacccta atgtgattga cctctatgat gtgtatgagg actcaaatgg    660
ggtgcacctt gtgttggagc tgtgttctgg tggagaactg tttgatagga ttgtggcaca    720
```

```
agataggtac tcagagactg aagctgcagg tgtggttcgc cagatagctt caggattaga    780
ggctattcat agagctaaca ttgtccacag agatttgaag cctgagaatt gccttttctt    840
ggatgtgagg agggactctc ctcttaagat catggacttt gggttgagtt ctgttgagga    900
attcactgac ccagttgttg gtttgtttgg atccattgat tacgtttcac cagaggctct    960
ttctcaaggg aagataacta ccaagagtga catgtggtct ctgggggtga ttctatatat   1020
cttgctctca gggtatccac ctttcattgc tcaaaataat cgccagaaac aacaaatgat   1080
aatgaatggg aatttcagtt tctatgagaa gacatggaag ggcattaccc gttcagcgaa   1140
gcaactgatt tcagatcttt tgattgttga tcctagtaga agacctagtg ctcaagatct   1200
tctgagtcat ccatgggtgg taggtgacaa ggccaaagat gatgcaatgg accctgagat   1260
tgtctcaaga ttgcagagct caacgctag gcgcaaactg cgtgcagttg caattgcaag   1320
tatttggagc accacaatct tcctcagaac caaaaaactg aaatccttgg tgggaacaca   1380
tgatctcaca gaagaggaaa ttgaaaatct caggatgagt tttaagaaga tatgtgtgag   1440
tggggacaat gccactctat ctgagtttga ggaggtgctg aaagcaatga acatgccatc   1500
actgatccct ctagcaccgc gaatatttga cttatttgac gacaaccgag atggaacagt   1560
tgacatgaga gagatactat gtggtttttc cagcttcaaa aactccaaag gggatgatgc   1620
tctccgtttg tgcttccaga tgtatgcaca agatcgatcc gggtgcatca ccaaggaaga   1680
agtagcatcc atgctcagag cttttgccaga agactgtctc ccaactgaca tcactgaacc   1740
tggcaaattg gatgagatat ttgacctaat ggatgccaac agtgatggaa aagttacctt   1800
tgatgaattc aaagctgcta tgcagagaga tagctctctc caagacgtag ttctctcttc   1860
tcttcgccca caatagttct cctaattttc attaatttat tgtattatta actatggtat   1920
tttaaaatgg agtagtacta gtgttgtcct tttctttttc ttcttcctgg cctgggccat   1980 tcttttttgct gacttattga tactatagga agaaaaagga ttggattact atatagtgaa   2040
tttttgcttt tgacagttat ctatgaactt ctgcgttctc atgttgttcg tcaa          2094
```

<210> SEQ ID NO 22
<211> LENGTH: 1878
<212> TYPE: DNA
<213> ORGANISM: Phaseolus vulgaris

<400> SEQUENCE: 22

```
tctcaaccgt tcaacacgc gttttgaagg ctcctcctat catttttta acaaacaaat      60 tcctttgtcc ctgcaaattt tctgagtctt caagattcct tagtttccaa gactctgtgt   120
gcagcacacc accatggggt atgaaaccag aatactctca gatgagtatg aagtctcaga   180
ggttctagga agaggtggat tttctgttgt cagaaaaggc acaagaaaat caagtagtga   240
caccaaaagc cttgtagcca tcaaaaccct gagaaggtca ggaactgcct caagccccag   300
ctacccttct gggtttccaa gaccaaaggg tggagagaag agcacagcag ctatgatggg   360
gttcccctca gggagacaag tctcagtctc agatgccttg ctcaccaatg agattcttgt   420
gatgaggaga atagtggaaa acgtttcacc acaccctaat gtgattgacc tttatgatgt   480
gtatgaggac tccaatggag tgcaccttgt gttggagctg tgctctggtg gggaattgtt   540
tgataggatt gtagcacaag ataggtactc agagactgaa gctgcaggtg tggttcgcca   600
gatagcttca ggattagagg ctattcatag agctaacatt gtgcacaggg acttgaagcc   660
tgagaattgt cttttcttgg atgtgaggag ggactcccct cttaagatca tggactttgg   720
```

```
attgagttct gttgaagaat tcactgaccc agttgttggt ttgtttggat ccattgatta    780
tgtttcacca gaggctcttt ctcaagggaa gataactacc aagagtgaca tgtggtctct    840
tggagtgatt ctatacatct tactctctgg gtatccacct ttcattgctc agaccaatcg    900
ccagaaacaa caaatgataa tgaatgggaa tttcagtttc tatgagaaga catggaaggg    960
cattactcaa tcagcaaaac agctaatttc agatcttctg actatagatc ctagcaggag   1020
acctagtgct caagatcttc tgagtcatcc atgggtggta ggtgacaaag ccaaggatga   1080
tgcaatggac cctgagattg tctcaagatt gcagagcttc aacgcaagac gcaaattgcg   1140
tgcagctgca attgctagtg tttggagctc cacaatcttc ctcagaacca aaaagctgaa   1200
atccttggtg ggaacacatg atctcacagc agaggaaatt gaaaacctca ggataaattt   1260
taagaaaata tgtgtgaatg agacaatgc cactctctct gagtttgaag aggtgctgaa   1320
agcaatgaat atgccatcac tgatccctct agcaccacga atatttgact tgtttgacaa   1380
caaccgtgat ggaacagttg acatgagaga gatactttgt ggcttttcca gcttcaaaaa   1440
ctccaaagga gatgatgctc tccgtttgtg cttccagatg tatgacacag atcgatcagg   1500
gtgcatcacc aaggaagaag tagcatccat gctcagagct ttaccagaag agtgtctacc   1560
tgctgatatc actgaacctg ggaaactgga tgagatattt gacagaatgg atgccaacag   1620
tgatggaaaa gttacctttg atgaattcaa agctgccatg cagagagata gctctttgca   1680
agaccttctt ctctcttctc taagaccaca atcttaactc ttcaaatttc cattgatcta   1740
tatgctattg ttatcaacca tgcacaacta tttttgtcct ttttgtccct tcacactgta   1800
ggaaaaaaca ctattccagg actatacact gatgttgttc catctaactt ttgcttagac   1860
tcatgttaat taagtatg                                                1878
```

<210> SEQ ID NO 23
<211> LENGTH: 1548
<212> TYPE: DNA
<213> ORGANISM: Arachis hypogaea

<400> SEQUENCE: 23

```
atgggatatg aaaccagaaa gctctctgat gagtatgaag tttcagaaat tctaggaaga     60
ggtggattct ctgttgtcag gaaaggcata aaaaaatcaa gcagtgatga gaaaactcat    120
gttgccataa agacactaag aagagtaagt gtcttctcta caaccctgg ttgtttacca    180 agagagagga gcaacatggg gtttcccaca tggagacagg tttcagtatc agatgctctt    240
ctcaccaatg agatccttgt gatgaggaag atagtcgaaa atgtgtcgcc acatccgaat    300
gtggttgacc tctatgatgt ttatgaggac tcgaatggtg ttcatcttgt tttggagctg    360
tgttctggcg gtgagctgtt tgatcgcatt gtggcacagg ataggtactc agagactgag    420
gctgcgacag ttattcgcca gattgcggcg ggcttagagg ctattcataa agcaaacatt    480
gtccatagag acttgaagcc tgagaattgc ttgttcttgg acaagaggaa ggattctcct    540
ctaaagatca tggatttcgg tttgagctct gttgaagagt ttactgatcc agttgttggt    600
ttgtttggtt ccattgatta tgtttcaccg gaggctcttt ctcaaggaaa gattactact    660
aagagtgaca tgtggtctct agggttaatt ttgtacatct tattatctgg atatccgcct    720
ttcattgctc agtctaatcg ccaaaaacaa caaatgataa tgaatgggaa cttcagcttc    780
tatgagaaga catggaaggg catttctcaa tcagcaaagc aattgatttc gagtcttctg    840
acagttgatc ctagtaggag acctagtgcg caggagctcc tgagtcatcc atgggtcata    900
ggtgatgtag ccaaagatgt tcaaatggac cctgagattg tctcaaggtt gcaaagcttc    960
```

```
aatgctcgtc gcaagctccg ggcagctgca attgcaagcg tatggagcac cacagtgttc   1020
ttgagaacca agaaactgaa atccttgata ggatcctatg atcttacaga agaggaaatt   1080
gaaagtctca ggatacactt caagaagata tgtggaaatg gggacaatgc cacgctctct   1140
aagtttgagg aggtactgaa agcaataaat atgccatcac taattcctct agcaccacgc   1200
atatttgact tgttcgacaa caaccgtgat ggaacggttg acatgcgaga gattttatgt   1260
gggctttcca gcctcaagaa ttccaaagga gatgatgccc tccgtttgtg cttccagatg   1320
tatgatgcag atcgatccgg gtgtatcaca aggaagaag tagcatccat gcttagagct    1380
ttgccggata ctgtcttcc cgttgatatc acggaacctg gcaaattgga cgagattttc     1440
gacagaatgg atgccaacag tgatggaaaa gtcacctttg aggaattcaa agctgctatg   1500
caaagagata gctctctcca agacgtagtc ctctcttctc ttcgtccca               1548

<210> SEQ ID NO 24
<211> LENGTH: 1716
<212> TYPE: DNA
<213> ORGANISM: Petunia x hybrida

<400> SEQUENCE: 24
gcggggagtg ctttgatggg acaaaaggaa gatacaagaa gtctaagtga tgaatatgaa     60
gtaacagaca tacttggaag aggtggcttt tcagtagtaa ggagaggaag aacacgtagc    120
agtgaagaag ttgccattaa gacactccgg cgattcggac cgccggagaa gaaagaattt    180
agtaggtcta ctactcatgt taattctcga ccagctgcac aggctttaat atctgaaact    240
ttgttgacaa atgagctgtt agttatgagg aagattgtgg aagatgtttc acctcatcct    300
aatgttatac atctgtatga cgtttgtgag gattcttcag gtgttcatct catcttggag    360
ctttgttgtg gtggggagct ctttgatcgg attgttgggc aagcaaggta taacgaggca    420
ggcgcagctg cagtggtgag acagatagct aagggtcttg aggcactaca tggggcaagt    480
atagttcata gggacttgaa accagagaac tgtctattct tgaacaagga tgagaattca    540
ccactgaaaa tcatggactt tggactcagc tctattgagg attttgccaa tccagtggtt    600
ggtttatttg gttccataga ttatgtttca ccagaagcac tttcaagggg aaacatcact    660
agcaaaagtg atatttggtc acttggagta atcctttaca ttctcctatc cgggtaccca    720
cctttcttcg caccgtccaa tcggcaaaag caacaaatga tattaaacgg ggagttcagt    780
tttgatgaga aacatggaa aaatatttcg tcatccgcaa acagctaat atccagtctt      840 ttgaaagtta tcctaacat gagacctact gctcaagaga tacttgaaca cccatgggtg    900
acaggagact tggcaaagca agaacagatg gatgccgaaa ttgtatctcg cctgcaaagc    960
ttcaatgctc ggcgcaagtt cagggcggca gctatggcta gtgtgttaag cagtagtttc   1020
tccttgagaa ctaagaaatt gaagaagttg gttggttcct atgacctcaa gcctgaagaa   1080
ttggaaaacc tcagccacaa cttcaagaaa atatgcaaaa atggagaaaa tgcaacttta   1140
ttggaatttg aagaggtcct gaaagctatg gaaatgtcat ctttagtccc tttagctcct   1200
cggatattcg atctatttga caacaatcgt gatggaacag tagatatgag agagatcata   1260
ggtggcttct ctagcctcaa gtattcccaa ggggatgatg cacttcgtct ttgtttccag   1320
atgtatgata cagatcggtc aggctgcatt agcaaggaag aggtcgcatc catgttaaga   1380
gcacttcctg aagactgcct tccaatggat ataacagaac ctggaaaaact tgatgagata   1440 tttgatttaa tggatgcaaa tagtgatggt aaagtcactt tgatgagtt cagagctgcc    1500
```

| | |
|---|---|
| atgcaaagag atagctctct tcaagatgta gttctctcct ctcttcgtcc cactttaatt | 1560 |
| cctttattat ttaattttcc ttttagcata ctagttgtat taatctctaa ccttctatga | 1620 |
| caatgattta tttttttatt cgcaactgag aaaaagggca tggaattaat ttgaaagctt | 1680 |
| tatcgaacgc taaaaaaaaa aaaaaaaaaa aaaaaa | 1716 |

<210> SEQ ID NO 25
<211> LENGTH: 1847
<212> TYPE: DNA
<213> ORGANISM: Sesbania rostrata

<400> SEQUENCE: 25

| | |
|---|---|
| gggaattcaa agacttgatt tttttgtttt gttttgtgca ccaccatggg atatgaaacc | 60 |
| agaaggctct cagatgagta tgaggtttca gatgttctag aagaggtgg attttctgtt | 120 |
| gtcagaaaag gtaccaaaaa atcaagcagt gagaaaacct tagtagccat caaaacactg | 180 |
| agaaggttag gtgcctctaa taacaaccct tctggtttac caaaaacaaa aggtggagag | 240 |
| aaaagcatag caactatgat ggggttcccc acatggagac aagtttcagt ctcagatgcc | 300 |
| ttgttgacca atgagattct tgtcatgagg aggatagtgg aaaatgtttc acctcacccc | 360 |
| aatgtgattg acctctatga tgtgtatgag gactcaaatg gggttcatct tgtgcttgag | 420 |
| ctttgttctg gtggggaatt gtttgatagg attgtggcac aagataggta ctcagagact | 480 |
| gaagctgcag ctgtggttcg ccagatagca gcaggattaa aggctattca taaagctaac | 540 |
| attgttcata gggacttgaa gcctgagaat tgcctttttt tggataccag gaaggactct | 600 |
| cctctcaaga tcatggactt tgggttgagt tctgttgaag aatttactga ccctgttgtt | 660 |
| ggtttgtttg gatccattga ttatgtttca ccagaggctc tttctcaagg aaagataact | 720 |
| actaagagtg acatgtggtc tctaggagta attctatata tcttactctc tgggtatcca | 780 |
| cctttcattg ctccgtctaa tcgccaaaaa caacaaatga tagtgaacgg gaatttcagt | 840 |
| ttctatgaga agacttggaa gggcatttcc caatcagcaa agcaattgat ttcaagtctt | 900 |
| ctgactgttg atcctagcaa gagacccagt gctcaacagc ttctgagtca tccatgggtt | 960 |
| ataggtgaga aagccaaaga tgatcaaatg gaccctgaaa ttgtctcaag gctgcagagc | 1020 |
| tttaatgcaa gacgcaaact gcgtgcagct gcaattgcta gtgtttggag ctccacagtc | 1080 |
| ttcctcagaa ccaaaaaact gagatccttg gtaggaaccc atgatctcaa agaagaggaa | 1140 |
| attgaaaacc tcaggataca tttcaagaag atatgtgcaa atggagacaa tgccactctc | 1200 |
| tctgagtttg aggaggtgct gaaagcaatg aaatatgccat cattgatccc tctagcacct | 1260 |
| cgtatatttg acttgtttga caacaaccgt gatggaacag ttgacatgcg agagatacta | 1320 |
| tgtgggtttt ctagtctcaa gaactccaaa ggagatgatg ctctccgttt gtgcttccag | 1380 |
| atgtatgaca cagatcgatc cgggtgcatc acaaaggaag aagtagcatc tatgctgaga | 1440 |
| gctttgccag atgattgtct tccagctgat atcactgaac ctggcaaatt ggatgagata | 1500 |
| tttgatttaa tggatgcaaa tagtgatgga aaagttacct tgatgaatt caaagctgct | 1560 |
| atgcagagag atagctctct tcaagatgta gtcctctctt ctcttcgccc ataatccttt | 1620 |
| tattatgaca taatattcac actacaagga aaagtgtaat gcagtactaa acagggtgaa | 1680 |
| actgtgccat ctaacttctg ctatgacaat taggaacttt tgcattttca tgttatacaa | 1740 |
| gctagctagc tacctacctg agtcttgaaa ctgcaattga gtagcagaaa gctaacatgt | 1800 |
| tcatcttgaa tcgaacaaat tcttccaaat ttagttttta ttgcatc | 1847 |

<210> SEQ ID NO 26
<211> LENGTH: 1572
<212> TYPE: DNA
<213> ORGANISM: Artificial
<220> FEATURE:
<223> OTHER INFORMATION: Modified DMI3 polynucleotide

<400> SEQUENCE: 26

```
atgggatatg gaacaagaaa actctcagat gaatatgaag tttcagaaat tctaggtaga      60
ggtggatttt ctgttgttag aaaaggtaca aaaaaatcaa gcattgaaga agaaaaatca     120
caatcacaag tagcaatcaa aaccctaaga aggttaggtg cttcaaataa ccctagtgga     180
ttaccaagaa aaaagatat tggagaaaaa agcacaatag ggttccctac aatgagacaa      240
gtttcagttt cagatacatt actaacaaat gagatacttg taatgagacg aatagtcgaa     300
aacgtttcgc cacatccaaa tgtgattgat ctttatgatg tatatgagga cacaaatggt     360
gttcatcttg ttcttgagct tgttccggt ggtgaacttt tcgataggat tgttgcacaa      420
gataagtata gtgagactga agctgcaact gtggttcatc aaatagcttc agggttagaa     480
gctgttcata gagctaatat agttcataga gatttgaaac ctgaaaattg tcttttttta     540
gatgttagga aagattctcc tcttaagatt atggattttg ggttgagttc tgttgaagag     600
tttactgatc ctgttgttgg tttgtttgga tctattgatt atgtttcacc tgaggctctt     660
tctcaaggaa agattactac taagagtgat atgtggtctc ttgggggttat tctatatatc    720
ttactttcag ggtatccacc tttcattgcc caaaataatc gccaaaaaca acaaatgata    780
atgaatggga attttagttt ttatgagaag gattggaagg gaatttcaca accagcaaag    840
aatttgattt caagtctttt aaccgttgat cctagcaaga gacctagtgc tcttgagctt    900
ctaagtgatc catgggtcaa aggtgagaaa gccaaagatg ttcaaatgga ccctgagatt    960
gtctcaaggc tacaaagctt taatgcaaga cgtaaacttc gtgcagctgc aattgctagt   1020
gtttggagct ccacaatctt ccttagaaca aaaaaattga atcattggt tggatcctat    1080
gatcttaaag aagaggaaat tgaaaatctc aggatgcatt tcaagaagat atgtgcagat    1140
agagacaatg caactctgtc agagtttgag gaggtgttaa aagcaatgaa tatgttatca    1200
ttgatcccctt ttgcttctcg tatatttgat ttgtttgaca caaccgtga tggaacagtt   1260
gacatgcgtg agatactttg tggattttcc agtctcaaga attccaaagg agaggatgct    1320
cttcgtttgt gcttccagat gtatgataca gatagatcag gctgcatcag caaagaggaa    1380
gtagcatcca tgctcagggc tttgccatat gattgtcttc caactgatat cactgaacct    1440
ggaaaattgg atgagatttt tgacttaatg gatgctaata atgatggaaa agttacatttt   1500
gatgaattca agctgctat gcaaagagat agctctcttc aagatgtagt tctctcttct    1560
attcgtccat aa                                                        1572
```

<210> SEQ ID NO 27
<211> LENGTH: 1572
<212> TYPE: DNA
<213> ORGANISM: Artificial
<220> FEATURE:
<223> OTHER INFORMATION: Modified DMI3 polynucleotide

<400> SEQUENCE: 27

```
atgggatatg gaacaagaaa actctcagat gaatatgaag tttcagaaat tctaggtaga      60
ggtggatttt ctgttgttag aaaaggtaca aaaaaatcaa gcattgaaga agaaaaatca     120
caatcacaag tagcaatcaa aaccctaaga aggttaggtg cttcaaataa ccctagtgga     180
```

```
ttaccaagaa aaaaagatat tggagaaaaa agcacaatag ggttccctac aatgagacaa    240
gtttcagttt cagatacatt actaacaaat gagatacttg taatgagacg aatagtcgaa    300
aacgtttcgc cacatccaaa tgtgattgat ctttatgatg tatatgagga cacaaatggt    360
gttcatcttg ttcttgagct ttgttccggt ggtgaacttt tcgataggat tgttgcacaa    420
gataagtata gtgagactga agctgcaact gtggttcatc aaatagcttc agggttagaa    480
gctgttcata gagctaatat agttcataga gatttgaaac ctgaaaattg tctttttta    540
gatgttagga aagattctcc tcttaagatt atggattttg ggttgagttc tgttgaagag    600
tttactgatc ctgttgttgg tttgtttgga tctattgatt atgtttcacc tgaggctctt    660
tctcaaggaa agattactac taagagtgat atgtggtctc ttggggttat tctatatatc    720
ttactttcag ggtatccacc tttcattgcc caaaataatc gccaaaaaca acaaatgata    780
atgaatggga attttagttt ttatgagaag atttggaagg gaatttcaca accagcaaag    840
aatttgattt caagtctttt aaccgttgat cctagcaaga gacctagtgc tcttgagctt    900
ctaagtgatc catgggtcaa aggtgagaaa gccaaagatg ttcaaatgga ccctgagatt    960
gtctcaaggc tacaaagctt taatgcaaga cgtaaacttc gtgcagctgc aattgctagt   1020
gtttggagct ccacaatctt ccttagaaca aaaaaattga aatcattggt tggatcctat   1080
gatcttaaag aagaggaaat tgaaaatctc aggatgcatt tcaagaagat atgtgcagat   1140
agagacaatg caactctgtc agagtttgag gaggtgttaa aagcaatgaa tatgttatca   1200
ttgatccctt ttgcttctcg tatatttgat ttgtttgaca acaaccgtga tggaacagtt   1260
gacatgcgtg agatactttg tggattttcc agtctcaaga attccaaagg agaggatgct   1320
cttcgtttgt gcttccagat gtatgataca gatagatcag gctgcatcag caaagaggaa   1380
gtagcatcca tgctcagggc tttgccatat gattgtcttc caactgatat cactgaacct   1440
ggaaaattgg atgagatttt tgacttaatg gatgctaata atgatggaaa agttacattt   1500
gatgaattca aagctgctat gcaaagagat agctctcttc aagatgtagt tctctcttct   1560
attcgtccat aa                                                        1572
```

<210> SEQ ID NO 28
<211> LENGTH: 523
<212> TYPE: PRT
<213> ORGANISM: Medicago truncatula

<400> SEQUENCE: 28

```
Met Gly Tyr Gly Thr Arg Lys Leu Ser Asp Glu Tyr Glu Val Ser Glu
1               5                   10                  15

Ile Leu Gly Arg Gly Gly Phe Ser Val Val Arg Lys Gly Thr Lys Lys
            20                  25                  30

Ser Ser Ile Glu Glu Glu Lys Ser Gln Ser Gln Val Ala Ile Lys Thr
        35                  40                  45

Leu Arg Arg Leu Gly Ala Ser Asn Asn Pro Ser Gly Leu Pro Arg Lys
    50                  55                  60

Lys Asp Ile Gly Glu Lys Ser Thr Ile Gly Phe Pro Thr Met Arg Gln
65                  70                  75                  80

Val Ser Val Ser Asp Thr Leu Leu Thr Asn Glu Ile Leu Val Met Arg
                85                  90                  95

Arg Ile Val Glu Asn Val Ser Pro His Pro Asn Val Ile Asp Leu Tyr
            100                 105                 110

Asp Val Tyr Glu Asp Thr Asn Gly Val His Leu Val Leu Glu Leu Cys
        115                 120                 125
```

Ser Gly Gly Glu Leu Phe Asp Arg Ile Val Ala Gln Asp Lys Tyr Ser
130                 135                 140

Glu Thr Glu Ala Ala Thr Val Val His Gln Ile Ala Ser Gly Leu Glu
145                 150                 155                 160

Ala Val His Arg Ala Asn Ile Val His Arg Asp Leu Lys Pro Glu Asn
                165                 170                 175

Cys Leu Phe Leu Asp Val Arg Lys Asp Ser Pro Leu Lys Ile Met Asp
                180                 185                 190

Phe Gly Leu Ser Ser Val Glu Glu Phe Thr Asp Pro Val Val Gly Leu
                195                 200                 205

Phe Gly Ser Ile Asp Tyr Val Ser Pro Glu Ala Leu Ser Gln Gly Lys
210                 215                 220

Ile Thr Thr Lys Ser Asp Met Trp Ser Leu Gly Val Ile Leu Tyr Ile
225                 230                 235                 240

Leu Leu Ser Gly Tyr Pro Pro Phe Ile Ala Gln Asn Asn Arg Gln Lys
                245                 250                 255

Gln Gln Met Ile Met Asn Gly Asn Phe Ser Phe Tyr Glu Lys Thr Trp
                260                 265                 270

Lys Gly Ile Ser Gln Pro Ala Lys Asn Leu Ile Ser Ser Leu Leu Thr
                275                 280                 285

Val Asp Pro Ser Lys Arg Pro Ser Ala Leu Glu Leu Leu Ser Asp Pro
290                 295                 300

Trp Val Lys Gly Glu Lys Ala Lys Asp Val Gln Met Asp Pro Glu Ile
305                 310                 315                 320

Val Ser Arg Leu Gln Ser Phe Asn Ala Arg Arg Lys Leu Arg Ala Ala
                325                 330                 335

Ala Ile Ala Ser Val Trp Ser Ser Thr Ile Phe Leu Arg Thr Lys Lys
                340                 345                 350

Leu Lys Ser Leu Val Gly Ser Tyr Asp Leu Lys Glu Glu Ile Glu
                355                 360                 365

Asn Leu Arg Met His Phe Lys Lys Ile Cys Ala Asp Arg Asp Asn Ala
                370                 375                 380

Thr Leu Ser Glu Phe Glu Glu Val Leu Lys Ala Met Asn Met Leu Ser
385                 390                 395                 400

Leu Ile Pro Phe Ala Ser Arg Ile Phe Asp Leu Phe Asp Asn Asn Arg
                405                 410                 415

Asp Gly Thr Val Asp Met Arg Glu Ile Leu Cys Gly Phe Ser Ser Leu
                420                 425                 430

Lys Asn Ser Lys Gly Glu Asp Ala Leu Arg Leu Cys Phe Gln Met Tyr
                435                 440                 445

Asp Thr Asp Arg Ser Gly Cys Ile Ser Lys Glu Glu Val Ala Ser Met
450                 455                 460

Leu Arg Ala Leu Pro Tyr Asp Cys Leu Pro Thr Asp Ile Thr Glu Pro
465                 470                 475                 480

Gly Lys Leu Asp Glu Ile Phe Asp Leu Met Asp Ala Asn Asn Asp Gly
                485                 490                 495

Lys Val Thr Phe Asp Glu Phe Lys Ala Ala Met Gln Arg Asp Ser Ser
                500                 505                 510

Leu Gln Asp Val Val Leu Ser Ser Ile Arg Pro
                515                 520

<210> SEQ ID NO 29
<211> LENGTH: 518

<212> TYPE: PRT
<213> ORGANISM: Lotus japonicus

<400> SEQUENCE: 29

```
Met Gly Tyr Asp Gln Thr Arg Lys Leu Ser Asp Glu Tyr Glu Ile Ser
1               5                   10                  15

Glu Ile Leu Gly Arg Gly Gly Phe Ser Val Val Arg Lys Gly Thr Lys
            20                  25                  30

Lys Ser Gly Asn Glu Lys Thr Gln Val Ala Ile Lys Thr Leu Arg Arg
        35                  40                  45

Leu Gly Ser Ser Pro Ser Gly Thr Gly Gly Gln Lys Ser Thr Ala
    50                  55                  60

Thr Val Met Gly Phe Pro Ser Leu Arg Gln Val Ser Val Ser Asp Ala
65                  70                  75                  80

Leu Leu Thr Asn Glu Ile Leu Val Met Arg Arg Ile Val Glu Asn Val
                85                  90                  95

Ser Pro His Pro Asn Val Ile Asp Leu Tyr Asp Val Cys Glu Asp Ser
            100                 105                 110

Asn Gly Val His Leu Val Leu Glu Leu Cys Ser Gly Gly Glu Leu Phe
        115                 120                 125

Asp Arg Ile Val Ala Gln Asp Lys Tyr Ala Glu Thr Glu Ala Ala Ala
130                 135                 140

Val Val Arg Gln Ile Ala Ala Gly Leu Glu Ala Val His Lys Ala Asp
145                 150                 155                 160

Ile Val His Arg Asp Leu Lys Pro Glu Asn Cys Leu Phe Leu Asp Ser
                165                 170                 175

Arg Lys Asp Ser Pro Leu Lys Ile Met Asp Phe Gly Leu Ser Ser Val
            180                 185                 190

Glu Glu Phe Thr Asp Pro Val Val Gly Leu Phe Gly Ser Ile Asp Tyr
        195                 200                 205

Val Ser Pro Glu Ala Leu Ser Gln Gly Lys Ile Thr Ala Lys Ser Asp
210                 215                 220

Met Trp Ser Leu Gly Val Ile Leu Tyr Ile Leu Leu Ser Gly Tyr Pro
225                 230                 235                 240

Pro Phe Ile Ala Gln Asn Asn Arg Gln Lys Gln Met Ile Ile Asn
            245                 250                 255

Gly Asn Phe Ser Phe Tyr Glu Lys Thr Trp Lys Gly Ile Thr Gln Ser
        260                 265                 270

Ala Lys Gln Leu Ile Ser Ser Leu Leu Thr Val Asp Pro Ser Lys Arg
    275                 280                 285

Pro Ser Ala Gln Glu Leu Leu Ser His Pro Trp Val Arg Gly Asp Lys
290                 295                 300

Ala Lys Asp Glu Gln Met Asp Pro Glu Ile Val Ser Arg Leu Gln Ser
305                 310                 315                 320

Phe Asn Ala Arg Arg Lys Leu Arg Ala Ala Ile Ala Ser Val Trp
                325                 330                 335

Ser Ser Thr Ile Phe Leu Arg Thr Lys Lys Leu Arg Ser Leu Val Gly
            340                 345                 350

Thr Tyr Asp Leu Lys Glu Glu Ile Glu Ser Leu Arg Ile His Phe
        355                 360                 365

Lys Lys Ile Cys Gly Asn Gly Asp Asn Ala Thr Leu Ser Glu Phe Val
    370                 375                 380

Glu Val Leu Lys Ala Met Lys Met Pro Ser Leu Ile Pro Leu Ala Pro
385                 390                 395                 400
```

```
Arg Ile Phe Asp Leu Phe Asp Asn Asn Arg Asp Gly Thr Ile Asp Met
            405                 410                 415

Arg Glu Ile Leu Cys Gly Phe Ser Ser Leu Lys Asn Ser Lys Gly Asp
            420                 425                 430

Asp Ala Leu Arg Leu Cys Phe Gln Met Tyr Asp Thr Asp Arg Ser Gly
            435                 440                 445

Cys Ile Thr Lys Glu Glu Val Ala Ser Met Leu Cys Ala Leu Pro Glu
450                 455                 460

Glu Cys Leu Pro Ala Asp Ile Thr Glu Pro Gly Lys Leu Asp Glu Ile
465                 470                 475                 480

Phe Asp Leu Met Asp Ala Asn Ser Asp Gly Lys Val Thr Phe Glu Glu
            485                 490                 495

Phe Lys Ala Ala Met Gln Arg Asp Ser Ser Leu Gln Asp Met Leu Leu
            500                 505                 510

Ser Ser Leu Arg Pro Ser
            515

<210> SEQ ID NO 30
<211> LENGTH: 527
<212> TYPE: PRT
<213> ORGANISM: Glycine max

<400> SEQUENCE: 30

Met Gly Asn Glu Thr Arg Lys Leu Ser Asp Glu Tyr Glu Val Ser Glu
1               5                   10                  15

Val Leu Gly Arg Gly Gly Phe Ser Val Val Arg Lys Gly Thr Lys Lys
            20                  25                  30

Ser Ser Ser Asp Thr Lys Thr His Val Ala Ile Lys Thr Leu Arg Arg
        35                  40                  45

Val Gly Thr Ala Ser Asn Ser Asn Asn Pro Ser Gly Phe Pro Arg Pro
50                  55                  60

Lys Gly Gly Glu Lys Lys Ser Thr Ala Ala Met Met Gly Phe Pro Thr
65                  70                  75                  80

Trp Arg Gln Val Ser Val Ser Asp Ala Leu Leu Thr Asn Glu Ile Leu
                85                  90                  95

Val Met Arg Arg Ile Val Glu Asn Val Ser Pro His Pro Asn Val Ile
            100                 105                 110

Asp Leu Tyr Asp Val Tyr Glu Asp Ser Asn Gly Val His Leu Val Leu
        115                 120                 125

Glu Leu Cys Ser Gly Gly Glu Leu Phe Asp Arg Ile Val Ala Gln Asp
    130                 135                 140

Arg Tyr Ser Glu Thr Glu Ala Ala Gly Val Val Arg Gln Ile Ala Ser
145                 150                 155                 160

Gly Leu Glu Ala Ile His Arg Ala Asn Ile Val His Arg Asp Leu Lys
                165                 170                 175

Pro Glu Asn Cys Leu Phe Leu Asp Val Arg Arg Asp Ser Pro Leu Lys
            180                 185                 190

Ile Met Asp Phe Gly Leu Ser Ser Val Glu Glu Phe Thr Asp Pro Val
        195                 200                 205

Val Gly Leu Phe Gly Ser Ile Asp Tyr Val Ser Pro Glu Ala Leu Ser
    210                 215                 220

Gln Gly Lys Ile Thr Thr Lys Ser Asp Met Trp Ser Leu Gly Val Ile
225                 230                 235                 240

Leu Tyr Ile Leu Leu Ser Gly Tyr Pro Pro Phe Ile Ala Gln Asn Asn
```

```
                245                 250                 255
Arg Gln Lys Gln Gln Met Ile Met Asn Gly Asn Phe Ser Phe Tyr Glu
            260                 265                 270

Lys Thr Trp Lys Gly Ile Thr Arg Ser Ala Lys Gln Leu Ile Ser Asp
        275                 280                 285

Leu Leu Ile Val Asp Pro Ser Arg Pro Ser Ala Gln Asp Leu Leu
    290                 295                 300

Ser His Pro Trp Val Val Gly Asp Lys Ala Lys Asp Asp Ala Met Asp
305                 310                 315                 320

Pro Glu Ile Val Ser Arg Leu Gln Ser Phe Asn Ala Arg Arg Lys Leu
                325                 330                 335

Arg Ala Val Ala Ile Ala Ser Ile Trp Ser Thr Thr Ile Phe Leu Arg
            340                 345                 350

Thr Lys Lys Leu Lys Ser Leu Val Gly Thr His Asp Leu Thr Glu Glu
        355                 360                 365

Glu Ile Glu Asn Leu Arg Met Ser Phe Lys Lys Ile Cys Val Ser Gly
    370                 375                 380

Asp Asn Ala Thr Leu Ser Glu Phe Glu Glu Val Leu Lys Ala Met Asn
385                 390                 395                 400

Met Pro Ser Leu Ile Pro Leu Ala Pro Arg Ile Phe Asp Leu Phe Asp
                405                 410                 415

Asp Asn Arg Asp Gly Thr Val Asp Met Arg Glu Ile Leu Cys Gly Phe
            420                 425                 430

Ser Ser Phe Lys Asn Ser Lys Gly Asp Asp Ala Leu Arg Leu Cys Phe
        435                 440                 445

Gln Met Tyr Asp Thr Asp Arg Ser Gly Cys Ile Thr Lys Glu Glu Val
    450                 455                 460

Ala Ser Met Leu Arg Ala Leu Pro Glu Asp Cys Leu Pro Thr Asp Ile
465                 470                 475                 480

Thr Glu Pro Gly Lys Leu Asp Glu Ile Phe Asp Leu Met Asp Ala Asn
                485                 490                 495

Ser Asp Gly Lys Val Thr Phe Asp Glu Phe Lys Ala Ala Met Gln Arg
            500                 505                 510

Asp Ser Ser Leu Gln Asp Val Val Leu Ser Ser Leu Arg Pro Gln
        515                 520                 525

<210> SEQ ID NO 31
<211> LENGTH: 527
<212> TYPE: PRT
<213> ORGANISM: Phaseolus vulgaris

<400> SEQUENCE: 31

Met Gly Tyr Glu Thr Arg Ile Leu Ser Asp Glu Tyr Glu Val Ser Glu
1               5                   10                  15

Val Leu Gly Arg Gly Phe Ser Val Val Arg Lys Gly Thr Arg Lys
            20                  25                  30

Ser Ser Ser Asp Thr Lys Ser Leu Val Ala Ile Lys Thr Leu Arg Arg
        35                  40                  45

Ser Gly Thr Ala Ser Ser Pro Ser Tyr Pro Ser Gly Phe Pro Arg Pro
    50                  55                  60

Lys Gly Gly Glu Lys Ser Thr Ala Ala Met Met Gly Phe Pro Ser Gly
65              70                  75                  80

Arg Gln Val Ser Val Ser Asp Ala Leu Leu Thr Asn Glu Ile Leu Val
                85                  90                  95
```

```
Met Arg Arg Ile Val Glu Asn Val Ser Pro His Pro Asn Val Ile Asp
                100                 105                 110

Leu Tyr Asp Val Tyr Glu Asp Ser Asn Gly Val His Leu Val Leu Glu
        115                 120                 125

Leu Cys Ser Gly Gly Glu Leu Phe Asp Arg Ile Val Ala Gln Asp Arg
    130                 135                 140

Tyr Ser Glu Thr Glu Ala Ala Gly Val Val Arg Gln Ile Ala Ser Gly
145                 150                 155                 160

Leu Glu Ala Ile His Arg Ala Asn Ile Val His Arg Asp Leu Lys Pro
                165                 170                 175

Glu Asn Cys Leu Phe Leu Asp Val Arg Arg Asp Ser Pro Leu Lys Ile
        180                 185                 190

Met Asp Phe Gly Leu Ser Ser Val Glu Glu Phe Thr Asp Pro Val Val
    195                 200                 205

Gly Leu Phe Gly Ser Ile Asp Tyr Val Ser Pro Glu Ala Leu Ser Gln
        210                 215                 220

Gly Lys Ile Thr Thr Lys Ser Asp Met Trp Ser Leu Gly Val Ile Leu
225                 230                 235                 240

Tyr Ile Leu Leu Ser Gly Tyr Pro Pro Phe Ile Ala Gln Thr Asn Arg
                245                 250                 255

Gln Lys Gln Gln Met Ile Met Asn Gly Asn Phe Ser Phe Tyr Glu Lys
        260                 265                 270

Thr Trp Lys Gly Ile Thr Gln Ser Ala Lys Gln Leu Ile Ser Asp Leu
    275                 280                 285

Leu Thr Ile Asp Pro Ser Arg Arg Pro Ser Ala Gln Asp Leu Leu Ser
290                 295                 300

His Pro Trp Val Val Gly Asp Lys Ala Lys Asp Asp Ala Met Asp Pro
305                 310                 315                 320

Glu Ile Val Ser Arg Leu Gln Ser Phe Asn Ala Arg Arg Lys Leu Arg
                325                 330                 335

Ala Ala Ala Ile Ala Ser Val Trp Ser Ser Thr Ile Phe Leu Arg Thr
        340                 345                 350

Lys Lys Leu Lys Ser Leu Val Gly Thr His Asp Leu Thr Ala Glu Glu
    355                 360                 365

Ile Glu Asn Leu Arg Ile Asn Phe Lys Lys Ile Cys Val Asn Gly Asp
370                 375                 380

Asn Ala Thr Leu Ser Glu Phe Glu Glu Val Leu Lys Ala Met Asn Met
385                 390                 395                 400

Pro Ser Leu Ile Pro Leu Ala Pro Arg Ile Phe Asp Leu Phe Asp Asn
                405                 410                 415

Asn Arg Asp Gly Thr Val Asp Met Arg Glu Ile Leu Cys Gly Phe Ser
        420                 425                 430

Ser Phe Lys Asn Ser Lys Gly Asp Asp Ala Leu Arg Leu Cys Phe Gln
    435                 440                 445

Met Tyr Asp Thr Asp Arg Ser Gly Cys Ile Thr Lys Glu Glu Val Ala
    450                 455                 460

Ser Met Leu Arg Ala Leu Pro Glu Glu Cys Leu Pro Ala Asp Ile Thr
465                 470                 475                 480

Glu Pro Gly Lys Leu Asp Glu Ile Phe Asp Arg Met Asp Ala Asn Ser
                485                 490                 495

Asp Gly Lys Val Thr Phe Asp Glu Phe Lys Ala Ala Met Gln Arg Asp
        500                 505                 510

Ser Ser Leu Gln Asp Leu Leu Leu Ser Ser Leu Arg Pro Gln Ser
```

```
                 515                 520                 525

<210> SEQ ID NO 32
<211> LENGTH: 516
<212> TYPE: PRT
<213> ORGANISM: Arachis hypogaea

<400> SEQUENCE: 32

Met Gly Tyr Glu Thr Arg Lys Leu Ser Asp Glu Tyr Glu Val Ser Glu
1               5                   10                  15

Ile Leu Gly Arg Gly Gly Phe Ser Val Val Arg Lys Gly Ile Lys Lys
            20                  25                  30

Ser Ser Ser Asp Glu Lys Thr His Val Ala Ile Lys Thr Leu Arg Arg
        35                  40                  45

Val Ser Val Phe Ser Thr Thr Pro Gly Cys Leu Pro Arg Glu Arg Ser
    50                  55                  60

Asn Met Gly Phe Pro Thr Trp Arg Gln Val Ser Val Ser Asp Ala Leu
65                  70                  75                  80

Leu Thr Asn Glu Ile Leu Val Met Arg Lys Ile Val Glu Asn Val Ser
                85                  90                  95

Pro His Pro Asn Val Val Asp Leu Tyr Asp Val Tyr Glu Asp Ser Asn
            100                 105                 110

Gly Val His Leu Val Leu Glu Leu Cys Ser Gly Gly Glu Leu Phe Asp
        115                 120                 125

Arg Ile Val Ala Gln Asp Arg Tyr Ser Glu Thr Glu Ala Ala Thr Val
    130                 135                 140

Ile Arg Gln Ile Ala Ala Gly Leu Glu Ala Ile His Lys Ala Asn Ile
145                 150                 155                 160

Val His Arg Asp Leu Lys Pro Glu Asn Cys Leu Phe Leu Asp Lys Arg
                165                 170                 175

Lys Asp Ser Pro Leu Lys Ile Met Asp Phe Gly Leu Ser Ser Val Glu
            180                 185                 190

Glu Phe Thr Asp Pro Val Val Gly Leu Phe Gly Ser Ile Asp Tyr Val
        195                 200                 205

Ser Pro Glu Ala Leu Ser Gln Gly Lys Ile Thr Thr Lys Ser Asp Met
    210                 215                 220

Trp Ser Leu Gly Val Ile Leu Tyr Ile Leu Leu Ser Gly Tyr Pro Pro
225                 230                 235                 240

Phe Ile Ala Gln Ser Asn Arg Gln Lys Gln Gln Met Ile Met Asn Gly
                245                 250                 255

Asn Phe Ser Phe Tyr Glu Lys Thr Trp Lys Gly Ile Ser Gln Ser Ala
            260                 265                 270

Lys Gln Leu Ile Ser Ser Leu Leu Thr Val Asp Pro Ser Arg Arg Pro
        275                 280                 285

Ser Ala Gln Glu Leu Leu Ser His Pro Trp Val Ile Gly Asp Val Ala
    290                 295                 300

Lys Asp Val Gln Met Asp Pro Glu Ile Val Ser Arg Leu Gln Ser Phe
305                 310                 315                 320

Asn Ala Arg Arg Lys Leu Arg Ala Ala Ala Ile Ala Ser Val Trp Ser
                325                 330                 335

Thr Thr Val Phe Leu Arg Thr Lys Lys Leu Lys Ser Leu Ile Gly Ser
            340                 345                 350

Tyr Asp Leu Thr Glu Glu Glu Ile Glu Ser Leu Arg Ile His Phe Lys
        355                 360                 365
```

```
Lys Ile Cys Gly Asn Gly Asp Asn Ala Thr Leu Ser Lys Phe Glu Glu
    370                 375                 380

Val Leu Lys Ala Ile Asn Met Pro Ser Leu Ile Pro Leu Ala Pro Arg
385                 390                 395                 400

Ile Phe Asp Leu Phe Asp Asn Asn Arg Asp Gly Thr Val Asp Met Arg
                405                 410                 415

Glu Ile Leu Cys Gly Leu Ser Ser Leu Lys Asn Ser Lys Gly Asp Asp
                420                 425                 430

Ala Leu Arg Leu Cys Phe Gln Met Tyr Asp Ala Asp Arg Ser Gly Cys
            435                 440                 445

Ile Thr Lys Glu Glu Val Ala Ser Met Leu Arg Ala Leu Pro Asp Asp
    450                 455                 460

Cys Leu Pro Val Asp Ile Thr Glu Pro Gly Lys Leu Asp Glu Ile Phe
465                 470                 475                 480

Asp Arg Met Asp Ala Asn Ser Asp Gly Lys Val Thr Phe Glu Glu Phe
                485                 490                 495

Lys Ala Ala Met Gln Arg Asp Ser Ser Leu Gln Asp Val Val Leu Ser
                500                 505                 510

Ser Leu Arg Pro
            515

<210> SEQ ID NO 33
<211> LENGTH: 534
<212> TYPE: PRT
<213> ORGANISM: Petunia x hybrida

<400> SEQUENCE: 33

Met Gly Gln Lys Glu Asp Thr Arg Ser Leu Ser Asp Glu Tyr Glu Val
1               5                   10                  15

Thr Asp Ile Leu Gly Arg Gly Gly Phe Ser Val Val Arg Arg Gly Arg
                20                  25                  30

Thr Arg Ser Ser Glu Glu Val Ala Ile Lys Thr Leu Arg Arg Phe Gly
            35                  40                  45

Pro Pro Glu Lys Lys Glu Phe Ser Arg Ser Thr Thr His Val Asn Ser
50                  55                  60

Arg Pro Ala Ala Gln Ala Leu Ile Ser Glu Thr Leu Leu Thr Asn Glu
65                  70                  75                  80

Leu Leu Val Met Arg Lys Ile Val Glu Asp Val Ser Pro His Pro Asn
                85                  90                  95

Val Ile His Leu Tyr Asp Val Cys Glu Asp Ser Ser Gly Val His Leu
                100                 105                 110

Ile Leu Glu Leu Cys Cys Gly Gly Glu Leu Phe Asp Arg Ile Val Gly
            115                 120                 125

Gln Ala Arg Tyr Asn Glu Ala Gly Ala Ala Ala Val Arg Gln Ile
            130                 135                 140

Ala Lys Gly Leu Glu Ala Leu His Gly Ala Ser Ile Val His Arg Asp
145                 150                 155                 160

Leu Lys Pro Glu Asn Cys Leu Phe Leu Asn Lys Asp Glu Asn Ser Pro
                165                 170                 175

Leu Lys Ile Met Asp Phe Gly Leu Ser Ser Ile Glu Asp Phe Ala Asn
                180                 185                 190

Pro Val Val Gly Leu Phe Gly Ser Ile Asp Tyr Val Ser Pro Glu Ala
            195                 200                 205

Leu Ser Arg Gly Asn Ile Thr Ser Lys Ser Asp Ile Trp Ser Leu Gly
            210                 215                 220
```

```
Val Ile Leu Tyr Ile Leu Leu Ser Gly Tyr Pro Pro Phe Phe Ala Pro
225                 230                 235                 240

Ser Asn Arg Gln Lys Gln Gln Met Ile Leu Asn Gly Glu Phe Ser Phe
            245                 250                 255

Asp Glu Lys Thr Trp Lys Asn Ile Ser Ser Ser Ala Lys Gln Leu Ile
            260                 265                 270

Ser Ser Leu Leu Lys Val Asp Pro Asn Met Arg Pro Thr Ala Gln Glu
            275                 280                 285

Ile Leu Glu His Pro Trp Val Thr Gly Asp Leu Ala Lys Gln Glu Gln
290                 295                 300

Met Asp Ala Glu Ile Val Ser Arg Leu Gln Ser Phe Asn Ala Arg Arg
305                 310                 315                 320

Lys Phe Arg Ala Ala Ala Met Ala Ser Val Leu Ser Ser Ser Phe Ser
                325                 330                 335

Leu Arg Thr Lys Lys Leu Lys Lys Leu Val Gly Ser Tyr Asp Leu Lys
            340                 345                 350

Pro Glu Glu Leu Glu Asn Leu Ser His Asn Phe Lys Lys Ile Cys Lys
            355                 360                 365

Asn Gly Glu Asn Ala Thr Leu Leu Glu Phe Glu Val Leu Lys Ala
370                 375                 380

Met Glu Met Ser Ser Leu Val Pro Leu Ala Pro Arg Ile Phe Asp Leu
385                 390                 395                 400

Phe Asp Asn Asn Arg Asp Gly Thr Val Asp Met Arg Glu Ile Ile Gly
                405                 410                 415

Gly Phe Ser Ser Leu Lys Tyr Ser Gln Gly Asp Asp Ala Leu Arg Leu
            420                 425                 430

Cys Phe Gln Met Tyr Asp Thr Asp Arg Ser Gly Cys Ile Ser Lys Glu
            435                 440                 445

Glu Val Ala Ser Met Leu Arg Ala Leu Pro Gly Asp Cys Leu Pro Met
450                 455                 460

Asp Ile Thr Glu Pro Gly Lys Leu Asp Glu Ile Phe Asp Leu Met Asp
465                 470                 475                 480

Ala Asn Ser Asp Gly Lys Val Thr Phe Asp Glu Phe Arg Ala Ala Met
                485                 490                 495

Gln Arg Asp Ser Ser Leu Gln Asp Val Val Leu Ser Ser Leu Arg Pro
            500                 505                 510

Thr Leu Ile Pro Leu Leu Phe Asn Phe Pro Phe Ser Ile Leu Val Val
            515                 520                 525

Leu Ile Ser Asn Leu Leu
    530

<210> SEQ ID NO 34
<211> LENGTH: 522
<212> TYPE: PRT
<213> ORGANISM: Sesbania rostrata

<400> SEQUENCE: 34

Met Gly Tyr Glu Thr Arg Arg Leu Ser Asp Glu Tyr Glu Val Ser Asp
1               5                   10                  15

Val Leu Gly Arg Gly Gly Phe Ser Val Val Arg Lys Gly Thr Lys Lys
                20                  25                  30

Ser Ser Ser Glu Lys Thr Leu Val Ala Ile Lys Thr Leu Arg Arg Leu
            35                  40                  45

Gly Ala Ser Asn Asn Asn Pro Ser Gly Leu Pro Lys Thr Lys Gly Gly
```

-continued

```
                50                  55                  60
Glu Lys Ser Ile Ala Thr Met Met Gly Phe Pro Thr Trp Arg Gln Val
 65                  70                  75                  80

Ser Val Ser Asp Ala Leu Leu Thr Asn Glu Ile Leu Val Met Arg Arg
                 85                  90                  95

Ile Val Glu Asn Val Ser Pro His Pro Asn Val Ile Asp Leu Tyr Asp
            100                 105                 110

Val Tyr Glu Asp Ser Asn Gly Val His Leu Val Leu Glu Leu Cys Ser
        115                 120                 125

Gly Gly Glu Leu Phe Asp Arg Ile Val Ala Gln Asp Arg Tyr Ser Glu
    130                 135                 140

Thr Glu Ala Ala Ala Val Val Arg Gln Ile Ala Ala Gly Leu Glu Ala
145                 150                 155                 160

Ile His Lys Ala Asn Ile Val His Arg Asp Leu Lys Pro Glu Asn Cys
                165                 170                 175

Leu Phe Leu Asp Thr Arg Lys Asp Ser Pro Leu Lys Ile Met Asp Phe
            180                 185                 190

Gly Leu Ser Ser Val Glu Glu Phe Thr Asp Pro Val Val Gly Leu Phe
        195                 200                 205

Gly Ser Ile Asp Tyr Val Ser Pro Glu Ala Leu Ser Gln Gly Lys Ile
    210                 215                 220

Thr Thr Lys Ser Asp Met Trp Ser Leu Gly Val Ile Leu Tyr Ile Leu
225                 230                 235                 240

Leu Ser Gly Tyr Pro Pro Phe Ile Ala Pro Ser Asn Arg Gln Lys Gln
                245                 250                 255

Gln Met Ile Val Asn Gly Asn Phe Ser Phe Tyr Glu Lys Thr Trp Lys
            260                 265                 270

Gly Ile Ser Gln Ser Ala Lys Gln Leu Ile Ser Ser Leu Leu Thr Val
        275                 280                 285

Asp Pro Ser Lys Arg Pro Ser Ala Gln Gln Leu Leu Ser His Pro Trp
    290                 295                 300

Val Ile Gly Glu Lys Ala Lys Asp Asp Gln Met Asp Pro Glu Ile Val
305                 310                 315                 320

Ser Arg Leu Gln Ser Phe Asn Ala Arg Arg Lys Leu Arg Ala Ala Ala
                325                 330                 335

Ile Ala Ser Val Trp Ser Ser Thr Val Phe Leu Arg Thr Lys Lys Leu
            340                 345                 350

Arg Ser Leu Val Gly Thr His Asp Leu Lys Glu Glu Ile Glu Asn
        355                 360                 365

Leu Arg Ile His Phe Lys Lys Ile Cys Ala Asn Gly Asp Asn Ala Thr
    370                 375                 380

Leu Ser Glu Phe Glu Val Leu Lys Ala Met Asn Met Pro Ser Leu
385                 390                 395                 400

Ile Pro Leu Ala Pro Arg Ile Phe Asp Leu Phe Asp Asn Asn Arg Asp
                405                 410                 415

Gly Thr Val Asp Met Arg Glu Ile Leu Cys Gly Phe Ser Ser Leu Lys
            420                 425                 430

Asn Ser Lys Gly Asp Ala Leu Arg Leu Cys Phe Gln Met Tyr Asp
        435                 440                 445

Thr Asp Arg Ser Gly Cys Ile Thr Lys Glu Glu Val Ala Ser Met Leu
    450                 455                 460

Arg Ala Leu Pro Asp Asp Cys Leu Pro Ala Asp Ile Thr Glu Pro Gly
465                 470                 475                 480
```

```
Lys Leu Asp Glu Ile Phe Asp Leu Met Asp Ala Asn Ser Asp Gly Lys
                485                 490                 495

Val Thr Phe Asp Glu Phe Lys Ala Ala Met Gln Arg Asp Ser Ser Leu
            500                 505                 510

Gln Asp Val Val Leu Ser Ser Leu Arg Pro
        515                 520

<210> SEQ ID NO 35
<211> LENGTH: 523
<212> TYPE: PRT
<213> ORGANISM: Artificial
<220> FEATURE:
<223> OTHER INFORMATION: Modified DMI3 polypeptide

<400> SEQUENCE: 35

Met Gly Tyr Gly Thr Arg Lys Leu Ser Asp Glu Tyr Glu Val Ser Glu
1               5                   10                  15

Ile Leu Gly Arg Gly Gly Phe Ser Val Val Arg Lys Gly Thr Lys Lys
            20                  25                  30

Ser Ser Ile Glu Glu Glu Lys Ser Gln Ser Gln Val Ala Ile Lys Thr
        35                  40                  45

Leu Arg Arg Leu Gly Ala Ser Asn Asn Pro Ser Gly Leu Pro Arg Lys
    50                  55                  60

Lys Asp Ile Gly Glu Lys Ser Thr Ile Gly Phe Pro Thr Met Arg Gln
65                  70                  75                  80

Val Ser Val Ser Asp Thr Leu Leu Thr Asn Glu Ile Leu Val Met Arg
                85                  90                  95

Arg Ile Val Glu Asn Val Ser Pro His Pro Asn Val Ile Asp Leu Tyr
            100                 105                 110

Asp Val Tyr Glu Asp Thr Asn Gly Val His Leu Val Leu Glu Leu Cys
        115                 120                 125

Ser Gly Gly Glu Leu Phe Asp Arg Ile Val Ala Gln Asp Lys Tyr Ser
    130                 135                 140

Glu Thr Glu Ala Ala Thr Val Val His Gln Ile Ala Ser Gly Leu Glu
145                 150                 155                 160

Ala Val His Arg Ala Asn Ile Val His Arg Asp Leu Lys Pro Glu Asn
                165                 170                 175

Cys Leu Phe Leu Asp Val Arg Lys Asp Ser Pro Leu Lys Ile Met Asp
            180                 185                 190

Phe Gly Leu Ser Ser Val Glu Glu Phe Thr Asp Pro Val Val Gly Leu
        195                 200                 205

Phe Gly Ser Ile Asp Tyr Val Ser Pro Glu Ala Leu Ser Gln Gly Lys
    210                 215                 220

Ile Thr Thr Lys Ser Asp Met Trp Ser Leu Gly Val Ile Leu Tyr Ile
225                 230                 235                 240

Leu Leu Ser Gly Tyr Pro Pro Phe Ile Ala Gln Asn Asn Arg Gln Lys
                245                 250                 255

Gln Gln Met Ile Met Asn Gly Asn Phe Ser Phe Tyr Glu Lys Asp Trp
            260                 265                 270

Lys Gly Ile Ser Gln Pro Ala Lys Asn Leu Ile Ser Ser Leu Leu Thr
        275                 280                 285

Val Asp Pro Ser Lys Arg Pro Ser Ala Leu Glu Leu Leu Ser Asp Pro
    290                 295                 300

Trp Val Lys Gly Glu Lys Ala Lys Asp Val Gln Met Asp Pro Glu Ile
305                 310                 315                 320
```

```
Val Ser Arg Leu Gln Ser Phe Asn Ala Arg Arg Lys Leu Arg Ala Ala
            325                 330                 335

Ala Ile Ala Ser Val Trp Ser Ser Thr Ile Phe Leu Arg Thr Lys Lys
            340                 345                 350

Leu Lys Ser Leu Val Gly Ser Tyr Asp Leu Lys Glu Glu Glu Ile Glu
            355                 360                 365

Asn Leu Arg Met His Phe Lys Lys Ile Cys Ala Asp Arg Asp Asn Ala
            370                 375                 380

Thr Leu Ser Glu Phe Glu Glu Val Leu Lys Ala Met Asn Met Leu Ser
385                 390                 395                 400

Leu Ile Pro Phe Ala Ser Arg Ile Phe Asp Leu Phe Asp Asn Asn Arg
            405                 410                 415

Asp Gly Thr Val Asp Met Arg Glu Ile Leu Cys Gly Phe Ser Ser Leu
            420                 425                 430

Lys Asn Ser Lys Gly Glu Asp Ala Leu Arg Leu Cys Phe Gln Met Tyr
            435                 440                 445

Asp Thr Asp Arg Ser Gly Cys Ile Ser Lys Glu Glu Val Ala Ser Met
            450                 455                 460

Leu Arg Ala Leu Pro Tyr Asp Cys Leu Pro Thr Asp Ile Thr Glu Pro
465                 470                 475                 480

Gly Lys Leu Asp Glu Ile Phe Asp Leu Met Asp Ala Asn Asn Asp Gly
            485                 490                 495

Lys Val Thr Phe Asp Glu Phe Lys Ala Ala Met Gln Arg Asp Ser Ser
            500                 505                 510

Leu Gln Asp Val Val Leu Ser Ser Ile Arg Pro
            515                 520

<210> SEQ ID NO 36
<211> LENGTH: 523
<212> TYPE: PRT
<213> ORGANISM: Artificial
<220> FEATURE:
<223> OTHER INFORMATION: Modified DMI3 polypeptide

<400> SEQUENCE: 36

Met Gly Tyr Gly Thr Arg Lys Leu Ser Asp Glu Tyr Glu Val Ser Glu
1               5                   10                  15

Ile Leu Gly Arg Gly Gly Phe Ser Val Val Arg Lys Gly Thr Lys Lys
            20                  25                  30

Ser Ser Ile Glu Glu Glu Lys Ser Gln Ser Gln Val Ala Ile Lys Thr
            35                  40                  45

Leu Arg Arg Leu Gly Ala Ser Asn Asn Pro Ser Gly Leu Pro Arg Lys
50                  55                  60

Lys Asp Ile Gly Glu Lys Ser Thr Ile Gly Phe Pro Thr Met Arg Gln
65                  70                  75                  80

Val Ser Val Ser Asp Thr Leu Leu Thr Asn Glu Ile Leu Val Met Arg
            85                  90                  95

Arg Ile Val Glu Asn Val Ser Pro His Pro Asn Val Ile Asp Leu Tyr
            100                 105                 110

Asp Val Tyr Glu Asp Thr Asn Gly Val His Leu Val Leu Glu Leu Cys
            115                 120                 125

Ser Gly Gly Glu Leu Phe Asp Arg Ile Val Ala Gln Asp Lys Tyr Ser
            130                 135                 140

Glu Thr Glu Ala Ala Thr Val Val His Gln Ile Ala Ser Gly Leu Glu
145                 150                 155                 160
```

Ala Val His Arg Ala Asn Ile Val His Arg Asp Leu Lys Pro Glu Asn
            165                 170                 175

Cys Leu Phe Leu Asp Val Arg Lys Asp Ser Pro Leu Lys Ile Met Asp
            180                 185                 190

Phe Gly Leu Ser Ser Val Glu Glu Phe Thr Asp Pro Val Gly Leu
        195                 200                 205

Phe Gly Ser Ile Asp Tyr Val Ser Pro Glu Ala Leu Ser Gln Gly Lys
            210                 215                 220

Ile Thr Thr Lys Ser Asp Met Trp Ser Leu Gly Val Ile Leu Tyr Ile
225                 230                 235                 240

Leu Leu Ser Gly Tyr Pro Pro Phe Ile Ala Gln Asn Asn Arg Gln Lys
            245                 250                 255

Gln Gln Met Ile Met Asn Gly Asn Phe Ser Phe Tyr Glu Lys Ile Trp
            260                 265                 270

Lys Gly Ile Ser Gln Pro Ala Lys Asn Leu Ile Ser Ser Leu Leu Thr
            275                 280                 285

Val Asp Pro Ser Lys Arg Pro Ser Ala Leu Glu Leu Leu Ser Asp Pro
            290                 295                 300

Trp Val Lys Gly Glu Lys Ala Lys Asp Val Gln Met Asp Pro Glu Ile
305                 310                 315                 320

Val Ser Arg Leu Gln Ser Phe Asn Ala Arg Arg Lys Leu Arg Ala Ala
            325                 330                 335

Ala Ile Ala Ser Val Trp Ser Ser Thr Ile Phe Leu Arg Thr Lys Lys
            340                 345                 350

Leu Lys Ser Leu Val Gly Ser Tyr Asp Leu Lys Glu Glu Ile Glu
            355                 360                 365

Asn Leu Arg Met His Phe Lys Lys Ile Cys Ala Asp Arg Asp Asn Ala
            370                 375                 380

Thr Leu Ser Glu Phe Glu Glu Val Leu Lys Ala Met Asn Met Leu Ser
385                 390                 395                 400

Leu Ile Pro Phe Ala Ser Arg Ile Phe Asp Leu Phe Asp Asn Asn Arg
            405                 410                 415

Asp Gly Thr Val Asp Met Arg Glu Ile Leu Cys Gly Phe Ser Ser Leu
            420                 425                 430

Lys Asn Ser Lys Gly Glu Asp Ala Leu Arg Leu Cys Phe Gln Met Tyr
            435                 440                 445

Asp Thr Asp Arg Ser Gly Cys Ile Ser Lys Glu Glu Val Ala Ser Met
            450                 455                 460

Leu Arg Ala Leu Pro Tyr Asp Cys Leu Pro Thr Asp Ile Thr Glu Pro
465                 470                 475                 480

Gly Lys Leu Asp Glu Ile Phe Asp Leu Met Asp Ala Asn Asn Asp Gly
            485                 490                 495

Lys Val Thr Phe Asp Glu Phe Lys Ala Ala Met Gln Arg Asp Ser Ser
            500                 505                 510

Leu Gln Asp Val Val Leu Ser Ser Ile Arg Pro
            515                 520

<210> SEQ ID NO 37
<211> LENGTH: 1569
<212> TYPE: DNA
<213> ORGANISM: Medicago truncatula

<400> SEQUENCE: 37
atgttggtgg aacttgcagt tactctattg ctcattgctc tcttcttaca cttgcgtcca    60

```
acacctactg caaaatcaaa ggctcttcgc caccttccaa atccaccaag ccctaaacca    120
cgtcttccat tcataggtca tcttcacctt ttggataacc cacttcttca ccacactctt    180
atcaagttag gaaagcgtta tggccctttg tacactcttt actttggttc catgcctacc    240
gttgttgcat ccactcctga cttgtttaaa cttttccttc aaacccatga agctacttcc    300
tttaacacaa gattccaaac ctctgctatt agtcgtctta cctatgacaa ctctgttgct    360
atggttccat ttgcacctta ttggaagttt attagaaagc ttatcatgaa cgacttgctc    420
aacgccacca ctgttaacaa attgaggcca ttgaggagcc gagaaatcct taaggttctt    480
aaggtcatgg ctaatagtgc tgaaactcaa cagccacttg atgtcactga ggagcttctc    540
aagtggacaa acagcacaat ctctaccatg atgttgggtg aggccgaaga ggttagagat    600
attgctcgtg atgttcttaa gatctttgga gaatatagtg ttacaaactt tatttggcct    660
ttgaacaagt ttaagtttgg aaactatgat aagagaactg aggagatttt caataagtat    720
gatcctatca ttgaaaaggt tatcaagaaa cgacaagaga ttgtgaacaa agaaaaaaat    780
ggagaaatcg tagaaggcga gcagaatgtt gttttttctg cactttgct tgaatttgca    840
caagatgaga ccatggagat caaaattaca aaggaacaaa tcaagggtct tgttgtggat    900
ttttctctg caggaacaga ctccaccgcc gtgtctacag aatggacttt atcagagctc    960
atcaataatc ctagagtgtt gaagaaagct cgagaggaga ttgactctgt tgtgggaaaa   1020
gatagactgg ttgatgaatc agatgttcag aatcttcctt acattaaagc catcgtaaaa   1080
gaagcatttc gcttgcaccc accactacct gtagtcaaaa gaaatgtac acaagaatgt   1140
gagatcgacg ggtatgtggt tccagaagga gcactaatac ttttcaatgt ctgggcagtg   1200
ggaagagacc caaatatttg ggtaaagcca ttggaatttc gtccagagag gttcatagaa   1260
aatgttggtg aaggtgaagc agcttcaatt gatcttaggg gtcaacattt cacacttcta   1320
ccatttgggt ctggaagaag gatgtgtcct ggagtcaatt tggctactgc aggaatggcc   1380
acaatgattg catctattat ccaatgcttc gatctccaag tacctggtca acatggagaa   1440
atattgaatg gtgattatgc taaggttagc atggaagaga gacctggtct cacagttcca   1500
agggcacata atctcatgtg tgttcctctt gcaagagctg gtgtcgcaga taaacttctt   1560
tcctcctaa                                                           1569
```

<210> SEQ ID NO 38
<211> LENGTH: 1569
<212> TYPE: DNA
<213> ORGANISM: Lotus japonicus

<400> SEQUENCE: 38

```
atgttggtgg aacttgcatt agcattactg gccatagctc tgttcttaca tttacgtccc     60
acaccaactg ccaaatccaa ggcccttcgt caccttccaa accctccaag tcccaagcct    120
cgtcttccat tcgttggaca ccttcacctt ttggaccaac cacttctcca ccactccctc    180
atcaaactcg gcgagcgata tgggcctttg tactctctct attttggatc catgcccacc    240
gttgttgcct caacccctga actcttcaaa ctcttccttc agacccatga ggcctcttcc    300
ttcaacacaa ggttccaaac ctctgccatt aggcgcctca cctatgacaa ctctgttgcc    360
atggtccctt ttgctcctta ttggaagttc atcaggaaga tcatcatgaa cgacctcctc    420
aacgccacca ccgtcaacaa gttgaggcct tgaggagcc aagagattcg taaggttctg    480
aaggctatgg cacatagtgc ggaatctcaa caaccccctta atgtcactga ggagcttctc    540
```

```
aagtggacaa acaacaccat ctctcgaatg atgttggggg aggctgaaga ggtcagagat      600
attgctcgtg aggtgcttaa gatcttcggg gaatatagtc tcacagactt catttggcca      660
ttgaagaagc tcaaggttgg acagtatgaa aagagaatag atgagatatt taacaaattc      720
gaccccgtca ttgagaaggt catcaagaaa cgccaagaga taataaagag gagaaaagag      780
agagatggag aacttgagga gggtgagcaa agtgtagttt tcctcgatac tttgcttgaa      840
tttgctgaag atgagaccat ggaaatcaaa atcacaaagg aacaaattaa gggtcttgta      900
gtggatttct tctctgcagg gacagattcg acagctgtgg caacagactg ggctctatca      960
gagctcatca acaacccgag ggtgctgaag aaagcaagag aggaagttga agtgttgtt      1020 ggaaagata gacttgttga tgaagcagat attcaaaatc ttccatacat tagagccatc      1080
gtgaaggaga cattccgcat gcatcctcca ctccctgttg ttaagagaaa gtgtgtacaa      1140
gaatgtgagc tcaacggtta cgtgatccca gagggagcac tgatactctt caacgtgtgg      1200
gccgtgcaaa gagatcccaa atactgggag ggcccatccg aattccgtcc tgagaggttt      1260
ttaactgctg aaggggagc aacctccatt gatcttagag ccagaatttt cgagcttctc      1320
ccatttgggt ctggaaggag gatgtgtcca ggtgtgaatt tggcaactgc aggaatggcc      1380
acattgcttg catctgttat ccaatgcttt gatttacagg ttgtgggtca aaagggcaaa      1440
ttattgaaag gaagtgatgc caaagttagc atggaagaga gtcctggtct cactgttcca      1500
agggcacata atctgatgtg cgttccactt gcaagaacca acgtcacatc tgaactcctt      1560
tcctcataa                                                              1569

<210> SEQ ID NO 39
<211> LENGTH: 2723
<212> TYPE: DNA
<213> ORGANISM: Glycine max

<400> SEQUENCE: 39
atgtgtttct ggggttattg cctcttgagt tcaattgcaa cttgttaagc aaatcagccg       60
gcttaagacc taagcaacac aagcaagggc tttaggtttc aaaaaaaggt ttcaattttt      120
tttaatatta atatatctca aaaaaattat tgtaaaatta tatttgaaaa taagttttaa      180
ttaaaatatt ataactaacc gttaatcttt ttattggtat tataaataat aatcaatgag      240
caacaattct tcaccgacat catatctttg ttttaaaaaa ataataattt taataaaatta     300 tttgatgaat aaataaaaga ttttattctt aaatttattt taaatctctt tgcgtccttg      360
aaaagtccat gatacaggat gagatatttg actatttgac tagaaacgta gtaggtgata      420
tatggacatt tcctggttta ttttatattc ttaaaaaata acaattcaat cgaatgtagt      480
tgccaaattt taataaataa ataaaagaa gcattcatcg aattcttcgt cttttatgag       540
tgtaaaacaa aacattgaat taggaacaat tattatcacg ttacttaaaa taaaatatac      600
taaaaccgtt gaatgaaatc ttcatatttg ataagtgtag gtagaccac aacacaaaca      660 ttgaatagaa taaatttccc cgtacagtgt cgtccactat gtggctataa aatggaagca      720
ttgaaggttg tttcctcagg ccaagatctt ggatagtaat taacctcact caaactcggg      780
atcacagaaa ccaacaacag ttcttgcact gaggtttcac gatgttgctg aacttgcac      840 ttggttttgtt tgtgttagct ttgtttctgc acttgcgtcc cacaccaagt gcaaaatcaa      900
aagcacttcg ccacctccca aaccctccaa gcccaaagcc tcgtcttccc ttcattggcc      960
accttcacct cttaaaagat aaacttctcc actatgcact catcgatctc tccaaaaagc     1020 atggccccttt attctctctc tccttcggct ccatgccaac cgtcgttgcc tccacccctg     1080
```

| | |
|---|---|
| agttgttcaa gctcttcctc caaacccacg aggcaacttc cttcaacaca aggttccaaa | 1140 |
| cctctgccat aagacgcctc acttacgaca actctgtggc catggttcca ttcggacctt | 1200 |
| actggaagtt cgtgaggaag ctcatcatga cgaccttct caacgccacc accgtcaaca | 1260 |
| agctcaggcc tttgaggacc caacagatcc gcaagttcct tagggttatg cccaaagcg | 1320 |
| cagaggccca gaagcccctt gacgtcaccg aggagcttct caaatggacc aacagcacca | 1380 |
| tctccatgat gatgctcggc gaggctgagg agatcagaga catcgctcgc gaggttctta | 1440 |
| agatcttcgg cgaatacagc ctcactgact tcatctggcc tttgaagtat ctcaaggttg | 1500 |
| gaaagtatga agaggatt gatgacatct tgaacaagtt cgaccctgtc gttgaaaggg | 1560 |
| tcatcaagaa gcgccgtgag atcgtcagaa ggagaaagaa cggagaagtt gttgagggcg | 1620 |
| aggccagcgg cgtcttcctc gacactttgc ttgaattcgc tgaggacgag accatggaga | 1680 |
| tcaaaattac caaggagcaa atcaagggcc ttgttgtcgt aagtttcctt cttctctcct | 1740 |
| actttattac tttctttcat tcatcatatg tattggcatt aaatagtata ctatatgaga | 1800 |
| aaatatgtta cgcactcacg gtgtaaagat atgtggtgtt tttttaaaaa gagatacaga | 1860 |
| agttgctttt atgcatgtat gttaacgtat atttactcaa gtggaaacta attaattctc | 1920 |
| aattttgggt atgtaggact ttttctctgc agggacagat tccactgcgg tggcaacaga | 1980 |
| gtgggcattg gcagagctca tcaacaatcc caggtgttg caaaaggctc gtgaggaggt | 2040 |
| ctacagtgtt gtgggcaaag atagactcgt tgacgaagtt gacactcaaa accttcctta | 2100 |
| cattagggcc attgtgaagg agacattccg aatgcaccca ccactcccag tggtcaaaag | 2160 |
| aaagtgcaca gaagagtgtg agattaatgg gtatgtgatc ccagagggag cattggttct | 2220 |
| tttcaatgtt tggcaagtag aagggaccc caaatactgg gacagaccat cagaattccg | 2280 |
| tcccgagagg ttcttagaaa ctggtgctga aggggaagca gggcctcttg atcttagggg | 2340 |
| ccagcatttc caactcctcc catttgggtc tgggaggaga atgtgccctg gtgtcaattt | 2400 |
| ggctacttca ggaatggcaa cacttcttgc atctcttatc caatgctttg acctgcaagt | 2460 |
| gctgggccct caaggacaaa tattgaaagg tgatgatgcc aaagttagca tggaagagag | 2520 |
| agctggcctc acggttccaa gggcacatag tctcgtttgt gttccacttg caaggatcgg | 2580 |
| cgttgcatct aaactccttt cttaattaag ataatcatca tatacaatag tagtgtcttg | 2640 |
| ccatcgcagt tgcttttat gtattcataa tcatcatttc aataaggtgt gactggtact | 2700 |
| taatcaagta attaaggtta cat | 2723 |

<210> SEQ ID NO 40
<211> LENGTH: 1566
<212> TYPE: DNA
<213> ORGANISM: Trifolium pratense

<400> SEQUENCE: 40

| | |
|---|---|
| atgttgctgg aacttgcact tggtttattg gttttggctc tgtttctgca cttgcgtccc | 60 |
| acacccactg caaaatcaaa agcacttcgc catctcccaa acccaccaag cccaaagcct | 120 |
| cgtcttccct tcataggaca ccttcatctc ttaaaagaca aacttctcca ctacgcactc | 180 |
| atcgacctct ccaaaaaaca tggtccctta ttctctctct actttggctc catgccaacc | 240 |
| gttgttgcct ccacaccaga attgttcaag ctcttcctcc aaacgcacga ggcaacttcc | 300 |
| ttcaacacaa ggttccaaac ctcagccata agacgcctca cctatgatag ctcagtggcc | 360 |
| atggttccct tcggaccta ctggaagttc gtgaggaagc tcatcatgaa cgaccttctc | 420 |

| aacgccacca ctgtaaacaa gttgaggcct ttgaggaccc aacagatccg caagttcctt | 480 |
| agggttatgg cccaaggcgc agaggcacag aagcccttg acttgaccga ggagcttctg | 540 |
| aaatggacca acagcaccat ctccatgatg atgctcggcg aggctgagga gatcagagac | 600 |
| atcgctcgcg aggttcttaa gatctttggc gaatacagcc tcactgactt catctggcca | 660 |
| ttgaagcatc tcaaggttgg aaagtatgag aagaggatcg acgacatctt gaacaagttc | 720 |
| gaccctgtcg ttgaaagagt catcaagaag cgccgtgaga tcgtgaggag agaaagaaac | 780 |
| ggagaggttg ttgagggtga ggtcagcggg gttttccttg cactttgct tgaattcgct | 840 |
| gaggatgaga ccacggagat caaaatcacc aaggaccaca tcaagggtct tgttgtcgac | 900 |
| ttttctcgg caggaacaga ctccacagcg gtggcaacag agtgggcatt ggcagaactc | 960 |
| atcaacaatc ctaaggtgtt ggaaaaggct cgtgaggagg tctacagtgt tgtgggaaag | 1020 |
| gacagacttg tggacgaagt tgacactcaa aaccttcctt acattagagc aatcgtgaag | 1080 |
| gagacattcc gcatgcaccc gccactccca gtggtcaaaa gaaagtgcac agaagagtgt | 1140 |
| gagattaatg gatatgtgat cccagaggga gcattgattc tcttcaatgt atggcaagta | 1200 |
| ggaagagacc ccaaatactg ggacagacca tcggagttcc gtcctgagag gttcctagag | 1260 |
| acagggctg aaggggaagc aaggcctctt gatcttaggg gacaacattt tcaacttctc | 1320 |
| ccatttgggt ctgggaggag aatgtgccct ggagtcaatc tggctacttc gggaatggca | 1380 |
| acacttcttg catctcttat tcagtgcttt gacttgcaag tgctgggtcc acaaggacag | 1440 |
| atattgaagg gtggtgacgc caaagttagc atggaagaga gggccggcct cactgttcca | 1500 |
| agggcacata gtcttgtctg tgttccactt gcaaggatcg gcgttgcatc taaactcctt | 1560 |
| tcttaa | 1566 |

<210> SEQ ID NO 41
<211> LENGTH: 1563
<212> TYPE: DNA
<213> ORGANISM: Pisum sativum

<400> SEQUENCE: 41

| atgttgctgg aacttgcact tggttttgttt gtgttagctt tgtttctgca cttgcgtccc | 60 |
| acaccaagcg caaaatcaaa agcacttcgc cacctcccaa accctccaag cccaaagcct | 120 |
| cgtcttccct tcattggcca ccttcacctc ttaaaagata aacttctcca ctatgcactc | 180 |
| atcgatctct ccaaaaagca tggccccctta ttctctctct ccttcggctc catgccaacc | 240 |
| gtcgttgcct ccacccctga gttgttcaag ctcttcctcc aagcccacga ggcaacttcc | 300 |
| ttcagcacaa ggttccaaac tctgccgta agacgcctca cttacgacaa ctctgtggcc | 360 |
| atggttccat tcggacctta ctggaagttc gtgaggaagc tcatcatgaa cgaccttctc | 420 |
| aacgccacca ccgtcaacga gctcaggcct ttgaggaccc aacagatccg caagttcctt | 480 |
| agggttatgg cccaaagcgc agaggcccag aagcccttg acgtcaccga ggagcttctc | 540 |
| aaatggacca acagcaccat ctccatgatg atgctcggcg aggctgagga gatcagagac | 600 |
| atcgctcgcg aggtccttaa gatcttcggc gaatacagcc tcactgactt catctggcct | 660 |
| ttgaagtatc tcaaggttgg aaagtatgag aagaggattg atgacatctt gaacaagttc | 720 |
| gaccctgtcg ttgaaagggt catcaagaag cgccgtgaga tcgtcagaag gagaaagaac | 780 |
| ggagaagttg ttgagggcga ggccagcggc gtcttcctcg cactttgct tgaattcgct | 840 |
| gaggacgaga ccatggagat caaaattacc aaggagcaaa tcaagggcct tgttgtcgac | 900 |
| ttttctctg cagggacaga ttccacagcg gtggcaacag agtgggcatt ggcagagctc | 960 |

| | |
|---|---|
| atcaacaatc ccagggtgtt gcaaaaggct cgtgaggagg tctacagtgt tgtgggcaaa | 1020 |
| gatagactcg ttgacgaagt cgacactcaa aaccttcctt acattagggc cattgtgaag | 1080 |
| gagacattcc gaatgcaccc accactccca gtggtcaaaa gaaagtgcac agaagagtgt | 1140 |
| gagattaatg ggtatgtgat cccagaggga gcattggttc ttttcaatgt ttggcaagta | 1200 |
| ggaaaggacc ccaaatactg ggacagacca tcagaattcc gtcccgagag gttcttagaa | 1260 |
| actggcgctg aaggggaagc agggcctctt gatcttaggg gccagcattt ccaactcctc | 1320 |
| ccatttgggt ctggaggag aatgtgccct ggtgtcaatt tggctacttc aggaatggca | 1380 |
| acacttcttg catctcttat ccaatgcttt gacctgcaag tgctgggccc tcaaggacaa | 1440 |
| atattgaaag gtgacgatgc caaagttagc atggaagaga gagctggcct caccgttcca | 1500 |
| agggcacata gtctcgtttg tgttccactt gcaaggatcg gcgttgcatc taaactcctt | 1560 |
| tct | 1563 |

<210> SEQ ID NO 42
<211> LENGTH: 1497
<212> TYPE: DNA
<213> ORGANISM: Beta vulgaris

<400> SEQUENCE: 42

| | |
|---|---|
| tctgcacttg cgtcccacac ccactgcaaa atcaaaagca cttcgccatc tcccaaaccc | 60 |
| accaagccca agcctcgtc tttcccttcat aggacacctt catctcttaa aagacaaact | 120 |
| tctccactac gcactcatcg acctctccaa aaaacatggt cccttattct ctcactactt | 180 |
| tggctccatg ccaaccgttg ttgcctccac accagaattg ttcaagctct tcctccaaac | 240 |
| gaacgaggca acttccttca acacaaggtt ccaaacctca gccataagac gcctcaccta | 300 |
| tgatagctca gtggccatgg ttcccttcgg accttactgg aagttcgtga ggaagctcat | 360 |
| catgaacgac cttctcaacg ccaccactgt aaacaagttg aggccttga ggacccaaca | 420 |
| gatccgcaag ttccttaggg ctatggccca aggcgcagag gcacggaagc cccttgactt | 480 |
| gaccgaggag cttctgaaat gggccaacag caccatctcc atgatgatgc tcggcgaggc | 540 |
| tgaggagatc agagacatcg ctcgcgaggt tcttaagatc tttggcgaat acagcctcac | 600 |
| tgacttcatc tggccattga agcatctcaa ggttggaaag tatgagaaga ggatcgacga | 660 |
| catcttgaac aagttcgacc ctgtcgttga aagagtcatc aagaagcgcc gtgagatcgt | 720 |
| gaggaggaga aagaacggag aggttgttga gggtgaggtc agcggggttt ccttgacac | 780 |
| tttgcttgaa ttcgctgagg atgagaccat ggagatcaaa atcaccaagg accacaccaa | 840 |
| gggtcttgtt gtcgacttct tctcggcagg aacagactcc acagcggtgg caacagagtg | 900 |
| ggcattggca gaactcatca acaatcctaa ggtgttggaa aaggctcgtg aggaggtcta | 960 |
| cagtgttgtg ggaaaggaca gacttgtgga cgaagttgac actcaaaaacc ttccttacat | 1020 |
| tagagcaatc gtgaaggaga cattccgcat gcacccgcca ctcccagtgg tcaaaagaaa | 1080 |
| gtgcacagaa gagtgtgaga ttaatggata tgtgatccca gagggagcat tgattccctt | 1140 |
| caatgtatgg caagtaggaa gagacccaa atactgggac agaccatcgg agttccgtcc | 1200 |
| tgagaggttc ctagagacag gggctgaagg ggaagcaagg cctcttgatc ttaggggaca | 1260 |
| acattttcaa cttctcccat ttgggtctgg gaggagaatg tgccctggag tcaatctggc | 1320 |
| tacttcggga acggcaacac ttcttgcatc tcttattcag tgctttgact tgcaagtgct | 1380 |
| gggtccacag ggacagatat tgaagggtgg tgacgccaaa gttagcatgg aagagagagc | 1440 |

| | |
|---|---|
| cggcctcact gttccaaggg cacatagtct tgtctgtgtt ccacttgcaa ggatcgg | 1497 |

<210> SEQ ID NO 43
<211> LENGTH: 1501
<212> TYPE: DNA
<213> ORGANISM: Vicia villosa

<400> SEQUENCE: 43

| | |
|---|---|
| tgtttctgca cttgcgtccc acacccactg caaaatcaaa agcacttcgc catctcccaa | 60 |
| acccaccaag cccaaagcct cgtcttccct tcataggaca ccttcatctc ttaaaagaca | 120 |
| aacttctcca ctacgcactc atcgacctct ccaaaaaaca tggtcccttt ttctctctct | 180 |
| actttggctc catgccaacc gttgttgcct ccacaccaga attgttcaag ctcttcctcc | 240 |
| aaacgcacga ggcaacttcc ttcaacacaa ggttccaaac ctcagccata agacgcctca | 300 |
| cctatgatag cttagtggcc atggttccct tcggacctta ctggaagttc gtgaggaagc | 360 |
| tcatcatgaa cgaccttctc aacgccacca ctgtaaacaa gttgaggcct ttgaggaccc | 420 |
| aacagatccg caagttcctt agggttatgg cccaaggcgc agaggcacag aagccccttg | 480 |
| acttgaccga ggagcttctg aaatggacca acagcaccat ctctatgatg atgctcggcg | 540 |
| aggctgagga gatcagagac atcgctcgcg aggttcttaa gatctatggc gaatacagcc | 600 |
| tcactgactt catctggcca ttgaagcatc tcaaggttgg aaagtatgag aagaggatcg | 660 |
| acgacatctt gaacaagttc gaccctgtcg ttgaaagagt catcaagaag cgccgtgaga | 720 |
| tcgtgaggag gagaaagaac ggagaggttg ttgagggtga ggtcagcggg gttttccttg | 780 |
| acactttgct tgaattcgct gaggatgaga ccacggagat caaaatcacc aaggaccaca | 840 |
| tcaagggtct tgttgtcgac ttttctcgg caggaataga ctccacagcg gtggcaacag | 900 |
| agtgggcatt ggcagaactc atcaacaatc ctaaggtgtt ggaaaaggct cgtgaggagg | 960 |
| tctacagtgt tgtgggaaag gacagacttg tggacgaagt tgacactcaa aaccttcctt | 1020 |
| acattagagc aatcgtgaag gagacattcc gcatgcaccc gccactccca gtggtcaaaa | 1080 |
| gaaagtgcac agaagagtgt gagattaatg gatatgtgat cccagaggga gcattgattc | 1140 |
| tcttcaatgt atggcaagta ggaagggacc ccaaatactg ggacagacca tcggagttcc | 1200 |
| gtcctgagag gttcctagag acaggggctg aaggggaagc aaggcctctt gatcttaggg | 1260 |
| gacaacattt tcaacttctc ccatttgggt ctgggagggg aatgtgccct ggagtcaatc | 1320 |
| tggctacttc gggaatggca acacttcttg catctcttat tcagtgcttt gacttgcaag | 1380 |
| tgctgggtcc acaaggacag atattgaagg gtggtgacgc caaagttagc atggaagaga | 1440 |
| gggccggcct cactgttcca agggcacata gtcttgtctg tgttccactt gcaaggatcg | 1500 |
| g | 1501 |

<210> SEQ ID NO 44
<211> LENGTH: 1899
<212> TYPE: DNA
<213> ORGANISM: Caragana arborescens

<400> SEQUENCE: 44

| | |
|---|---|
| aagatcaaag aaacacaaaa caaacaccat gttggtggaa ctagcaatta ctctattagt | 60 |
| gatagctctg ttcctacacc ttcgtcccac accttctgca aaatcaaaag ccttcgcca | 120 |
| ccttccaaac ccaccgagtc caaaacctcg tcttcctttc ataggtcacc ttcacctttt | 180 |
| agacaaacct cttctccacc agtccctcat ccgtctcagc gaacgctatg gccccttata | 240 |
| ctctctctac tttggttcca tgcctaccgt tgttgcctcc acccctgaat tgttcaaact | 300 |

```
cttccttcaa acccacgagg cttcttcctt caacaccagg ttccaaacct ctgccatcag      360
acgccttacc tacgataact ccgttgccat ggttcccttt ggaccttact ggaagttcat      420
cagaaagctc atcatgaacg accttctaaa cgccacaacc gtcaacaagt tgagaccctt      480
gaggagccag gaaatccgta aggttcttaa ggtgatggca cagagcgcgg aaactcaaca      540
gccacttaat gtcaccgagg agcttctcaa gtggaccaac agcaccatct ctaggatgat      600
gttgggtgag gctgaagaga ttagagacat tgctcgtgat gtgcttaaga tctttggaga      660
gtatagtctt acggatttca tttggccatt gaagaaactc aaggttggac agtatgagaa      720
gagaatagat gatattttca acaggtttga ccctgtcatt gaaaaggtca tcaagaaacg      780
ccaggagatt aggaagagaa gaaaggagag aaatggtgaa cttgaagagg gtgagcagag      840
tgttgttttt cttgatactt tgcttgattt tgctgaggay gagaccatgg agatcaaaat      900
taccaaggaa caaatcaagg gtcttattgt ggatttcttc tcagcaggga cagattcaac      960
ggcagtggca acagactatg ctttgtcaga gctaatcaac aaccccaggg tgttgcaaaa     1020
agcgcgagag gaagtcgata tgttgtgggg aaaagataga ctggttgacg aatcagatgt     1080
tcaaaacctt cctttcatta gagcaatcgt gaaggagaca ttccgtatgc acccgccact     1140
acccgttgtg aaaagaaaat gtacacaaga gtgtgagata gacggttttg tgatcccaga     1200
gggagcattg atactttttca atgtttgggc tgttggaaga gacccaaagt actgggaaag     1260
gccctcggaa tttcgtcctg agaggttctt acaaaatgct ggtgaagggg aagtaggttc     1320
aattgatctt aggggccaac atttccaact tttgccattt gggtctggta ggagaatgtg     1380
ccctggagtc aatttggcta ctgcaggaat ggctacactt cttgcatctg ttattcagtg     1440
ctttgacctg caagtaccgg gcccacaagg agaactattg aaaggtgatg atgccaaggt     1500
tagcatggaa gagagacctg tcttacagt tccaagggcg aataatctca tgtgtgttcc     1560
tcttgctaga gcaggtgttg cagctaaact tctttcctcc taaaaacaca gtacaacaca     1620
gcacaaccac aagaatgttg ctatggatgg tgttttttta tatttgtagt aataatcatt     1680
ttcaataagg tatcattgag agacaatgag tccaagttcc cccggcacat gggctgctgg     1740
aagagtcaca tatatattta tcgtctcaat taaactctct ttgatgtaat tttcatcttt     1800
gttttttctt tttccttttt gtcaccgaag aagtgttgta cttgtaacag cttatatcta     1860 taattttttac gaaaaaaaaa aaaaaaaaaa aaaaaaaaa                            1899

<210> SEQ ID NO 45
<211> LENGTH: 1770
<212> TYPE: DNA
<213> ORGANISM: Vigna unguiculata

<400> SEQUENCE: 45
aggccaaaat cttggtgtca catagcctca agctcgggat ctcacaaaaa caaaggtcaa       60
gcaaacacat acacaaccat gttgctcgaa attacaattg gtttgttggt gctggctttg      120 ttttttgcact tgcgtcccac acccactgct aaatcaaagg cccttcgcca ccttccaaac      180
cctcctagtc caaaacctcg tcttccattc attggtcacc ttcaccttct aaaagacaaa      240
cttctccact atgccctcat agattatccc aaaacctatg gcccttttgta ctctctctac      300 tttgggtcta tgccaaccgt tgttgcctcc tcccctgagt tgttcaaact cttccttcaa      360
acccacgagg ctgcttcctt caacacaagg ttccaaacct ctgccattag gcgcctcact      420
tatgacaact cagtggccat ggttcccttt ggaccttact ggaagttcat caggaagctc      480
```

-continued

| | |
|---|---|
| atcatgaacg acctcctcaa cgccaccacc gtcaacaagt tgaggcccct caggacccaa | 540 |
| cagatccgca agttcctcaa ggtcatggcc caaagcgcac aggctcagca gccccttaac | 600 |
| gtcaccgagg agcttctcaa gtggaccaac agcactatct ccatgatgat gttgggtgag | 660 |
| gctgaagaga ttagagatat cgctcgtgag gtgcttaaga ttttcgggga gtacagtctc | 720 |
| actgacttca tctggcccct gaagaagctt aagtttggac agtacgagaa gaggatcgat | 780 |
| gaaatattca caagttcga ccctgtcatc gagagggtta ttaagaagcg ccgagagatc | 840 |
| atgagaagga gaaagaacgg agaagccgtt gaggaagagc agagcggagt cttcctcgac | 900 |
| actttgcttc aattcgctga ggacgagacc atggagatca aaattaccaa ggagcagatc | 960 |
| aagggtcttg ttgtcgactt cttctcagca ggaacagatt ccacagccgt ggcaactgag | 1020 |
| tgggctttgg cagagctgat caacaaccct agggtgttgc agaaggctcg ggaggaggtg | 1080 |
| tacagtgttg tggggaaaga tagactggtt gatgaagttg atactcaaaa ccttccttac | 1140 |
| atcagggcga ttgtgaagga gacattccgc atgcacccac cactcccagt ggtgaagaga | 1200 |
| aagtgtgtgg aggagtgtga gattgagggg tatgtgatcc cagagggagc attgatactt | 1260 |
| ttcaatgtgt gggctgtagg aagagaccct aaatactggg acagaccatt ggagtttcgt | 1320 |
| cctgagagat tcctagaaac tggagctgaa ggagaagctg ggcctcttga tcttaggggc | 1380 |
| caacatttca ctcttctccc atttgggtca ggtagaagaa tgtgccctgg agtgaatttg | 1440 |
| gctacttcag gtatggcaac acttcttgca tctgttatcc agtgctttga ccttcaagtg | 1500 |
| gtgggcccac aaggacaaat attgaaaggc aatgacgcca agtgagcat ggaagagaga | 1560 |
| gctggactca cggttccgag ggcacataat ctggagtgtg ttccagttgc aaggacaagc | 1620 |
| gttgcagcta aactcctttc ctagttcaca acatatatac aacaacagtg tcttgccact | 1680 |
| catgcttttg cttttgtgtg ttaataataa tcgtttcaat aaggtgtctt tgataacgaa | 1740 |
| gtcagacaca ttcacatgta aaaaaaaaaa | 1770 |

<210> SEQ ID NO 46
<211> LENGTH: 522
<212> TYPE: PRT
<213> ORGANISM: Medicago truncatula

<400> SEQUENCE: 46

Met Leu Val Glu Leu Ala Val Thr Leu Leu Ile Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Asp Asn Pro Leu Leu His Thr Leu Ile Lys Leu Gly
    50                  55                  60

Lys Arg Tyr Gly Pro Leu Tyr Thr Leu Tyr Phe Gly Ser Met Pro Thr
65                  70                  75                  80

Val Val Ala Ser Thr Pro Asp Leu Phe Lys Leu Phe Leu Gln Thr His
                85                  90                  95

Glu Ala Thr Ser Phe Asn Thr Arg Phe Gln Thr Ser Ala Ile Ser Arg
            100                 105                 110

Leu Thr Tyr Asp Asn Ser Val Ala Met Val Pro Phe Ala Pro Tyr Trp
        115                 120                 125

Lys Phe Ile Arg Lys Leu Ile Met Asn Asp Leu Leu Asn Ala Thr Thr
    130                 135                 140

Val Asn Lys Leu Arg Pro Leu Arg Ser Arg Glu Ile Leu Lys Val Leu
145                 150                 155                 160

Lys Val Met Ala Asn Ser Ala Glu Thr Gln Gln Pro Leu Asp Val Thr
            165                 170                 175

Glu Glu Leu Leu Lys Trp Thr Asn Ser Thr Ile Ser Thr Met Met Leu
                180                 185                 190

Gly Glu Ala Glu Val Arg Asp Ile Ala Arg Asp Val Leu Lys Ile
        195                 200                 205

Phe Gly Glu Tyr Ser Val Thr Asn Phe Ile Trp Pro Leu Asn Lys Phe
    210                 215                 220

Lys Phe Gly Asn Tyr Asp Lys Arg Thr Glu Glu Ile Phe Asn Lys Tyr
225                 230                 235                 240

Asp Pro Ile Ile Glu Lys Val Ile Lys Lys Arg Gln Glu Ile Val Asn
                245                 250                 255

Lys Arg Lys Asn Gly Glu Ile Val Glu Gly Gln Asn Val Val Phe
                260                 265                 270

Leu Asp Thr Leu Leu Glu Phe Ala Gln Asp Glu Thr Met Glu Ile Lys
        275                 280                 285

Ile Thr Lys Glu Gln Ile Lys Gly Leu Val Val Asp Phe Phe Ser Ala
    290                 295                 300

Gly Thr Asp Ser Thr Ala Val Ser Thr Glu Trp Thr Leu Ser Glu Leu
305                 310                 315                 320

Ile Asn Asn Pro Arg Val Leu Lys Lys Ala Arg Glu Glu Ile Asp Ser
                325                 330                 335

Val Val Gly Lys Asp Arg Leu Val Asp Glu Ser Asp Val Gln Asn Leu
            340                 345                 350

Pro Tyr Ile Lys Ala Ile Val Lys Glu Ala Phe Arg Leu His Pro Pro
        355                 360                 365

Leu Pro Val Val Lys Arg Lys Cys Thr Gln Glu Cys Glu Ile Asp Gly
    370                 375                 380

Tyr Val Val Pro Glu Gly Ala Leu Ile Leu Phe Asn Val Trp Ala Val
385                 390                 395                 400

Gly Arg Asp Pro Lys Tyr Trp Val Lys Pro Leu Glu Phe Arg Pro Glu
                405                 410                 415

Arg Phe Ile Glu Asn Val Gly Glu Gly Glu Ala Ala Ser Ile Asp Leu
            420                 425                 430

Arg Gly Gln His Phe Thr Leu Leu Pro Phe Gly Ser Gly Arg Arg Met
        435                 440                 445

Cys Pro Gly Val Asn Leu Ala Thr Ala Gly Met Ala Thr Met Ile Ala
    450                 455                 460

Ser Ile Ile Gln Cys Phe Asp Leu Gln Val Pro Gly Gln His Gly Glu
465                 470                 475                 480

Ile Leu Asn Gly Asp Tyr Ala Lys Val Ser Met Glu Glu Arg Pro Gly
                485                 490                 495

Leu Thr Val Pro Arg Ala His Asn Leu Met Cys Val Pro Leu Ala Arg
            500                 505                 510

Ala Gly Val Ala Asp Lys Leu Leu Ser Ser
        515                 520

<210> SEQ ID NO 47
<211> LENGTH: 522
<212> TYPE: PRT
<213> ORGANISM: Lotus japonicus

<400> SEQUENCE: 47

```
Met Leu Val Glu Leu Ala Leu Ala Leu Leu Ala Ile Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Val Gly His Leu
        35                  40                  45

His Leu Leu Asp Gln Pro Leu Leu His His Ser Leu Ile Lys Leu Gly
50                  55                  60

Glu Arg Tyr Gly Pro Leu Tyr Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Ser Ser Phe Asn Thr Arg Phe Gln Thr Ser Ala Ile Arg Arg
                100                 105                 110

Leu Thr Tyr Asp Asn Ser Val Ala Met Val Pro Phe Ala Pro Tyr Trp
            115                 120                 125

Lys Phe Ile Arg Lys Ile Ile Met Asn Asp Leu Leu Asn Ala Thr Thr
        130                 135                 140

Val Asn Lys Leu Arg Pro Leu Arg Ser Gln Glu Ile Arg Lys Val Leu
145                 150                 155                 160

Lys Ala Met Ala His Ser Ala Glu Ser Gln Gln Pro Leu Asn Val Thr
                165                 170                 175

Glu Glu Leu Leu Lys Trp Thr Asn Asn Thr Ile Ser Arg Met Met Leu
                180                 185                 190

Gly Glu Ala Glu Glu Val Arg Asp Ile Ala Arg Glu Val Leu Lys Ile
            195                 200                 205

Phe Gly Glu Tyr Ser Leu Thr Asp Phe Ile Trp Pro Leu Lys Lys Leu
        210                 215                 220

Lys Val Gly Gln Tyr Glu Lys Arg Ile Asp Glu Ile Phe Asn Lys Phe
225                 230                 235                 240

Asp Pro Val Ile Glu Lys Val Ile Lys Lys Arg Gln Glu Ile Ile Lys
                245                 250                 255

Arg Arg Lys Glu Arg Asp Gly Glu Leu Glu Gly Glu Gln Ser Val
                260                 265                 270

Val Phe Leu Asp Thr Leu Leu Glu Phe Ala Glu Asp Glu Thr Met Glu
            275                 280                 285

Ile Lys Ile Thr Lys Glu Gln Ile Lys Gly Leu Val Val Asp Phe Phe
        290                 295                 300

Ser Ala Gly Thr Asp Ser Thr Ala Val Ala Thr Asp Trp Ala Leu Ser
305                 310                 315                 320

Glu Leu Ile Asn Asn Pro Arg Val Leu Lys Lys Ala Arg Glu Glu Val
                325                 330                 335

Glu Ser Val Val Gly Lys Asp Arg Leu Val Asp Glu Ala Asp Ile Gln
            340                 345                 350

Asn Leu Pro Tyr Ile Arg Ala Ile Val Lys Glu Thr Phe Arg Met His
        355                 360                 365

Pro Pro Leu Pro Val Val Lys Arg Lys Cys Val Gln Glu Cys Glu Leu
        370                 375                 380

Asn Gly Tyr Val Ile Pro Glu Gly Ala Leu Ile Leu Phe Asn Val Trp
385                 390                 395                 400

Ala Val Gln Arg Asp Pro Lys Tyr Trp Glu Gly Pro Ser Glu Phe Arg
                405                 410                 415
```

```
Pro Glu Arg Phe Leu Thr Ala Glu Gly Ala Thr Ser Ile Asp Leu
            420                 425                 430

Arg Gly Gln Asn Phe Glu Leu Leu Pro Phe Gly Ser Gly Arg Arg Met
        435                 440                 445

Cys Pro Gly Val Asn Leu Ala Thr Ala Gly Met Ala Thr Leu Leu Ala
    450                 455                 460

Ser Val Ile Gln Cys Phe Asp Leu Gln Val Val Gly Gln Lys Gly Lys
465                 470                 475                 480

Leu Leu Lys Gly Ser Asp Ala Lys Val Ser Met Glu Glu Ser Pro Gly
                485                 490                 495

Leu Thr Val Pro Arg Ala His Asn Leu Met Cys Val Pro Leu Ala Arg
            500                 505                 510

Thr Asn Val Thr Ser Glu Leu Leu Ser Ser
            515                 520

<210> SEQ ID NO 48
<211> LENGTH: 521
<212> TYPE: PRT
<213> ORGANISM: Glycine max

<400> SEQUENCE: 48

Met Leu Leu Glu Leu Ala Leu Gly Leu Phe Val Leu Ala Leu Phe Leu
1               5                   10                  15

His Leu Arg Pro Thr Pro Ser Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Ser Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
130                 135                 140

Val Asn Lys Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys Tyr Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Ala Ser Gly Val Phe
            260                 265                 270
```

```
Leu Asp Thr Leu Leu Glu Phe Ala Glu Asp Glu Thr Met Glu Ile Lys
            275                 280                 285

Ile Thr Lys Glu Gln Ile Lys Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
            325                 330                 335

Val Val Gly Lys Asp Arg Leu Val Asp Glu Val Asp Thr Gln Asn Leu
        340                 345                 350

Pro Tyr Ile Arg Ala Ile Val Lys Glu Thr Phe Arg Met His Pro Pro
    355                 360                 365

Leu Pro Val Val Lys Arg Lys Cys Thr Glu Glu Cys Glu Ile Asn Gly
370                 375                 380

Tyr Val Ile Pro Glu Gly Ala Leu Val Leu Phe Asn Val Trp Gln Val
385                 390                 395                 400

Gly Arg Asp Pro Lys Tyr Trp Asp Arg Pro Ser Glu Phe Arg Pro Glu
            405                 410                 415

Arg Phe Leu Glu Thr Gly Ala Glu Gly Glu Ala Gly Pro Leu Asp Leu
        420                 425                 430

Arg Gly Gln His Phe Gln Leu Leu Pro Phe Gly Ser Gly Arg Arg Met
    435                 440                 445

Cys Pro Gly Val Asn Leu Ala Thr Ser Gly Met Ala Thr Leu Leu Ala
450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Glu Arg Ala Gly
            485                 490                 495

Leu Thr Val Pro Arg Ala His Ser Leu Val Cys Val Pro Leu Ala Arg
        500                 505                 510

Ile Gly Val Ala Ser Lys Leu Leu Ser
    515                 520

<210> SEQ ID NO 49
<211> LENGTH: 521
<212> TYPE: PRT
<213> ORGANISM: Trifolium pratense

<400> SEQUENCE: 49

Met Leu Leu Glu Leu Ala Leu Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
            85                  90                  95

Glu Ala Thr Ser Phe Asn Thr Arg Phe Gln Thr Ser Ala Ile Arg Arg
        100                 105                 110

Leu Thr Tyr Asp Ser Ser Val Ala Met Val Pro Phe Gly Pro Tyr Trp
```

```
            115                 120                 125
Lys Phe Val Arg Lys Leu Ile Met Asn Asp Leu Leu Asn Ala Thr Thr
130                 135                 140
Val Asn Lys Leu Arg Pro Leu Arg Thr Gln Gln Ile Arg Lys Phe Leu
145                 150                 155                 160
Arg Val Met Ala Gln Gly Ala Glu Ala Gln Lys Pro Leu Asp Leu Thr
                165                 170                 175
Glu Glu Leu Leu Lys Trp Thr Asn Ser Thr Ile Ser Met Met Met Leu
                180                 185                 190
Gly Glu Ala Glu Glu Ile Arg Asp Ile Ala Arg Glu Val Leu Lys Ile
                195                 200                 205
Phe Gly Glu Tyr Ser Leu Thr Asp Phe Ile Trp Pro Leu Lys His Leu
210                 215                 220
Lys Val Gly Lys Tyr Glu Lys Arg Ile Asp Asp Ile Leu Asn Lys Phe
225                 230                 235                 240
Asp Pro Val Val Glu Arg Val Ile Lys Lys Arg Arg Glu Ile Val Arg
                245                 250                 255
Arg Arg Lys Asn Gly Glu Val Glu Gly Glu Val Ser Gly Val Phe
                260                 265                 270
Leu Asp Thr Leu Leu Glu Phe Ala Glu Asp Glu Thr Thr Glu Ile Lys
                275                 280                 285
Ile Thr Lys Asp His Ile Lys Gly Leu Val Val Asp Phe Phe Ser Ala
290                 295                 300
Gly Thr Asp Ser Thr Ala Val Ala Thr Glu Trp Ala Leu Ala Glu Leu
305                 310                 315                 320
Ile Asn Asn Pro Lys Val Leu Glu Lys Ala Arg Glu Glu Val Tyr Ser
                325                 330                 335
Val Val Gly Lys Asp Arg Leu Val Asp Glu Val Asp Thr Gln Asn Leu
                340                 345                 350
Pro Tyr Ile Arg Ala Ile Val Lys Glu Thr Phe Arg Met His Pro Pro
                355                 360                 365
Leu Pro Val Val Lys Arg Lys Cys Thr Glu Glu Cys Glu Ile Asn Gly
370                 375                 380
Tyr Val Ile Pro Glu Gly Ala Leu Ile Leu Phe Asn Val Trp Gln Val
385                 390                 395                 400
Gly Arg Asp Pro Lys Tyr Trp Asp Arg Pro Ser Glu Phe Arg Pro Glu
                405                 410                 415
Arg Phe Leu Glu Thr Gly Ala Glu Gly Glu Ala Arg Pro Leu Asp Leu
                420                 425                 430
Arg Gly Gln His Phe Gln Leu Leu Pro Phe Gly Ser Gly Arg Arg Met
                435                 440                 445
Cys Pro Gly Val Asn Leu Ala Thr Ser Gly Met Ala Thr Leu Leu Ala
                450                 455                 460
Ser Leu Ile Gln Cys Phe Asp Leu Gln Val Leu Gly Pro Gln Gly Gln
465                 470                 475                 480
Ile Leu Lys Gly Gly Asp Ala Lys Val Ser Met Glu Glu Arg Ala Gly
                485                 490                 495
Leu Thr Val Pro Arg Ala His Ser Leu Val Cys Val Pro Leu Ala Arg
                500                 505                 510
Ile Gly Val Ala Ser Lys Leu Leu Ser
                515                 520

<210> SEQ ID NO 50
```

```
<211> LENGTH: 521
<212> TYPE: PRT
<213> ORGANISM: Pisum sativum

<400> SEQUENCE: 50

Met Leu Leu Glu Leu Ala Leu Gly Leu Phe Val Leu Ala Leu Phe Leu
1               5                   10                  15

His Leu Arg Pro Thr Pro Ser Ala Lys Ser Lys Ala Leu Arg His Leu
            20                  25                  30

Pro Asn Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Lys His Gly Pro Leu Phe Ser Leu Ser Phe Gly Ser Met Pro Thr
65                  70                  75                  80

Val Val Ala Ser Thr Pro Glu Leu Phe Lys Leu Phe Leu Gln Ala His
                85                  90                  95

Glu Ala Thr Ser Phe Ser Thr Arg Phe Gln Thr Ser Ala Val Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
    130                 135                 140

Val Asn Glu Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys Tyr Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Ala Ser Gly Val Phe
            260                 265                 270

Leu Asp Thr Leu Leu Glu Phe Ala Glu Asp Thr Met Glu Ile Lys
        275                 280                 285

Ile Thr Lys Glu Gln Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Val Leu Phe Asn Val Trp Gln Val
```

```
                385                 390                 395                 400

Gly Lys Asp Pro Lys Tyr Trp Asp Arg Pro Ser Glu Phe Arg Pro Glu
            405                 410                 415

Arg Phe Leu Glu Thr Gly Ala Glu Gly Ala Gly Pro Leu Asp Leu
        420                 425                 430

Arg Gly Gln His Phe Gln Leu Leu Pro Phe Gly Ser Gly Arg Arg Met
            435                 440                 445

Cys Pro Gly Val Asn Leu Ala Thr Ser Gly Met Ala Thr Leu Leu Ala
        450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Arg Ala Gly
            485                 490                 495

Leu Thr Val Pro Arg Ala His Ser Leu Val Cys Val Pro Leu Ala Arg
            500                 505                 510

Ile Gly Val Ala Ser Lys Leu Leu Ser
            515                 520

<210> SEQ ID NO 51
<211> LENGTH: 499
<212> TYPE: PRT
<213> ORGANISM: Beta vulgaris

<400> SEQUENCE: 51

Leu His Leu Arg Pro Thr Pro Thr Ala Lys Ser Lys Ala Leu Arg His
1               5                   10                  15

Leu Pro Asn Pro Pro Ser Pro Lys Pro Arg Leu Pro Phe Ile Gly His
                20                  25                  30

Leu His Leu Leu Lys Asp Lys Leu Leu His Tyr Ala Leu Ile Asp Leu
            35                  40                  45

Ser Lys Lys His Gly Pro Leu Phe Ser His Tyr Phe Gly Ser Met Pro
    50                  55                  60

Thr Val Val Ala Ser Thr Pro Glu Leu Phe Lys Leu Phe Leu Gln Thr
65              70                  75                  80

Asn Glu Ala Thr Ser Phe Asn Thr Arg Phe Gln Thr Ser Ala Ile Arg
                85                  90                  95

Arg Leu Thr Tyr Asp Ser Ser Val Ala Met Val Pro Phe Gly Pro Tyr
            100                 105                 110

Trp Lys Phe Val Arg Lys Leu Ile Met Asn Asp Leu Leu Asn Ala Thr
        115                 120                 125

Thr Val Asn Lys Leu Arg Pro Leu Arg Thr Gln Gln Ile Arg Lys Phe
    130                 135                 140

Leu Arg Ala Met Ala Gln Gly Ala Glu Ala Arg Lys Pro Leu Asp Leu
145                 150                 155                 160

Thr Glu Glu Leu Leu Lys Trp Ala Asn Ser Thr Ile Ser Met Met Met
                165                 170                 175

Leu Gly Glu Ala Glu Glu Ile Arg Asp Ile Ala Arg Glu Val Leu Lys
            180                 185                 190

Ile Phe Gly Glu Tyr Ser Leu Thr Asp Phe Ile Trp Pro Leu Lys His
        195                 200                 205

Leu Lys Val Gly Lys Tyr Glu Lys Arg Ile Asp Asp Ile Leu Asn Lys
    210                 215                 220

Phe Asp Pro Val Val Glu Arg Val Ile Lys Arg Arg Glu Ile Val
225                 230                 235                 240
```

-continued

```
Arg Arg Arg Lys Asn Gly Glu Val Val Gly Glu Val Ser Gly Val
            245                 250                 255

Phe Leu Asp Thr Leu Leu Glu Phe Ala Glu Asp Glu Thr Met Glu Ile
        260                 265                 270

Lys Ile Thr Lys Asp His Thr Lys Gly Leu Val Val Asp Phe Phe Ser
            275                 280                 285

Ala Gly Thr Asp Ser Thr Ala Val Ala Thr Glu Trp Ala Leu Ala Glu
        290                 295                 300

Leu Ile Asn Asn Pro Lys Val Leu Glu Lys Ala Arg Glu Glu Val Tyr
305                 310                 315                 320

Ser Val Val Gly Lys Asp Arg Leu Val Asp Glu Val Asp Thr Gln Asn
                325                 330                 335

Leu Pro Tyr Ile Arg Ala Ile Val Lys Glu Thr Phe Arg Met His Pro
            340                 345                 350

Pro Leu Pro Val Val Lys Arg Lys Cys Thr Glu Glu Cys Glu Ile Asn
        355                 360                 365

Gly Tyr Val Ile Pro Glu Gly Ala Leu Ile Pro Phe Asn Val Trp Gln
    370                 375                 380

Val Gly Arg Asp Pro Lys Tyr Trp Asp Arg Pro Ser Glu Phe Arg Pro
385                 390                 395                 400

Glu Arg Phe Leu Glu Thr Gly Ala Gly Glu Ala Arg Pro Leu Asp
                405                 410                 415

Leu Arg Gly Gln His Phe Gln Leu Leu Pro Phe Gly Ser Gly Arg Arg
            420                 425                 430

Met Cys Pro Gly Val Asn Leu Ala Thr Ser Gly Thr Ala Thr Leu Leu
        435                 440                 445

Ala Ser Leu Ile Gln Cys Phe Asp Leu Gln Val Leu Gly Pro Gln Gly
    450                 455                 460

Gln Ile Leu Lys Gly Gly Asp Ala Lys Val Ser Met Glu Glu Arg Ala
465                 470                 475                 480

Gly Leu Thr Val Pro Arg Ala His Ser Leu Val Cys Val Pro Leu Ala
                485                 490                 495

Arg Ile Gly

<210> SEQ ID NO 52
<211> LENGTH: 500
<212> TYPE: PRT
<213> ORGANISM: Vicia villosa

<400> SEQUENCE: 52

Phe Leu His Leu Arg Pro Thr Pro Thr Ala Lys Ser Lys Ala Leu Arg
1               5                   10                  15

His Leu Pro Asn Pro Ser Pro Lys Pro Arg Leu Pro Phe Ile Gly
            20                  25                  30

His Leu His Leu Leu Lys Asp Lys Leu Leu His Tyr Ala Leu Ile Asp
        35                  40                  45

Leu Ser Lys Lys His Gly Pro Leu Phe Ser Leu Tyr Phe Gly Ser Met
    50                  55                  60

Pro Thr Val Val Ala Ser Thr Pro Glu Leu Phe Lys Leu Phe Leu Gln
65                  70                  75                  80

Thr His Glu Ala Thr Ser Phe Asn Thr Arg Phe Gln Thr Ser Ala Ile
                85                  90                  95

Arg Arg Leu Thr Tyr Asp Ser Leu Val Ala Met Val Pro Phe Gly Pro
            100                 105                 110
```

Tyr Trp Lys Phe Val Arg Lys Leu Ile Met Asn Asp Leu Leu Asn Ala
            115                 120                 125

Thr Thr Val Asn Lys Leu Arg Pro Leu Arg Thr Gln Gln Ile Arg Lys
130                 135                 140

Phe Leu Arg Val Met Ala Gln Gly Ala Glu Ala Gln Lys Pro Leu Asp
145                 150                 155                 160

Leu Thr Glu Glu Leu Leu Lys Trp Thr Asn Ser Thr Ile Ser Met Met
                165                 170                 175

Met Leu Gly Glu Ala Glu Glu Ile Arg Asp Ile Ala Arg Glu Val Leu
            180                 185                 190

Lys Ile Tyr Gly Glu Tyr Ser Leu Thr Asp Phe Ile Trp Pro Leu Lys
        195                 200                 205

His Leu Lys Val Gly Lys Tyr Glu Lys Arg Ile Asp Asp Ile Leu Asn
    210                 215                 220

Lys Phe Asp Pro Val Val Glu Arg Val Ile Lys Lys Arg Arg Glu Ile
225                 230                 235                 240

Val Arg Arg Arg Lys Asn Gly Glu Val Val Glu Gly Glu Val Ser Gly
                245                 250                 255

Val Phe Leu Asp Thr Leu Leu Glu Phe Ala Glu Asp Glu Thr Thr Glu
            260                 265                 270

Ile Lys Ile Thr Lys Asp His Ile Lys Gly Leu Val Val Asp Phe Phe
        275                 280                 285

Ser Ala Gly Ile Asp Ser Thr Ala Val Ala Thr Glu Trp Ala Leu Ala
    290                 295                 300

Glu Leu Ile Asn Asn Pro Lys Val Leu Glu Lys Ala Arg Glu Glu Val
305                 310                 315                 320

Tyr Ser Val Val Gly Lys Asp Arg Leu Val Asp Glu Val Asp Thr Gln
                325                 330                 335

Asn Leu Pro Tyr Ile Arg Ala Ile Val Lys Glu Thr Phe Arg Met His
            340                 345                 350

Pro Pro Leu Pro Val Val Lys Arg Lys Cys Thr Glu Glu Cys Glu Ile
        355                 360                 365

Asn Gly Tyr Val Ile Pro Glu Gly Ala Leu Ile Leu Phe Asn Val Trp
    370                 375                 380

Gln Val Gly Arg Asp Pro Lys Tyr Trp Asp Arg Pro Ser Glu Phe Arg
385                 390                 395                 400

Pro Glu Arg Phe Leu Glu Thr Gly Ala Glu Gly Ala Arg Pro Leu
                405                 410                 415

Asp Leu Arg Gly Gln His Phe Gln Leu Leu Pro Phe Gly Ser Gly Arg
            420                 425                 430

Gly Met Cys Pro Gly Val Asn Leu Ala Thr Ser Gly Met Ala Thr Leu
        435                 440                 445

Leu Ala Ser Leu Ile Gln Cys Phe Asp Leu Gln Val Leu Gly Pro Gln
    450                 455                 460

Gly Gln Ile Leu Lys Gly Gly Asp Ala Lys Val Ser Met Glu Glu Arg
465                 470                 475                 480

Ala Gly Leu Thr Val Pro Arg Ala His Ser Leu Val Cys Val Pro Leu
                485                 490                 495

Ala Arg Ile Gly
            500

<210> SEQ ID NO 53
<211> LENGTH: 524
<212> TYPE: PRT

<213> ORGANISM: Caragana arborescens

<400> SEQUENCE: 53

```
Met Leu Val Glu Leu Ala Ile Thr Leu Leu Val Ile Ala Leu Phe Leu
1               5                   10                  15

His Leu Arg Pro Thr Pro Ser Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Asp Lys Pro Leu Leu His Gln Ser Leu Ile Arg Leu Ser
    50                  55                  60

Glu Arg Tyr Gly Pro Leu Tyr Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Ser Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Ile Arg Lys Leu Ile Met Asn Asp Leu Leu Asn Ala Thr Thr
130                 135                 140

Val Asn Lys Leu Arg Pro Leu Arg Ser Gln Glu Ile Arg Lys Val Leu
145                 150                 155                 160

Lys Val Met Ala Gln Ser Ala Glu Thr Gln Gln Pro Leu Asn Val Thr
                165                 170                 175

Glu Glu Leu Leu Lys Trp Thr Asn Ser Thr Ile Ser Arg Met Met Leu
            180                 185                 190

Gly Glu Ala Glu Glu Ile Arg Asp Ile Ala Arg Asp Val Leu Lys Ile
        195                 200                 205

Phe Gly Glu Tyr Ser Leu Thr Asp Phe Ile Trp Pro Leu Lys Lys Leu
    210                 215                 220

Lys Val Gly Gln Tyr Glu Lys Arg Ile Asp Asp Ile Phe Asn Arg Phe
225                 230                 235                 240

Asp Pro Val Ile Glu Lys Val Ile Lys Lys Arg Gln Glu Ile Arg Lys
                245                 250                 255

Arg Arg Lys Glu Arg Asn Gly Glu Leu Glu Glu Gly Gln Ser Val
            260                 265                 270

Val Phe Leu Asp Thr Leu Leu Asp Phe Ala Glu Asp Glu Thr Met Glu
        275                 280                 285

Ile Lys Ile Thr Lys Glu Gln Ile Lys Gly Leu Ile Val Asp Phe Phe
    290                 295                 300

Ser Ala Gly Thr Asp Ser Thr Ala Val Ala Thr Asp Tyr Ala Leu Ser
305                 310                 315                 320

Glu Leu Ile Asn Asn Pro Arg Val Leu Gln Lys Ala Arg Glu Glu Val
                325                 330                 335

Asp Ser Val Val Gly Lys Asp Arg Leu Val Asp Glu Ser Asp Val Gln
            340                 345                 350

Asn Leu Pro Phe Ile Arg Ala Ile Val Lys Glu Thr Phe Arg Met His
        355                 360                 365

Pro Pro Leu Pro Val Val Lys Arg Lys Cys Thr Gln Glu Cys Glu Ile
    370                 375                 380

Asp Gly Phe Val Ile Pro Glu Gly Ala Leu Ile Leu Phe Asn Val Trp
385                 390                 395                 400
```

Ala Val Gly Arg Asp Pro Lys Tyr Trp Glu Arg Pro Ser Glu Phe Arg
            405                 410                 415

Pro Glu Arg Phe Leu Gln Asn Ala Gly Glu Gly Glu Val Gly Ser Ile
        420                 425                 430

Asp Leu Arg Gly Gln His Phe Gln Leu Leu Pro Phe Gly Ser Gly Arg
        435                 440                 445

Arg Met Cys Pro Gly Val Asn Leu Ala Thr Ala Gly Met Ala Thr Leu
    450                 455                 460

Leu Ala Ser Val Ile Gln Cys Phe Asp Leu Gln Val Pro Gly Pro Gln
465                 470                 475                 480

Gly Glu Leu Leu Lys Gly Asp Asp Ala Lys Val Ser Met Glu Glu Arg
                485                 490                 495

Pro Gly Leu Thr Val Pro Arg Ala Asn Asn Leu Met Cys Val Pro Leu
            500                 505                 510

Ala Arg Ala Gly Val Ala Ala Lys Leu Leu Ser Ser
        515                 520

<210> SEQ ID NO 54
<211> LENGTH: 521
<212> TYPE: PRT
<213> ORGANISM: Vigna unguiculata

<400> SEQUENCE: 54

Met Leu Leu Glu Ile Thr Ile Gly Leu Leu Val Leu Ala Leu Phe Leu
1               5                   10                  15

His Leu Arg Pro Thr Pro Thr Ala Lys Ser Lys Ala Leu Arg His Leu
            20                  25                  30

Pro Asn Pro Pro Ser Pro Lys Pro Arg Leu Pro Phe Ile Gly His Leu
        35                  40                  45

His Leu Leu Lys Asp Lys Leu Leu His Tyr Ala Leu Ile Asp Leu Ser
    50                  55                  60

Lys Thr Tyr Gly Pro Leu Tyr Ser Leu Tyr Phe Gly Ser Met Pro Thr
65                  70                  75                  80

Val Val Ala Ser Ser Pro Glu Leu Phe Lys Leu Phe Leu Gln Thr His
                85                  90                  95

Glu Ala Ala Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Ile Arg Lys Leu Ile Met Asn Asp Leu Leu Asn Ala Thr Thr
    130                 135                 140

Val Asn Lys Leu Arg Pro Leu Arg Thr Gln Gln Ile Arg Lys Phe Leu
145                 150                 155                 160

Lys Val Met Ala Gln Ser Ala Gln Ala Gln Gln Pro Leu Asn Val Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys Lys Leu
    210                 215                 220

Lys Phe Gly Gln Tyr Glu Lys Arg Ile Asp Glu Ile Phe Asn Lys Phe
225                 230                 235                 240

Asp Pro Val Ile Glu Arg Val Ile Lys Lys Arg Glu Ile Met Arg
                245                 250                 255

```
Arg Arg Lys Asn Gly Glu Ala Val Glu Glu Gln Ser Gly Val Phe
            260                 265                 270

Leu Asp Thr Leu Leu Gln Phe Ala Glu Asp Glu Thr Met Glu Ile Lys
        275                 280                 285

Ile Thr Lys Glu Gln Ile Lys Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Val Glu Glu Cys Glu Ile Glu Gly
    370                 375                 380

Tyr Val Ile Pro Glu Gly Ala Leu Ile Leu Phe Asn Val Trp Ala Val
385                 390                 395                 400

Gly Arg Asp Pro Lys Tyr Trp Asp Arg Pro Leu Glu Phe Arg Pro Glu
                405                 410                 415

Arg Phe Leu Glu Thr Gly Ala Glu Gly Ala Gly Pro Leu Asp Leu
            420                 425                 430

Arg Gly Gln His Phe Thr Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Val Ile Gln Cys Phe Asp Leu Gln Val Val Gly Pro Gln Gly Gln
465                 470                 475                 480

Ile Leu Lys Gly Asn Asp Ala Lys Val Ser Met Glu Glu Arg Ala Gly
                485                 490                 495

Leu Thr Val Pro Arg Ala His Asn Leu Glu Cys Val Pro Val Ala Arg
            500                 505                 510

Thr Ser Val Ala Ala Lys Leu Leu Ser
        515                 520

<210> SEQ ID NO 55
<211> LENGTH: 1383
<212> TYPE: DNA
<213> ORGANISM: Petroselinum crispum

<400> SEQUENCE: 55 ctcgccttc aatggctcct acaacaataa ccgcattagc caaggagaaa acactaaact      60
tggactttgt gagggatgaa gacgagcgtc ccaaagttgc ttacaatcaa ttcagcaatg     120
aaattcccat tatttcttta gccggtttgg atgacgattc tgatggcagg agacccgaga    180
tatgtcgcaa aatagttaag gcttgtgaag actgggaat tttccaagtg gttgatcatg     240
gtattgacag cggcttgatt tccgagatga ctcgtctttc tcgtgaattc tttgctttgc    300
ctgctgagga aaaacttgag tatgatacaa ctggggaaa gagaggcggc tttactatat    360
ccactgttct tcagggtgac gacgctatgg attggcgtga gttcgttact tactttttcgt   420 acccaatcaa tgctcgggac tactcaagat ggcctaaaaa gcccgaagga tggagatcaa    480
ccacggaggt ttatagcgag aagttaatgg tgctaggtgc caagttactg gaagtgttat    540
cagaggccat ggggcttgag aaaggggatc ttactaaggc ttgtgtggat atggaacaga    600
```

```
aagtgttaat taattactat cccacgtgcc cccaacccga cttgacactt ggagtcagaa      660
ggcatacgga tccaggtact attaccattc tacttcagga catggttggt gggttacaag      720
ccaccaggga cggtggcaaa acttggatta ctgttcagcc tgtggaggga gcttttgttg      780
tcaatttggg cgatcatggt cattatttga gcaatgaaag gttcaggaat gctgaccacc      840
aagcagtagt gaattcaacc tctagcagat tgtcaattgc aactttccag aacccggctc      900
agaatgcgat agtatatcca ttaaagatca gggagggaga aaggcaatt  ctggatgagg     960 ccatcaccta cgctgaaatg tataagaaat gcatgactaa acatattgag gtggctactc     1020
ggaagaaatt ggccaaggag aaaaggttgc aagacgagaa agccaagctg agatgaaat      1080 ccaagagtgc agatgaaaat ttagcttagg ctttgtgcac tctaccatct acattatgtt     1140
ttgcgagttt gtgctccctg cattagtgaa tgatgtcatt tgcgagtttg tgctctctgc     1200
attagtgaat aatgtcattg ttcaattcca tgtctaaacg ctgaatacta tggagtcatg     1260
gtactctttg gttagaaatt cttacaatgt cgttctttta gagtccttaa taataataat     1320
tctcggagtg tttaattatg tttattatgt gctataatca atggtgtgtg ttattggcag     1380
aag                                                                   1383

<210> SEQ ID NO 56
<211> LENGTH: 1098
<212> TYPE: DNA
<213> ORGANISM: Cuminum cyminum

<400> SEQUENCE: 56
atggctccaa caacaattac tgcattggcc caagagaaaa cacttaactc tgattttgtc        60
cgggatgaag atgagcgccc caaagttgcc tacaatcagt tcagcactga gattcccatc       120
atttctttag ctggcatcga tgatgattcc aaaggcagga ggcctgaggt gtgtagaaaa       180
atagttgagg cctttgaaga ctggggcatt tttcaggtgg ttgatcacgg tgttgacagc       240
gctttgatct ccgaaatgtc tcgtctgtct cgtgaattct tcgctttgcc tgctgaggaa       300
aaactccggt atgataccac tggtggaaag agaggcggct tcactatctc cactcatcaa       360
cagggtgacg acgtgcggga ctggcgtgag tttgttactt attttcgta cccagtggat        420 gctcgggact actcaagatg gcctgagaag ccagagggat ggaggtcagt tacagaggtt       480
tatagtgaga agttgatggt tctaggtgcc aagttactgg aagtgttatc agaggccatg       540
gggcttgaca aagggggctct tacaaaggct tgtgtgaata tggaacagaa agtgctaatt      600
aattactatc ccacatgccc cgagccagac ttgacacttg agtcagaag  gcatacggat     660 ccaggtacta ttaccatttt gcttcaggac atggttggtg gttacaggc cacgagggat      720 ggcggcaaaa cctggatcac tgttcagcct gtggagggag ttttgtcgt caatttgggt      780 gatcatggtc attatttgag caatgggagg ttcaagaacg cggaccacca ggcagtagtg      840
aattcaacct caagcagatt gtcaatcgca actttccaga acccggctca gaacgctata     900
gtgtatccat taaagatcag ggagggtgag aagccaattc tggaggaggc catcacgtac     960
gcggagatgt ataagaaaaa catgactaaa catattgagg tggctacaca gaagaaattg     1020
gccaaggaga aagattgca agaagagaag gccaagctgg agacgaaaac caagagcgca      1080
gatggaattt tagcttag                                                    1098

<210> SEQ ID NO 57
<211> LENGTH: 1098
<212> TYPE: DNA
```

<213> ORGANISM: Aethusa cynapium

<400> SEQUENCE: 57

```
atggctccta caaccataac tgcattatcc caggagaaat cactaaactt agactttgtc      60
agggatgaag acgagcgtcc caaagttgct tacaatcagt tcagcaatga aattcccatc     120
atttctctag ctggtatgga tgatgattct aatggcagga gacccgagat atgtcgtaaa     180
atagtcgagg cattcgaaga ctggggaatt ttccaggtgg ttgatcacgg tattgacaaa     240
ggtttgattt ctcagatgtc tcgtctctct cgtgaattct ttgctttgcc tgctgaggaa     300
aaactccggt atgatacaac tggtggaaag agaggtggct ttactatctc cactcatctt     360
cagggtgacg atgttaagga ttggcgtgag ttcgttactt acttttcgta cccaatcgaa     420
gatcgggact actcaagatg gcctgaaaag ccagagggat ggaggtcaac cactgaggtt     480
tatagtgaga agttaatggt gctaggtgcc aagttactgg aagtgttgtc agaggccatg     540
gggcttgaga agaggctct tacaaaggct tgtgtgaata tggaacagaa agtgttaatc     600
aattactatc ccacatgccc cgaacccgac ttgacacttg gagtcagaag gcatacggat     660
ccaggtacta ttaccattct gcttcaggac atggttggtg gattacaggc tactagggat     720
ggcggcaaaa catggatcac tgttcagcct gtggaggag cttttgtggt caatttgggt     780
gaccatggtc attatttgag caatggaagg ttcaagaatg ctgaccacca agcagtagtg     840
aattcaactt ctagcagatt gtctattgca actttccaga acccggccca gaatgcgata     900
gtgtatccct aaaaatcag ggagggagaa aaggcaattc ttgatgaggc catcacctac     960
gctgaaatgt ataagaaaaa catgactaaa catattgagg tggctgccct gaagaaattg    1020
gccaaggaga aaaggctgca agatgagaag gccaagctgg agatgtaatc caagagtgca    1080
gatgaaaatt tagcttag                                                  1098
```

<210> SEQ ID NO 58
<211> LENGTH: 1095
<212> TYPE: DNA
<213> ORGANISM: Angelica archangelica

<400> SEQUENCE: 58

```
atggctccaa caactataac tgcattagcc caggagaaaa cactaaattt agcctttgtc      60
agggatgaag acgagcgtcc caaagttgcc tacaatcagt tcagcaatga aattcccatc     120
atttctttag ctggtatgga tgacgatact ggcaggagac cccagatatg tcgtaaaata     180
gttgaggcat tgaagactg ggaattttc caggtggttg atcacggcat tgacggcact     240
ttgatttctg agatgactcg tctttctcgt gaattctttg ctttgcctgc tgaggaaaaa     300
cttcggtatg atacaactgg tggaaagaga ggcggcttta ccatctccac tcatcttcag     360
ggtgacgatg ttaaggattg gcgtgagttc gttacttact tttcgtaccc aatcgatgat     420
cgggactact caagatggcc tgataagccc agggatgga ggtcaaccac ggaggtttat     480
agtgagaagt taatggtgct aggtgccaag ttacttgaag tgttatcaga ggccatgggg     540
cttgagaaag aggctcttac aaaggcttgt gtgaatatgg aacaaaaagt gttaatcaat     600
tactatccca cgtgccccga accgacttg acacttggag tcagaaggca tacggatcca     660
ggtactatta ccattctgct tcaggacatg gttggtggt acaggctac tagggatggt     720
ggcaaaactt ggattactgt tcagcctgtg gagggagctt ttgtggtcaa tttgggtgac     780
catggtcatt atttgagcaa tgggaggttc aagaatgctg accaccaagc agtagtgaat     840
tcaacctcta gcagattgtc tattgcaact ttccagaacc cggcccagaa tgcgatagtg     900
```

| | | |
|---|---|---|
| tatcccttga ggatcaggga gggagagaag gcagttcttg atgaggccat cacctacgct | 960 | |
| gaaatgtata agaaaaacat gactaaacat attgaggtgg ctaccctgaa gaaattggcc | 1020 | |
| aaggagaaaa ggttgcaaga ggaaaaggcc aagctggaga cggaatccaa gagtgcagat | 1080 | |
| ggaatttcag cttag | 1095 | |

<210> SEQ ID NO 59
<211> LENGTH: 1294
<212> TYPE: DNA
<213> ORGANISM: Apium graveolens

<400> SEQUENCE: 59

| | | |
|---|---|---|
| aaaaatggct ccatcaacta taactgcact gtctcaagag aagacactga acttagactt | 60 | |
| tgtgagggat gaagatgagc gtcccaaagt tgcttacaat caattcagca atgaagttcc | 120 | |
| catcatttct ttagctggtt tggatgacga ttctaatggc aggagagctg agatatgtcg | 180 | |
| taaaatagtt gaggctttcg aagaatgggg aattttccaa gttgttgatc acggtattga | 240 | |
| tagcggtttg atttctgaga tgagtcgtct ttctcgtgaa ttcttcgctt tgcctgctga | 300 | |
| ggaaaaactt gtgtatgata ccactggtga aagaaaggc ggctttacta tctccactca | 360 | |
| tcttcaggga gatgatgttc gggattggcg tgagtttgtt acttactttt cgtatccaat | 420 | |
| cagtgctcgg gactactcaa gatggcctaa aaagcccgag gggtggagat caaccacgga | 480 | |
| ggtttatagt gagaagttaa tggtgctagg tgccaagtta ctggaggtgt tatccgaggc | 540 | |
| aatggggctt gagaaagagg ctcttacaaa ggcttgtgtg gaaatggaac agaaagtgtt | 600 | |
| aattaattac tatcccacat gccccgaacc cgacttgacg ctaggtgtca gaaggcatac | 660 | |
| ggatccaggt actattacca ttctgcttca ggacatggtt ggtggtttac aggctactag | 720 | |
| ggatggcggc aaaacttgga ttactgttca gcctgtggag ggagctttg ttgtcaattt | 780 | |
| gggtgatcat ggtcattatt tgagcaatgg aaggttcagg aatgctgacc atcaagcagt | 840 | |
| agtgaattca acttccacca gattgtcaat tgcaactttc cagaacccgg ctcagaatgc | 900 | |
| gatagtatat ccgttaaaga tcagggaggg agagaaggca attctggatg aggccatcac | 960 | |
| ctacgctgaa atgtataaga aaaacatgac taaacatatt gcggtggcta cccagaagaa | 1020 | |
| attggccaag gagaaaggt tgcaagatga gaaggccaag atgaagatat gatcggagat | 1080 | |
| tgccagggca ggtggaattt aagctcagcc tttgtccacc ataccatcta tgtttcacga | 1140 | |
| agtttgtgct cgctgcgtta gtgaactatt gggccgttgg tcaatttcca tgtctaaatg | 1200 | |
| tcatggtctc ttttggtcag aaattcgaaa tgtcgtcttt ttagggactt tataataatt | 1260 | |
| ctaagtttgg gaggggtcaa aaaaaaaaaa aaaa | 1294 | |

<210> SEQ ID NO 60
<211> LENGTH: 1290
<212> TYPE: DNA
<213> ORGANISM: Conium maculatum

<400> SEQUENCE: 60

| | | |
|---|---|---|
| aaatggctcc tacaactata accgcattag cccaggagaa aacactaaac ttagcctttg | 60 | |
| tgagggatga agacgagcgt cccaaagttg cctacaatga attcagcaat gaaattccca | 120 | |
| taatttctct agctggtttg gaaaatgact ctgatgggag gagacccgag atatgtcgta | 180 | |
| aaatagtcga ggcttttgaa aactggggaa ttttccaagt ggctgatcat ggtattgaca | 240 | |
| gtgctttgat ttctgagatg tctcgtcttt ctcgtgaatt ctttgctttg cctgctgagg | 300 | |

| | |
|---|---|
| aaaaacttcg gtatgatacc actggtggaa agagaggcgg ctttactatc tccactcatc | 360 |
| ttcagggtga tgacgttcgg gattggcgtg aattcgttac ttactttcg tacccaatag | 420 |
| atgctcggga ctgctcgaga tggcctgata agcccgaggg atggaggtca atcacggagg | 480 |
| tttacagtga gaggttaatg gtgctaggtg ccaagttact ggaagtgtta tcagaggcca | 540 |
| tggggcttga gaaagaggct cttacaaagg cttgtgtgaa tatggaacag aaagtgttaa | 600 |
| ttaattacta tcccacgtgc cccgagcccg acttgacact ggagtcaga aggcatacgg | 660 |
| atccaggtac tattactgtt ctgcttcagg acatggttgg tgggttacag gctactaggg | 720 |
| atggtggcaa aacttggatt actgttcagc ctgtggaggg agcttttgtt gtcaatttgg | 780 |
| gtgatcatgg tcattatctg agcaatggaa ggttcaagaa tgctgaccac caagcggtag | 840 |
| taaattcaag ctctagcaga ttgtcaattg cgacattcca gaacccggct cagaatgcga | 900 |
| tagtttatcc attaaagatc agggagggag agaaggcaat tcttgatgag ccatcacct | 960 |
| acgccgaaat gtataagaaa aacatgacta aacatattga ggtggctacc ctcaagaaat | 1020 |
| tggccaagga gaaaaggttg caagatgaga aggccaacat ggagaagaaa tccaagagtg | 1080 |
| cacatggaat ttcagcttag gtgcatgatg gcatctaaat aatgtttctg gatttttgtag | 1140 |
| gtgaataata tcattgttaa attctgtcca aacgctgcgt acgatgtagt catggccctc | 1200 |
| tttggccgga aaatcggaca gtctcaatct ttctgagtac tcaataacag taattctaaa | 1260 |
| attttgaagt gtttgatgaa aaaaaaaaaa | 1290 |

<210> SEQ ID NO 61
<211> LENGTH: 1328
<212> TYPE: DNA
<213> ORGANISM: Daucus carota

<400> SEQUENCE: 61

| | |
|---|---|
| ggacttaaaa tggctccaac aactattact gcattggcca aggaaaaaac acttaactct | 60 |
| gattttgtcc gggatgagga tgagcgtccc aaagttgcct acaatcaatt cagcactgaa | 120 |
| attcccatta tttctttagc tggtatcgat gatgattcca atggcaggag acctgaggtg | 180 |
| tgtcgtaaaa tagtggaggc cttcgaagac tgggggattt tccaggtagt tgatcacggt | 240 |
| attgacagcg gtttgatcgc ggaaatgtct cgtctgtctc gtgaattctt tgctttgcct | 300 |
| gccgaggaga aacttcggta tgatactact ggtggaaaga gaggcggctt cactatctcc | 360 |
| actcatcttc agggtgacga tgtgaaggat tggcgtgagt ttgttgttta tttttcgtac | 420 |
| ccagtcgatg ctcgggacta ctcgagatgc cctgataagc ccgagggatg gaggtcagtt | 480 |
| acagaggttt atagtgagaa gttgatggcg ctaggtgcca agttactgga agtgctatca | 540 |
| gaggccatgg ggcttgaaaa agaggctctt acagaggctt gtgtgaatat ggaacagaaa | 600 |
| gtgttgatca attactatcc tacatgtccc caaccggact tgacacttgg agtcagaagg | 660 |
| cacacggatc cgggtacgat taccatttg cttcaggaca tggttggggg gttacaggct | 720 |
| accagggatg gcggcaaaac ttggattact gttcagcctg tcgagggagc ttttgtcgtc | 780 |
| aatttgggtg atcatggtca ttatttgagc aatggaaggt tcaagaatgc cgatcaccaa | 840 |
| gcagtagtga attcaacctc tagcagattg tccatcgcaa cttccagaa cccagctcag | 900 |
| aatgctatag tgtatccttt aaagatcagg gagggcgaga agccaattct tgaggaggcc | 960 |
| atgcacatacg ccgagatgta taagaaaaac atgactaaac atattgaggt ggctactcag | 1020 |
| aagaaattgg ccaaggagaa aagattgcag aacgagaagg ccaagctgga gacgaaattt | 1080 |
| tagcttaggc tttgtccatt atagtatcta tattatgttt tccgagtttg tgttatctac | 1140 |

-continued

```
aataatacag tagtkaatwa ggccatttt gttaatgtct aaatkctgcg tactgtggtc    1200
agagtwctgt kttaagaaat tcatacaata tcgttcttaa tcctaaactt tcgtgtgttt    1260
gattttgttc attctataca ataatttaat agttcattct attacagtta tgcgaaawaa    1320
aaaaaaaa                                                              1328
```

<210> SEQ ID NO 62
<211> LENGTH: 365
<212> TYPE: PRT
<213> ORGANISM: Petroselinum crispum

<400> SEQUENCE: 62

```
Met Ala Pro Thr Thr Ile Thr Ala Leu Ala Lys Glu Lys Thr Leu Asn
1               5                   10                  15

Leu Asp Phe Val Arg Asp Glu Asp Arg Pro Lys Val Ala Tyr Asn
            20                  25                  30

Gln Phe Ser Asn Glu Ile Pro Ile Ile Ser Leu Ala Gly Leu Asp Asp
        35                  40                  45

Asp Ser Asp Gly Arg Arg Pro Glu Ile Cys Arg Lys Ile Val Lys Ala
    50                  55                  60

Cys Glu Asp Trp Gly Ile Phe Gln Val Val Asp His Gly Ile Asp Ser
65                  70                  75                  80

Gly Leu Ile Ser Glu Met Thr Arg Leu Ser Arg Glu Phe Phe Ala Leu
                85                  90                  95

Pro Ala Glu Glu Lys Leu Glu Tyr Asp Thr Thr Gly Gly Lys Arg Gly
            100                 105                 110

Gly Phe Thr Ile Ser Thr Val Leu Gln Gly Asp Asp Ala Met Asp Trp
        115                 120                 125

Arg Glu Phe Val Thr Tyr Phe Ser Tyr Pro Ile Asn Ala Arg Asp Tyr
    130                 135                 140

Ser Arg Trp Pro Lys Lys Pro Glu Gly Trp Arg Ser Thr Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Glu Lys Gly Asp Leu Thr Lys Ala Cys Val
            180                 185                 190

Asp Met Glu Gln Lys Val Leu Ile Asn Tyr Tyr Pro Thr Cys Pro Gln
        195                 200                 205

Pro Asp Leu Thr Leu Gly Val Arg Arg His Thr Asp Pro Gly Thr Ile
    210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Arg
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Lys Ile Arg Glu Gly Glu Lys Ala Ile Leu Asp Glu Ala Ile Thr Tyr
305                 310                 315                 320

Ala Glu Met Tyr Lys Lys Cys Met Thr Lys His Ile Glu Val Ala Thr
                325                 330                 335
```

Arg Lys Lys Leu Ala Lys Glu Lys Arg Leu Gln Asp Glu Lys Ala Lys
                340                 345                 350

Leu Glu Met Lys Ser Lys Ser Ala Asp Glu Asn Leu Ala
        355                 360                 365

<210> SEQ ID NO 63
<211> LENGTH: 365
<212> TYPE: PRT
<213> ORGANISM: Cuminum cyminum

<400> SEQUENCE: 63

Met Ala Pro Thr Thr Ile Thr Ala Leu Ala Gln Glu Lys Thr Leu Asn
1               5                   10                  15

Ser Asp Phe Val Arg Asp Glu Asp Arg Pro Lys Val Ala Tyr Asn
            20                  25                  30

Gln Phe Ser Thr Glu Ile Pro Ile Ser Leu Ala Gly Ile Asp Asp
        35                  40                  45

Asp Ser Lys Gly Arg Arg Pro Glu Val Cys Arg Lys Ile Val Glu Ala
    50                  55                  60

Phe Glu Asp Trp Gly Ile Phe Gln Val Val Asp His Gly Val Asp Ser
65              70                  75                  80

Ala Leu Ile Ser Glu Met Ser Arg Leu Ser Arg Glu Phe Phe Ala Leu
                85                  90                  95

Pro Ala Glu Glu Lys Leu Arg Tyr Asp Thr Thr Gly Gly Lys Arg Gly
            100                 105                 110

Gly Phe Thr Ile Ser Thr His Gln Gln Gly Asp Asp Val Arg Asp Trp
        115                 120                 125

Arg Glu Phe Val Thr Tyr Phe Ser Tyr Pro Val Asp Ala Arg Asp Tyr
    130                 135                 140

Ser Arg Trp Pro Glu Lys Pro Glu Gly Trp Arg Ser Val Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Asp Lys Gly Ala Leu Thr Lys Ala Cys Val
            180                 185                 190

Asn Met Glu Gln Lys Val Leu Ile Asn Tyr Tyr Pro Thr Cys Pro Glu
        195                 200                 205

Pro Asp Leu Thr Leu Gly Val Arg Arg His Thr Asp Pro Gly Thr Ile
    210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Val Phe Val
                245                 250                 255

Val Asn Leu Gly Asp His Gly His Tyr Leu Ser Asn Gly Arg Phe Lys
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Lys Ile Arg Glu Gly Glu Lys Pro Ile Leu Glu Ala Ile Thr Tyr
305                 310                 315                 320

Ala Glu Met Tyr Lys Lys Asn Met Thr Lys His Ile Glu Val Ala Thr
                325                 330                 335

Gln Lys Lys Leu Ala Lys Glu Lys Arg Leu Gln Glu Glu Lys Ala Lys

```
                    340                 345                 350

Leu Glu Thr Lys Thr Lys Ser Ala Asp Gly Ile Leu Ala
            355                 360                 365

<210> SEQ ID NO 64
<211> LENGTH: 355
<212> TYPE: PRT
<213> ORGANISM: Aethusa cynapium

<400> SEQUENCE: 64

Met Ala Pro Thr Thr Ile Thr Ala Leu Ser Gln Glu Lys Ser Leu Asn
1               5                   10                  15

Leu Asp Phe Val Arg Asp Glu Asp Arg Pro Lys Val Ala Tyr Asn
            20                  25                  30

Gln Phe Ser Asn Glu Ile Pro Ile Ile Ser Leu Ala Gly Met Asp Asp
        35                  40                  45

Asp Ser Asn Gly Arg Arg Pro Glu Ile Cys Arg Lys Ile Val Glu Ala
    50                  55                  60

Phe Glu Asp Trp Gly Ile Phe Gln Val Val Asp His Gly Ile Asp Lys
65                  70                  75                  80

Gly Leu Ile Ser Gln Met Ser Arg Leu Ser Arg Glu Phe Phe Ala Leu
                85                  90                  95

Pro Ala Glu Glu Lys Leu Arg Tyr Asp Thr Thr Gly Gly Lys Arg Gly
            100                 105                 110

Gly Phe Thr Ile Ser Thr His Leu Gln Gly Asp Asp Val Lys Asp Trp
        115                 120                 125

Arg Glu Phe Val Thr Tyr Phe Ser Tyr Pro Ile Glu Asp Arg Asp Tyr
    130                 135                 140

Ser Arg Trp Pro Glu Lys Pro Glu Gly Trp Arg Ser Thr Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Glu Lys Glu Ala Leu Thr Lys Ala Cys Val
            180                 185                 190

Asn Met Glu Gln Lys Val Leu Ile Asn Tyr Tyr Pro Thr Cys Pro Glu
        195                 200                 205

Pro Asp Leu Thr Leu Gly Val Arg Arg His Thr Asp Pro Gly Thr Ile
    210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Lys
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Lys Ile Arg Glu Gly Glu Lys Ala Ile Leu Asp Glu Ala Ile Thr Tyr
305                 310                 315                 320

Ala Glu Met Tyr Lys Lys Asn Met Thr Lys His Ile Glu Val Ala Ala
                325                 330                 335

Leu Lys Lys Leu Ala Lys Glu Lys Arg Leu Gln Asp Glu Lys Ala Lys
            340                 345                 350
```

Leu Glu Met
        355

<210> SEQ ID NO 65
<211> LENGTH: 364
<212> TYPE: PRT
<213> ORGANISM: Angelica archangelica

<400> SEQUENCE: 65

Met Ala Pro Thr Thr Ile Thr Ala Leu Ala Gln Glu Lys Thr Leu Asn
1               5                   10                  15

Leu Ala Phe Val Arg Asp Glu Asp Glu Arg Pro Lys Val Ala Tyr Asn
            20                  25                  30

Gln Phe Ser Asn Glu Ile Pro Ile Ile Ser Leu Ala Gly Met Asp Asp
        35                  40                  45

Asp Thr Gly Arg Arg Pro Gln Ile Cys Arg Lys Ile Val Glu Ala Phe
    50                  55                  60

Glu Asp Trp Gly Ile Phe Gln Val Val Asp His Gly Ile Asp Gly Thr
65                  70                  75                  80

Leu Ile Ser Glu Met Thr Arg Leu Ser Arg Glu Phe Phe Ala Leu Pro
                85                  90                  95

Ala Glu Glu Lys Leu Arg Tyr Asp Thr Thr Gly Lys Arg Gly Gly
            100                 105                 110

Phe Thr Ile Ser Thr His Leu Gln Gly Asp Asp Val Lys Asp Trp Arg
        115                 120                 125

Glu Phe Val Thr Tyr Phe Ser Tyr Pro Ile Asp Asp Arg Asp Tyr Ser
    130                 135                 140

Arg Trp Pro Asp Lys Pro Gln Gly Trp Arg Ser Thr Thr Glu Val Tyr
145                 150                 155                 160

Ser Glu Lys Leu Met Val Leu Gly Ala Lys Leu Leu Glu Val Leu Ser
                165                 170                 175

Glu Ala Met Gly Leu Glu Lys Glu Ala Leu Thr Lys Ala Cys Val Asn
            180                 185                 190

Met Glu Gln Lys Val Leu Ile Asn Tyr Tyr Pro Thr Cys Pro Glu Pro
        195                 200                 205

Asp Leu Thr Leu Gly Val Arg Arg His Thr Asp Pro Gly Thr Ile Thr
    210                 215                 220

Ile Leu Leu Gln Asp Met Val Gly Gly Leu Gln Ala Thr Arg Asp Gly
225                 230                 235                 240

Gly Lys Thr Trp Ile Thr Val Gln Pro Val Glu Gly Ala Phe Val Val
                245                 250                 255

Asn Leu Gly Asp His Gly His Tyr Leu Ser Asn Gly Arg Phe Lys Asn
            260                 265                 270

Ala Asp His Gln Ala Val Val Asn Ser Thr Ser Ser Arg Leu Ser Ile
        275                 280                 285

Ala Thr Phe Gln Asn Pro Ala Gln Asn Ala Ile Val Tyr Pro Leu Arg
    290                 295                 300

Ile Arg Glu Gly Glu Lys Ala Val Leu Asp Glu Ala Ile Thr Tyr Ala
305                 310                 315                 320

Glu Met Tyr Lys Lys Asn Met Thr Lys His Ile Glu Val Ala Thr Leu
                325                 330                 335

Lys Lys Leu Ala Lys Glu Lys Arg Leu Gln Glu Glu Lys Ala Lys Leu
            340                 345                 350

Glu Thr Glu Ser Lys Ser Ala Asp Gly Ile Ser Ala
        355                 360

<210> SEQ ID NO 66
<211> LENGTH: 355
<212> TYPE: PRT
<213> ORGANISM: Apium graveolens

<400> SEQUENCE: 66

```
Met Ala Pro Ser Thr Ile Thr Ala Leu Ser Gln Glu Lys Thr Leu Asn
1               5                   10                  15

Leu Asp Phe Val Arg Asp Glu Asp Arg Pro Lys Val Ala Tyr Asn
            20                  25                  30

Gln Phe Ser Asn Glu Val Pro Ile Ile Ser Leu Ala Gly Leu Asp Asp
            35                  40                  45

Asp Ser Asn Gly Arg Arg Ala Glu Ile Cys Arg Lys Ile Val Glu Ala
        50                  55                  60

Phe Glu Glu Trp Gly Ile Phe Gln Val Val Asp His Gly Ile Asp Ser
65                  70                  75                  80

Gly Leu Ile Ser Glu Met Ser Arg Leu Ser Arg Glu Phe Phe Ala Leu
                85                  90                  95

Pro Ala Glu Glu Lys Leu Val Tyr Asp Thr Thr Gly Glu Lys Lys Gly
            100                 105                 110

Gly Phe Thr Ile Ser Thr His Leu Gln Gly Asp Asp Val Arg Asp Trp
            115                 120                 125

Arg Glu Phe Val Thr Tyr Phe Ser Tyr Pro Ile Ser Ala Arg Asp Tyr
        130                 135                 140

Ser Arg Trp Pro Lys Lys Pro Glu Gly Trp Arg Ser Thr Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Glu Lys Glu Ala Leu Thr Lys Ala Cys Val
            180                 185                 190

Glu Met Glu Gln Lys Val Leu Ile Asn Tyr Tyr Pro Thr Cys Pro Glu
            195                 200                 205

Pro Asp Leu Thr Leu Gly Val Arg Arg His Thr Asp Pro Gly Thr Ile
        210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Arg
            260                 265                 270

Asn Ala Asp His Gln Ala Val Val Asn Ser Thr Ser Thr Arg Leu Ser
            275                 280                 285

Ile Ala Thr Phe Gln Asn Pro Ala Gln Asn Ala Ile Val Tyr Pro Leu
        290                 295                 300

Lys Ile Arg Glu Gly Glu Lys Ala Ile Leu Asp Glu Ala Ile Thr Tyr
305                 310                 315                 320

Ala Glu Met Tyr Lys Lys Asn Met Thr Lys His Ile Ala Val Ala Thr
                325                 330                 335

Gln Lys Lys Leu Ala Lys Glu Lys Arg Leu Gln Asp Glu Lys Ala Lys
            340                 345                 350

Met Lys Ile
        355
```

-continued

<210> SEQ ID NO 67
<211> LENGTH: 365
<212> TYPE: PRT
<213> ORGANISM: Conium maculatum

<400> SEQUENCE: 67

Met Ala Pro Thr Thr Ile Thr Ala Leu Ala Gln Glu Lys Thr Leu Asn
1               5                   10                  15

<212> TYPE: PRT
<213> ORGANISM: Daucus carota

<400> SEQUENCE: 68

```
Met Ala Pro Thr Thr Ile Thr Ala Leu Ala Lys Glu Lys Thr Leu Asn
1               5                   10                  15

Ser Asp Phe Val Arg Asp Glu Asp Arg Pro Lys Val Ala Tyr Asn
            20                  25                  30

Gln Phe Ser Thr Glu Ile Pro Ile Ile Ser Leu Ala Gly Ile Asp Asp
                35                  40                  45

Asp Ser Asn Gly Arg Arg Pro Glu Val Cys Arg Lys Ile Val Glu Ala
    50                  55                  60

Phe Glu Asp Trp Gly Ile Phe Gln Val Val Asp His Gly Ile Asp Ser
65                  70                  75                  80

Gly Leu Ile Ala Glu Met Ser Arg Leu Ser Arg Glu Phe Phe Ala Leu
                85                  90                  95

Pro Ala Glu Glu Lys Leu Arg Tyr Asp Thr Thr Gly Gly Lys Arg Gly
                100                 105                 110

Gly Phe Thr Ile Ser Thr His Leu Gln Gly Asp Asp Val Lys Asp Trp
            115                 120                 125

Arg Glu Phe Val Val Tyr Phe Ser Tyr Pro Val Asp Ala Arg Asp Tyr
        130                 135                 140

Ser Arg Cys Pro Asp Lys Pro Glu Gly Trp Arg Ser Val Thr Glu Val
145                 150                 155                 160

Tyr Ser Glu Lys Leu Met Ala Leu Gly Ala Lys Leu Leu Glu Val Leu
                165                 170                 175

Ser Glu Ala Met Gly Leu Glu Lys Glu Ala Leu Thr Glu Ala Cys Val
            180                 185                 190

Asn Met Glu Gln Lys Val Leu Ile Asn Tyr Tyr Pro Thr Cys Pro Gln
                195                 200                 205

Pro Asp Leu Thr Leu Gly Val Arg Arg His Thr Asp Pro Gly Thr Ile
        210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly Tyr Leu Ser Asn Gly Arg Phe Lys
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Lys Ile Arg Glu Gly Glu Lys Pro Ile Leu Glu Ala Met Thr Tyr
305                 310                 315                 320

Ala Glu Met Tyr Lys Lys Asn Met Thr Lys His Ile Glu Val Ala Thr
                325                 330                 335

Gln Lys Lys Leu Ala Lys Glu Lys Arg Leu Gln Asn Glu Lys Ala Lys
            340                 345                 350

Leu Glu Thr Lys Phe
            355
```

<210> SEQ ID NO 69
<211> LENGTH: 1884
<212> TYPE: DNA
<213> ORGANISM: Medicago truncatula

<400> SEQUENCE: 69

```
ctctagagat ggtttcatta gtgtaacgta tacactataa aatgctcaag gaggtaatcc        60
aaatcccaca atcatttctc aactattctc atgagttttc atttccaata taaagacaat       120
aaccaagatg atttctcagc caatcttatt agctttgatt ctattcctcc tcttccttct       180
ccaactcttt tgtttaaga gaaacaacag agcaaggag cacttacctt accctccaag         240
tccactagca ataccaataa ttggtcatct tcatctcctc aaaccctcg ttcatcaagc        300
ctttcgcgac ctctctgatc gatatggacc ccttatatcc cttcgacttg gttctgttcc      360
atttatcgtt gttagttccc catcactcgc aaaagagttg ctcaaaacaa acgagcttgt      420
ttattcttcc cgtaaaatga acattgccat caacacagtt gtctacgatg atgctacttt      480
tgcttttgcc cctatggggg catattggaa attcatcaaa aagcttagta cctttgagct      540
cttaggcaac cggactattg acaattcttt accaattcga actcgagaac tcaacgagtt      600
cattcaaact ttggaaaata aatccaaggt tgaagaaagc gtgaacctca ctcaagcttt      660
gttgaagctt ccaacaaca taatatcacg gatgatgttg agcattgaga gctcaggaac       720
ggatagtcag gctgaacagg cgaggacgtt ggttcgagat gtgacccaaa ttttcgggga      780
atttaacatt tcggatttta taggattttg caagaacttg gactttcaag gtctcaaaaa      840
gagggcattg gatatacata agaggtatga tgcttttctg gagaagttaa tttgtgatcg      900
tgaggaatca cgaaggaaag ccaaggttga gggtggttgt gaggatagag acgaaaaagt      960
gaaggattt cttgatatgt tgcttgatgt tttcgaggcc aaagaatgtg aggtcgactt      1020
tactaggaac catatcaaat cgttgatctt ggattacttc acagcagcta cagatacaac     1080
tgccatttca ttggaatgga caatagcaga actgttcaac aatccaatag tactgaagaa     1140
agcacaagaa gaggtggaga gaataatagg gaaggaaaga ctagtatgtg aagcagacat     1200
tccaaaccttt cctttatatac aagccattat aaaagaaaca ttgaggcttc acccaccact     1260
accgatgatt gctaggaaag gaacaaaaga ttgtgtggtc gatgggaaaa tgatcaaaaa     1320
aggctcaata gtttgtgtga acatttgggc tattggaagg gactcaaaga cttggaaaaa     1380
cccactagag tttaggcctg aaaggttttt agaatctgga aaagagagtg agatagatat     1440
caaagggcat gactttgagt tgttgccatt tggttctgga aggagaggtt gcccggggat     1500
gcctttggcc atgcgcgaat tgccgactgt gattggagct ttagtacaat gcttgagtg      1560
gaagatgctt gactctgaag gtaaattatt agatcaaggc aaaacaatcg atatggatga    1620
acggcctgga ttgactgctc ctagagccaa tgatcttttt tgcattccag ttgcaagatt    1680
gaatttgatt cctttggttc aattgtagtg taaagcaatt gcgataaggt attatgaaaa    1740
tttctttcaa attgttttc tgggccaagg gcctaatata agataacttt atttattgta    1800
tgtttatttt aatttaatac tcactccgtc ccaaattgta cgacgttttg agcatttaac     1860
atatattaag aaatataatt aata                                           1884
```

<210> SEQ ID NO 70
<211> LENGTH: 1569
<212> TYPE: DNA
<213> ORGANISM: Lotus japonicus

<400> SEQUENCE: 70

```
atgttggtgg aacttgcatt agcattactg gccatagctc tgttcttaca tttacgtccc        60
acaccaactg ccaaatccaa ggcccttcgt caccttccaa accctccaag tcccaagcct       120
```

```
cgtcttccat tcgttggaca ccttcacctt ttggaccaac cacttctcca ccactccctc    180
atcaaactcg gcgagcgata tgggcctttg tactctctct attttggatc catgcccacc    240
gttgttgcct caacccctga actcttcaaa ctcttccttc agacccatga ggcctcttcc    300
ttcaacacaa ggttccaaac ctctgccatt aggcgcctca cctatgacaa ctctgttgcc    360
atggtccctt ttgctcctta ttggaagttc atcaggaaga tcatcatgaa cgacctcctc    420
aacgccacca ccgtcaacaa gttgaggcct tgaggagcc aagagattcg taaggttctg     480
aaggctatgg cacatagtgc ggaatctcaa caacccctta atgtcactga ggagcttctc    540
aagtggacaa acaacaccat ctctcgaatg atgttggggg aggctgaaga ggtcagagat    600
attgctcgtg aggtgcttaa gatcttcggg aatatagtc tcacagactt catttggcca     660
ttgaagaagc tcaaggttgg acagtatgaa aagagaatag atgagatatt taacaaattc    720
gaccccgtca ttgagaaggt catcaagaaa cgccaagaga taataaagag gagaaaagag    780
agagatggag aacttgagga gggtgagcaa agtgtagttt cctcgatac tttgcttgaa     840
tttgctgaag atgagaccat ggaaatcaaa atcacaaagg aacaaattaa gggtcttgta    900
gtggatttct tctctgcagg gacagattcg acagctgtgg caacagactg ggctctatca    960
gagctcatca acaacccgag ggtgctgaag aaagcaagag aggaagttga aagtgttgtt   1020
ggaaaagata gacttgttga tgaagcagat attcaaaatc ttccatacat tagagccatc   1080
gtgaaggaga cattccgcat gcatcctcca ctccctgttg ttaagagaaa gtgtgtacaa   1140
gaatgtgagc tcaacggtta cgtgatccca gagggagcac tgatactctt caacgtgtgg   1200
gccgtgcaaa gagatcccaa atactgggag ggcccatccg aattccgtcc tgagaggttt   1260
ttaactgctg aaggggagc aacctccatt gatcttagag ccagaatttt cgagcttctc    1320
ccatttgggt ctggaaggag gatgtgtcca ggtgtgaatt tggcaactgc aggaatggcc   1380
acattgcttg catctgttat ccaatgcttt gatttacagg ttgtgggtca aaagggcaaa   1440
ttattgaaag gaagtgatgc caaagttagc atggaagaga gtcctggtct cactgttcca   1500
agggcacata atctgatgtg cgttccactt gcaagaacca acgtcacatc tgaactcctt   1560
tcctcataa                                                            1569

<210> SEQ ID NO 71
<211> LENGTH: 1919
<212> TYPE: DNA
<213> ORGANISM: Glycine max

<400> SEQUENCE: 71
gatggtcatt ttcctaatta atcaaaccaa ccaccaacaa gatgatttct gagtccctct      60
tggtagtatt cctcattgtc ttcatttctg cttcccttct caaactcttg tttgtgagag     120
aaaacaaacc aaaggcccac ttgaagaacc caccaagccc acctgcaata cccataatag    180
gtcatctcca cctccttaaa cccctcatcc atcactcatt ccgagacctc tctctccgat    240
atgggcccct cctaagcctt cgaattggtt ccgttaagtt catagttgca agcacccat     300
cactcgccca agagtttctc aagaccaacg agctcacata ctcttcccgc aaaatgaaca    360
tggccatcaa catggtcact taccacaacg ccacgtttgc gtttgcacct tacgacactt    420
actggaagtt catgaaaaaa ctaagcacca ctgagctctt gggaaacaaa accctcggac    480
acttcctacc tattcggacg agggaagttc atgacatcat tcaattttgt ttccataaat    540
caaaggccca agagagcgtg aacctcaccg aagcgctttt gagtctttcc aacaacgtaa    600
tatcgcagat gatgttgagc attaagagct ccggtacaga cagccaggca gagcaggcac    660
```

```
ggactttggt tcgtgaagtg acgcagattt tcggggagtt taacgtgtcg gatttcttag    720
gtttctgcaa aaacttggac ttgcaaggtt tcaggaagag ggcattggac atacataaga    780
ggtacgatgc tctgctagag aagatcatct ctgatcgtga ggagttgaga aggaaatcaa    840
aggtagacgg ctgcgaagat ggagatgatg agaaagtgaa ggattttctt gacattttgt    900
tggatgttgc tgagcagaaa gaatgcgagg tccagttaac tcggaccat gtcaaatcat    960 tgatcttgga ttattttacg gcagctactg acacaactgc catatcagtg gaatggacaa   1020
tagcagaact atttaacaat ccaaaggtgt aaagaaagc gcaagaggaa gttgatagag   1080
tcaccggaaa cacgcaatta gtgtgtgaag cagacattcc aaaccttcct tatattcatg   1140
ccatcataaa agaaacaatg agacttcacc cgccaatacc aatgattatg aggaaaggaa   1200
tcgaagactg cgtggttaat ggaaacatga ttccaaaagg ttcaatagtt tgtgtaaaca   1260
tttgggctat gggaagggac ccaaatatct ggaagaaccc tttagaattc aagccagaga   1320
ggtttctaga aggtgaagga agtgctatag ataccaaagg gcatcatttt gagttgttgc   1380
catttggcag tggaaggaga gggtgtcctg gaatgccttt ggccatgcgt gaattgccca   1440
ccatcattgg agcactcata caatgctttg agtggaagat gttaggttca caaggtgaaa   1500
tcttagatca tggaagaagc ttaatcagta tggatgaacg gccaggattg actgccccaa   1560
gggccaatga tcttattggc attcctgttg cacgattgaa tcccactcct tttcgtcaaa   1620
tgtagtttat tgtcaaggga atttgtgaca acaaagagtt atacgtgcca actaataagt   1680
atttccatga aaaatagag tcagtattat ttccatgata aactcatgca gtttgatatt   1740
atggtaggtg tatgagttga aaaatgttct ttcaaatcgt atttgtggtg taatatatct   1800
aagatattat gattatgatg agtgtaggag ctggaaaatg ttccttctat gtattttttt   1860
aattcaaata aagacgaaat tgaataaaaa ttatcttgtt gcaaaaaaaa aaaaaaaa    1919
```

<210> SEQ ID NO 72
<211> LENGTH: 1770
<212> TYPE: DNA
<213> ORGANISM: Perilla frutescens crispa

<400> SEQUENCE: 72

```
tgtcgacgga gcaagtggaa atggcactgt acgccgccct cttcctcctg tccgccgccg     60
tggtccgctc cgttctggat cgaaaacgcg ggcggccgcc ctaccctccc gggccgttcc    120
ctcttcccat catcggccac ttacacctcc tcgggccgag actccaccaa accttccacg    180
atctgtccca acggtacggg cccttaatgc agctccgcct cgggtccatc cgctgcgtca    240
ttgctgcctc gccggagctc gccaaggaat gcctcaagac acacgagctc gtcttctcct    300
cccgcaaaca ctccaccgcc attgatatcg tcacctacga ttcatcctct gctttctctc    360
cctacgggcc ttactggaaa ttcatcaaga aattatgcac ctacgagctg ctcggggccc    420
gaaatctcgc ccactttcag cccatcagga ctctcgaagt caagtctttc ctccaaattc    480
ttatgcgcaa gggtgaatcg ggggagagct tcaacgtgac tgaggagctc gtgaagctga    540
cgagcaacgt catatcgcat atgatgctga gcatacggtg ttcagagacg gagtcggagg    600
cggaggcggc gaggacggtg attcgggagg tcacgcagat atttggggag ttcgacgtct    660
ccgacatcat atggcttttgt aagaacttcg atttccaagg tataaggaag cggtccgagg    720
atatccagag gagatatgat gctctgctgg agaagatcat caccgacaga gagaagcaga    780
ggcggaccca cggcggcggt ggcggcggcg gggaagccaa ggattttctt gacatgttcc    840
```

| | |
|---|---|
| tcgacataat ggagagcggg aaagccgaag ttaaattcac gagggagcat ctcaaagctt | 900 |
| tgattctgga tttcttcacc gccggcaccg acacgacggc gatcgtgtgt gaatgggcga | 960 |
| tagcagaagt gatcaacaat ccaaatgtgt tgaagaaagc tcaagaagag attgccaaca | 1020 |
| tcgtcggatt cgacagaatt ctgcaagaat ccgacgcccc aaatctgccc taccttcaag | 1080 |
| ccctcatcaa agaaacattc cggctccacc ctccaatccc aatgctggcg aggaaatcga | 1140 |
| tctccgactg cgtcatcgac ggctacatga ttccggccaa cacgctgctc ttcgtcaacc | 1200 |
| tctggtccat ggggcggaac cctaaaatct gggactaccc gacggcgttc cagccggaga | 1260 |
| ggtttctgga gaaggaaaag gccgccatcg atgttaaagg gcagcatttt gagctgctac | 1320 |
| cgttcggaac gggcaggaga ggctgcccag ggatgctttt agccattcag gaggtggtca | 1380 |
| tcataattgg gacgatgatt caatgcttcg attggaagct gcccgacggc tccggccatg | 1440 |
| ttgatatggc agaacggcca gggctcacgg caccgcgaga gaccgatttg ttttgccgtg | 1500 |
| tggtgccgcg agttgatccg ttggttgttt ccacccagtg atcacccct ttaaatttat | 1560 |
| taatgatata ttttattttt gagaaaaaat aaaaatgcta attgttttgt ttcatgatgt | 1620 |
| aattgttaat tagtttctat tgtgcgctgt cgcgtgtcgc gtggcttaag ataagattgt | 1680 |
| atcattggta cctaggatgt attttcattt tcaataaatt attttgtgct gtgtatatta | 1740 |
| aaaaaaaaaa agaaaaaaaa aaaaaaaaa | 1770 |

<210> SEQ ID NO 73
<211> LENGTH: 1697
<212> TYPE: DNA
<213> ORGANISM: Gerbera x hybrida

<400> SEQUENCE: 73

| | |
|---|---|
| atgtcctaac acaacccaac accatgaata cactccaact catcttcctc ctcttcttct | 60 |
| tcccaacctt actcttcctc tactgtctcc cctacaaaag aaaccaaaac caccgccgtc | 120 |
| ttccgccgtc cccgccatct tttccgatca tcggccacct ccaccatctc ggcccactca | 180 |
| tccaccaatc cttccacgct ctctccactc gctacggctc tctaatccac ctccgtctcg | 240 |
| gctcagtccc atgcgtcgtc gtttcaaccc cagacctcgc caaagacttc ctcaaaacaa | 300 |
| acgaactcgc gttctcatca agaaaacact ccttagccat cgaccacatc acctatggcg | 360 |
| tagcatttgc attcgcacca tatggaactt actggaagtt catcaagaaa ctcttcacag | 420 |
| tggagctttt gggcacccag aatctcagcc atttcctacc cattcgaacc catgaaattc | 480 |
| gcgagcttct tcgaacgtta atggtgaaat ctagggcaaa ggagagagta aacttgacgg | 540 |
| aagagttgtt gaagttgacc aacaatgtga taagtcaaat gatgatgagc attaggtgtt | 600 |
| cggggacgaa tagtgaggct gatgaagcaa agaatcttgt tcgggaagtg accaaaattt | 660 |
| ttggacagtt taatgtttca gatttcatat ggttttgtaa gaacatagat ttgcaagggt | 720 |
| ttaagaagag gtacgagggt acacatagaa gatatgatgc tttgcttgaa aggattataa | 780 |
| tggggaggga agaaaataga agaagaggga agataaaaga tggtgaaggg aaagattttc | 840 |
| ttgatatgtt acttgatgtt ttggaggatg gtaaggcaga gattaaaatt actagagacc | 900 |
| acatcaaagc cttgattttg gactttctta cagctgggac ggataccacc gcgattgcaa | 960 |
| ttgaatgggc actagtcgaa ttgataaaca acccgaacgc tctcgagaaa gcaagacaag | 1020 |
| agattgatca ggtcatcggt gatgagaggc tagttcaaga atcagacacg cctaacctcc | 1080 |
| cttatatcca agctatcata aaggaagccc tacgacttca cccaccaatc ccaatgttga | 1140 |
| ttcgcaagtc aacagaaaat gtaattgttc aggggtatga catcccagcc ggcaccttgt | 1200 |

```
tgtttgtcaa tatttggtcc attggaagaa acccctcaatg ttgggaaacc cctttagagt    1260
tcaagcctca tcggtttttg gatggtggtg accttaaaag ctctttagat attaaaggcc    1320
acaattttca actattgcct tttgggacgg ggaggagagg gtgtcctggt gttaatttgg    1380
ccatgagaga actctcagtg gtgattgcaa acctcataca atgctttgat tgggatgttg    1440
taggtgaacg actattgaat acagatgaac gtgctggatt gacggctcca agggcggtag    1500
attttgtgtg tgttccattg gaacgaggaa acactttgaa gattcttggt tcaaactaaa    1560
tttatttgtt gttgctttct tgatggcagt cggtctatct ataggtcata ataccttggg    1620
actcacgtgt ttgaatctta atacgctttt agtacattgc ttatcgtata tcttgggtat    1680
gcatgaaaaa aaaaaaa                                                    1697
```

<210> SEQ ID NO 74
<211> LENGTH: 1836
<212> TYPE: DNA
<213> ORGANISM: Gentiana triflora

<400> SEQUENCE: 74

```
acctcacagt atatcataat gatgcttctt gactttttt actctgcttc cattttcgtc      60
ctctcaatcc tcctcttccg tgcaatctac accaccaaaa accgccgtct ccgcctcccg     120
ccgagcccat tcgggttacc aatcatcggc catctccacc tcctcggccc caaaatccac    180
cattctttcc acaacctcta caaacgctac ggcccaatat tccatcttcg tctcggatct    240
aatcgttgta ttgtagtctc caccectgaa ctagctaaag aattcctcaa aacccatgaa    300
ctcgatttcg cttaccggaa aaacagctcc gccattagtc tttaacctta ccatgtttct    360
ttcgcttttg caccttatgg tccctactgg aaatacatca agaaaatcac tacttaccag    420
ctactgggta accggaatct cacccatttc gaaccaattc gaagactgga aacgaatcgg    480
gttctttacg atttgatggt gagttctaaa catggcaaat cagtgaattt aacagaggag    540
atgataaaat tgacgagcaa catcatttca cagatgatgt taagtatccg atgttcagat    600
acagagtccg gagctacgaa tgtacggaac gttatccggg atgtgactga actgttcgga    660
gagttcgatg tttcggatat aatatggttt tgtaagaaca ctgatttgca agggattaaa    720
aagagggcta acggtataca tgaaaggtac gatgctttgt tggagaagat catttcggac    780
agagaaagaa ccagaattgt tgagaagaag aacagcggtg ctggcggtgg aagcggcgac    840
ggtgagagga atgatttttct tgatattctg atggatgcaa tggaagatga cacgtcggaa    900
gtcaagttat ccagaaaatca tatcaaagct ataatcttgg acttcctaac agctgcaaca    960
gatacaacag ccatatcact agaatgggca ttgtctgagc tcattaacaa tccaagggtc   1020
ctaaagaaag cacaagaaga aatcaacaat gtggttggaa atcaacggct agtaaaagag   1080
ttagacactc ctaattttccc ctacattaag gcaataatta agaaacatt tcgtcttcac    1140 ccacccatcc cgatggtcat tcgaaaatca gctaacgaca tccaagtggc tggatatgac   1200
gtaccaaaaa atacgatgct tttcgtgaac atttggtcta ttggaaggaa tcccagttac   1260
tgggagaagg cgtcggagtt ttccccggag agatttttgg ctgatacaga tggtggcggt   1320
ttgagtcaca tggatataaa cggcagtat ttcgagctta tgccgtttgg tactggaagg   1380
agaggttgtc ctgggatgcc gttagccatg caagaattac caactgttct ttcgcttatg    1440
atacaatgtt tcgattatat tccgcttgat ttcaagggag aaaaggctga agggttatg    1500 gacatgagtg aacggccagg actgactgct ccgagggcga atgagttgat gtgtttgctt   1560
```

| | |
|---|---|
| aaaccgcgaa ttgatcttcc aaatctcctt ggtaatgtaa agggtgagta gatgacattt | 1620 |
| gtgaggatgt gttttaact agtcgataat tatttatcga ctaataatgt gatttaagag | 1680 |
| aagtatgggg accaactttt agttgtttca atttgtccaa gggtgtgaat gtaataagat | 1740 |
| ataagttgca tgttcatctt tcttgtatcc gagttatttt gatcttaatg aattctctat | 1800 |
| ttaattataa aaaaaaaaaa aaaaaaaaaa aaaaaa | 1836 |

<210> SEQ ID NO 75
<211> LENGTH: 1706
<212> TYPE: DNA
<213> ORGANISM: Antirrhinum majus

<400> SEQUENCE: 75

| | |
|---|---|
| gctttacaca cacacacaca cacacacaca caaacaaaaa tgtctacact tgtctacagc | 60 |
| acactcttca tcctctcaac cctcctcctc accctcctaa cccgcacccg ccgcaagacc | 120 |
| cgcccgcccg gcccattagc cctcccctta ataggccact tacacctcct cggcccaaag | 180 |
| ctccaccaca ccttccacca attctcccaa cgctacggcc cgctcatcca gctctacctc | 240 |
| ggctccgtcc catgcgtcgt cgcttccacg cccgaactcg cccgcgaatt cctcaagacg | 300 |
| cacgaactcg acttctcgtc ccgcaagcac tccaccgcca tcgacatcgt cacgtacgac | 360 |
| tcctcgttcg ccttcgcgcc gtacgggccg tactggaaat tcatcaagaa attatgtact | 420 |
| tacgagctac tgggtgcccg gaacttgagc catttccagc ccattagagc tttggaggtc | 480 |
| aacagtttct tgagaatttt gtacgagaaa acagagcaga acagagtgt taatgtgact | 540 |
| gaggagcttg tgaagctgac gagtaatgtg atcagtaaca tgatgttggg gatcaggtgt | 600 |
| tcggggacgg aaggggaggc ggaggtggcg aggacggtga tagggaggt gacgcagata | 660 |
| tttgggggagt ttgatgtgtc ggagattgtt tggttttgta agaatttgga tctgcagggg | 720 |
| attaggaaga ggtcggagga tattaggagg aggtatgatg ctttgttgga gaagattatt | 780 |
| agtgataggg agaggttgag gttgaggggg ggtggtggtg gaggggtgg agaggtgaag | 840 |
| gatttttgg atatgttgtt ggatgtgatg gagagtgaga atcggaggt ggagtttacg | 900 |
| agggagcatc tcaaagcttt gattctggat ttcttcactg ccggtacaga cacaacagca | 960 |
| atcacaacag aatgggcaat agcagaactc attagcaatc caaatgtact caaaaaagct | 1020 |
| caagaagaga tggacaaagt cataggatca caaaggttgt tgcaagaatc cgacgcccct | 1080 |
| aacttgcctt acctcaacgc gatcataaaa gaaacgttcc gtctccaccc tccaatcccc | 1140 |
| atgctcacta gaaaatcaat ttctgacgtt gtggtcaacg ggtacacgat ccctgccaaa | 1200 |
| acgctattgt ttgtcaacct tggtccatg gaaggaatc ctaactactg ggaaaatccg | 1260 |
| atggagttcc gacccgagag gtttctcgag aaagggaccg ggtcgataga cgttaaaggg | 1320 |
| cagcatttcg agttgctgcc gtttggcacg ggcaggcggg gctgcccggg gatgttgtta | 1380 |
| ggcatgcagg agttgtttag tattatcggg gctatggtgc agtgcttcga ttggaaactg | 1440 |
| cccgatggtg tgaagtcggt cgacatgacc gagcggcccg ggttgacggc tccacgtgcc | 1500 |
| aatgatttgg tgtgccaatt ggtgccacgg attgacccgg tcgttgtctc cggaccgtga | 1560 |
| acctaaggt agtatcgata atctgtttaa ttaaattgtt atttgttgtg aggatttgat | 1620 |
| ttttgttatg tatgattatg cgtggattaa gataagcctg caaggacaaa ttcccttct | 1680 |
| ttgattgatg tcaatgagtt tgtgtc | 1706 |

<210> SEQ ID NO 76
<211> LENGTH: 1846

```
<212> TYPE: DNA
<213> ORGANISM: Theobroma cacao

<400> SEQUENCE: 76
aatcctgtgg gttgagaaaa tttgtcacca aaactctctc tttcagtctg agttgaggta    60
gccatgttgc ttcaactcct gtcgtattcc accctctaca ttgcttcgtt ttttcttgtg   120
aaaacaatat taatctccat caacaaccgt cccaagcttc ccccaggccc cattgcctta   180
ccagtcatcg gccacctcca cctccttggc cccttcattc atcaaacttt ccacaagttc   240
tcctcccgct atggtccctt aatgtatctc cgtcttggct ctattgggtg cgtcgtggcc   300
tctaacccag agcttgcaaa agagcttctc aaaacttacg agctggcatt cgccgccgc    360
atgcacaccg ctgccattac ccaccttaca tacgactctt cctttgcctt tgcaccctac   420
ggaccttact ggaaattcat aaaaaagttt agcacctatg agctcctagg taaccgaact   480
cttagccagt ttcttcccgt tcggaccaag gaattgcact gtttcattaa gtttcttctt   540
gacaggtcta aagcaggcga aagcgtgaat gtaactcaag agctgttgaa attaaccaac   600
aacacaatat cacagatgat gctgagcatg aggtgctcgg ggagtggaaa ccccgccgat   660
ggggttcgag ctctagtgag ggaggtgact gagatcttcg gagagttcaa catctcagac   720
agtatatggt tttgcaaaaa ctgggatctg cagggattcc gaaggagatt tgaggacata   780
catagaaggt atgacgcttt gttggagaga atcataagag atcgcgagga agtaagaaaa   840
agcaagaaag agtgtgacca acgagacaat ggaaatgagg tcaaggattt tctggacatg   900
atgcttgatg tattggaaaa tgataactcg gagatccaat taaccagaaa tcacattaag   960
gccttggttt tggatttctt gacagccggt acggatacaa cagcaattgt acttgaatgg  1020
gcactggcag agctcatcaa caacccggaa gtgctaaaac tagctcaaaa agagattgat  1080
caagttgtgg gaacaagcag gttggtagaa gaatcggaca gtcctcgtct ccaatacatc  1140
caagccatca ttaaggaaac ttttcggctc cacccaccgg tcccgatgat cagcagaaaa  1200
tcaatccaat catgcaaaat taagggatac accatccctg ccgactgttt ggtgttcgta  1260
aacatttggg ctataggaag ggatcccacg gtctgggcag atccattgag gtttcagcct  1320
gagaggttcc tgaaatccta tgagggagat catagttcag ggcctataga tgttagaggc  1380
ctccattatc agctgttgcc tttcggtaca gggaggaggg gctgccctgg tgcttcttta  1440
gcaatgcagg agctgcccac cactctggca gccatgattc agtgctttga ctggaagcct  1500
gcggctactt caaagactgg agatggtgtt gacatgtctg aacggcctgg acttacggct  1560
cccagggcaa aggatctgga gtgtgttcca gttgcacgct tcacacccag tctttgcaac  1620
ttaagcaggt gaccacttac gtatgatgtg atgagcaatc gagcatcagt ctcccccgtt  1680
ctcccgattt cctaggctct gtgtctttag cgtgttacga gtgatgtgac tgtgatggca  1740
tgcatttagg tagaaataaa tgcaattata ttgcatattt gcttgccaaa aacaaaataa  1800
aaaaaatgta ttaatagttt atgaattttt ctgtttggtt tatttc                 1846

<210> SEQ ID NO 77
<211> LENGTH: 1907
<212> TYPE: DNA
<213> ORGANISM: Camellia sinensis

<400> SEQUENCE: 77
ttttcctttc ctagtttcta tttaaagcaa catataattt ctcgaatgca taatttctct    60
tgaaatcaag ccaagatgtt tgacttaatc tccattgcca ccttattctt tgttattatc   120
```

```
tccaccacca tcctcctcct ctccataaac cacttcaaaa aaccaccaca tctccgccgc    180
cgtctcagcc tcccaccaac cccttcgcc ctgccaatca tcggccacct ccacctcctc    240
ggccccatca tccaccgctc cttccatgac ctctcctccc gctacggccc cttgtttcac    300
ctccgcctcg gctcagtccc atgcttcgtg gtctccactc cagagctcgc aaaagagttc    360
ctcttgacac atgagctcaa gttctcatct cgcagggatt ccatcgccat ccaacgcctc    420
acctatgact ctgcattcgc cttcgcccct tacggtccct actggaaatt cctaaagaag    480 cttttgtactt gtgatcttct cggcgctcgt agtatcaatc attttcttcc cacacggacc    540
cgtgaactac actgctttgt tcgacttctc atcgacaagg ccgtggcttg tgaacctgtc    600
aacatcacta aagagctttc aacgctcgcc aacaatatca tctctcaaat gatgattggt    660
gtaaggtgtt cggggacgac aggagaggct gaggaggcta caactcttgc ccgcgaggtg    720
acgaagatat tcggagagtt taatgtgtcg gattttatgt gggttatcag gaactttgat    780
ttgcaggggt ttaggaagag agttgaggat atatacacaa ggtatgatgc gttgctggaa    840
aggattatca caaacaggga agaagtcaga gaaaagaacg tacaagaaag aaaattgggt    900
gttggagaag gtcatcacgt caaggatttt cttgatctat tgcttgatgt tttggaagag    960
gaccattcgg agattaactt cagtagagat aacattaagg gcttgatttt ggatttcttc   1020
accgcaggaa cagatacatc atctattgca attgaatggg cattagcaga gctgatcaac   1080
aatccaagag tgctccaaaa agcacaagag gagattgata atgtggttgg gaaacatcgg   1140
ttagtaagcg aatcacacgg tccaaatctt ccatacatcc aagccatcat aagggaagca   1200
cttcggcttc accctccagt ccccttgatc acaagaaaat caatagagga ctgcatgatc   1260
caaggataca acatcccagc caactccatg ctatttgtga atgtttggtc tcttgctaga   1320
aatcccaagt attgggatag cccactggac ttccttgcctg agcgattctt aaggcccgaa   1380
aagggtggcc cagtgggccc aacagatgtt aagggccaac atttccagct attacccttt   1440
ggtactggga ggagaggctg ccctggtact tctttggcca tgcaagagct gcctgctatg   1500
ctagcagcaa tgattcagtg tttcgagtgg aaggttgtga atcagagtgg ggatgtgatg   1560
aacggtgatg gagcgcttga tatgactgaa caacccggga tgacagctcc gagggcccat   1620
gatcttgtgt gcatgccgat accacgaatc gatcaacttt atgcccttct tgatccatag   1680
tttatgctaa ggcaaggatt ctcagtagtt aaaattttg tgcccaataa atttctaatc    1740
gcatgatttt gtcgtcaata aaagttgtga aatacaatca tacgattaag aaggcaatat   1800
gaataaggga taaagatttt ggaatagagg atctgtacct ttgtgctatg atttgcccaa   1860
tattgctctc tttaacctat ttttagaaaa aaaaaaaaaa aaaaaa                   1907
```

<210> SEQ ID NO 78
<211> LENGTH: 1530
<212> TYPE: DNA
<213> ORGANISM: Plectranthus barbatus

<400> SEQUENCE: 78

```
atggaccatg tcgaagccgc tctcttcgcc gccatcttcc tcctctccgc cgccctcctc     60
aaccaccttc tcaccggaaa acgccgccag aacgcttacc ctcccggccc gttccctctt    120
cccatcatcg gccacttaca ccttctcggg ccgagactcc accacccttc cacgatctg    180 acccaacggt atgggccctt gatgcaggtc cgcctcggct ccatccgctg tgtcatcgcc    240
gccacgccag agctggcaaa ggaattcctc aagacgagcg agctcgtctt ctccgctcgg    300
aagcactcaa ccgccattga tatcgtcacc tacgaatcct ccttcgcttt ctcccctac    360
```

```
ggcccctact ggaaatacat caagaaatta tgcacctacg agctgctcgg ggccaggaat      420
ctcaaccact ttctcccgat tcgaacgatt gaagtcaaga ctttcttaga agctctcatg      480
caaaagggta aaacggggga gaggttgaac gtgacggagg agctggtgaa gctgacgagc      540
aacgtgatat cgcagatgat gctgagcata cggtgctcgg ggacggaggg ggagacggag      600
gcggtgagga ctgtgattcg ggaggtgacg cagatatttg gggagttcga cgttgcagac      660
attatttggt tttgcaagaa cttcgatttc caagggataa ggaagaggtc ggaggatata      720
cagaggaggt atgatgcttt gctggagaag atcatcaccg accgggagaa gcagcggcgg      780
acgcagcacg gcggcgaggc caaggatttt ctggacatgt ttctggatat aatgaagagt      840
gggaaagctg aagtcaattt caccagggac catctcaagg ctctcattct ggatttcttc      900
accgccggca ccgacactac ggccattgtc gtcggatggg cgatagcaga gctcatcaac      960
aaccctaatg tgctgaagaa agctcaagcc gagatcgata aagtcgtcgg actccacaga     1020
atcctgcaag aatccgacgg tccaaatctg ccctaccttc acgccgtcat caaagaaaca     1080
ttccggcttc atcctcccat ccccatgctg tcgaggaaat caatctccga ctgcgtgatc     1140
gacggctaca cgataccggc caacacactg ctgttcgtca acatctggtc catggggcgg     1200
aaccctaaaa tctgggacaa cccgatggcg ttccggccgg agaggtttct ggagaaggaa     1260
aaaaccggca tcgacattaa agggcagcat ttcgagcttc tgccgtttgg cacgggcagg     1320
aggggctgcc ccgggatgct gctcgccatt cgggaggtgg tcgttataat tgggaccgtg     1380
attcagtgct ttgactggaa gcttcccgtc gacgatgtct ccggccttgt ggacatgacg     1440
gagcggccgg ggctcacggc gccgagagct gacgatttga tttgtcgtgt ggtgccgcga     1500
gttgatcctt tggttgtttc cggccattga                                       1530

<210> SEQ ID NO 79
<211> LENGTH: 1566
<212> TYPE: DNA
<213> ORGANISM: Lonicera japonica

<400> SEQUENCE: 79
atgtggatct ttgacctcac aatctcgttc accacactcc tcttcctcat cttcaccacc       60
gccctcctac tcctcctcaa ggttttcaag aaaaaccaca aactccgacc gccgcctagc      120
cccttcaccc taccgataat cggccacctc cacctcctcg gccccctcat ccaccagtcc      180
ttccatcgcc tctccaccct ctatggcccc ttaatccagc tcaaaatcgg ctacatccca      240
tgcgttgttg cctcaactcc cgagctagca aaagaatttt taaaaacaca cgaactcgcg      300
ttctcctcgc gtaaacactc cgctgccatt aaactcctca cctacgatgt atcatttgct      360 ttttcacccct acggtcccta ttggaaattc atcaaaaaaa catgcacctt gaacttttg      420 ggcacacgta acatgaacca ctttctcccc attaggacca cgagattcg tcgtttctta      480 caagtgatgt tagaaaaagc caaggctagt gagggggtga acgtgactga agagttgatc      540
aagctcacga acaacgttat ctctcaaatg atgtttagta ctcggagctc ggggaccgag      600
ggggaggcgg aggagatgag gacattggta cgtgaggtga ctcaaatatt cggagaattt      660
aatgtttcgt attttataaa gttgtgtaag aacattgata ttggagggtt taagaagaga      720
agtaaggata tacaaaaaag gtatgatgct ttgttggaga agataataag tgagagggag      780
agtgaaagag caagaagggg taaaaataga gagactttag ggaggaagg agggaaagat       840 tttcttgata tgatgcttga tactatggag gatggcaagt gtgaagttga gataacaaga      900
```

```
gatcacatta aggccttggt tttggatttc ttaactgcgg ccacggatac aactgcgatt   960
gctgttgaat ggacattagc cgagcttatc agcaacccgg aagtgttcga taaagctcga  1020
gaggagatcg ataaagtcgt agggaagcac aggctagtca cagaattgga cacgccaaat  1080
cttccctaca tccacgcgat cataaaggaa agttttcggc ttcacccgcc aattcctctg  1140
ctcataagaa aatcagtcca agattgcacg gtaggtggct accacatctc ggctaacacc  1200 atacttttg tcaatatttg ggccatcggg cgaaatccca agtattggga agcccaatg   1260 aagttctggc ccgaaagatt tcttgaatcc aatgggccag gtccagtggg ctctatggat  1320
attaagggcc atcattatga gcttttgcct tttgggagtg ggagaagggg ttgccccggg  1380
atggctttag ccatgcaaga actgcccgtg gtgctcgccg ccatgataca atgctttaat  1440
tggaagccgg tgacattgga cggagaggaa ctggatatga gtgagcggcc tggtctaact  1500
gctccaagag cccacgatct tgtatgcgtt ccctccgctc gaattaattc tttcgataat  1560
ttttaa                                                             1566
```

<210> SEQ ID NO 80
<211> LENGTH: 526
<212> TYPE: PRT
<213> ORGANISM: Medicago truncatula

<400> SEQUENCE: 80

```
Met Ile Ser Gln Pro Ile Leu Leu Ala Leu Ile Leu Phe Leu Leu Phe
1               5                   10                  15

Leu Leu Gln Leu Phe Leu Phe Lys Arg Asn Asn Arg Ala Lys Glu His
            20                  25                  30

Leu Pro Tyr Pro Pro Ser Pro Leu Ala Ile Pro Ile Ile Gly His Leu
        35                  40                  45

His Leu Leu Lys Pro Leu Val His Gln Ala Phe Arg Asp Leu Ser Asp
    50                  55                  60

Arg Tyr Gly Pro Leu Ile Ser Leu Arg Leu Gly Ser Val Pro Phe Ile
65                  70                  75                  80

Val Val Ser Ser Pro Ser Leu Ala Lys Glu Phe Leu Lys Thr Asn Glu
                85                  90                  95

Leu Val Tyr Ser Ser Arg Lys Met Asn Ile Ala Ile Asn Thr Val Val
            100                 105                 110

Tyr Asp Asp Ala Thr Phe Ala Phe Ala Pro Tyr Gly Ala Tyr Trp Lys
        115                 120                 125

Phe Ile Lys Lys Leu Ser Thr Phe Glu Leu Leu Gly Asn Arg Thr Ile
    130                 135                 140

Gly Gln Phe Leu Pro Ile Arg Thr Arg Glu Leu Asn Glu Phe Ile Gln
145                 150                 155                 160

Thr Leu Glu Asn Lys Ser Lys Val Glu Glu Ser Val Asn Leu Thr Gln
                165                 170                 175

Ala Leu Leu Lys Leu Ser Asn Asn Ile Ile Ser Arg Met Met Leu Ser
            180                 185                 190

Ile Glu Ser Ser Gly Thr Asp Ser Gln Ala Glu Gln Ala Arg Thr Leu
        195                 200                 205

Val Arg Asp Val Thr Gln Ile Phe Gly Glu Phe Asn Ile Ser Asp Phe
    210                 215                 220

Ile Gly Phe Cys Lys Asn Leu Asp Phe Gln Gly Leu Lys Lys Arg Ala
225                 230                 235                 240

Leu Asp Ile His Lys Arg Tyr Asp Ala Phe Leu Glu Lys Leu Ile Cys
                245                 250                 255
```

-continued

Asp Arg Glu Glu Ser Arg Arg Lys Ala Lys Val Gly Gly Cys Glu
            260                 265                 270

Asp Arg Asp Glu Lys Val Lys Asp Phe Leu Asp Met Leu Asp Val
            275                 280                 285

Phe Glu Ala Lys Glu Cys Glu Val Asp Phe Thr Arg Asn His Ile Lys
290                 295                 300

Ser Leu Ile Leu Asp Tyr Phe Thr Ala Ala Thr Asp Thr Thr Ala Ile
305                 310                 315                 320

Ser Leu Glu Trp Thr Ile Ala Glu Leu Phe Asn Asn Pro Ile Val Leu
                325                 330                 335

Lys Lys Ala Gln Glu Glu Val Glu Arg Ile Ile Gly Lys Glu Arg Leu
                340                 345                 350

Val Cys Glu Ala Asp Ile Pro Asn Leu Pro Tyr Ile Gln Ala Ile Ile
                355                 360                 365

Lys Glu Thr Leu Arg Leu His Pro Pro Leu Pro Met Ile Ala Arg Lys
                370                 375                 380

Gly Thr Lys Asp Cys Val Val Asp Gly Lys Met Ile Lys Lys Gly Ser
385                 390                 395                 400

Ile Val Cys Val Asn Ile Trp Ala Ile Gly Arg Asp Ser Lys Thr Trp
                405                 410                 415

Lys Asn Pro Leu Glu Phe Arg Pro Glu Arg Phe Leu Glu Ser Gly Lys
                420                 425                 430

Glu Ser Glu Ile Asp Ile Lys Gly His Asp Phe Glu Leu Leu Pro Phe
                435                 440                 445

Gly Ser Gly Arg Arg Gly Cys Pro Gly Met Pro Leu Ala Met Arg Glu
                450                 455                 460

Leu Pro Thr Val Ile Gly Ala Leu Val Gln Cys Phe Glu Trp Lys Met
465                 470                 475                 480

Leu Asp Ser Glu Gly Lys Leu Leu Asp Gln Gly Lys Thr Ile Asp Met
                485                 490                 495

Asp Glu Arg Pro Gly Leu Thr Ala Pro Arg Ala Asn Asp Leu Phe Cys
                500                 505                 510

Ile Pro Val Ala Arg Leu Asn Leu Ile Pro Leu Val Gln Leu
                515                 520                 525

<210> SEQ ID NO 81
<211> LENGTH: 522
<212> TYPE: PRT
<213> ORGANISM: Lotus japonicus

<400> SEQUENCE: 81

Met Leu Val Glu Leu Ala Leu Ala Leu Ala Ile Ala Leu Phe Leu
1               5                   10                  15

His Leu Arg Pro Thr Pro Thr Ala Lys Ser Lys Ala Leu Arg His Leu
                20                  25                  30

Pro Asn Pro Pro Ser Pro Lys Pro Arg Leu Pro Phe Val Gly His Leu
                35                  40                  45

His Leu Leu Asp Gln Pro Leu Leu His Ser Leu Ile Lys Leu Gly
                50                  55                  60

Glu Arg Tyr Gly Pro Leu Tyr Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Ser Ser Phe Asn Thr Arg Phe Gln Thr Ser Ala Ile Arg Arg

```
                    100                 105                 110
Leu Thr Tyr Asp Asn Ser Val Ala Met Val Pro Phe Ala Pro Tyr Trp
            115                 120                 125
Lys Phe Ile Arg Lys Ile Ile Met Asn Asp Leu Leu Asn Ala Thr Thr
130                 135                 140
Val Asn Lys Leu Arg Pro Leu Arg Ser Gln Glu Ile Arg Lys Val Leu
145                 150                 155                 160
Lys Ala Met Ala His Ser Ala Glu Ser Gln Gln Pro Leu Asn Val Thr
                165                 170                 175
Glu Glu Leu Leu Lys Trp Thr Asn Asn Thr Ile Ser Arg Met Met Leu
            180                 185                 190
Gly Glu Ala Glu Glu Val Arg Asp Ile Ala Arg Glu Val Leu Lys Ile
        195                 200                 205
Phe Gly Glu Tyr Ser Leu Thr Asp Phe Ile Trp Pro Leu Lys Lys Leu
    210                 215                 220
Lys Val Gly Gln Tyr Glu Lys Arg Ile Asp Glu Ile Phe Asn Lys Phe
225                 230                 235                 240
Asp Pro Val Ile Glu Lys Val Ile Lys Lys Arg Gln Glu Ile Ile Lys
                245                 250                 255
Arg Arg Lys Glu Arg Asp Gly Glu Leu Glu Glu Gly Glu Gln Ser Val
            260                 265                 270
Val Phe Leu Asp Thr Leu Leu Glu Phe Ala Glu Asp Glu Thr Met Glu
        275                 280                 285
Ile Lys Ile Thr Lys Glu Gln Ile Lys Gly Leu Val Val Asp Phe Phe
    290                 295                 300
Ser Ala Gly Thr Asp Ser Thr Ala Val Ala Thr Asp Trp Ala Leu Ser
305                 310                 315                 320
Glu Leu Ile Asn Asn Pro Arg Val Leu Lys Lys Ala Arg Glu Glu Val
                325                 330                 335
Glu Ser Val Val Gly Lys Asp Arg Leu Val Asp Glu Ala Asp Ile Gln
            340                 345                 350
Asn Leu Pro Tyr Ile Arg Ala Ile Val Lys Glu Thr Phe Arg Met His
        355                 360                 365
Pro Pro Leu Pro Val Val Lys Arg Cys Val Gln Glu Cys Glu Leu
    370                 375                 380
Asn Gly Tyr Val Ile Pro Glu Gly Ala Leu Ile Leu Phe Asn Val Trp
385                 390                 395                 400
Ala Val Gln Arg Asp Pro Lys Tyr Trp Glu Gly Pro Ser Glu Phe Arg
                405                 410                 415
Pro Glu Arg Phe Leu Thr Ala Glu Gly Ala Thr Ser Ile Asp Leu
            420                 425                 430
Arg Gly Gln Asn Phe Glu Leu Leu Pro Phe Gly Ser Gly Arg Arg Met
        435                 440                 445
Cys Pro Gly Val Asn Leu Ala Thr Ala Gly Met Ala Thr Leu Leu Ala
    450                 455                 460
Ser Val Ile Gln Cys Phe Asp Leu Gln Val Val Gly Gln Lys Gly Lys
465                 470                 475                 480
Leu Leu Lys Gly Ser Asp Ala Lys Val Ser Met Glu Glu Ser Pro Gly
                485                 490                 495
Leu Thr Val Pro Arg Ala His Asn Leu Met Cys Val Pro Leu Ala Arg
            500                 505                 510
Thr Asn Val Thr Ser Glu Leu Leu Ser Ser
        515                 520
```

<210> SEQ ID NO 82
<211> LENGTH: 527
<212> TYPE: PRT
<213> ORGANISM: Glycine max

<400> SEQUENCE: 82

```
Met Ile Ser Glu Ser Leu Leu Val Val Phe Leu Ile Val Phe Ile Ser
1               5                   10                  15

Ala Ser Leu Leu Lys Leu Leu Phe Val Arg Glu Asn Lys Pro Lys Ala
            20                  25                  30

His Leu Lys Asn Pro Pro Ser Pro Pro Ala Ile Pro Ile Ile Gly His
        35                  40                  45

Leu His Leu Leu Lys Pro Leu Ile His His Ser Phe Arg Asp Leu Ser
    50                  55                  60

Leu Arg Tyr Gly Pro Leu Leu Ser Leu Arg Ile Gly Ser Val Lys Phe
65                  70                  75                  80

Ile Val Ala Ser Thr Pro Ser Leu Ala Gln Glu Phe Leu Lys Thr Asn
                85                  90                  95

Glu Leu Thr Tyr Ser Ser Arg Lys Met Asn Met Ala Ile Asn Met Val
            100                 105                 110

Thr Tyr His Asn Ala Thr Phe Ala Phe Ala Pro Tyr Asp Thr Tyr Trp
        115                 120                 125

Lys Phe Met Lys Lys Leu Ser Thr Thr Glu Leu Leu Gly Asn Lys Thr
    130                 135                 140

Leu Gly His Phe Leu Pro Ile Arg Thr Arg Glu Val His Asp Ile Ile
145                 150                 155                 160

Gln Phe Leu Phe His Lys Ser Lys Ala Gln Glu Ser Val Asn Leu Thr
                165                 170                 175

Glu Ala Leu Leu Ser Leu Ser Asn Asn Val Ile Ser Gln Met Met Leu
            180                 185                 190

Ser Ile Lys Ser Ser Gly Thr Asp Ser Gln Ala Glu Gln Ala Arg Thr
        195                 200                 205

Leu Val Arg Glu Val Thr Gln Ile Phe Gly Glu Phe Asn Val Ser Asp
    210                 215                 220

Phe Leu Gly Phe Cys Lys Asn Leu Asp Leu Gln Gly Phe Arg Lys Arg
225                 230                 235                 240

Ala Leu Asp Ile His Lys Arg Tyr Asp Ala Leu Leu Glu Lys Ile Ile
                245                 250                 255

Ser Asp Arg Glu Glu Leu Arg Arg Lys Ser Lys Val Asp Gly Cys Glu
            260                 265                 270

Asp Gly Asp Asp Glu Lys Val Lys Asp Phe Leu Asp Ile Leu Leu Asp
        275                 280                 285

Val Ala Glu Gln Lys Glu Cys Glu Val Gln Leu Thr Arg Asn His Val
    290                 295                 300

Lys Ser Leu Ile Leu Asp Tyr Phe Thr Ala Ala Thr Asp Thr Thr Ala
305                 310                 315                 320

Ile Ser Val Glu Trp Thr Ile Ala Glu Leu Phe Asn Asn Pro Lys Val
                325                 330                 335

Leu Lys Lys Ala Gln Glu Glu Val Asp Arg Val Thr Gly Asn Thr Gln
            340                 345                 350

Leu Val Cys Glu Ala Asp Ile Pro Asn Leu Pro Tyr Ile His Ala Ile
        355                 360                 365

Ile Lys Glu Thr Met Arg Leu His Pro Pro Ile Pro Met Ile Met Arg
```

```
            370                 375                 380
Lys Gly Ile Glu Asp Cys Val Asn Gly Asn Met Ile Pro Lys Gly
385                 390                 395                 400

Ser Ile Val Cys Val Asn Ile Trp Ala Met Gly Arg Asp Pro Asn Ile
                405                 410                 415

Trp Lys Asn Pro Leu Glu Phe Lys Pro Glu Arg Phe Leu Glu Gly Glu
                420                 425                 430

Gly Ser Ala Ile Asp Thr Lys Gly His His Phe Glu Leu Leu Pro Phe
            435                 440                 445

Gly Ser Gly Arg Arg Gly Cys Pro Gly Met Pro Leu Ala Met Arg Glu
            450                 455                 460

Leu Pro Thr Ile Ile Gly Ala Leu Ile Gln Cys Phe Glu Trp Lys Met
465                 470                 475                 480

Leu Gly Ser Gln Gly Glu Ile Leu Asp His Gly Arg Ser Leu Ile Ser
                485                 490                 495

Met Asp Glu Arg Pro Gly Leu Thr Ala Pro Arg Ala Asn Asp Leu Ile
                500                 505                 510

Gly Ile Pro Val Ala Arg Leu Asn Pro Thr Pro Phe Arg Gln Met
            515                 520                 525

<210> SEQ ID NO 83
<211> LENGTH: 506
<212> TYPE: PRT
<213> ORGANISM: Perilla frutescens crispa

<400> SEQUENCE: 83

Met Ala Leu Tyr Ala Ala Leu Phe Leu Leu Ser Ala Ala Val Val Arg
1               5                   10                  15

Ser Val Leu Asp Arg Lys Arg Gly Arg Pro Pro Tyr Pro Pro Gly Pro
                20                  25                  30

Phe Pro Leu Pro Ile Ile Gly His Leu His Leu Leu Gly Pro Arg Leu
            35                  40                  45

His Gln Thr Phe His Asp Leu Ser Gln Arg Tyr Gly Pro Leu Met Gln
        50                  55                  60

Leu Arg Leu Gly Ser Ile Arg Cys Val Ile Ala Ala Ser Pro Glu Leu
65                  70                  75                  80

Ala Lys Glu Cys Leu Lys Thr His Glu Leu Val Phe Ser Ser Arg Lys
                85                  90                  95

His Ser Thr Ala Ile Asp Ile Val Thr Tyr Asp Ser Ser Phe Ala Phe
            100                 105                 110

Ser Pro Tyr Gly Pro Tyr Trp Lys Phe Ile Lys Lys Leu Cys Thr Tyr
            115                 120                 125

Glu Leu Leu Gly Ala Arg Asn Leu Ala His Phe Gln Pro Ile Arg Thr
        130                 135                 140

Leu Glu Val Lys Ser Phe Leu Gln Ile Leu Met Arg Lys Gly Glu Ser
145                 150                 155                 160

Gly Glu Ser Phe Asn Val Thr Glu Glu Leu Val Lys Leu Thr Ser Asn
                165                 170                 175

Val Ile Ser His Met Met Leu Ser Ile Arg Cys Ser Glu Thr Glu Ser
            180                 185                 190

Glu Ala Glu Ala Ala Arg Thr Val Ile Arg Glu Val Thr Gln Ile Phe
        195                 200                 205

Gly Glu Phe Asp Val Ser Asp Ile Ile Trp Leu Cys Lys Asn Phe Asp
    210                 215                 220
```

```
Phe Gln Gly Ile Arg Lys Arg Ser Glu Asp Ile Gln Arg Arg Tyr Asp
225                 230                 235                 240

Ala Leu Leu Glu Lys Ile Ile Thr Asp Arg Glu Lys Gln Arg Arg Thr
                245                 250                 255

His Gly Gly Gly Gly Gly Gly Glu Ala Lys Asp Phe Leu Asp Met
                260                 265                 270

Phe Leu Asp Ile Met Glu Ser Gly Lys Ala Glu Val Lys Phe Thr Arg
                275                 280                 285

Glu His Leu Lys Ala Leu Ile Leu Asp Phe Phe Thr Ala Gly Thr Asp
                290                 295                 300

Thr Thr Ala Ile Val Cys Glu Trp Ala Ile Ala Glu Val Ile Asn Asn
305                 310                 315                 320

Pro Asn Val Leu Lys Lys Ala Gln Glu Glu Ile Ala Asn Ile Val Gly
                325                 330                 335

Phe Asp Arg Ile Leu Gln Glu Ser Asp Ala Pro Asn Leu Pro Tyr Leu
                340                 345                 350

Gln Ala Leu Ile Lys Glu Thr Phe Arg Leu His Pro Pro Ile Pro Met
                355                 360                 365

Leu Ala Arg Lys Ser Ile Ser Asp Cys Val Ile Asp Gly Tyr Met Ile
370                 375                 380

Pro Ala Asn Thr Leu Leu Phe Val Asn Leu Trp Ser Met Gly Arg Asn
385                 390                 395                 400

Pro Lys Ile Trp Asp Tyr Pro Thr Ala Phe Gln Pro Glu Arg Phe Leu
                405                 410                 415

Glu Lys Glu Lys Ala Ala Ile Asp Val Lys Gly Gln His Phe Glu Leu
                420                 425                 430

Leu Pro Phe Gly Thr Gly Arg Arg Gly Cys Pro Gly Met Leu Leu Ala
                435                 440                 445

Ile Gln Glu Val Val Ile Ile Gly Thr Met Ile Gln Cys Phe Asp
                450                 455                 460

Trp Lys Leu Pro Asp Gly Ser Gly His Val Asp Met Ala Glu Arg Pro
465                 470                 475                 480

Gly Leu Thr Ala Pro Arg Glu Thr Asp Leu Phe Cys Arg Val Val Pro
                485                 490                 495

Arg Val Asp Pro Leu Val Val Ser Thr Gln
                500                 505

<210> SEQ ID NO 84
<211> LENGTH: 511
<212> TYPE: PRT
<213> ORGANISM: Gerbera x hybrida

<400> SEQUENCE: 84

Met Asn Thr Leu Gln Leu Ile Phe Leu Leu Phe Phe Pro Thr Leu
1               5                   10                  15

Leu Phe Leu Tyr Cys Leu Pro Tyr Lys Arg Asn Gln Asn His Arg Arg
                20                  25                  30

Leu Pro Pro Ser Pro Pro Ser Phe Pro Ile Ile Gly His Leu His His
                35                  40                  45

Leu Gly Pro Leu Ile His Gln Ser Phe His Ala Leu Ser Thr Arg Tyr
                50                  55                  60

Gly Ser Leu Ile His Leu Arg Leu Gly Ser Val Pro Cys Val Val Val
65                  70                  75                  80

Ser Thr Pro Asp Leu Ala Lys Asp Phe Leu Lys Thr Asn Glu Leu Ala
                85                  90                  95
```

```
Phe Ser Ser Arg Lys His Ser Leu Ala Ile Asp His Ile Thr Tyr Gly
                100                 105                 110

Val Ala Phe Ala Phe Ala Pro Tyr Gly Thr Tyr Trp Lys Phe Ile Lys
            115                 120                 125

Lys Leu Phe Thr Val Glu Leu Leu Gly Thr Gln Asn Leu Ser His Phe
    130                 135                 140

Leu Pro Ile Arg Thr His Glu Ile Arg Glu Leu Leu Arg Thr Leu Met
145                 150                 155                 160

Val Lys Ser Arg Ala Lys Glu Arg Val Asn Leu Thr Glu Glu Leu Leu
                165                 170                 175

Lys Leu Thr Asn Asn Val Ile Ser Gln Met Met Met Ser Ile Arg Cys
            180                 185                 190

Ser Gly Thr Asn Ser Glu Ala Asp Glu Ala Lys Asn Leu Val Arg Glu
        195                 200                 205

Val Thr Lys Ile Phe Gly Gln Phe Asn Val Ser Asp Phe Ile Trp Phe
    210                 215                 220

Cys Lys Asn Ile Asp Leu Gln Gly Phe Lys Lys Arg Tyr Glu Gly Thr
225                 230                 235                 240

His Arg Arg Tyr Asp Ala Leu Leu Glu Arg Ile Ile Met Gly Arg Glu
                245                 250                 255

Glu Asn Arg Arg Arg Gly Lys Ile Lys Asp Gly Glu Gly Lys Asp Phe
            260                 265                 270

Leu Asp Met Leu Leu Asp Val Leu Glu Asp Gly Lys Ala Glu Ile Lys
        275                 280                 285

Ile Thr Arg Asp His Ile Lys Ala Leu Ile Leu Asp Phe Leu Thr Ala
    290                 295                 300

Gly Thr Asp Thr Thr Ala Ile Ala Ile Glu Trp Ala Leu Val Glu Leu
305                 310                 315                 320

Ile Asn Asn Pro Asn Ala Leu Glu Lys Ala Arg Gln Glu Ile Asp Gln
                325                 330                 335

Val Ile Gly Asp Glu Arg Leu Val Gln Glu Ser Asp Thr Pro Asn Leu
            340                 345                 350

Pro Tyr Ile Gln Ala Ile Ile Lys Glu Ala Leu Arg Leu His Pro Pro
        355                 360                 365

Ile Pro Met Leu Ile Arg Lys Ser Thr Glu Asn Val Ile Val Gln Gly
    370                 375                 380

Tyr Asp Ile Pro Ala Gly Thr Leu Leu Phe Val Asn Ile Trp Ser Ile
385                 390                 395                 400

Gly Arg Asn Pro Gln Cys Trp Glu Thr Pro Leu Glu Phe Lys Pro His
                405                 410                 415

Arg Phe Leu Asp Gly Asp Leu Lys Ser Ser Leu Asp Ile Lys Gly
            420                 425                 430

His Asn Phe Gln Leu Leu Pro Phe Gly Thr Gly Arg Arg Gly Cys Pro
        435                 440                 445

Gly Val Asn Leu Ala Met Arg Glu Leu Ser Val Val Ile Ala Asn Leu
    450                 455                 460

Ile Gln Cys Phe Asp Trp Asp Val Val Gly Glu Arg Leu Leu Asn Thr
465                 470                 475                 480

Asp Glu Arg Ala Gly Leu Thr Ala Pro Arg Ala Val Asp Phe Val Cys
                485                 490                 495

Val Pro Leu Glu Arg Gly Asn Thr Leu Lys Ile Leu Gly Ser Asn
            500                 505                 510
```

<210> SEQ ID NO 85
<211> LENGTH: 530
<212> TYPE: PRT
<213> ORGANISM: Gentiana triflora

<400> SEQUENCE: 85

```
Met Met Leu Leu Asp Phe Phe Tyr Ser Ala Ser Ile Phe Val Leu Ser
1               5                   10                  15

Ile Leu Leu Phe Arg Ala Ile Tyr Thr Thr Lys Asn Arg Arg Leu Arg
            20                  25                  30

Leu Pro Pro Ser Pro Phe Gly Leu Pro Ile Ile Gly His Leu His Leu
        35                  40                  45

Leu Gly Pro Lys Ile His His Ser Phe His Asn Leu Tyr Lys Arg Tyr
    50                  55                  60

Gly Pro Ile Phe His Leu Arg Leu Gly Ser Asn Arg Cys Ile Val Val
65                  70                  75                  80

Ser Thr Pro Glu Leu Ala Lys Glu Phe Leu Lys Thr His Glu Leu Asp
                85                  90                  95

Phe Ala Tyr Arg Lys Asn Ser Ser Ala Ile Ser Leu Leu Thr Tyr His
            100                 105                 110

Val Ser Phe Ala Phe Ala Pro Tyr Gly Pro Tyr Trp Lys Tyr Ile Lys
        115                 120                 125

Lys Ile Thr Thr Tyr Gln Leu Leu Gly Asn Arg Asn Leu Thr His Phe
    130                 135                 140

Glu Pro Ile Arg Arg Leu Glu Thr Asn Arg Val Leu Tyr Asp Leu Met
145                 150                 155                 160

Val Ser Ser Lys His Gly Lys Ser Val Asn Leu Thr Glu Glu Met Ile
                165                 170                 175

Lys Leu Thr Ser Asn Ile Ile Ser Gln Met Met Leu Ser Ile Arg Cys
            180                 185                 190

Ser Asp Thr Glu Ser Gly Ala Thr Asn Val Arg Asn Val Ile Arg Asp
        195                 200                 205

Val Thr Glu Leu Phe Gly Glu Phe Asp Val Ser Asp Ile Ile Trp Phe
    210                 215                 220

Cys Lys Asn Thr Asp Leu Gln Gly Ile Lys Lys Arg Ala Asn Gly Ile
225                 230                 235                 240

His Glu Arg Tyr Asp Ala Leu Leu Glu Lys Ile Ile Ser Asp Arg Glu
                245                 250                 255

Arg Thr Arg Ile Val Glu Lys Lys Asn Ser Gly Ala Gly Gly Gly Ser
            260                 265                 270

Gly Asp Gly Glu Arg Asn Asp Phe Leu Asp Ile Leu Met Asp Ala Met
        275                 280                 285

Glu Asp Asp Thr Ser Glu Val Lys Leu Ser Arg Asn His Ile Lys Ala
    290                 295                 300

Ile Ile Leu Asp Phe Leu Thr Ala Ala Thr Asp Thr Thr Ala Ile Ser
305                 310                 315                 320

Leu Glu Trp Ala Leu Ser Glu Leu Ile Asn Asn Pro Arg Val Leu Lys
                325                 330                 335

Lys Ala Gln Glu Glu Ile Asn Asn Val Val Gly Asn Gln Arg Leu Val
            340                 345                 350

Lys Glu Leu Asp Thr Pro Asn Phe Pro Tyr Ile Lys Ala Ile Ile Lys
        355                 360                 365

Glu Thr Phe Arg Leu His Pro Pro Ile Pro Met Val Ile Arg Lys Ser
    370                 375                 380
```

```
Ala Asn Asp Ile Gln Val Ala Gly Tyr Asp Val Pro Lys Asn Thr Met
385                 390                 395                 400

Leu Phe Val Asn Ile Trp Ser Ile Gly Arg Asn Pro Ser Tyr Trp Glu
            405                 410                 415

Lys Ala Ser Glu Phe Ser Pro Glu Arg Phe Leu Ala Asp Thr Asp Gly
        420                 425                 430

Gly Gly Leu Ser His Met Asp Ile Asn Gly Gln Tyr Phe Glu Leu Met
            435                 440                 445

Pro Phe Gly Thr Gly Arg Arg Gly Cys Pro Gly Met Pro Leu Ala Met
        450                 455                 460

Gln Glu Leu Pro Thr Val Leu Ser Leu Met Ile Gln Cys Phe Asp Tyr
465                 470                 475                 480

Ile Pro Leu Asp Phe Lys Gly Glu Lys Ala Glu Arg Val Met Asp Met
            485                 490                 495

Ser Glu Arg Pro Gly Leu Thr Ala Pro Arg Ala Asn Glu Leu Met Cys
        500                 505                 510

Leu Leu Lys Pro Arg Ile Asp Leu Pro Asn Leu Leu Gly Asn Val Lys
            515                 520                 525

Gly Glu
    530

<210> SEQ ID NO 86
<211> LENGTH: 506
<212> TYPE: PRT
<213> ORGANISM: Antirrhinum majus

<400> SEQUENCE: 86

Met Ser Thr Leu Val Tyr Ser Thr Leu Phe Ile Leu Ser Thr Leu Leu
1               5                   10                  15

Leu Thr Leu Leu Thr Arg Thr Arg Arg Lys Thr Arg Pro Pro Gly Pro
            20                  25                  30

Leu Ala Leu Pro Leu Ile Gly His Leu His Leu Gly Pro Lys Leu
        35                  40                  45

His His Thr Phe His Gln Phe Ser Gln Arg Tyr Gly Pro Leu Ile Gln
50                  55                  60

Leu Tyr Leu Gly Ser Val Pro Cys Val Val Ala Ser Thr Pro Glu Leu
65                  70                  75                  80

Ala Arg Glu Phe Leu Lys Thr His Glu Leu Asp Phe Ser Ser Arg Lys
            85                  90                  95

His Ser Thr Ala Ile Asp Ile Val Thr Tyr Asp Ser Ser Phe Ala Phe
        100                 105                 110

Ala Pro Tyr Gly Pro Tyr Trp Lys Phe Ile Lys Lys Leu Cys Thr Tyr
    115                 120                 125

Glu Leu Leu Gly Ala Arg Asn Leu Ser His Phe Gln Pro Ile Arg Ala
130                 135                 140

Leu Glu Val Asn Ser Phe Leu Arg Ile Leu Tyr Glu Lys Thr Glu Gln
145                 150                 155                 160

Lys Gln Ser Val Asn Val Thr Glu Glu Leu Val Lys Leu Thr Ser Asn
            165                 170                 175

Val Ile Ser Asn Met Met Leu Gly Ile Arg Cys Ser Gly Thr Glu Gly
        180                 185                 190

Glu Ala Glu Val Ala Arg Thr Val Ile Arg Glu Val Thr Gln Ile Phe
    195                 200                 205

Gly Glu Phe Asp Val Ser Glu Ile Val Trp Phe Cys Lys Asn Leu Asp
```

```
              210                 215                 220
Leu Gln Gly Ile Arg Lys Arg Ser Glu Asp Ile Arg Arg Tyr Asp
225                 230                 235                 240

Ala Leu Leu Glu Lys Ile Ile Ser Asp Arg Glu Arg Leu Arg Leu Arg
                245                 250                 255

Gly Gly Gly Gly Gly Gly Gly Glu Val Lys Asp Phe Leu Asp Met
            260                 265                 270

Leu Leu Asp Val Met Glu Ser Glu Lys Ser Glu Val Glu Phe Thr Arg
                275                 280                 285

Glu His Leu Lys Ala Leu Ile Leu Asp Phe Phe Thr Ala Gly Thr Asp
    290                 295                 300

Thr Thr Ala Ile Thr Thr Glu Trp Ala Ile Ala Glu Leu Ile Ser Asn
305                 310                 315                 320

Pro Asn Val Leu Lys Lys Ala Gln Glu Glu Met Asp Lys Val Ile Gly
                325                 330                 335

Ser Gln Arg Leu Leu Gln Glu Ser Asp Ala Pro Asn Leu Pro Tyr Leu
                340                 345                 350

Asn Ala Ile Ile Lys Glu Thr Phe Arg Leu His Pro Pro Ile Pro Met
            355                 360                 365

Leu Thr Arg Lys Ser Ile Ser Asp Val Val Asn Gly Tyr Thr Ile
    370                 375                 380

Pro Ala Lys Thr Leu Leu Phe Val Asn Leu Trp Ser Met Gly Arg Asn
385                 390                 395                 400

Pro Asn Tyr Trp Glu Asn Pro Met Glu Phe Arg Pro Glu Arg Phe Leu
                405                 410                 415

Glu Lys Gly Thr Gly Ser Ile Asp Val Lys Gly Gln His Phe Glu Leu
                420                 425                 430

Leu Pro Phe Gly Thr Gly Arg Arg Gly Cys Pro Gly Met Leu Leu Gly
            435                 440                 445

Met Gln Glu Leu Phe Ser Ile Ile Gly Ala Met Val Gln Cys Phe Asp
                450                 455                 460

Trp Lys Leu Pro Asp Gly Val Lys Ser Val Asp Met Thr Glu Arg Pro
465                 470                 475                 480

Gly Leu Thr Ala Pro Arg Ala Asn Asp Leu Val Cys Gln Leu Val Pro
                485                 490                 495

Arg Ile Asp Pro Val Val Val Ser Gly Pro
            500                 505

<210> SEQ ID NO 87
<211> LENGTH: 520
<212> TYPE: PRT
<213> ORGANISM: Theobroma cacao

<400> SEQUENCE: 87

Met Met Leu Gln Leu Leu Ser Tyr Ser Thr Leu Tyr Ile Ala Ser Phe
1               5                   10                  15

Phe Leu Val Lys Thr Ile Leu Ile Ser Ile Asn Asn Arg Pro Lys Leu
                20                  25                  30

Pro Pro Gly Pro Ile Ala Leu Pro Val Ile Gly His Leu His Leu Leu
            35                  40                  45

Gly Pro Phe Ile His Gln Thr Phe His Lys Phe Ser Ser Arg Tyr Gly
    50                  55                  60

Pro Leu Met Tyr Leu Arg Leu Gly Ser Ile Gly Cys Val Val Ala Ser
65                  70                  75                  80
```

-continued

```
Asn Pro Glu Leu Ala Lys Glu Leu Leu Lys Thr Tyr Glu Leu Ala Phe
                 85                  90                  95

Ala Ala Arg Met His Thr Ala Ala Ile Thr His Leu Thr Tyr Asp Ser
            100                 105                 110

Ser Phe Ala Phe Ala Pro Tyr Gly Pro Tyr Trp Lys Phe Ile Lys Lys
        115                 120                 125

Phe Ser Thr Tyr Glu Leu Leu Gly Asn Arg Thr Leu Ser Gln Phe Leu
130                 135                 140

Pro Val Arg Thr Lys Glu Leu His Arg Phe Ile Lys Phe Leu Leu Asp
145                 150                 155                 160

Arg Ser Lys Ala Gly Glu Ser Val Asn Val Thr Gln Glu Leu Leu Lys
                165                 170                 175

Leu Thr Asn Asn Thr Ile Ser Gln Met Met Leu Ser Met Arg Cys Ser
            180                 185                 190

Gly Ser Gly Asn Pro Ala Asp Gly Val Arg Ala Leu Val Arg Glu Val
        195                 200                 205

Thr Glu Ile Phe Gly Glu Phe Asn Ile Ser Asp Ser Ile Trp Phe Cys
210                 215                 220

Lys Ser Trp Asp Leu Gln Gly Phe Arg Arg Phe Glu Asp Ile His
225                 230                 235                 240

Arg Arg Tyr Asp Ala Leu Leu Glu Arg Ile Ile Arg Asp Arg Glu Glu
                245                 250                 255

Val Arg Lys Ser Lys Lys Glu Cys Asp Gln Arg Asp Asn Gly Asn Glu
            260                 265                 270

Val Lys Asp Phe Leu Asp Met Met Leu Asp Val Leu Glu Asn Asp Asn
        275                 280                 285

Ser Glu Met Gln Leu Thr Arg Asn His Ile Lys Ala Leu Val Leu Asp
290                 295                 300

Phe Leu Thr Ala Gly Thr Asp Thr Thr Ala Ile Val Leu Glu Trp Ala
305                 310                 315                 320

Leu Ala Glu Leu Ile Asn Asn Pro Glu Val Leu Lys Leu Ala Gln Lys
                325                 330                 335

Glu Ile Asp Gln Val Val Gly Thr Ser Arg Leu Val Glu Glu Ser Asp
            340                 345                 350

Ser Pro Arg Leu Gln Tyr Ile Gln Ala Ile Ile Lys Glu Thr Phe Arg
        355                 360                 365

Leu His Pro Pro Val Pro Met Ile Ser Arg Lys Ser Ile Gln Ser Cys
370                 375                 380

Lys Ile Lys Gly Tyr Thr Ile Pro Ala Asp Cys Leu Val Phe Val Asn
385                 390                 395                 400

Ile Trp Ala Ile Gly Arg Asp Pro Thr Val Trp Ala Asp Pro Leu Arg
                405                 410                 415

Phe Gln Pro Glu Arg Phe Leu Lys Ser Tyr Glu Gly Asp His Ser Ser
            420                 425                 430

Gly Pro Ile Asp Val Arg Gly Leu His Tyr Gln Leu Leu Pro Phe Gly
        435                 440                 445

Thr Gly Arg Arg Gly Cys Pro Gly Ala Ser Leu Ala Met Gln Glu Leu
450                 455                 460

Pro Thr Thr Leu Ala Ala Met Ile Gln Cys Phe Asp Trp Lys Pro Ala
465                 470                 475                 480

Ala Thr Ser Lys Thr Gly Asp Gly Val Asp Met Ser Glu Arg Pro Gly
                485                 490                 495

Leu Thr Ala Pro Arg Ala Lys Asp Leu Glu Cys Val Pro Val Ala Arg
```

```
                      500                 505                 510
Phe Thr Pro Thr Val Phe Ala Thr
            515                 520

<210> SEQ ID NO 88
<211> LENGTH: 534
<212> TYPE: PRT
<213> ORGANISM: Camellia sinensis

<400> SEQUENCE: 88

Met Phe Asp Leu Ile Ser Ile Ala Thr Leu Phe Val Ile Ile Ser
1               5                   10                  15

Thr Thr Ile Leu Leu Leu Ser Ile Asn His Phe Lys Lys Pro His
                20                  25                  30

Leu Arg Arg Arg Leu Ser Leu Pro Pro Thr Pro Phe Ala Leu Pro Ile
            35                  40                  45

Ile Gly His Leu His Leu Leu Gly Pro Ile Ile His Arg Ser Phe His
        50                  55                  60

Asp Leu Ser Ser Arg Tyr Gly Pro Leu Phe His Leu Arg Leu Gly Ser
65                  70                  75                  80

Val Pro Cys Phe Val Ser Thr Pro Glu Leu Ala Lys Glu Phe Leu
                85                  90                  95

Leu Thr His Glu Leu Lys Phe Ser Ser Arg Arg Asp Ser Ile Ala Ile
                100                 105                 110

Gln Arg Leu Thr Tyr Asp Ser Ala Phe Ala Phe Ala Pro Tyr Gly Pro
            115                 120                 125

Tyr Trp Lys Phe Leu Lys Lys Leu Cys Thr Cys Asp Leu Leu Gly Ala
        130                 135                 140

Arg Ser Ile Asn His Phe Leu Pro Thr Arg Thr Arg Glu Leu His Cys
145                 150                 155                 160

Phe Val Arg Leu Leu Ile Asp Lys Ala Val Ala Cys Glu Pro Val Asn
                165                 170                 175

Ile Thr Lys Glu Leu Ser Thr Leu Ala Asn Asn Ile Ile Ser Gln Met
            180                 185                 190

Met Ile Gly Val Arg Cys Ser Gly Thr Thr Gly Glu Ala Glu Ala
        195                 200                 205

Thr Thr Leu Ala Arg Glu Val Thr Lys Ile Phe Gly Glu Phe Asn Val
210                 215                 220

Ser Asp Phe Met Trp Val Ile Arg Asn Phe Asp Leu Gln Gly Phe Arg
225                 230                 235                 240

Lys Arg Val Glu Asp Ile Tyr Thr Arg Tyr Asp Ala Leu Leu Glu Arg
                245                 250                 255

Ile Ile Thr Asn Arg Glu Glu Val Arg Glu Lys Asn Val Gln Glu Arg
            260                 265                 270

Lys Leu Gly Val Gly Glu Gly His His Val Lys Asp Phe Leu Asp Leu
        275                 280                 285

Leu Leu Asp Val Leu Glu Glu Asp His Ser Glu Ile Asn Phe Ser Arg
    290                 295                 300

Asp Asn Ile Lys Gly Leu Ile Leu Asp Phe Phe Thr Ala Gly Thr Asp
305                 310                 315                 320

Thr Ser Ser Ile Ala Ile Glu Trp Ala Leu Ala Glu Leu Ile Asn Asn
                325                 330                 335

Pro Arg Val Leu Gln Lys Ala Gln Glu Glu Ile Asp Asn Val Val Gly
            340                 345                 350
```

```
Lys His Arg Leu Val Ser Glu Ser His Gly Pro Asn Leu Pro Tyr Ile
            355                 360                 365

Gln Ala Ile Ile Arg Glu Ala Leu Arg Leu His Pro Pro Val Pro Leu
        370                 375                 380

Ile Thr Arg Lys Ser Ile Glu Asp Cys Met Ile Gln Gly Tyr Asn Ile
385                 390                 395                 400

Pro Ala Asn Ser Met Leu Phe Val Asn Val Trp Ser Leu Ala Arg Asn
                405                 410                 415

Pro Lys Tyr Trp Asp Ser Pro Leu Asp Phe Leu Pro Glu Arg Phe Leu
            420                 425                 430

Arg Pro Glu Lys Gly Gly Pro Val Gly Pro Thr Asp Val Lys Gly Gln
        435                 440                 445

His Phe Gln Leu Leu Pro Phe Gly Thr Gly Arg Arg Gly Cys Pro Gly
    450                 455                 460

Thr Ser Leu Ala Met Gln Glu Leu Pro Ala Met Leu Ala Ala Met Ile
465                 470                 475                 480

Gln Cys Phe Glu Trp Lys Val Val Asn Gln Ser Gly Asp Val Met Asn
                485                 490                 495

Gly Asp Gly Ala Leu Asp Met Thr Glu Gln Pro Gly Met Thr Ala Pro
            500                 505                 510

Arg Ala His Asp Leu Val Cys Met Pro Ile Pro Arg Ile Asp Gln Leu
        515                 520                 525

Tyr Ala Leu Leu Asp Pro
    530

<210> SEQ ID NO 89
<211> LENGTH: 509
<212> TYPE: PRT
<213> ORGANISM: Plectranthus barbatus

<400> SEQUENCE: 89

Met Asp His Val Glu Ala Ala Leu Phe Ala Ala Ile Phe Leu Leu Ser
1               5                   10                  15

Ala Ala Leu Leu Asn His Leu Leu Thr Gly Lys Arg Arg Gln Asn Ala
            20                  25                  30

Tyr Pro Pro Gly Pro Phe Pro Leu Pro Ile Ile Gly His Leu His Leu
        35                  40                  45

Leu Gly Pro Arg Leu His His Thr Phe His Asp Leu Thr Gln Arg Tyr
    50                  55                  60

Gly Pro Leu Met Gln Val Arg Leu Gly Ser Ile Arg Cys Val Ile Ala
65                  70                  75                  80

Ala Thr Pro Glu Leu Ala Lys Glu Phe Leu Lys Thr Ser Glu Leu Val
                85                  90                  95

Phe Ser Ala Arg Lys His Ser Thr Ala Ile Asp Ile Val Thr Tyr Glu
            100                 105                 110

Ser Ser Phe Ala Phe Ser Pro Tyr Gly Pro Tyr Trp Lys Tyr Ile Lys
        115                 120                 125

Lys Leu Cys Thr Tyr Glu Leu Leu Gly Ala Arg Asn Leu Asn His Phe
    130                 135                 140

Leu Pro Ile Arg Thr Ile Glu Val Lys Thr Phe Leu Glu Ala Leu Met
145                 150                 155                 160

Gln Lys Gly Lys Thr Gly Glu Arg Leu Asn Val Thr Glu Glu Leu Val
                165                 170                 175

Lys Leu Thr Ser Asn Val Ile Ser Gln Met Met Leu Ser Ile Arg Cys
            180                 185                 190
```

```
Ser Gly Thr Glu Gly Glu Thr Glu Ala Val Arg Thr Val Ile Arg Glu
    195                 200                 205

Val Thr Gln Ile Phe Gly Glu Phe Asp Val Ala Asp Ile Ile Trp Phe
210                 215                 220

Cys Lys Asn Phe Asp Phe Gln Gly Ile Arg Lys Arg Ser Glu Asp Ile
225                 230                 235                 240

Gln Arg Arg Tyr Asp Ala Leu Leu Glu Lys Ile Ile Thr Asp Arg Glu
                245                 250                 255

Lys Gln Arg Arg Thr Gln His Gly Gly Glu Ala Lys Asp Phe Leu Asp
            260                 265                 270

Met Phe Leu Asp Ile Met Lys Ser Gly Lys Ala Glu Val Asn Phe Thr
        275                 280                 285

Arg Asp His Leu Lys Ala Leu Ile Leu Asp Phe Phe Thr Ala Gly Thr
    290                 295                 300

Asp Thr Thr Ala Ile Val Val Gly Trp Ala Ile Ala Glu Leu Ile Asn
305                 310                 315                 320

Asn Pro Asn Val Leu Lys Lys Ala Gln Ala Glu Ile Asp Lys Val Val
                325                 330                 335

Gly Leu His Arg Ile Leu Gln Glu Ser Asp Gly Pro Asn Leu Pro Tyr
            340                 345                 350

Leu Asn Ala Val Ile Lys Glu Thr Phe Arg Leu His Pro Pro Ile Pro
        355                 360                 365

Met Leu Ser Arg Lys Ser Ile Ser Asp Cys Val Ile Asp Gly Tyr Thr
    370                 375                 380

Ile Pro Ala Asn Thr Leu Leu Phe Val Asn Ile Trp Ser Met Gly Arg
385                 390                 395                 400

Asn Pro Lys Ile Trp Asp Asn Pro Met Ala Phe Arg Pro Glu Arg Phe
                405                 410                 415

Leu Glu Lys Glu Lys Thr Gly Ile Asp Ile Lys Gly Gln His Phe Glu
            420                 425                 430

Leu Leu Pro Phe Gly Thr Gly Arg Arg Gly Cys Pro Gly Met Leu Leu
        435                 440                 445

Ala Ile Arg Glu Val Val Val Ile Ile Gly Thr Val Ile Gln Cys Phe
    450                 455                 460

Asp Trp Lys Leu Pro Val Asp Asp Val Ser Gly Leu Val Asp Met Thr
465                 470                 475                 480

Glu Arg Pro Gly Leu Thr Ala Pro Arg Ala Asp Asp Leu Ile Cys Arg
                485                 490                 495

Val Val Pro Arg Val Asp Pro Leu Val Val Ser Gly His
            500                 505

<210> SEQ ID NO 90
<211> LENGTH: 521
<212> TYPE: PRT
<213> ORGANISM: Lonicera japonica

<400> SEQUENCE: 90

Met Trp Ile Phe Asp Leu Thr Ile Ser Phe Thr Thr Leu Leu Phe Leu
1               5                   10                  15

Ile Phe Thr Thr Ala Leu Leu Leu Leu Lys Val Phe Lys Lys Asn
                20                  25                  30

His Lys Leu Arg Pro Pro Ser Pro Phe Thr Leu Pro Ile Ile Gly
            35                  40                  45

His Leu His Leu Leu Gly Pro Leu Ile His Gln Ser Phe His Arg Leu
```

-continued

```
            50                  55                  60
Ser Thr Leu Tyr Gly Pro Leu Ile Gln Leu Lys Ile Gly Tyr Ile Pro
65                  70                  75                  80

Cys Val Val Ala Ser Thr Pro Glu Leu Ala Lys Glu Phe Leu Lys Thr
                85                  90                  95

His Glu Leu Ala Phe Ser Ser Arg Lys His Ser Ala Ala Ile Lys Leu
            100                 105                 110

Leu Thr Tyr Asp Val Ser Phe Ala Phe Ser Pro Tyr Gly Pro Tyr Trp
            115                 120                 125

Lys Phe Ile Lys Lys Thr Cys Thr Phe Glu Leu Leu Gly Thr Arg Asn
            130                 135                 140

Met Asn His Phe Leu Pro Ile Arg Thr Asn Glu Ile Arg Arg Phe Leu
145                 150                 155                 160

Gln Val Met Leu Glu Lys Ala Lys Ala Ser Glu Gly Val Asn Val Thr
                165                 170                 175

Glu Glu Leu Ile Lys Leu Thr Asn Asn Val Ile Ser Gln Met Met Phe
            180                 185                 190

Ser Thr Arg Ser Ser Gly Thr Glu Gly Glu Ala Glu Glu Met Arg Thr
            195                 200                 205

Leu Val Arg Glu Val Thr Gln Ile Phe Gly Glu Phe Asn Val Ser Asp
210                 215                 220

Phe Ile Lys Leu Cys Lys Asn Ile Asp Ile Gly Gly Phe Lys Lys Arg
225                 230                 235                 240

Ser Lys Asp Ile Gln Lys Arg Tyr Asp Ala Leu Leu Glu Lys Ile Ile
                245                 250                 255

Ser Glu Arg Glu Ser Glu Arg Ala Arg Arg Gly Lys Asn Arg Glu Thr
            260                 265                 270

Leu Gly Glu Glu Gly Gly Lys Asp Phe Leu Asp Met Met Leu Asp Thr
            275                 280                 285

Met Glu Asp Gly Lys Cys Glu Val Glu Ile Thr Arg Asp His Ile Lys
290                 295                 300

Ala Leu Val Leu Asp Phe Leu Thr Ala Ala Thr Asp Thr Thr Ala Ile
305                 310                 315                 320

Ala Val Glu Trp Thr Leu Ala Glu Leu Ile Ser Asn Pro Glu Val Phe
                325                 330                 335

Asp Lys Ala Arg Glu Glu Ile Asp Lys Val Val Gly Lys His Arg Leu
            340                 345                 350

Val Thr Glu Leu Asp Thr Pro Asn Leu Pro Tyr Ile His Ala Ile Ile
            355                 360                 365

Lys Glu Ser Phe Arg Leu His Pro Pro Ile Pro Leu Leu Ile Arg Lys
            370                 375                 380

Ser Val Gln Asp Cys Thr Val Gly Gly Tyr His Ile Ser Ala Asn Thr
385                 390                 395                 400

Ile Leu Phe Val Asn Ile Trp Ala Ile Gly Arg Asn Pro Lys Tyr Trp
                405                 410                 415

Glu Ser Pro Met Lys Phe Trp Pro Glu Arg Phe Leu Glu Ser Asn Gly
            420                 425                 430

Pro Gly Pro Val Gly Ser Met Asp Ile Lys Gly His His Tyr Glu Leu
            435                 440                 445

Leu Pro Phe Gly Ser Gly Arg Arg Gly Cys Pro Gly Met Ala Leu Ala
            450                 455                 460

Met Gln Glu Leu Pro Val Val Leu Ala Ala Met Ile Gln Cys Phe Asn
465                 470                 475                 480
```

```
Trp Lys Pro Val Thr Leu Asp Gly Glu Glu Leu Asp Met Ser Glu Arg
            485                 490                 495

Pro Gly Leu Thr Ala Pro Arg Ala His Asp Leu Val Cys Val Pro Ser
        500                 505                 510

Ala Arg Ile Asn Ser Phe Asp Asn Phe
        515                 520

<210> SEQ ID NO 91
<211> LENGTH: 6429
<212> TYPE: DNA
<213> ORGANISM: Medicago truncatula

<400> SEQUENCE: 91
cctttaatga cggatagtgg tacggtatat cattgaatac ttaagattca tccccttgcg      60
gggcttgcag tatactgcat tttaggcaaa aaaaaaatga tgttgtaaca aactctgaaa     120
atttcaggct tattgtgtgt aggatgccgc ggcatttttta tttgtctttc aactgtgatc     180
cagtaacgga gaaatttgtt gattattgtt atattgattg ttccttttctt atgtcttaac     240 tactacagag tcttttttttt agtcgcacga catttagaac ctcaactttt ccaagtagag     300
cctggtgtat ctgtattagg ggcattacaa ttgtcttagg atacgtttgg attggtggag     360
tgaaaagtcg caaaagctgt gaagtttgac atgatgtcat agcacctatt gaggagttaa     420
acatctcgaa ttaagttgtg ccgtcggaaa acgctcttag cgcaatatct tcatttcact     480
gtgaatgcac tagcaggtcg gaaaacgctc ttagcgcaat atcttcattt cactgtgaat     540
gcactagcag atggcacgat gaacaacctc tcatgaagtc tctgttggga tctactcatt     600
gggtagaaat tcgaaatcaa agccattgct atagtccagc agaaacatat caaatagagt     660
ttaaataagc ttaaagattc tgagtgcatt ttgtttcagc tttaaaaaaa atagattttg     720
agttaaaaaa tctctagaga ttttaaaaaa aatctaaagc tatttctatt tgtttactat     780
cataaaaaat cattttttcta agatttaaag ctcttacact tgagttcttt atgtttagaa     840
aaaaaataga ttttggaaaa gctacttgaa atagcttttc atttttaaagc taaaaatgat     900 ttttttaata aaatggattt ttttaaaatc taaaacaaat actaaaaaaa taaaaaaagt     960
gattttttta gatcaaaaat agattttttt caaaaaaatc caaaacaatc gggccctcta    1020
tgaaaacatg agaatttaag ctaaccagaa cttaaacttc gttaaaaatt gttgaaaata    1080
ctgattataa aagagataag ggatataaat attacacaca ataatttatg tcctcacccc    1140
tatattatta aacataaaat gtcaataatg ataggcactg ttttgtaggt caatctttga    1200
cttgtcacca agaaatgaaa tgctgccgac tcatcaaaga aggagccttt aatttatttg    1260
ttttttacta taatattggg acactaccgc ttaatagtag taactaatct tagttggaga    1320
atttgaaaaa caaataagat gtgctcttca atttcaacca aaaattttct atatgcatga    1380
gacagaaatt aaaactccga ccatatgttt aaaaagccta atctcttgt ctgttcaacc     1440 aatatatttt tgatggagcc tctaattact aattagtgat taatcaaata ttaatttga    1500 aactcaactc tcagcctatg tcacagtgtg aaaaaagcta aaagagtag ccttgtcttt     1560 tttgttgaaa atttgggaaa cttattgccg gatgaaccga atataccctt tgaatgataa    1620
cgccatttca tgttttgact ctaatattca aaactcaaaa gtccaaacta atacatgtat    1680 tttttttatta aaaaaataat attagcaatc aaagtctatt tcttgtactc cctccggtca    1740
tatttataat caaaaaataa ttttttttgat acattgaata ttaactaat gtatctaaca    1800 tataaatgtg accggaaata ttaattattc gatgaactta aaaaattatt ttttacttat    1860
```

```
aaatgtgacc agaatgtgta ctaattatgc ctgcaatgat gcacatgtga agacattatt    1920
attaatgcta ctactactat tgtcatgatt tttgaaaata ttatctacaa tcgtagatga    1980
ccattagctt aaataaataa aggtccagtt tatttagact ggattttgta tgagttttt    2040 ttttatctaa taattagcct aattctttac ttctaaaaat attcttataa atatttacag    2100
ggaaattaaa aattaaatta atcttttta tgaagaaaa ttaaattaat cataaaattc     2160
aaaatatgta gattaatttt gatttacgct aaaaccatta tataaagata cataatcatt    2220
tcaagtaaaa aaagatacat aatcatatgg agattatctt aatcattttt ttaaatactt    2280
ttcacctcta cctcaacgag cagcagttaa aacagggaaa ctactaataa actatcgtaa    2340
tgatgtgaca tgcaagattt gttttagctg ttggttcaac tagaagccaa gccttaaaat    2400
cttttttgct tatttaaatg ctaccttatt gtaattgata ttaaaggata caagtagttt    2460
ttatttttat tttttaaata tcatatcatt cacttcaaag ttaaaaatta ttcttttgaa    2520
atatgaagat ccgtttaaaa agctaacatt tctcaacaga cgctctttca tatgtaccaa    2580
ctcgattaga tatcatactt gtatagttac gagatatagt tatttataaa ccgtatcgtg    2640
tcatattata ttggtagatg aaataatata atatactgta taatttgtct aacaagacta    2700
gttgcatgat taggagacgt gcctaatcat gtccttatct ttttgtcctt aaagtaacca    2760
aaaatagagt tgcaaaggtg ttatatctac ttgttttaat atgtttaatt ctgcaaatga    2820
tacatcacaa attatatata tataatagat taagtgtgta ggtacatgta tcttctatag    2880
caaccataga ctcatttaga ggatcacttt aatatctaca ctgtaatcac actaactagt    2940
tgaataagtt gcattgtcaa gaaaaaataa ttagttcaat aggttaaacc aatgtgatta    3000
taattagatc agatcagctt tttgaatcgg aatagggggtc tgatctggct catgcagtcc    3060
atgagaaact accataatgt gattatttac tcgatggcat attaaccaat ttgattctaa    3120
gactttcacc caaaacattg ctctcaattc aagtagattg tgatatgtaa tggccggagt    3180
ttgaactcta aatttcttat gcgtttgatt tgttaaaaaa taaggatagg atatgacaac    3240
ttcaattgta aggtgtttaa tttgtaaaat tgttttttgga acatgacaaa ctagaggtca    3300
gagattggac gaaaactgaa attcttgacc ctcactaagc cacgacacaa ctttttgtct    3360
cacgtacacg ttgtctaaaa tatcaaaaag ttttttgtcc ataaaaattt gtataatacc    3420
aaaatagttt ttttttcata aaaagttgtc atgtgttgtt ctgctttgtg ttatgatgtt    3480
atgttcaata cttttggttt aacatatcaa acgcacccctt aaagatgaat ttctagtaat    3540
tatgttacgt gaccggaaaa aaaaaactttt cacccaaaat attgctatca attcatatgt    3600
tgattataga ttatgtcagg ttcttaatta gtatacgttt tttgagagga ggttgttgat    3660
attttttttt tgaaagactt gtatataaat acgactcact taacattatg attgtgcgca    3720
ttgaagaaga aaatgcaaaa atcctctctt aattattaat taaaaggaca ttaatgataa    3780
ttttacaatc tttttttttt tttgagagca atgataattt tacaatcatc ttcaatgtga    3840
tttcaattat gttcctgagg ttacaaagtc gaactcttaa taccgagata acacctcatc    3900
aacgtatact ttcaatttttt ttcactagtt tgattatttt cattaataat ttgagctaac    3960
tttatcatat catgtgaatg gagtgagatt aacaaaataa gattcactta agaacaaatg    4020
gatctggatt attcgaatat gagtcattac caactttact tgacctctttt tcactaaaaa    4080 agatggttaa gacataaaaa taagtttttag aaaaatatcat aaaactgttt gaaaaagatc    4140
aatttattat tcataattaa agagtaaata agataggtta gacaccttca tccgaattca    4200
```

```
aacccaagac cttgtagtat gtgagttctt ttacataatt ttttttacctt tacaaaaaag    4260
gtaaaaaaaa atagtataaa aaaaaaaaag atacataaat tttttttatac atgtctaatg    4320
atacttcttt tattgatcaa aacatcattt aaacaaaatc tttaaaagaa ctaatttcag    4380
taatcataaa atctttaaat ctaaaattca tcttgtaggg cttcttttttg gtaactttca   4440
ttttcatttc tttttttggtt ttagactttt agaagtattt gccccattct ttcccaacac   4500
ctctacttct tcgagatttc cacatatccg tgtgattatg ttaagaaagt caactcttat   4560
gtcaccttaa aagttgattc taatacagtt ttgtcatcta tgaccacaat aagacactat    4620
ataattaata tcaatgatca ataaggtgac aaatattggg atataagatt aggtgtactt    4680
cctctaaaaa aaattaggtc cttagttagt ttgtaaaata gtattagaga tttagtgtat    4740
attgttgtaa tataagtata taaccacctc attatagagg cactctttat gatttgtaac    4800
atacttaagg ttaaatatgt ttttggtccc tgtaaatatg tcaactttttc gttttagttt   4860
ctctaaaatt tcctttcaac ttttagtccc tcaaaaaaat ttcatcttca cttttggtcc    4920
ctcctttaaa ataaactcat atgtagaatt catatatttg aataaaattt tgcagaaaaa   4980
ttcttaatat tataagaatc tctcccaaaa aaatttagaa tttttttaaca aaacatgaat   5040
ttaatatgaa tttttatatt tttgtggtta aaaatttata ttaaatttat gttttgttaa    5100
aaaattctaa ttttttttttt ggaaaatatt tttacaatat tctacacatt tctgcacaat   5160
ttcattaaaa aaaaaaatac taaaattaac tttaaaatag gaaccaaaag tagtgattga   5220
aaattttata gggactaaaa gttgaaggaa aattttagag ggactaaaat gaaaagataa   5280
ttagggacca aaaacatatt taaccctact tattaattac catcaataca acaattatat    5340
tcttctttca ctaagtggag tcaaaagaaa tagtttatat gaaataataa tatcacaagt   5400
cacctacaca tataaatatt tgtataaagt gatggaacac acataaattt cattagataa    5460
aaaaacgaat aacacttgta cgtaactaat aatttatacg acatgactag actttaatgt   5520
tttacataac agaataaatt ttcacagtcc tataaagaat ttatggacgt gaggtgaaca    5580
aacattgctg aaacatgctt agcaaacaat gaaagcacca ccttaacagc ttcctatttt    5640
aatacaaaaa acaaccaatc aatgttccac aatatccctt tcataacacc atcatctaat   5700
tgcatcacct acggcatttt atttatttaa taatatcaaa aggtgaccaa aattgtcatt    5760
aaattaatca aaatgaccct cttttgcttga ttcaaaagct acaaatttttt ttcatttttta  5820
aacctgtcca ttaaatttcc acacacggtt ttctaacctt tgaagattaa ttttttaacat   5880
cacaatcttt tctctttcat tgtacacaag agacaaatga atggtacatg gaatcttttg    5940
agtattttttt tcactcttag atgtcatagc cactgctcta atatttagta tttattaatt    6000
ctattgacaa aaacaaaaat cagaaaaata tttactatta gtaaatgcca agttctaaga    6060
caaagtttat ttatctatat gcaagatttc tttcaagttt cacgtgtaaa ttgttgtagg   6120
aagctattcc tttaactgtt tcatgttaat tagttactac atgcttttgg aataaaacag    6180
ttcataaagt ctttctttca tttccttggt ttttgagaag aaaaaatagt tgctagctta    6240
ggttgaattt tcattgagta ttcaaaattc tctcccttgg ttttttgagaa gggtattgtg   6300
atgaataaag aattcagctg aaaattcatt tatgaaacct gaaagatctt agccaaaaac   6360
ctgtgttgaa aataagttca agcatcattc aagtgtttct ttataatcaa gcatctttaa    6420
agtgttgaa                                                            6429

<210> SEQ ID NO 92
<211> LENGTH: 791
```

```
<212> TYPE: DNA
<213> ORGANISM: Medicago truncatula

<400> SEQUENCE: 92
tcacaacatt tttatttcta taataataaa tttgttattt tcagaatatt ttttatttaa      60
taaaaataac caaacatttt ttcatcatta caacaggtat cttatctatt cattcaattt     120
aacttttact atttttttgtt ttcattatac ttaataatcc tcaacatcaa ttactaaaac    180
atcctaaaaa ctgaatttt taataaaaaa ggaatttcac ccctatgaaa ggatactatc     240
ctttgagcat gtgtgtgaaa agatggcttt tcctttataa tgttaacaat aaccttcaca    300
caaaataata ataataaatc ctcttaagac aaagtttagt gataatttgt cacatctaag   360
tttattatga gcaagtcaaa gataactata acttcataaa catttctgtt gtgacatcgt    420
gcaaccatca caaagctacg ccgtatgatg ggaggtggtc aaccacagaa ataaaaatga   480
gcttaattag actctgatag agtacacgtt tctactaaaa tcattccatc aatccaaaca    540
cgaccacaat ggcttttaca aaactgttaa ttaaagtgtg tttgtgactc gtcatcgttt    600
gtaacgggaa cttagagaca tatttgatgt aagacaacta tgtaaaccac tattaatgaa    660
cataatattt taaccaaaag attgcatttt ttttttctga agtaacaaca agaactcagt   720
aactattagt acatttttca ttttcactcg aactatacac gacttcctta ttggtgtaga    780
tgggacaata g                                                          791
```